United States Patent
Wallace et al.

(10) Patent No.: US 6,735,497 B2
(45) Date of Patent: May 11, 2004

(54) SYSTEMS AND METHODS FOR DISPENSING MEDICAL PRODUCTS

(75) Inventors: Robert L. Wallace, Pepperell, MA (US); Brian T. Hart, Bedford, MA (US); Richard D. Hart, Irving, TX (US); Arthur A. Berube, Hampstead, NH (US); Harold J. Liff, Lexington, MA (US); Liana Buciuman-Coman, Leominster, MA (US); James Dowling, Milford, NH (US); Steve Piantedosi, Gardner, MA (US)

(73) Assignee: Telepharmacy Solutions, Inc., North Billerica, MA (US)

( * ) Notice: Subject to any disclaimer, the term of this patent is extended or adjusted under 35 U.S.C. 154(b) by 0 days.

(21) Appl. No.: 10/105,059

(22) Filed: Mar. 22, 2002

(65) Prior Publication Data

US 2002/0173875 A1 Nov. 21, 2002

Related U.S. Application Data

(63) Continuation-in-part of application No. PCT/US00/26170, filed on Sep. 22, 2000, which is a continuation-in-part of application No. 09/454,359, filed on Dec. 3, 1999, now Pat. No. 6,564,121.
(60) Provisional application No. 60/155,446, filed on Sep. 22, 1999.

(51) Int. Cl.$^7$ .......................... G06F 17/00; G07F 11/00
(52) U.S. Cl. .................. 700/231; 700/232; 700/237; 221/2; 221/7
(58) Field of Search .................. 700/231, 232, 700/236, 237, 241; 221/2, 3, 7, 15

(56) References Cited

U.S. PATENT DOCUMENTS

| | | | |
|---|---|---|---|
| 4,847,764 A | 7/1989 | Halvorson | 364/413.02 |
| 4,857,713 A | 8/1989 | Brown | 235/375 |
| 5,014,875 A | 5/1991 | McLaughlin et al. | 221/2 |
| 5,314,243 A | * 5/1994 | McDonald et al. | 221/2 |
| 5,502,944 A | 4/1996 | Kraft et al. | 53/55 |

(List continued on next page.)

FOREIGN PATENT DOCUMENTS

| | | |
|---|---|---|
| NL | 9400 941 | 1/1996 |
| WO | WO 98/28676 | 7/1998 |
| WO | WO 99/10829 | 3/1999 |

OTHER PUBLICATIONS

Ukens, C., "Automation: Pharmacists' friend or foe?"; Drug Topics; 78–81 Oct. 4, 1999.

*Primary Examiner*—Gene O. Crawford
(74) *Attorney, Agent, or Firm*—Bowditch & Dewey, LLP

(57) ABSTRACT

The present invention relates to systems and methods for the remote dispensing of packaged and non-packaged medical products using networked communications systems. A preferred embodiment of the invention utilizes a network to provide for the secure delivery of confidential patient information and the sending of dispense instructions to a remote dispensing station. A preferred embodiment of the present invention relates to systems and methods of dispensing samples of drugs or other medical products. Another preferred embodiment of the invention provides a system and method for dispensing non-prescription medications.

26 Claims, 135 Drawing Sheets

U.S. PATENT DOCUMENTS

| | | | | |
|---|---|---|---|---|
| 5,564,803 A | * | 10/1996 | McDonald et al. | 312/215 |
| 5,713,485 A | | 2/1998 | Liff et al. | 221/2 |
| 5,745,366 A | * | 4/1998 | Higham et al. | 700/242 |
| 5,797,515 A | | 8/1998 | Liff et al. | 221/2 |
| 5,805,455 A | * | 9/1998 | Lipps | 700/231 |
| 5,842,976 A | | 12/1998 | Williamson | 600/300 |
| 5,850,344 A | | 12/1998 | Conkright | 364/479.01 |
| 5,860,563 A | | 1/1999 | Guerra et al. | 221/172 |
| 5,867,821 A | | 2/1999 | Ballantyne et al. | 705/2 |
| 5,873,488 A | | 2/1999 | Guerra | 221/220 |
| 5,884,806 A | | 3/1999 | Boyer et al. | 221/75 |
| 5,897,024 A | | 4/1999 | Coughlin et al. | 221/135 |
| 5,905,653 A | | 5/1999 | Higham et al. | 364/479.14 |
| 5,907,493 A | | 5/1999 | Boyer et al. | 364/479.01 |
| 5,924,074 A | | 7/1999 | Evans | 705/3 |
| 5,945,651 A | | 8/1999 | Chorosinski et al. | 235/375 |
| 5,950,630 A | * | 9/1999 | Portwood et al. | 128/897 |
| 5,950,632 A | | 9/1999 | Reber et al. | 128/898 |
| 5,963,452 A | | 10/1999 | Etoh et al. | 364/479.06 |
| 5,971,594 A | | 10/1999 | Sahai et al. | 364/479.12 |
| 5,991,731 A | | 11/1999 | Colon et al. | 705/3 |
| 6,003,006 A | | 12/1999 | Colella et al. | 705/2 |
| 6,004,020 A | | 12/1999 | Bartur | 364/479.06 |
| 6,021,392 A | | 2/2000 | Lester et al. | 705/2 |
| 6,032,155 A | | 2/2000 | de la Huerga | 707/104 |
| 6,039,467 A | | 3/2000 | Holmes | 364/479.01 |
| 6,109,774 A | * | 8/2000 | Holmes et al. | 700/237 |
| 6,112,502 A | | 9/2000 | Frederick et al. | 53/411 |
| 6,115,649 A | | 9/2000 | Sakata | 700/241 |
| 6,116,461 A | * | 9/2000 | Broadfield et al. | 221/98 |
| 6,119,932 A | * | 9/2000 | Maloney et al. | 235/380 |
| 6,138,865 A | * | 10/2000 | Gilmore | 221/2 |
| 6,151,536 A | * | 11/2000 | Arnold et al. | 700/237 |
| 6,169,707 B1 | * | 1/2001 | Newland | 221/2 |
| 6,330,491 B1 | | 12/2001 | Lion | 700/237 |

* cited by examiner

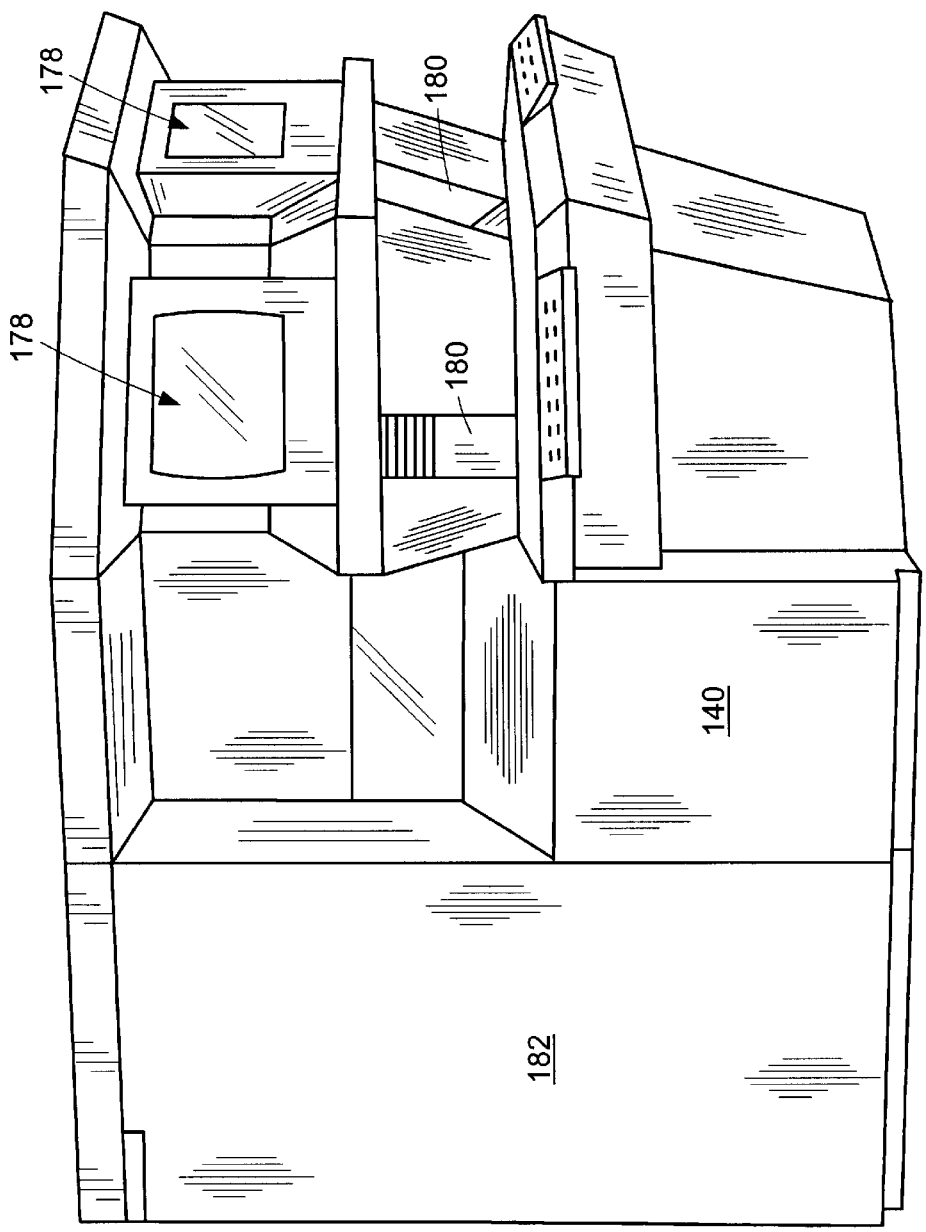

1) City 3 controls Host Pharmacy System in City 1 using internet to process a medication prescription

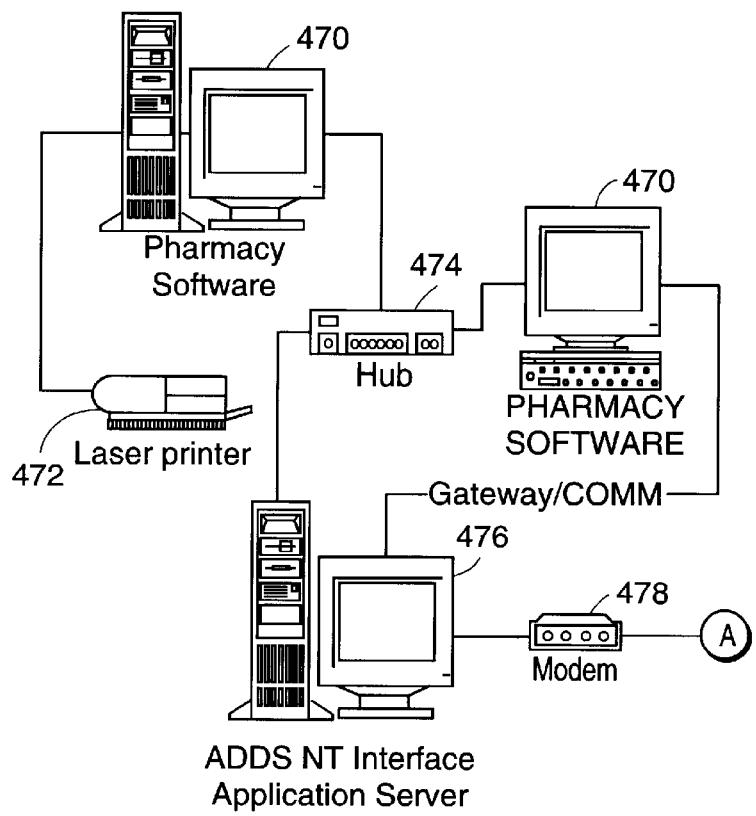
Figure 9A(1)
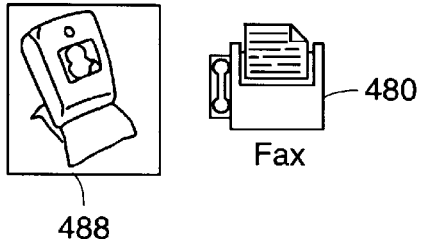
Figure 9A

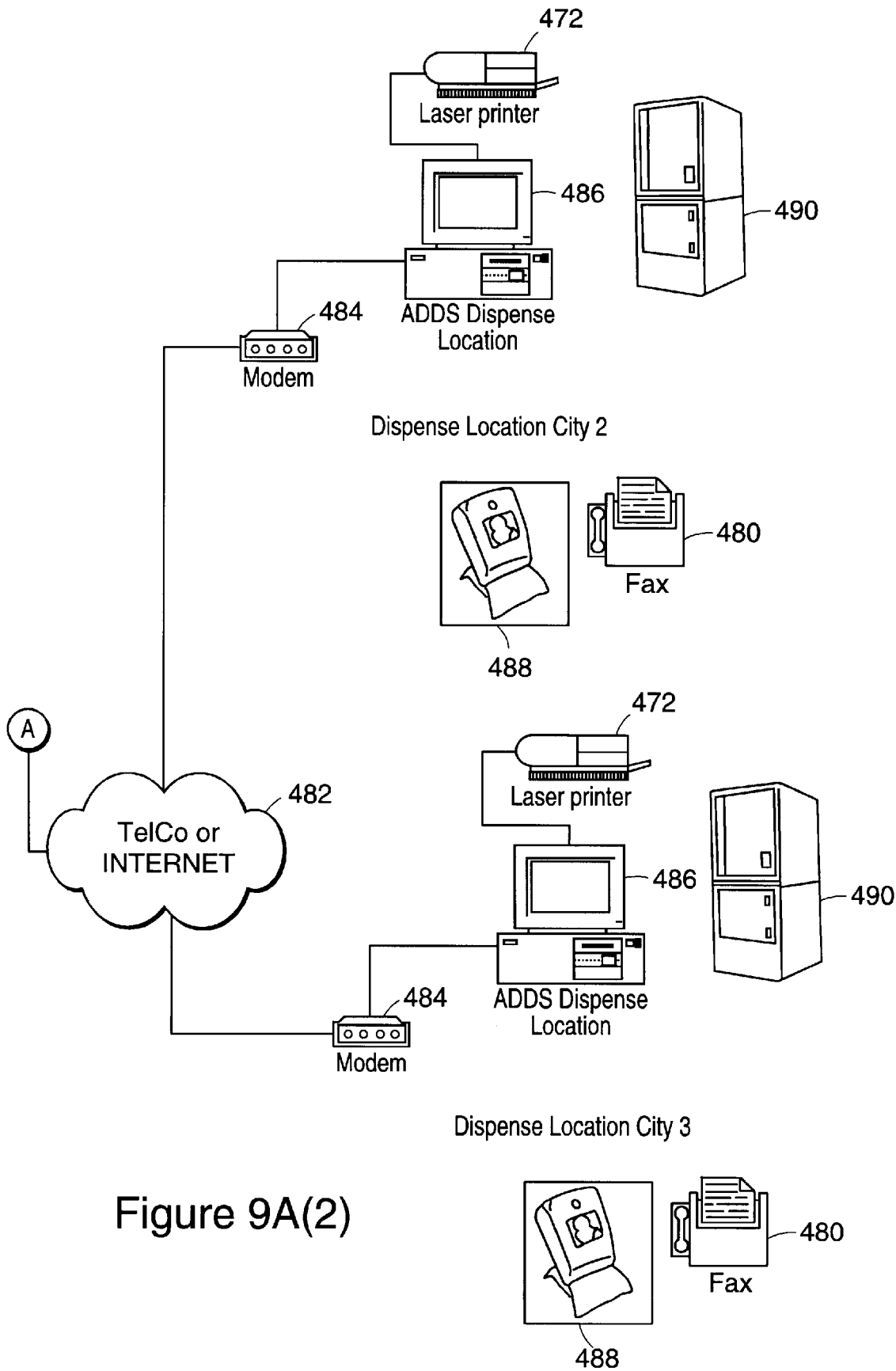
Figure 9A(2)

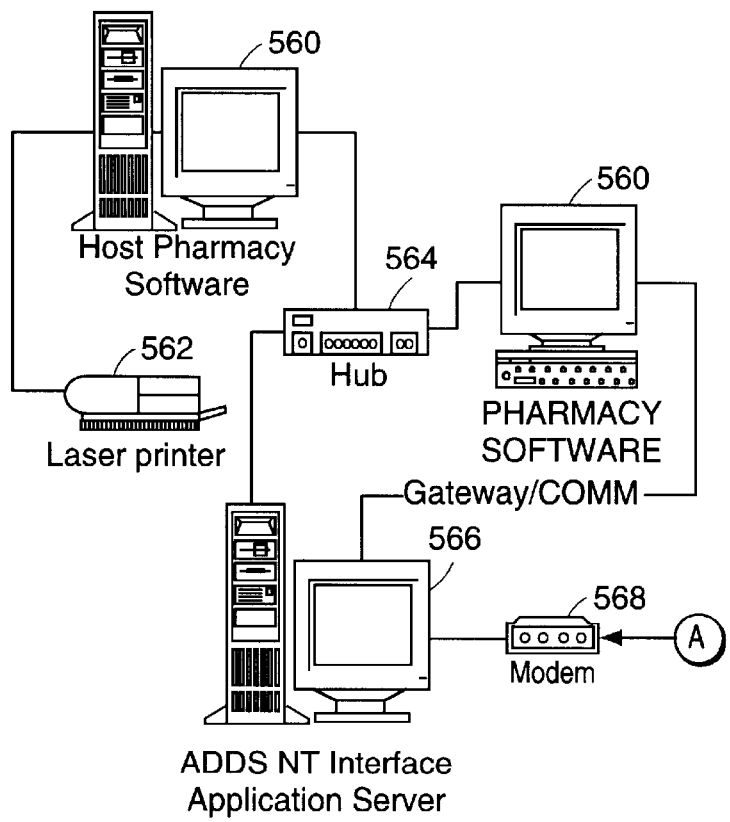
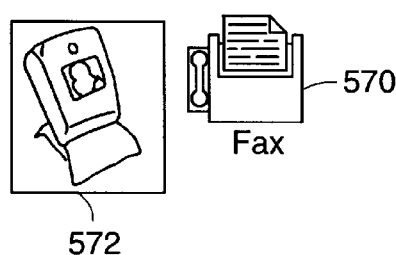
Figure 10A(1)
Figure 10A

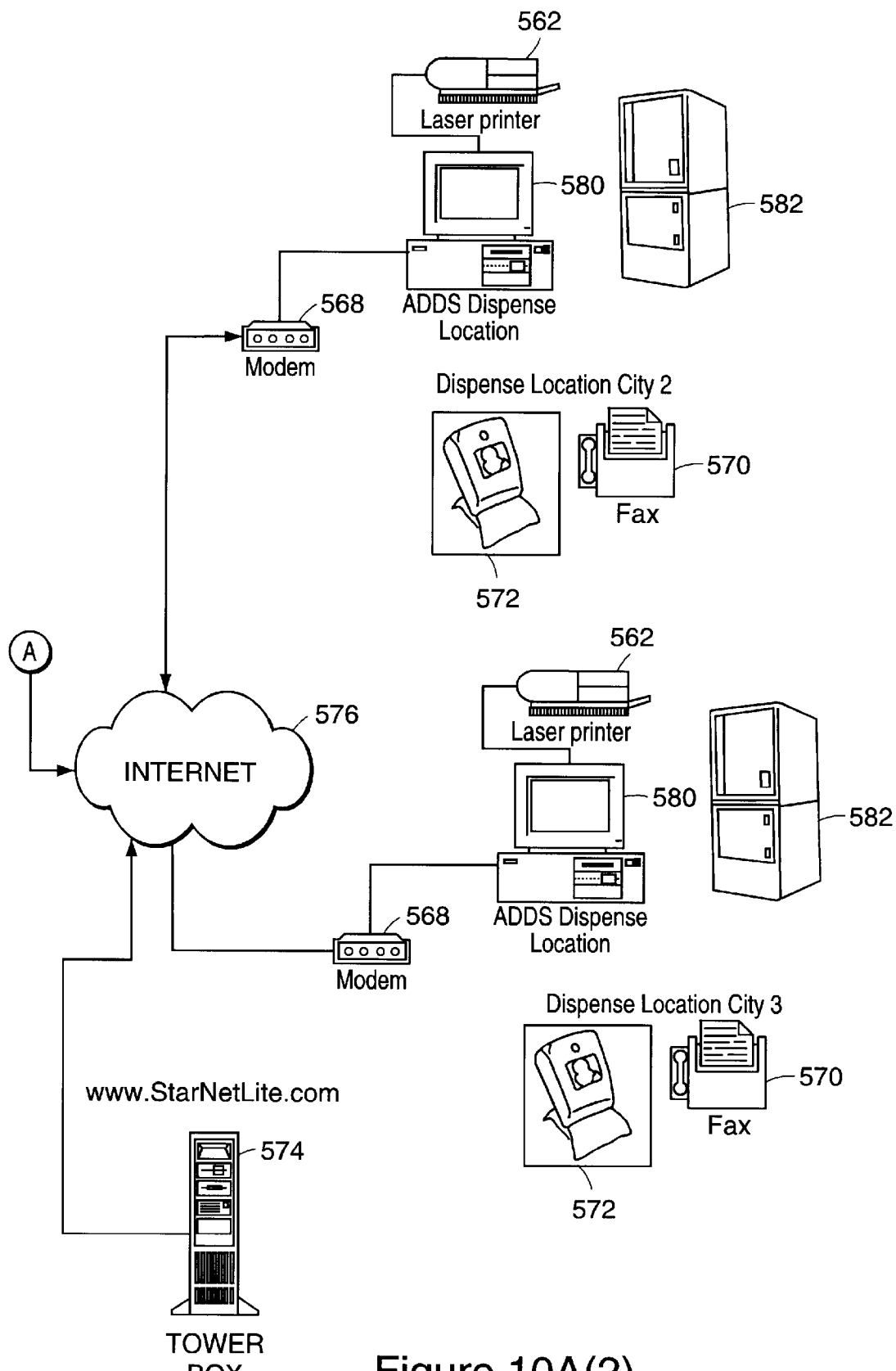
Figure 10A(2)

⑩ SELECT ONE OF THE PROVIDED SIGS 1436
OR USE THE SPACE AT THE BOTTOM
TO CREATE YOUR OWN.

1442

SIGS

| TAKE AS DIRECTED BY PRESCRIBER |
| TAKE AS DIRECTED BY PRESCRIBER |
| TAKE AS DIRECTED BY PRESCRIBER |
| TAKE AS DIRECTED BY PRESCRIBER |
| TAKE AS DIRECTED BY PRESCRIBER |
| TAKE AS DIRECTED BY PRESCRIBER |
| |

| CLEAR LOT NUMBER | ENTER NEW LOT NUMBER | CLEAR EXPIRATION DATE | ENTER NEW EXPIRATION DATE |
|---|---|---|---|
| | 2ND01M | | 20020101 |

[CLEAR SIGS]   [BACK TO MAIN]   [NEXT]
                                      1426

⑪ EDIT LOT AND EXPIRATION DATE
WHERE NECESSARY
1438

⑫ SELECT 'NEXT' TO PROCEED
1440

FIG. 16D

 CHECK ALL ENTRIES TO MAKE SURE THEY ARE CORRECT. CHECK THE PRINTER TO MAKE SURE IT HAS THE PROPER PAPER. — 1444

DISPENSE SUMMARY — 1442

PRESCRIBER: BERTHIUME RN, ELAINE

PATIENT: STEVEN PIANTEDOSI

MEDICATION

| QTY | DRUG, POTENCY, FORM | LOT | EXPIRE |
|---|---|---|---|
| 6 | PROZAC 10MG PULVULES(2-7s) | 3AC55M | 20010202 |

[SELECT ANOTHER MEDICATION] [BACK TO MAIN] [FINISH]

GIVE SAME PATIENT ADDITIONAL MEDICATIONS — 1446

SELECT 'BACK TO MAIN' TO START OVER — 1448

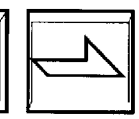 SELECT 'FINISH" TO PRINT LABEL(S) AND MONOGRAPH(S) FOR PATIENT. — 1450

FIG. 16E

7 ENTER THE QUANTITY ADDED, THE LOT
NUMBER, AND EXPIRATION DATE. — 1474

```
┌─ MEDICATION SUMMARY ─────────────────────────────┐
│ DRUG,POTENCY,FORM  [ZOLOFT 50MG TABLET]          │
│        MFG. [PFIZER]            GCN  [20201]     │
│ QTY PER PACKAGE [7]         ON HAND [102]        │
│ STORAGE LOCATION [PSY1]    LAST LOT [0210K99A]   │
│ WARNING CODES [   ]      LAST EXPIRY [20010401]  │
└──────────────────────────────────────────────────┘
┌─ AVAILABLE FOR EDITING ──────────────────────────┐
│   QTY ADDED [    ]    [ CLEAR QTY ]   ┌──────┐   │
│   LAST LOT [0210K99A] [ CLEAR LOT ]   │ SAVE │   │
│  LAST EXPIRY [20010401] [ CLEAR EXP ] └──────┘   │
└──────────────────────────────────────────────────┘
┌─────────┐ ┌───────────┐ ┌──────┐ ┌──────────┐
│ ANOTHER │ │MAINTENANCE│ │ MAIN │ │   QUIT   │
│MEDICATION│ │           │ │      │ │(NO SAVE) │
└─────────┘ └───────────┘ └──────┘ └──────────┘
```

8

AFTER ENTERING YOUR DATA AND MOVING THE
FOCUS (HIT THE TAB KEY), CHECK YOUR
ENTRIES. IF THEY ARE CORRECT HIT 'SAVE", IF — 1480
NOT, CHANGE YOUR ENTRIES OR HIT 'QUIT (NO
SAVE'.

FIG. 17C

⑥ TOUCH OR CLICK ON A FIELD TO
SET FOCUS. EDIT WHERE REQUIRED.
TO ADD ENTIRELY NEW ITEM, USE — 1496
'CLEAR ALL FIELDS'. THEN ENTER
ALL NEW DATA.

INVENTORY DATABASE EDITOR  1495

| | |
|---|---|
| DRUG,POTENCY,FORM | ACETAMINOPHEN 325MG TABLET |
| MFG | UDL |
| QTY PER PACKAGE | 1 |
| STORAGE LOCATION | PSY2 |
| WARNING CODES | |
| ON HAND | 29 |
| LAST LOT | 0384503 |
| LAST EXPIRY | 20010101 |
| BINBARCODE | 5107900202 |
| GCN | 16903 |
| NEW GCN | — 1306 |

SIG1
SIG2
SIG3
SIG4
SIG5
SIG6

[BACK] [GET NEW GCN] [APPLY NEW GCN] [CLEAR ALL FIELDS] [QUIT DON'T SAVE] [SAVE] [MAIN]

1332    1334

⑦ SELECT 'GET NEW GCN' IF NECESARY
AND THEN SELECT 'APPLY NEW GCN'. — 1498

⑧ SELECT 'SAVE' TO SAVE, THEN 'MAIN'
OR 'BACK' TO EXIT. SELECT 'QUIT
DON'T SAVE' (PRIOR TO SAVE) TO — 1310
RESTORE VALUES.

FIG. 18C (7A) SELECT A NEW GCN NUMBER BY PICKING THE ACTUAL MEDICATION OR IT'S CLOSEST THERAPUTIC EQUIVALENT. —1302

1300

GCN

| BN | |
|---|---|
| ACEPHEN 120MG | ACETAMINOPHEN |
| ACEPHEN 120MG | ACETAMINOPHEN |
| ACEPHEN 120MG | ACETAMINOPHEN |
| ACEPHEN 120MG | ACETAMINOPHEN |
| ACEPHEN 120MG | ACETAMINOPHEN |
| ACEPHEN 120MG | ACETAMINOPHEN |
| ACEPHEN 120MG | ACETAMINOPHEN |
| ACEPHEN 120MG | ACETAMINOPHEN |
| ACEPHEN 120MG | ACETAMINOPHEN |
| ACEPHEN 120MG | ACETAMINOPHEN |

 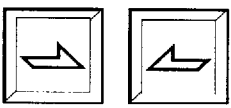   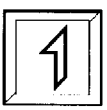 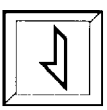 

(7B) SELECT 'BACK' TO RETURN TO INVENTORY DATABASE EDITOR. WHATEVER ITEM SELECTED WILL HAVE IT'S GCN NUMBER ADDED TO THE 'NEW GCN" TEXTBOX. —1308

FIG. 18D

PRESCRIBER DATABASE EDITOR

ENTER NEW NAME (LAST NAME FIRST)  1316

| BACK | CLEAR | ADD NAME TO DATABASE |

⑥ AFTER ENTERING A NEW NAME IN THE TEXT BOX, SELECT 'ADD NAME TO DATABASE.' THEN SELECT 'BACK'. ― 1318

Thank you for using the Non-Prescription Drug Dispenser

1. Pick up Drugs from Tray
2. Take Information from Printer

*Please wait, Getting Drugs and Printing Drug Information*

[Start Over] — 1574

[End] — 1568

1606

NEXT CLICK ON REPORTS

2882

| Telepharmacy Solutions, Inc. [ADD/EDIT PASSWORDS] |
|---|

Enter New User
- User Name: r
- User ID: r
- User Password: *
- Access Level: 3

Assign Privilages
- ☑ Dispense   ☑ Exit
- ☑ NewRx   ☑ Add/Edit Inventory
- ☑ Add/Edit Patient   ☑ Reload Inventory
- ☑ Resources   ☑ Add/Edit Prescriber
- ☑ Reports   ☑ Refills
- ☑ Reverse   ☑ Delete Script
- ☑ Assign Users   ☑ Special

Select User To Edit
- Lauren
- r
- ss
- STEVEN

UP / DOWN

2880

CLEAR   DELETE   SAVE   MAIN MENU

Figure 85

FROM THE RESOURCE SCREEN SELECT RETURN/WASTE

ON THE RETURN/WASTE SCREEN SELECT A TRANSACTION.
THEN PRESS "SELECT"

| RxNUMBER | DATE | LAST NAME | FIRST NAME | DOB | BRAND NA |
|---|---|---|---|---|---|
| 6002573 | 8/6/01 | MCCOY | VICKIE | | PREMA |
| 6005383 | 7/30/01 | LAPOSA | MARY A | | PAXIL |
| 6002573 | 7/30/01 | MCCOY | VICKIE | | PREMA |
| 6005330 | 7/29/01 | MADSEN | DALE | | ALBUTE |
| 6005303 | 7/29/01 | WARD | GENE C | | GLYBUD |
| 6005275 | 7/29/01 | GRIFFITH | MARTIN E | | IBUPRO |

Telepharmacy Solutions, Inc. [RETURN \ WASTE UTILITY]
RETURN / WASTED

BACK  →  ←  FIRST  ↑  ↓  LAST  SELECT

Figure 92

THE SELECTED TRANSACTIONS' DETAIL ARE DISPLAYED ON THE LEFT.
NOTE THE CURRENT QTY DISPENSED ON RIGHT.

| | |
|---|---|
| RXNUMBER | 6005383 |
| FIRST NAME | MARY A |
| LAST NAME | LAPOSA |
| BRAND NAME: | PAXIL [PAROXETINE] 20 MG |
| GENERIC NAME: | PAXIL [PAROXETINE] 20 MG |
| STRENGTH: | 20 |
| DOSAGE FORM: | TAB |
| LOT: | |
| EXPIRY DATE: | |
| IEN: | |
| NDC: | 00029321113 |
| PRESCRIBER NAME: | DR. TORRETTA, LINDA |
| PRESCRIBER DEA#: | |
| DATE FILLED: | 7/30/01 |

CURRENT DATE / TIME: 8/6/01 4:32:10 PM
LOGGED IN USERS NAME: r — 3044
QTY DISPENSED: 12 — 3050
ENTER AMOUNT RETURNED
ENTER AMOUNT WASTED — 3052
ENTER ACTUAL QUANTITY DISPENSED
ENTER WITNESS USERID AND PASSWORD
USERID
PASSWORD

3040

BACK / DON'T SAVE  3042  SAVE / BACK  3046  3048  MAIN MENU

Figure 93

DISPENSE SUMMARY                          3060

PRESCRIBER: DOE, JOHN        PATIENT: TEST

| QTY | DRUG, POTENCY, FORM | LOT | EXPIRY | SIG |
|---|---|---|---|---|
| 1 | ACCUPRIL 10 MG QUINSAPRIL HCl TABLE | test | 20010101 | TAKE AS DIRECT |

SELECT ANOTHER MEDICATION (3062) | BACK TO MAIN (3064) | WRITE A SCRIPT (3068) | FINISH (3066)

INVENTORY DATABASE EDITOR

3260

| DRUG NAME | ACCUPRIL 10 MG QUINSAPRIL HCl TABLETS [1x7] | | |
|---|---|---|---|
| MFG | PARKE DAVIS | ON HAND | 50 |
| QTYPERPACK | 7 | GCN | 48692 |
| LOCATION | TEST | NEW GCN | |
| INSTITUTION | TELEPHARMACY SOLUTIONS | PIC | |

DRUG NAME

MFG

FIRST — LOT / EXP YYYY MMDD — QTY 0

SECOND — LOT / EXP YYYY MMDD — QTY 0

THIRD — LOT / EXP YYYY MMDD — QTY 0

NEW — LOT / EXP YYYY MMDD — QTY 0

SIG1 TAKE AS DIRECTED
SIG2 TAKE ONE TABLET DAILY
SIG3 TAKE TWO TABLETS DAILY
SIG4
SIG5
SIG6

COMMENT

BACK | GET NEW GCN | APPLY NEW GCN | CLEAR ALL FIELDS | SHIFT LOT EXP | QUIT DON'T SAVE | SAVE | MAIN

③ SELECT 'PRESCRIBER'

⑤ ENTER THE PRESCRIBER NAME

⑥ SELECT 'ADD NAME TO DATABASE'
(*) TO START OVER SELECT 'CLEAR'

③ SELECT DATABASE YOU WISH TO VIEW    3480

DATABASES

| INVENTORY | PRESCRIBER | TRANSACTIONS | LOAD |

| DrugNamePotency | MFG | PIC | OnHand |
|---|---|---|---|
| ACCUPRIL 10 | PARKE DAVIS | 5 | 98 |
| ACCUPRIL | PARKE DAVIS | 5 | 78 |
| BACITRACIN | FOUGERA | 5 | 50 |
| EFFEXOR | WYETH | 5 | 44 |

FIRST PAGE

LAST PAGE

| MAINTENANCE | DELETE | ADD | MAIN |

(*) THE TRANSACTION AND LOAD DATABASES ARE FOR VIEWING PURPOSES ONLY.

Figure 98C

VIEWING REPORTS

⑤ UNDER 'REPORT' THE DROP DOWN COMBO BOX CONTAINS OPTIONS FOR VIEWING THE SELECTED REPORT. YOU CAN' Print the report to a window', WHICH DISPLAYS THE REPORT ON THE MONITOR. YOU CAN SEND THE REPORT TO THE PRINTER OR CONVERT IT INTO AN EXCEL FILE.

⑥ BE CERTAIN TO SELECT 'Refresh Data'.

⑦ SELECT 'PRINT'

(*) SELECT 'Window Styles' TO ADJUST VIEWING OPTIONS

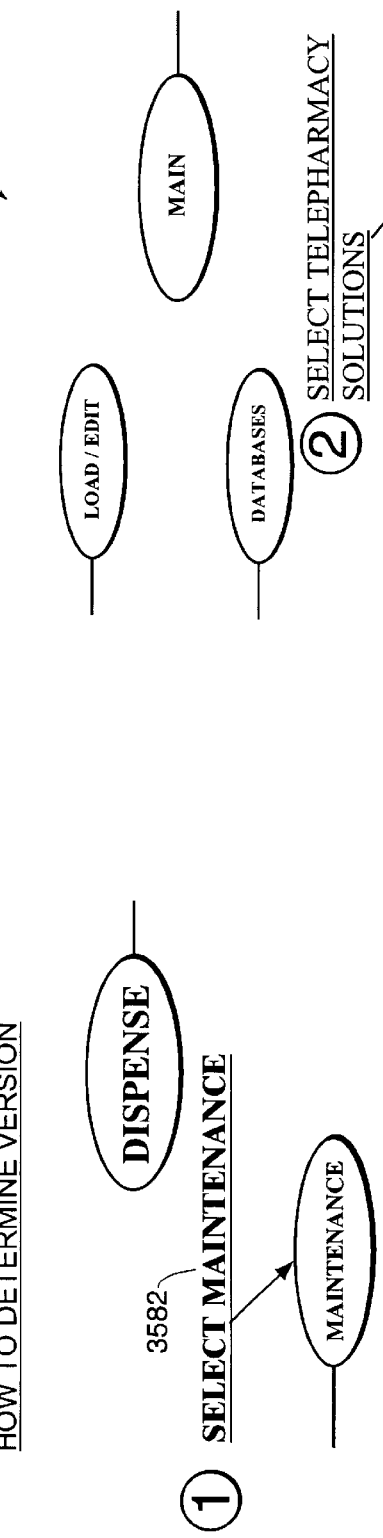
Figure 100B
Figure 100A
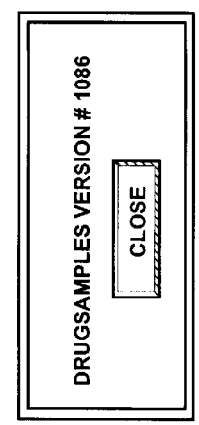
Figure 100C

HOW TO EXIT TO DESKTOP

WARNING SCREEN (CABINET)  3620

(*) WHEN DRUGSAMPLES.EXE IS INTIALLY EXECUTED OR THE 'CLOSE' BUTTON SELECTED. THE SCREEN BELOW IS

DISPENSE

STAND CLEAR
LET DOORS CLOSE

MAINTENANCE

REGISTERING FINGERPRINTS (CABINET)

SYSTEMS AND METHODS FOR DISPENSING MEDICAL PRODUCTS

REFERENCES TO RELATED APPLICATIONS

This is a continuation-in-part of International Application No. PCT/US00/26170 filed on Sep. 22, 2000, now Application No. WO 01/021131, which is a continuation-in-part application of U.S. application Ser. No. 09/454,359, filed on Dec. 3, 1999, now U.S. Pat. No. 6,564,121, issued May 13, 2003, which claims the benefit of U.S. Provisional Application No. 60/155,446 filed Sep. 22, 1999, the entire teachings of these applications being incorporated herein by reference.

BACKGROUND OF THE INVENTION

Automated pharmaceutical delivery systems have been in use for over thirty years. The initial purpose of such systems was to reduce the high rates of medication errors associated with manual distribution. In modern times, automated systems present more sophisticated advantages. These include: further reduction of errors, lower costs associated with pharmaceutical distribution, reduction of personnel, inventory control, substance control, automated documentation, and relieving professional pharmacists of many tasks.

The current state of the art of automated pharmaceutical delivery systems, otherwise known as medication management devices generally fall under three categories: automated devices in the central pharmacy area; automated devices in the patient care unit; and point-of-care information systems.

The primary goal of centrally-located devices is to replace or improve the current manual process for filling unit dose carts. These devices offer the advantage of a single, centralized inventory and a lower overall inventory. Disadvantages of such devices include their large size, high cost, and reliance on efficient delivery systems.

Patient care unit-based devices replace the traditional manual unit dose cart filling and delivery system and provide increased control over floor stock. Advantages of such systems include their smaller size and lower cost relative to centrally-located devices, immediate access to medications, and automated documentation of medication administration. Disadvantages include application to unit dose levels only, increased costs due to the maintenance of multiple inventories in multiple units, additional time required to restock multiple devices, and larger inventory.

Point-of-care systems are designed to enable immediate exchange of patient data at the bedside. Such systems allow for rapid access to patient information, fast documentation, integration of hospital information systems, and immediate verification of drug administration. Primary disadvantages of point-of-care systems include high cost associated with placing hardware in each room, networking the system, and security issues associated with personal data access.

The above-described systems offer solutions for medication management in large hospitals where the large expense associated with large centrally-located pharmacy systems, decentralized patient care units, and point-of-care systems at the bedside are justifiable for unit-dose dispensing and verification. These systems fail to address efficient and economical medication management at medium size facilities, for example health maintenance organizations which cannot justify the expenses associated with the large and costly aforementioned systems. Furthermore, while the above systems provide a solution for unit-dose dispensing for individual patients, they fail to address the issue of filling weekly or monthly prescriptions in a cost-effective manner.

SUMMARY OF THE INVENTION

The present invention relates to a method for remote dispensing of pharmaceuticals or other medical products using a distributed, interoperable, packet-switched network such as the Internet and to a system that combines computer hardware and software, including a computer network, a telecommunications capability, and a medical products dispensing cabinet to form a complete drug dispensing system. The medical products may include, but are not limited to, packaged or non-packaged pharmaceuticals or individual pills, caplets, tablets, liquids, or suspensions. This enables drug prescription dispensing in volume by a physician, pharmacist, or other licensed practitioner directly to the patient at a clinic, group practice, or other location outside a pharmacy or a hospital. The system provides a convenient, safe, automated, and low cost drug delivery system for the patient.

A preferred embodiment of the present invention is directed to an apparatus and method for automated dispensing of packaged and non-packaged pharmaceuticals. The remote control dispenser system of the invention includes a centralized computer network in conjunction with product release at a remote location. The centralized network communicates with the remote distribution point using standard Internet Protocols (IP) or higher level application protocols such as Hypertext Transport Protocol (HTTP). In another preferred embodiment, a web browser can be employed as a tool to provide for the controlled remote dispensing of packaged and non-packaged pharmaceuticals. In another preferred embodiment a customized web server can be employed as a tool to provide for the controlled remote dispensing of packaged and non-packaged pharmaceuticals. The systems and methods of the present invention provide for the efficient remote dispensing of medical products using widely available communications network technology while preserving the confidentiality of patient information and the safety of users based on restricted access to controlled substances.

A preferred system and method for remote dispensing of a medical product, such as, for example, a prescription pharmaceutical includes an authorization node, a dispensing node to distribute the authorized medical product, a controlling node that interfaces with the authorization node and the dispensing node and a transmission medium between the nodes. The authorization node can include a controller and appropriate software used by a pharmacist or a licensed physician. The dispensing node can include a housing having a plurality of bins which store encoded packages of medical products and a dispenser controller. The controlling node, which may be collocated with the authorization node, includes a customized web server to control the flow of information between the authorization and dispensing node.

A preferred embodiment of the present invention relates to systems and methods of dispensing samples of drugs or other medical products. Samples are often given to patients by physicians at clinics, offices, or hospitals. These samples are provided free of charge to physicians or institutions for distribution to patients. At present, there are no systematic procedures for controlling the distribution of samples and there are increasing requirements by regulatory and accrediting institutions to provide such controls.

Samples are usually packaged as unit doses in small foil and/or plastic containers with labels intended to identify a particular brand name or manufacturer so that the patient will then associate the particular medication with a particular source. Thus, the packaging for different samples from different sources tend to be varied in size and shape.

Thus, a system for containing and monitoring distribution in accordance with the present invention includes a number of trays or drawers in which the samples are stored, a control system that opens and closes the system to provide access to the user and secures the system to restrict unauthorized access.

A user identification system can be included that serves to identify those gaining access to the dispensing system. This system can include a computer containing a catalog of medications dispensed using the system as well as patient data, or alternatively, accessing such information using a communication network as described herein.

Another preferred embodiment of the present invention provides a system for dispensing non-prescription medications or other medical products that do not require a licensed physician or pharmacist to be involved in the transaction. Such a system can include a secure storage housing that dispenses individual packages based on credit card, debit card, cash, or other smart card transactions. The system can utilize features of the communications network, code reader, and dispensing systems described herein to provide for the distribution of "over the counter" medical products.

The systems and methods to dispense medical products in the preferred embodiments have an information display device for retrieving and caching information from a communication network during periodically established communication sessions. The display device includes a graphical display device, a communication transceiver connectable to a communication network that receives display data. The network can include the Internet or other local and wide area networks. The device also includes a microprocessor and a memory device that stores display data, at least one display template, and program information. The display templates include variable field identifiers. Further the program information comprises a display generator providing a modified template by replacing the variable field identifiers with corresponding display data, and displaying the modified template on the graphical display device. The microprocessor and the memory device record at least one dispensing operation value for a subset of data that are subsequently sent to the communication network. The display device formats textual data and graphical data for display on the touch screen.

The foregoing and other object and features and advantages of the invention will be apparent from the following more particular description of preferred embodiments of the invention, as illustrated in the accompanying drawings in which like reference characters refer to the same parts throughout the different views. The drawing are not necessarily to scale, emphasis instead being place upon illustrating the principles of the invention.

BRIEF DESCRIPTION OF THE DRAWINGS

FIG. 1E illustrates a dispensing unit having a plurality of workstations in accordance with the present invention.

FIG. 9A is a schematic block diagram illustrating a preferred embodiment of the remote control dispensing system which uses an internal data socket network configuration in accordance with the present invention.

FIG. 10A is a schematic block diagram of a preferred embodiment of the remote control dispensing system using the internet and host pharmacy system network configuration.

FIGS. 16A–16E illustrate views of the display screen that a user interfaces with during a dispense process to dispense a drug sample in accordance with a preferred embodiment of the present invention.

FIGS. 17A–17C illustrate views of the display screen that a user interfaces with during a maintenance process including loading medications in accordance with a preferred embodiment of the present invention which includes dispensing of drug samples.

FIGS. 18A–18D illustrate views of the display screen that a user interfaces with during a maintenance process including an inventory process in accordance with a preferred embodiment of the present invention which includes dispensing of drug samples.

FIGS. 19A–19C illustrate views of the display screen that a user interfaces with including a prescriber process in accordance with a preferred embodiment of the present invention which includes dispensing of drug samples.

FIG. 34 illustrates a view of a display screen showing in particular an ending screen that a user interfaces with to dispense a non-prescription drug in accordance with a preferred embodiment of the present invention.

FIG. 85 illustrates a view of a display screen of a user interface showing an access users screen for dispensing, tracking and returning of particular classes of drugs such as, for example, controlled drugs like narcotics in accordance with a preferred embodiment of the present invention.

FIG. 92 illustrates a view of a display screen of a user interface showing return/wasted information generated in accordance with a preferred embodiment of the present invention.

FIG. 93 illustrates a view of a display screen of a user interface showing the details of the selected transactions for an access level user in accordance with a preferred embodiment of the present invention.

FIGS. 94A–94D illustrate display screens in a user interface that is used in a system for dispensing samples of medical products showing displays for dispense summaries in accordance with a preferred embodiment of the present invention.

FIGS. 95A–95G illustrate display screens in a user interface that is used in a system for dispensing samples of medical products showing the methods of entering medical products to an inventory in accordance with a preferred embodiment of the present invention.

FIGS. 98A–98C illustrate display screens in a user interface that is used in a system for dispensing samples of medical products showing the methods for viewing a transaction or loading databases in accordance with a preferred embodiment of the present invention.

FIGS. 100A–100C illustrate display screens in a user interface that is used in a system for dispensing samples of medical products showing the method to determine the software version of the medical products in accordance with a preferred embodiment of the present invention.

DETAILED DESCRIPTION OF THE INVENTION

Figure 1A:
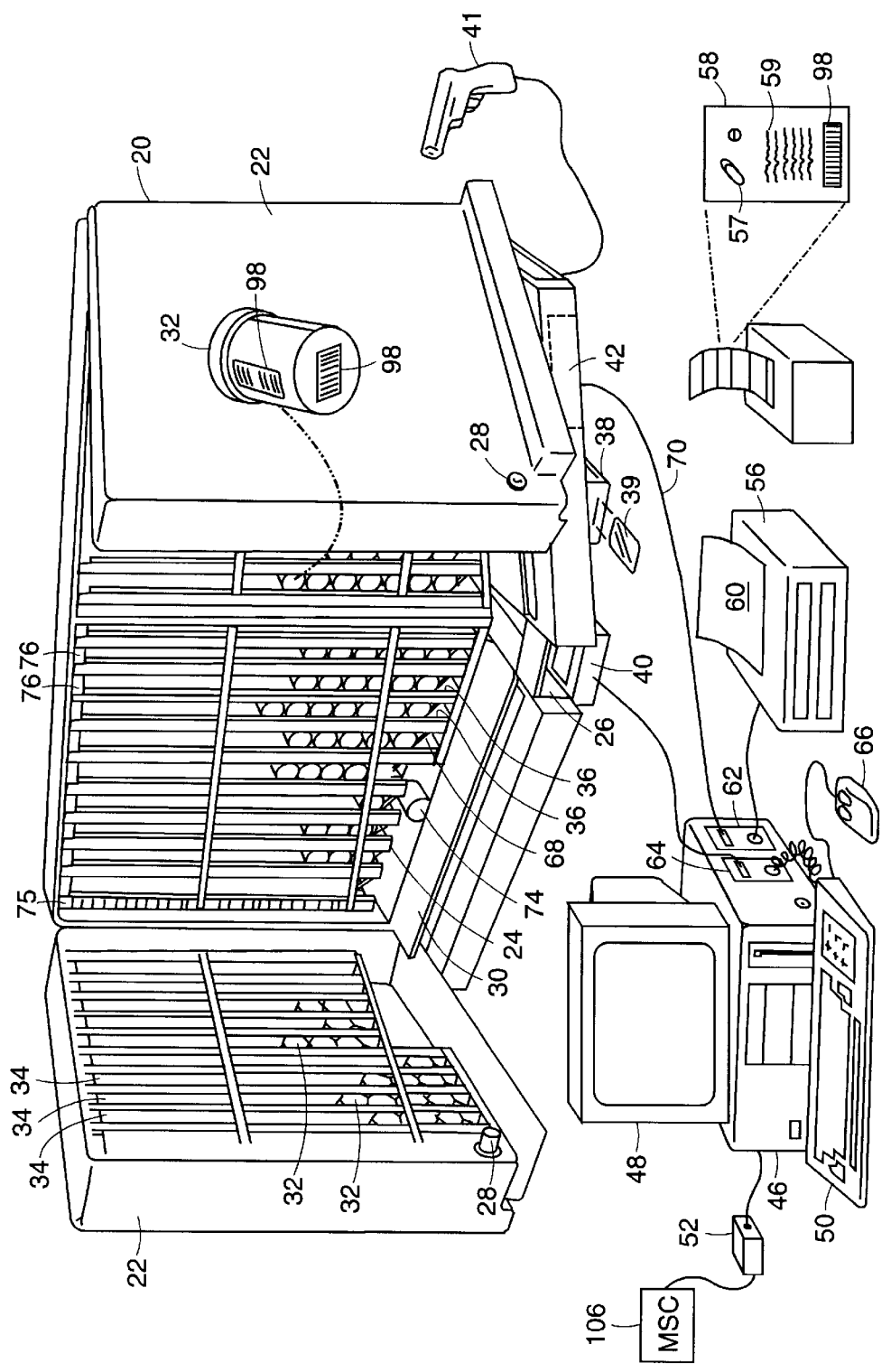
FIG. 1A is a diagram of a preferred embodiment of an automated drug dispensing system in accordance with the present invention.

The present invention relates to systems and methods for the remote dispensing of packaged and non-packaged medical products including the methods for controlling a drug dispensing system described in U.S. patent application Ser. No. 09/058,524 filed Apr. 10, 1998, which is a continuation of PCT/US96/16758, filed Oct. 18, 1996, which is a continuation-in-part of U.S. patent application Ser. No. 08/642,484 filed on May 3, 1996, now U.S. Pat. No. 5,797,515 which issued Aug. 25, 1998, which is a continuation-in-part of U.S. patent application Ser. No. 08/544,623 filed on Oct. 18, 1995, now U.S. Pat. No. 5,713,485 which issued Feb. 3, 1998, the entire contents of the above patents and applications being incorporated herein by reference.

The present invention provides safe pharmaceutical prescription dispensing directly by physicians, pharmacists, and other trained or licensed practitioners operating in small to medium size locations in a cost-effective manner. The dispensing locations can be remote from the location of a licensed practitioner such as, for example, a pharmacist. Prepackaged pharmaceuticals are stocked at nearby municipal service centers and distributed to the health care locations as needed. The inventory is continually and automatically monitored by a host computer at the location, and/or offsite on a central server. Inventory is ordered on a just-in-time basis by the computer. In this manner, prepackaged multiple-dose pharmaceuticals are available to practitioners at the health-care facility for immediate filling of patient prescriptions.

The present invention offers significant advantages to physician group practices. The system improves customer service and enhances the image of the group practice. Drug theft is prevented by securing the pharmaceuticals in a closed system on hand and inventory is kept low. The system meets state pharmacy, safety, and regulatory compliance laws, whereas many manual dispensing systems do not. A pharmaceutical distributor can handle all inventory planning, financing, maintenance, and ordering with minimal interaction with group practitioners. Disruptive telephone calls to the physician from pharmacists are minimized. Further, physicians can gain immediate access to a patient's pharmacy records currently unavailable to him.

Managed care providers, for example, Health Maintenance Organizations and Pharmacy Benefits Managers also realize significant advantages from the present invention. The invention increases the likelihood that a patient will receive the required treatment, because the pharmacy is available at the doctor's office. Labor costs for in-house pharmacies are reduced, allowing staff reductions or reassignments. In-house drug dispensing can be extended to physician-staffed satellite clinics and other locations not suitable economically for conventional pharmacies. The system enables automated patient compliance enhancing programs, drug utilization analysis, and the use of other emerging pharmacy management opportunities to reduce costs and improve patient compliance and wellness. Drug costs are reduced by formulary control, thereby encouraging generic substitution of name brand drugs. Inventory is tracked automatically by the drug distributor headquarters, thus preserving professional time for patient care.

The present invention also offers significant advantages to the patients. Drugs are provided immediately at the physician's office, avoiding an inconvenient trip to a pharmacy. This is particularly important to mobility-impaired patients and eliminates a major source of drug non-compliance. Electronic third-party payor cards such as smart cards can be used for drug purchases at the doctor's office. The patient can obtain prescription drugs at prices competitive with retail discounters. The physicians are able to track prescription compliance which can result in faster recovery.

The apparatus of a preferred embodiment of the invention will now be described. FIG. 1A is a diagram of an automated drug dispensing system in accordance with the present invention. The primary components of the system include a remote control dispenser (RCD) cabinet 20, a host computer 46, a modem 52, a document printer 56, and a label printer 54. The cabinet 20 includes a rack 24 comprising a plurality of bins, preferably in the shape of columns 34. Packages 32 such as drug bottles, containing pharmaceuticals of various types are distributed among—the columns 34, each column 34 containing a separate type of pharmaceutical, or multiple columns 34 containing the same pharmaceutical to help prevent stock outs on more frequently dispensed pharmaceuticals. A plurality of racks, for example, four racks 24 are enclosed in the cabinet 20 chamber, two in the main cabinet 20 and two on the doors 22. The doors are secured by locks 28.

A licensed user, for example, a doctor, pharmacist, nurse, or other medical practitioner qualified to fill patient prescriptions, operates the system at the host computer 46, using a keyboard 50 and mouse 66 for input and receiving visual feedback at a monitor 48. In an alternative preferred embodiment, a touch screen can be used for input. Using the keyboard 50, a user enters a command to request dispensing of a particular packaged pharmaceutical variety 32 for a particular patient. The computer 46 transmits the request via an interface 70 to a controller 42 located on the RCD cabinet 20. The controller 42 interprets the command sent from the computer 46 and enables a dispensing actuator 68 in the appropriate column 34. The lowest package 32 in the appropriate column 34 is released from the column 34 and ejected onto a ramp 30. The released package 74 slides down the ramp 30 into an opening 26, where the released package 74 is made available to the dispensing party for transfer to the patient. A barcode reader 40, located near the dispensing opening 26, reads a code 98 on the dispensed package 74 and transmits the barcode information to the computer 46, which informs the user whether the code 98 on the dispensed package 74 matches that which was requested by the user. The barcode 98 can be disposed on the side, top, and/or bottom of the package 32. In an alternative embodiment, a semiconductor chip can be embedded in the dispensed package which, when passed through an RF field, charges a capacitor. When the capacitor reaches an appropriate level, a weak RF signal is emitted. The signal can include approximately a 12 digit number. The semiconductor chip can also be used to uniquely identify a dispensed item.

In an automated embodiment of the system, sensors 36 located on each column 34 monitor the dispensing process and notify the controller 42 of any package jams. The sensors 36 also monitor inventory of the columns 34 and notify the computer 46 through controller 42 that a particular column is empty or near empty.

Alternatively, the prescription can be dispensed directly to the patient. A card reader 38, mounted directly on or near the cabinet, is adapted to receive a card 39 from a patient. The card is programmed with patient information that is stored in an electronic memory on the card by a licensed practitioner. The patient inserts the card 39 in the card reader 38 and receives his medication automatically from the cabinet. The medication bottle 32 may be filled with a single dose of medication for a particular patient, or can include weekly or monthly doses. This embodiment is especially useful in large institutions, such as prisons, where many individuals require medication on a regular basis.

Upon validating the barcode 98 or the unique electronic signature of the dispensed package 74, the computer generates a label 58 containing prescription information at a label printer 54 to be placed on the package, and generates a document 60 at a document printer 56 containing additional instructions for the patient or practitioner. A modem 52 enables periodic or continuous communication between the host computer 46 and other computers in the network so that a complete inventory and status of each remote control dispenser cabinet is available at all times. Several remote control dispenser cabinets 20 can be integrated into a single installation operated by a single computer 46. The cabinets 20 can each be individually connected to the host computer 46, or may be daisy-chained, with only one cabinet 20 in the chain connected to the host 46.

The RCD controller 42 receives commands from and transmits status information to the host computer 46 via the controller interface 70. A request command sent from the host computer 46 identifies the pharmaceutical package 32 to be dispensed. In response, the RCD controller 42 activates the appropriate dispenser 68, thereby releasing a single package of the variety requested. A parallel or serial I/O interface 62 at the host computer 46 provides a sufficient communication channel. The simplest interface is a unidirectional channel from the host computer 46 to the controller 42. A full duplex implementation allows the controller 42 to transfer status information back to the host 46. Status information may include errors such as package jams, empty columns, or other cabinet status. Availability of such information prevents inconsistencies in the database and provides the operator with recovery procedures. This would require adequate sensors 36 to be mounted in appropriate positions on the RCD cabinet 20.

The barcode reader 40 or an electronic digital signal reader can be mounted directly on the unit or can comprise a hand-held unit 41. It verifies proper loading of the RCD cabinet 20 and proper dispensing of each pharmaceutical package 32. Before a column 34 is loaded with packages 32, the column barcode label 76 is compared with the barcode label 98 of each package 32 inserted into the column 34. Each time a package 74 is dispensed from the cabinet 20, the package barcode label 98 is scanned by the barcode reader 40 to verify that the correct pharmaceutical has been dispensed. The barcode reader 40 is interfaced to the host computer 46, through a standard keyboard wedge 64. The wedge 64 makes the barcode reader 40 input via the barcode interface 72 appears to be coming from the keyboard 50. Such an interface is a simple and reliable interface to the pharmacy software operating on the computer 46. The barcode reader 40 must be highly reliable and provide a high first read rate. Label printing on the pharmaceutical packages 32 must be of high quality to accommodate this. The electronic digital signal reader interfaces with a communications port (comm port), a network interface card (NIC), or is in direct communication with the computer bus. During loading, the bottles are loaded into each column up to a certain height. The highest bottle in the column is positioned adjacent a barcoded column label 75 running along each column. Thus, the number of bottles in each column can be recorded at loading and tracked during use.

The host computer 46 runs the pharmacy software, provides a user interface, and supports the RCD controller 42, barcode reader 40, printer, electronic digital signal reader, and modem 52. A standard off-the-shelf personal computer and operating system are sufficient to meet these requirements. As described above, the keyboard 50 and mouse 66 receive input from the user and the monitor 48 provides visual feedback. The document printer 56 prints documentation 60 such as detailed instructions and a label printer 54 prints package labels 58, for example, prescription information 59 for adherence to the dispensed package 74. Using a combination label stock form, a single printer can be used to provide both the patient label and patient education material. The prescription label 58 may also include a printed picture of the pharmaceutical 57 contained on the bottle to provide additional safety.

The modem 52 provides a communication link between the municipal service center (MSC) 106 and the remote control dispenser 108. Through this link, inventory of each RCD cabinet 20 is automatically monitored and updated in the MSC 106 computer. The modem link also serves as a medium to issue restock orders, update pharmacy software running on the host computer 46, and provide remote diagnostics. The modem can be compatible with standard telephone lines and can be capable of transferring data at sufficient rates.

The pharmacy software operating on the host computer 46 is a standard commercial software package which provides standard administrative and accounting capabilities. The pharmacy software also supports the unique features of the remote control dispenser system. These include: data communication with the RCD controller 42 via parallel or serial I/O interface 62; network interface card (NIC); data communication with the barcode reader 40 via keyboard wedge 64; data communication with the municipal service center via modem 52; printing of labels 58 with the label printer 54 and printing of documentation 60 with the document printer 56.

The cabinet 20 and rack 24 are preferably fabricated from aluminum, stainless steel, or plastic to be fully compatible with a clinical setting. The rack 34 can be modified to provide for a diversity of packages including various box and bottle sizes, unit-of-use packaging, liquids, syringes, and various non-prescription products, for example, medical supplies.

The computer 46 can comprise a portable terminal, a notebook computer, or a hand-held personal digital assistant. Voice recognition or voice prompted software can be employed using a telephone or wireless local area network. Voice recognition systems can use a generic or a user-customized system and can include voice signatures. The objective is to maximize system flexibility and ease of use for the doctor and staff without compromising safety. The remote control dispenser system can be utilized as a free-standing system, as a local network integrated with physician office computers, or as a centralized network in conjunction with product release at a remote location.

Figure 1B:
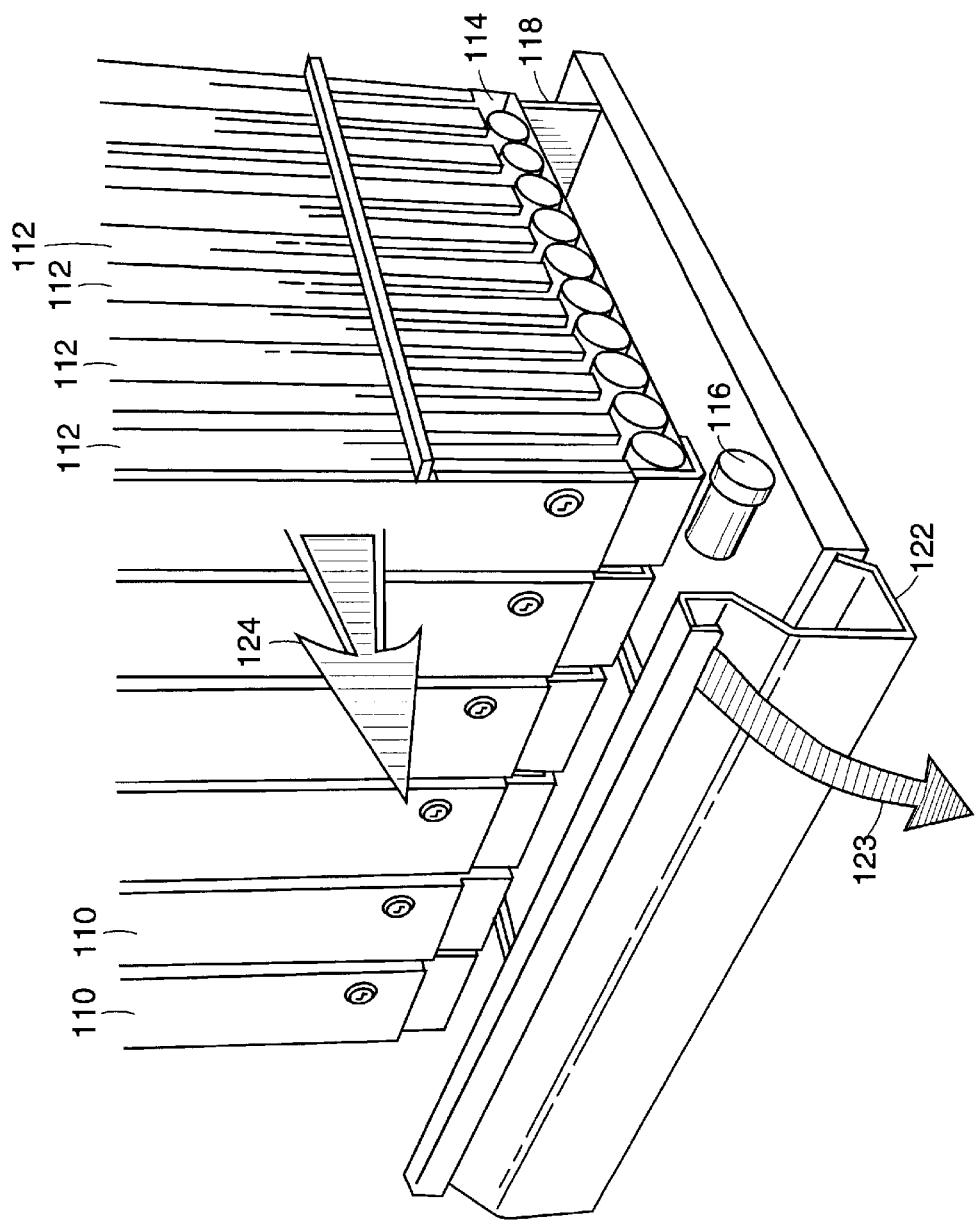
FIG. 1B is a perspective illustration of a rack of columns in accordance with the present invention.

FIG. 1B is a perspective illustration of a rack 110 of columns 112. Each column 112 includes a corresponding roller assembly 114, which is individually addressable by the controller to dispense a bottle 116 as shown. After dispensing, a pusher 118 pushes the dispensed bottle forward into an off-center tilt tray 121 and returns to its original position. The tilt tray 121 rotates in the direction shown by arrow 123 for removal of the dispensed bottle by the operator. Either a return spring or gravity returns the tilt tray 121 to its closed position. Note that the tilt tray 121 when opened by the operator prevents entry of the operator's hand or other objects into the rack area 110 to avoid pilferage.

To load the columns 112, each rack 110 of columns slides out in the direction shown by arrow 124. Each rack preferably includes a key lock at the top with a keying mechanism which retains the key until the rack is returned to its position, preventing loss of the key. After the columns are filled, the rack is returned to its normal position and the key is removed.

Figure 1D:
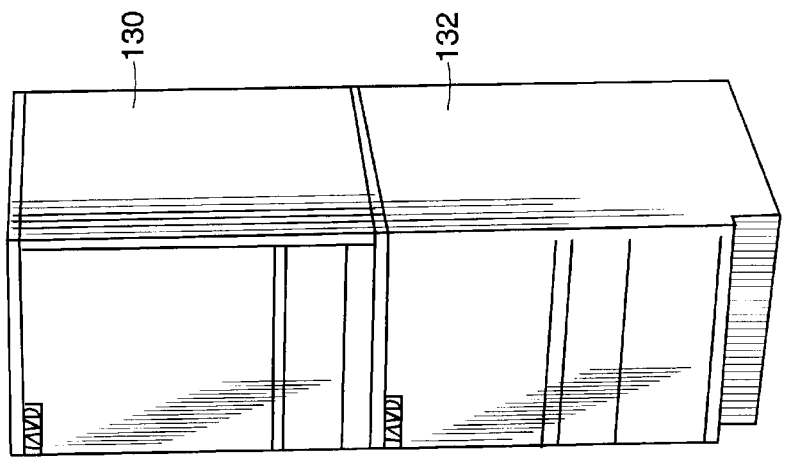
FIG. 1D is a perspective illustration of a system including helix and column dispensers in accordance with the present invention.
Figure 1C:
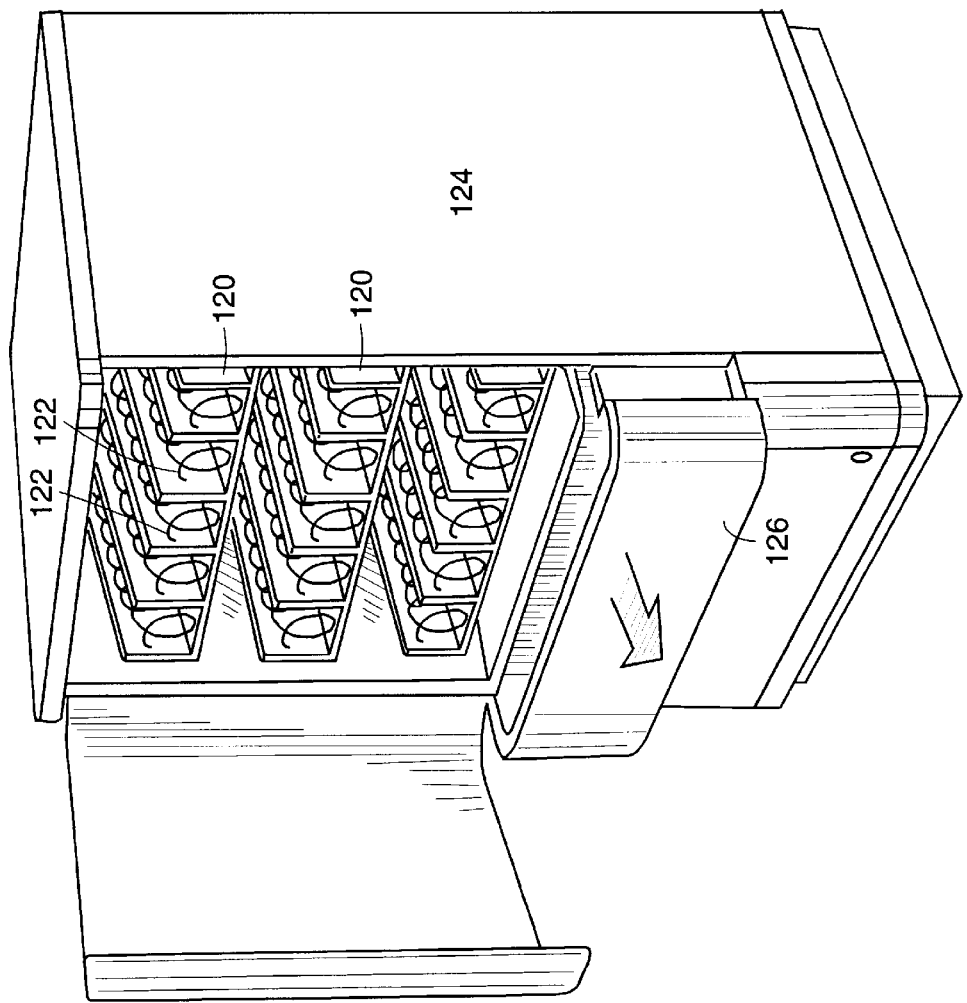
FIG. 1C is a perspective illustration of drawers of helix dispensers.

FIG. 1C is a perspective illustration of an alternative embodiment of the present invention. In this embodiment, drawers 120 of helix dispensers 122 are contained in a cabinet 124. The helix dispensers 122, when activated, rotate in a single direction. As the helix 122 rotates, any pharmaceutical packages disposed on the helix are pushed forward toward the front of the cabinet 124. One full rotation of the helix 122 will cause the outermost package to be released, causing the package to fall into the bin 126. After the package drops into the bin 126, an operator slides open the bin 126 and removes the package. While the bin is open, a door blocks the opening between the bin 126 and the dispensing area to prevent pilferage. The helix-dispensing unit described above is particularly suitable for packages of various non-standard sizes, for example boxes, bags, and kits. Larger-sized helixes 122 may be used for smaller packages. The helixes 122 are each individually driven by a stepper motor located in the rear of each tray.

FIG. 1D is a remote control dispenser embodiment well-suited for use in a doctor's office or in a small clinic. The top unit 130 includes a column dispenser as shown in FIG. 1B. The bottom unit 132 includes a helix dispenser as shown in FIG. 1C. This combination of dispensers covers a range of package styles for controlled substances, toolkits, and bandages for a typical clinic.

FIG. 1E is an illustration of an alternative dispensing unit. The unit includes a plurality of workstations 178, each workstation having a corresponding dispensing port 180. The unit further includes a cabinet 182 for storing a variety of pharmaceuticals and a conveyer means 184 for conveying a dispensed pharmaceutical from the cabinet area 182 and for distributing it to the appropriate dispensing port 180. Each workstation 178 also includes a printer for printing labels and instructions as described herein and a barcode reader for verifying that proper dispensing has occurred.

The workstation can alternatively be configured with integrated voice response software and hardware to permit external initiation of a refill order. In such a configuration, a patient telephones the workstation, enters a secret code and initiates refill dispensing. After dispensing has occurred, the workstation verifies such to the patient indicates a time for pick up. At the next opportunity, the operator of the workstation prepares the bottle label and instructions, and verifies that proper dispensing has occurred.

Figure 1F:
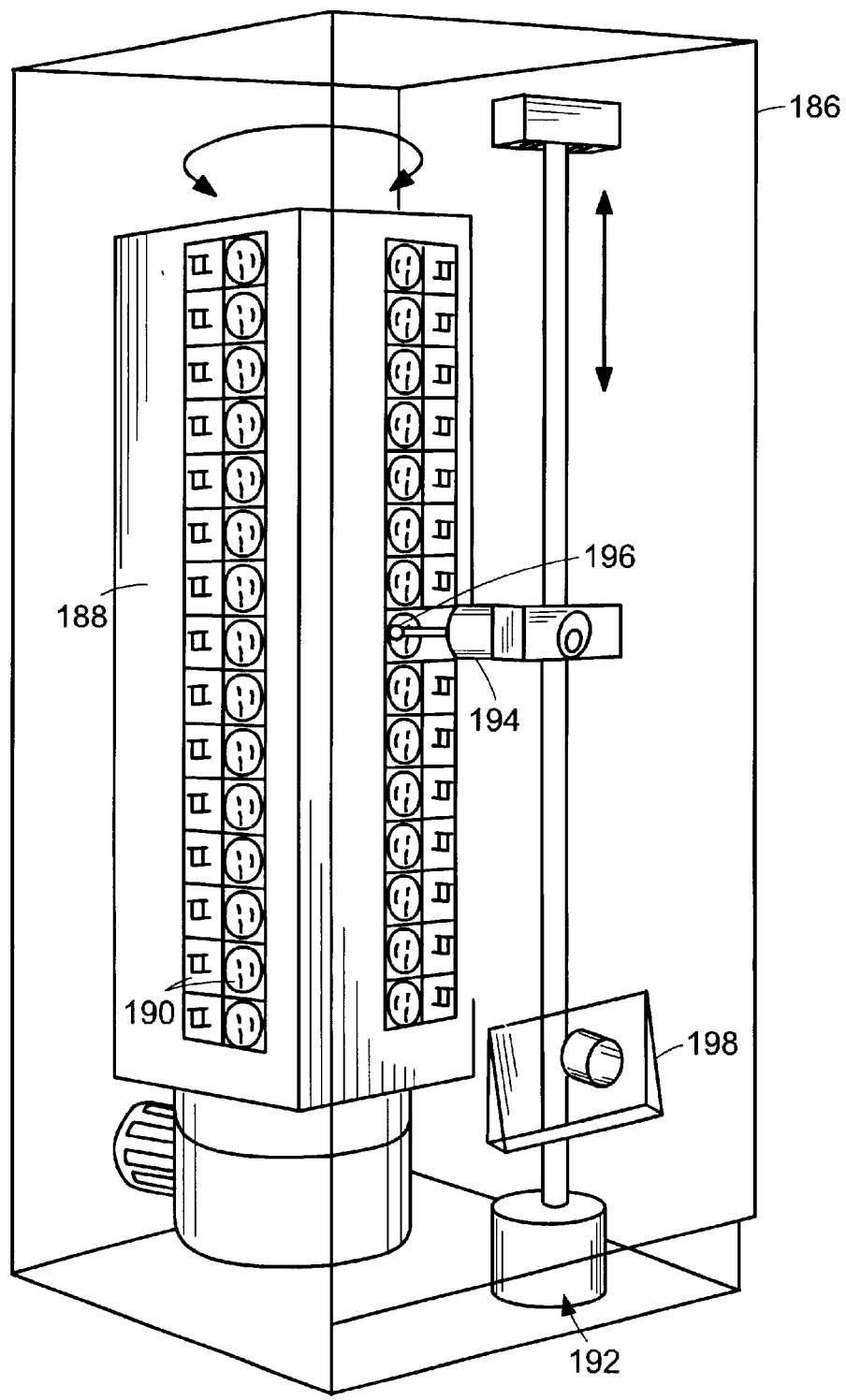
FIG. 1F illustrates a kiosk system in accordance with the present invention.

In a kiosk configuration as shown in FIG. 1F, a cabinet 186 encloses a carousel-type rotatable cabinet 188 containing a plurality of individually addressable locations 190. Upon receiving a dispensing signal, the carousel 188 rotates to align the correct column 190 with the dispenser 192. The dispenser 192 includes a grabber 194 which removes the bottle from its storage location 196. The grabber 194 conveys the pharmaceutical downward to dispensing drawer 198 and rotates to place the pharmaceutical in the drawer 198. The operator removes the pharmaceutical from the drawer and completes the dispensing process.

Figure 2:
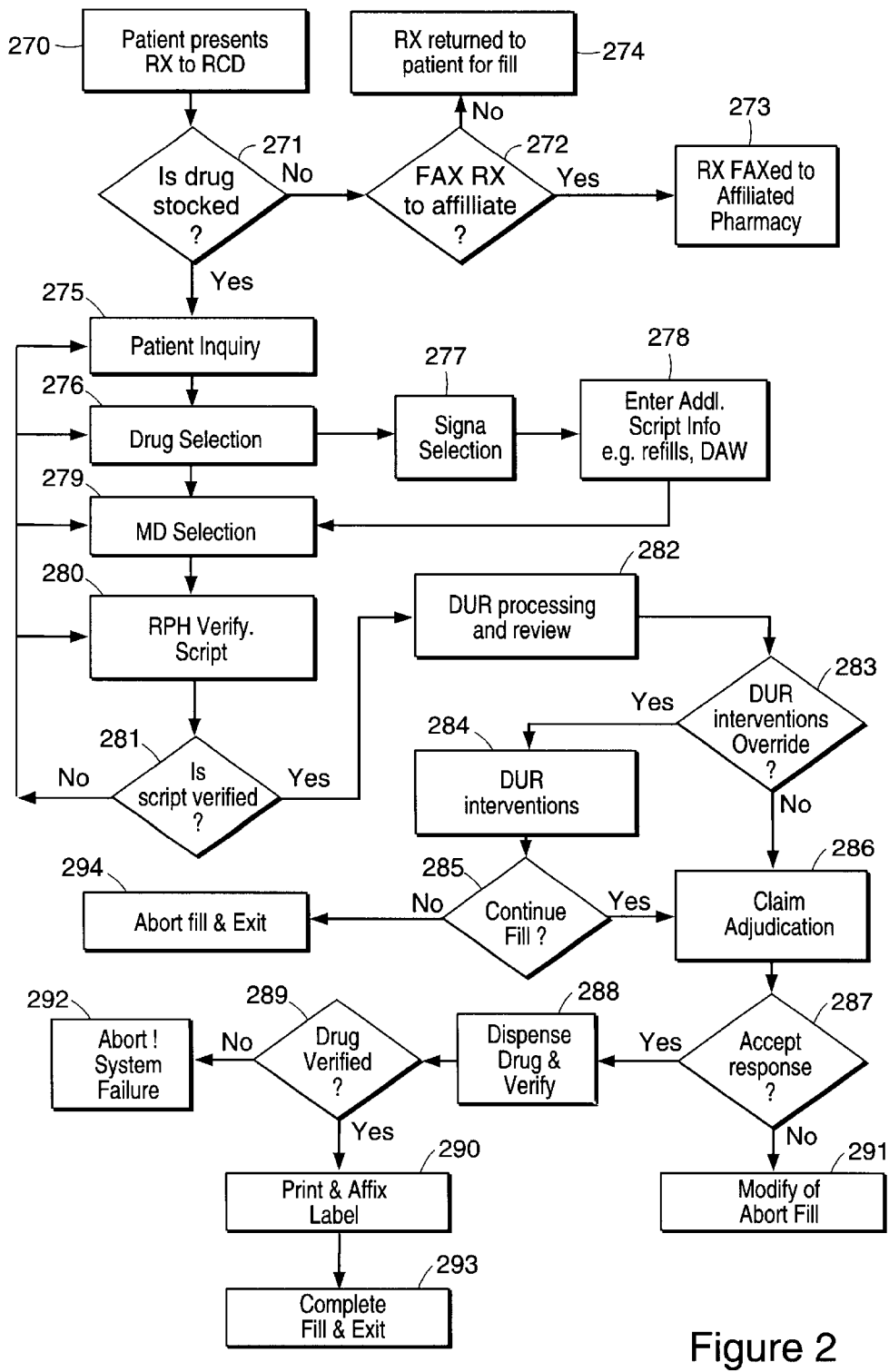
FIG. 2 is a flow diagram representing the processes performed by the pharmacy technician at a Remote Control Dispenser (RCD) in a remote dispense location and a registered pharmacist, R.Ph., at a remote control location in accordance with the present invention.

FIG. 2 is a flow diagram representing the processes performed by the pharmacy technician at an RCD and a registered pharmacist at the RPH workstation in accordance with the present invention. Initially, a patient presents a prescription to a technician at an RCD unit 270. The technician determines whether the drug is stocked in the RCD unit 271. If the pharmaceutical is not stocked, then the technician decides whether to electronically transfer via facsimile, email, or otherwise, the prescription to an affiliate 272. If the prescription is transferred to the affiliated pharmacy, 273, the patient may travel to that pharmacy to receive the pharmaceutical. Otherwise, the prescription is returned to the patient 274 to be filled at another RCD unit or by another pharmacist of the patient's choosing.

If the drug is stocked at the RCI unit, then patient data is retrieved 275, the drug is selected 276, the prescription signa is selected 277 and additional scripts may be entered 278. Following this, the identification number of the prescriber is entered 279 and all data is transmitted to the RPH workstation 280. At the RPH workstation, the pharmacist verifies the prescription 281 and performs a drug utilization review 282. If issues arise during the review, the pharmacist is immediately made aware of the conflict and given an opportunity to review and, if appropriate, override 283 the contraindications 284. If the pharmacist decides at this point to discontinue the dispensing 285, the process is aborted 294. If the pharmacist decides to continue the dispensing anyway 284 or there were no contra-indications 283 in the first place, then claim adjudication is performed 286. During adjudication 286, a patient's insurance information is automatically verified to determine whether the insurer will pay for the prescription, and if so, if any co-payment is required from the patient. If a negative response is received 287, drug dispensing is aborted 291. Otherwise, the drug is dispensed and verified with a barcode reader 288. If an improper drug was dispensed, the technician is notified to abort the process as a system failure has occurred 292. Upon system failure electronic notification is performed. Distribution headquarters or a regional dispensing location or agent can be notified by the RCD system of an incorrect dispense is shown. Electronic notification can take the form of a fax, email, file transfer, pager notification, or any other electronic transfer protocol. If verification is positive, a label is printed and affixed to the bottle 290. The technician then must scan an additional barcode that is created at the time of the printing. This barcode is located on the patient label now affixed to the dispensed item. If verification of this last barcode is positive, the prescription is dispensed to the patient by the technician 293.

Figure 3:
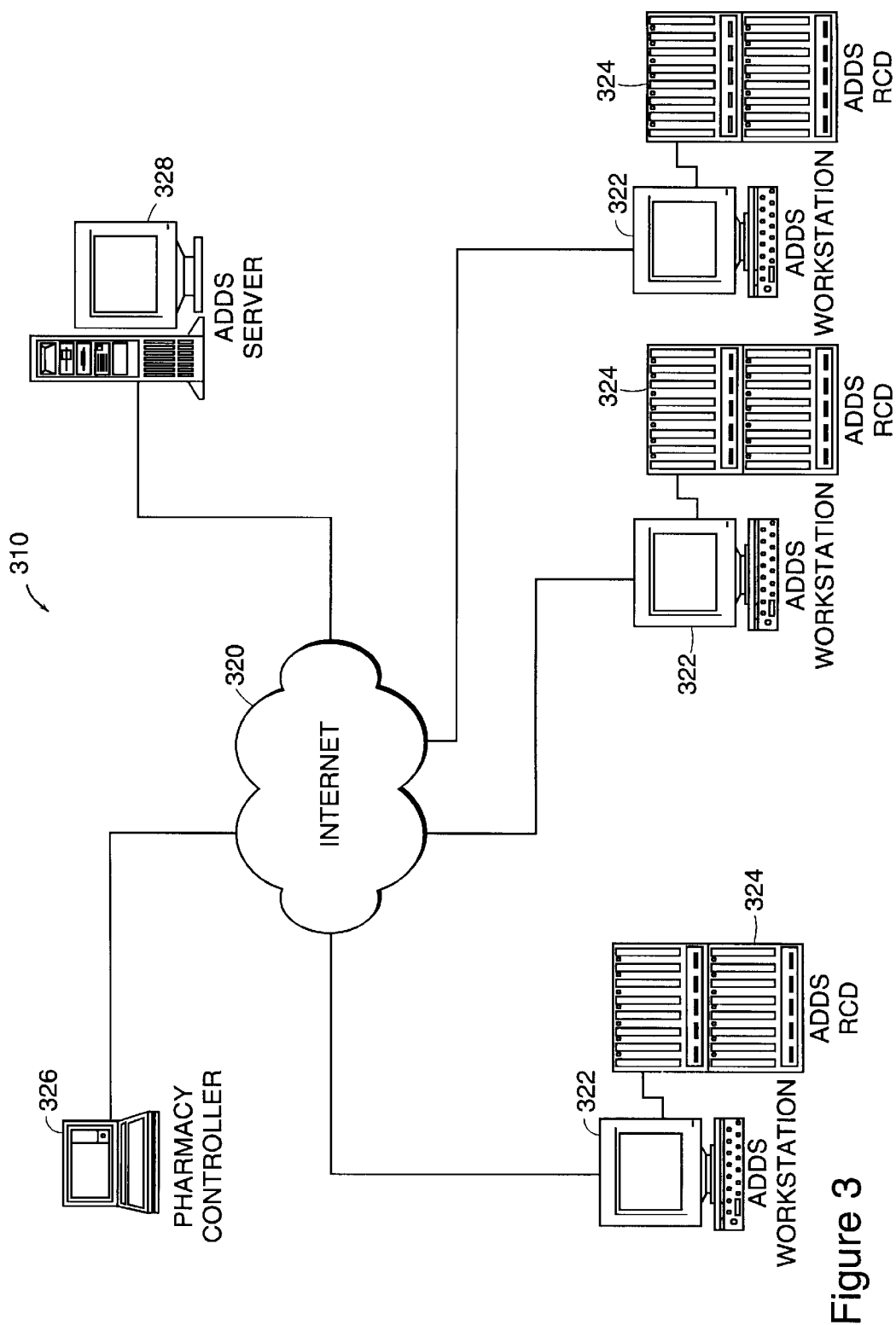
FIG. 3 is a schematic block diagram illustrating the drug dispensing system in accordance with the present invention.

Referring to FIG. 3, the drug dispensing system 310 of the present invention includes computers attached to a computer network system, for example, the Internet 320. Three of the systems are RCD workstations 322 which control the RCD hardware or dispensers 324. A computer system, represented by the laptop graphic, is the "Controlling Pharmacist" computer 326. Another computer 328 is a server running typical website type software.

The operating system of the workstations 322 is preferably a Windows basedsystem, for example, Windows NT systems with access to the Internet via a modem or via a connection to a Local Area Network (LAN), which has access to the Internet. Each workstation 322 uses a browser (for example, Microsoft Internet Explorer) to interact with the server 328. The interaction entails getting patient information entered, drug information, etc. Instead of a local executable, the Internet and a browser are used. The server 328 sends permission to each workstation 322 via the browser. The permission protocol is discussed in further details hereinafter.

In a particular embodiment, the server 328 runs Microsoft NT, Microsoft Internet Information Server (IIS) 4.0, ColdFusion™ and is connected to the Internet 320 via a static Internet Protocol (IP) address. A static or dynamic IP or a unique domain name can be used.

The server 328 contains and maintains all the information necessary to dispense a drug. It effectively functions as a "mainframe."

Once the dispense is appropriate that is there are no drug issues, and the patient can pay for the medication, the server 328 passes to the client browser the necessary codes to cause the RCD 324 to dispense the drug requested.

The pharmacy controller 326 is shown as a laptop to indicate pictorially that there is no attached hardware RCD's, etc. This system also requires access to the Internet 320 via a modem or LAN, and uses a browser to interact with the server 328 and the workstations 322.

The drug dispensing method of the present invention is predicated on the fact that most everybody has access to the Internet 320. When one logs onto the Internet 320 one gets an IP address, which uniquely identifies a user. Access to the Internet can be through an existing connection LAN, or using a Microsoft utility for example, dial-up networking. The workstation 322 using a bookmark, or Internet Explorer Favorites, or entering the domain name or IP address, connects to the server 328. The server 328, for example, WebDirectRx.com has a password gate; to control access and to establish which databases the workstation 322 has access to. This reduces any confusion regarding the inventory and dispense queues of networks, for example, in Utah, and Florida. The workstation 322 gets access from its user ID and password, plus a cookie that uniquely identifies the installation, to the correct databases. Examples are the inventory database, patient database, transaction database, and the dispense queue database.

The workstation 322 types into WebDirectRx.com the demographics of a new patient, or selects an existing patient. Another preferred embodiment has a host pharmacy or hospital network share access to patient records within its own nodes, or dispense sites. The workstation 322 selects and enters the Rx information. Rx Information is the data needed to process a drug Rx. It includes at least an account number, Rx#, Rx date, patient name, prescriber name, SIG, dosage, and insurance information. This information is placed into a queue database that is accessible for read only by the workstation 322. The Rx information is then available to a pharmacy controller account, who has READ/WRITE access to the queue. The pharmacy controller 326 uses a browser, and has gone through a password gate. The queue available to the pharmacy controller 326 is based upon the user ID entered to keep the different dispensing networks from sharing or intercepting data not pertinent unto itself.

The pharmacy controller 326 reviews the Rx information in the queue, processes the information through a Drug Utilization Review (DUR) Process, and performs adjudication as needed. Once these services are completed the pharmacy controller 326 places into a dispense queue the Rx information for the sending workstation 322. The sending workstation 322 in turn, sees it has an item in its queue, and dispenses that item using one of the methods to dispense a drug from hardware using the network as will be discussed later.

In a particular embodiment, the actual signal sent to the RCD 324 is triggered by the pharmacy controller 326, assuming the RCD is in a ready state to receive such a signal. Some states require the signal to be controlled by the pharmacy controller 326, versus the caregiver in front of the dispenser. The pharmacy controller can control quite a large network of workstations 322.

Figure 4A:
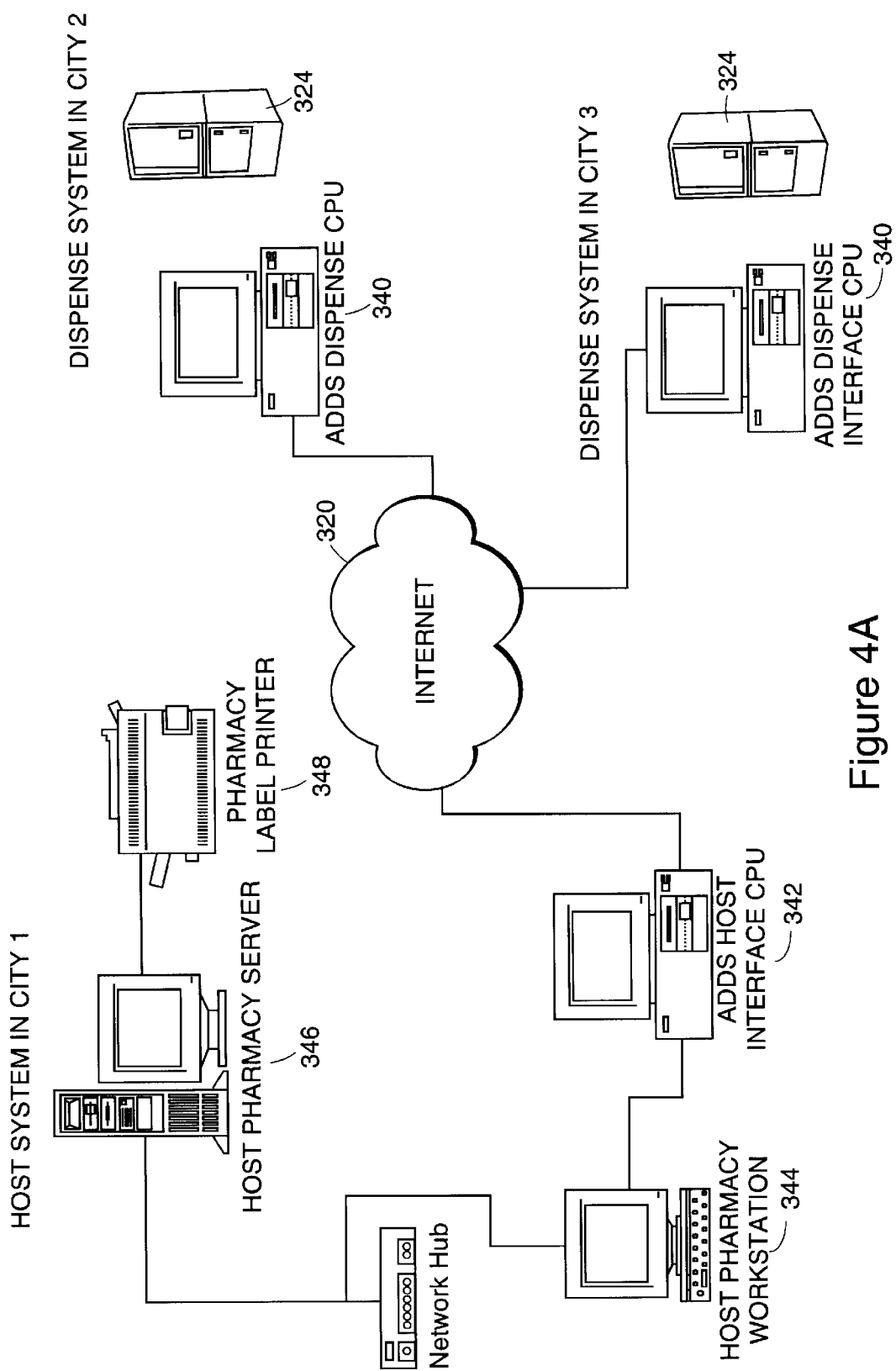
FIG. 4A is a schematic block diagram illustrating a drug dispensing system having a host system in one city and a remote drug dispensing system in different cities in accordance with the present invention.
Figure 4B:
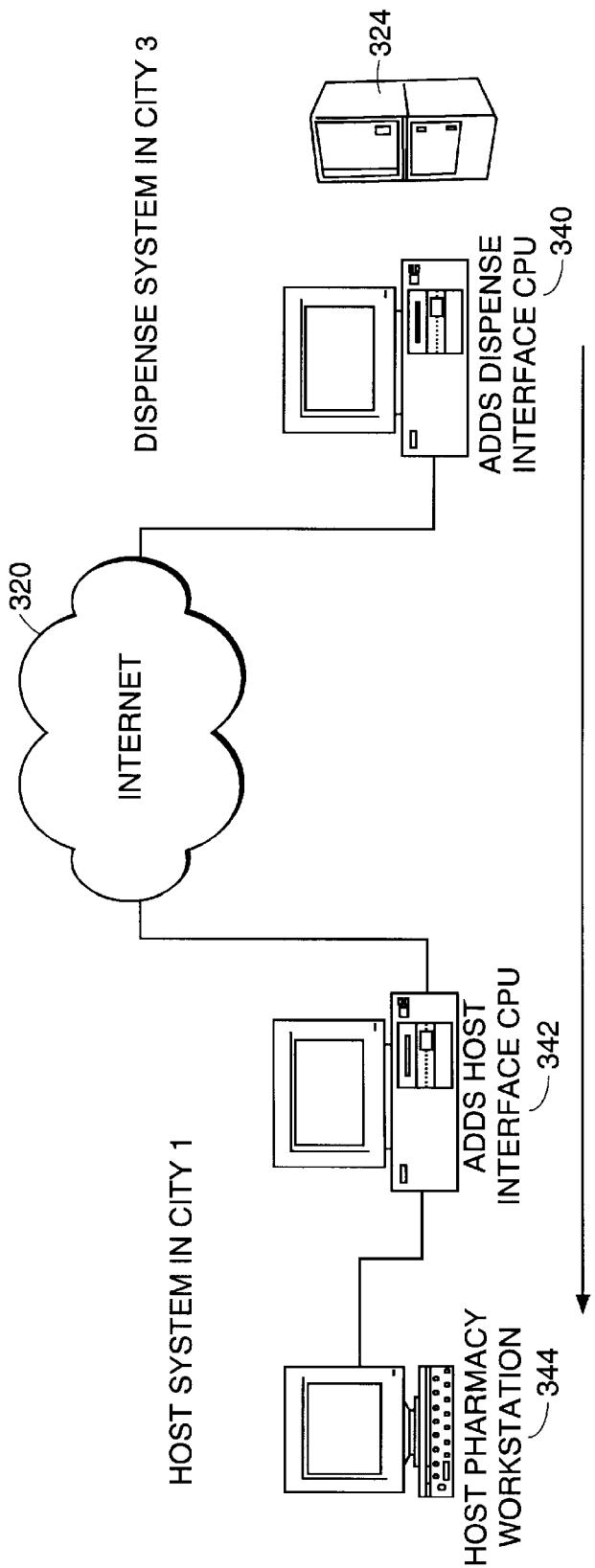
FIGS. 4B–4C are schematic block diagrams illustrating the transfer of information between the host system and the dispensing system in accordance with the present invention.
Figure 4C:
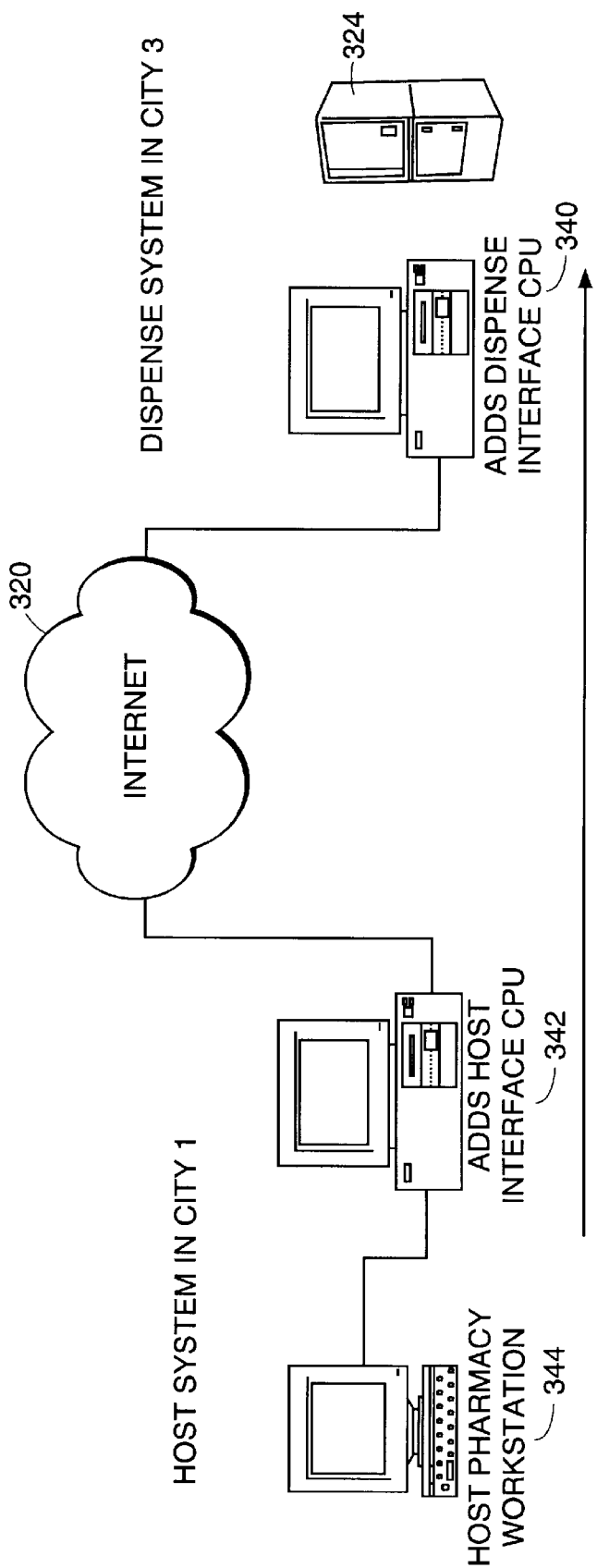

FIGS. 4A–4C schematically illustrates a host pharmacy system in city 1 connected to a remote dispensing system 340 in city 2 and city 3. The dispensing systems 340 are connected to a host interface controller 342 which acts as a gateway and passes control to the host pharmacy workstation 344. The information required to process a medication prescription for example, patient information, patient allergies, disease, and medication profile, is sent by the dispense interface central processing unit (CPU) 340 to the host interface CPU 342. The information is processed by the host pharmacy server 346 then is sent to a pharmacy label printer 348 which in turn prints out a pharmacy label for the requested medication. The pharmacist at the host pharmacy workstation 344 is sent the physician's prescription or a copy thereof. The physicians prescription can be in a variety of forms for example, a physician's called in instructions, an electronic version, a scanned in version from a scanner co-located with the remote dispensing RCD system 324. The pharmacist interprets the physician's prescription instructions against the label printed out by the printer 348. If acceptable, the pharmacist redirects the label to the host interface CPU 342 which now effectively acts as a network printer. The host interface CPU 342 parses the output based on a set of instructions and extracts out the prescription information, for example, the patients name, the name of the drug, SIGNA etc. The host interface CPU 342 then sends a signal, or dispense information, to the dispense interface CPU 340 in either city 2 or city 3 via the Internet 320. Upon receiving the signal, the dispense interface CPU 340 dispenses the appropriate medication from the RCD 324. In the alternative, the dispense interface reconstructs the information and presents it for dispensing from the RCD 324 by the co-located caregiver. As described previously with the dispense interface CPU 340 with respect to FIG. 2, the dispensed drug's barcode is scanned along with the printed label and provided to an end user.

Figure 5A:
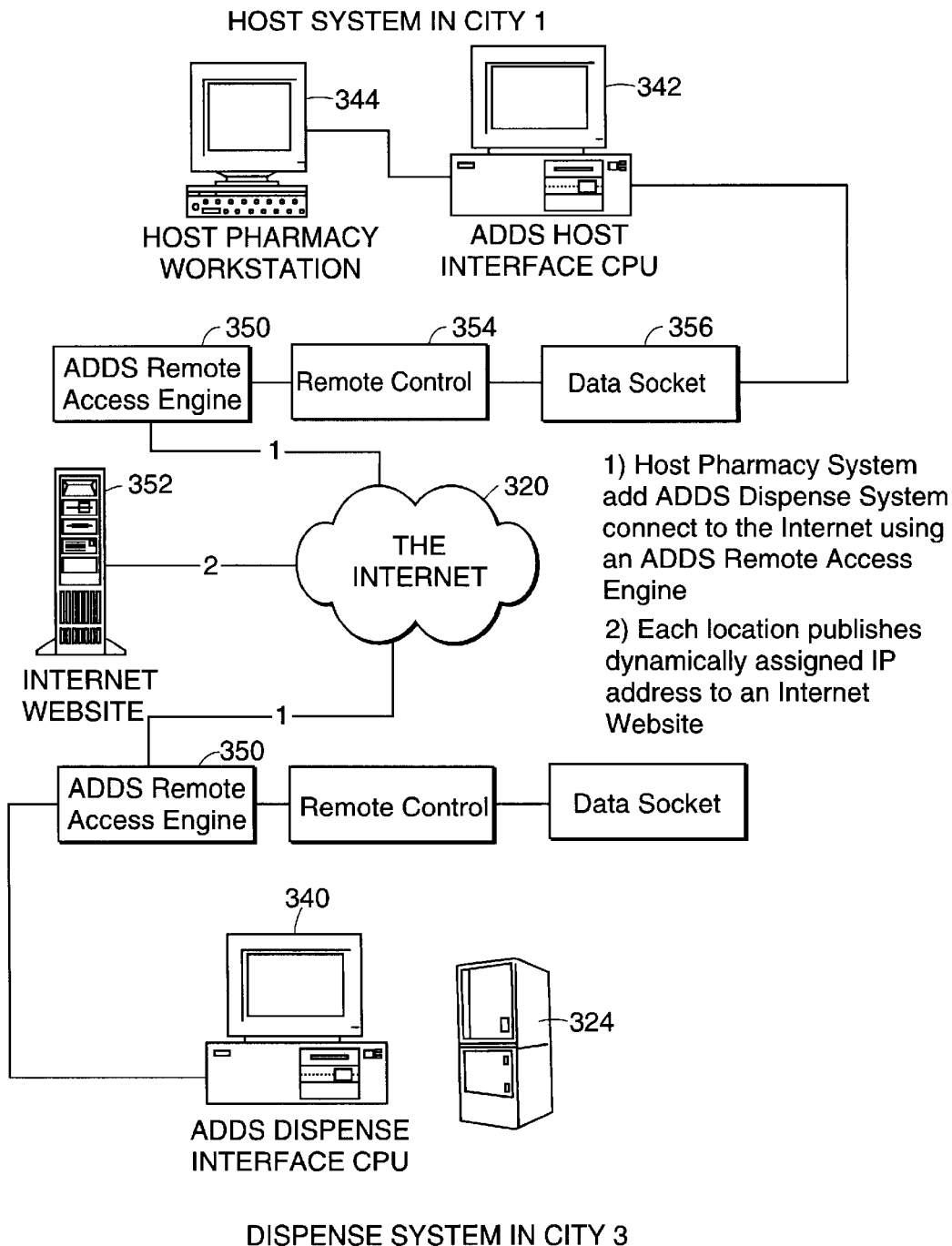
FIGS. 5A–5C are schematic block diagrams illustrating the sequence of the transfer of information between a host system and a remote drug dispensing system, using the Internet, in accordance with the present invention.
Figure 5B:
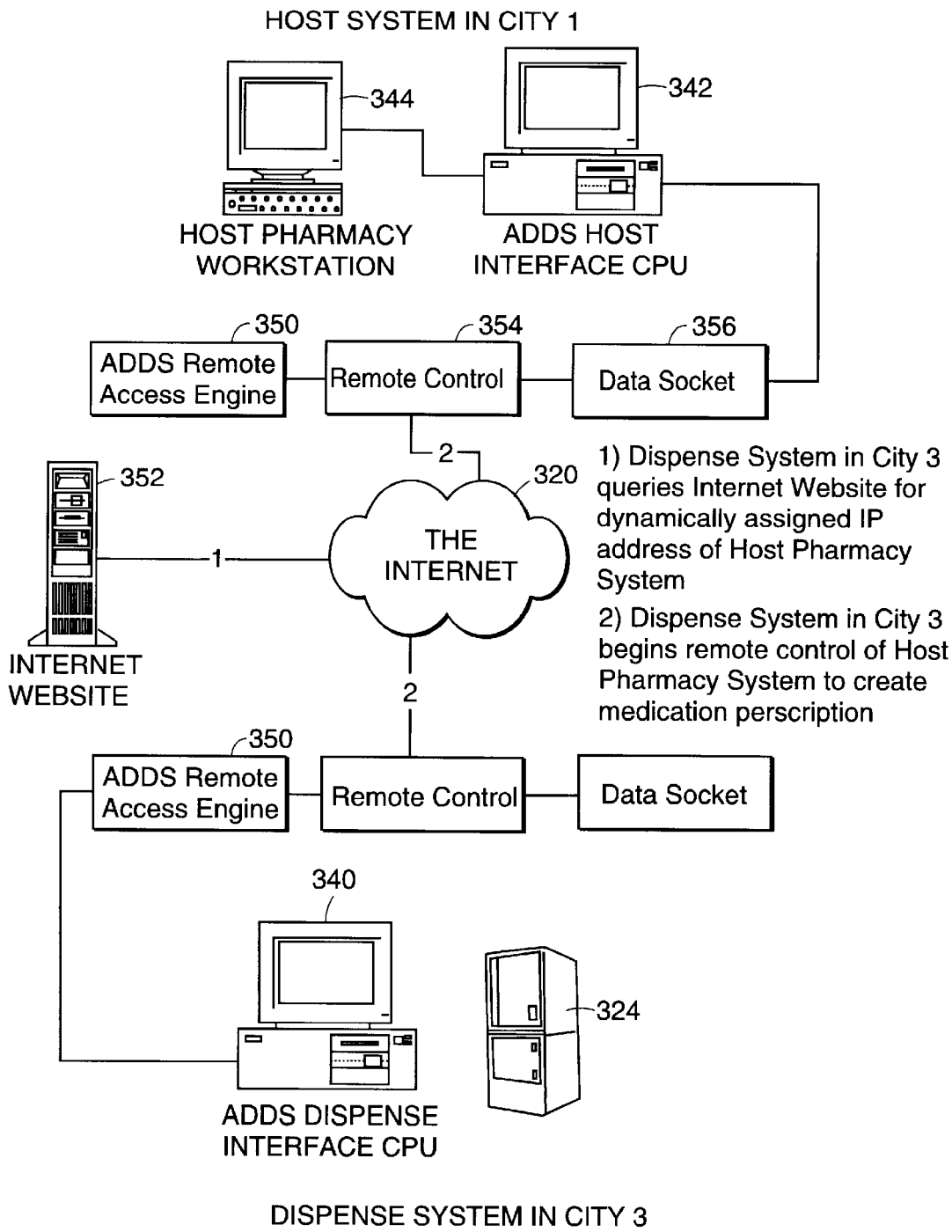
Figure 5C:
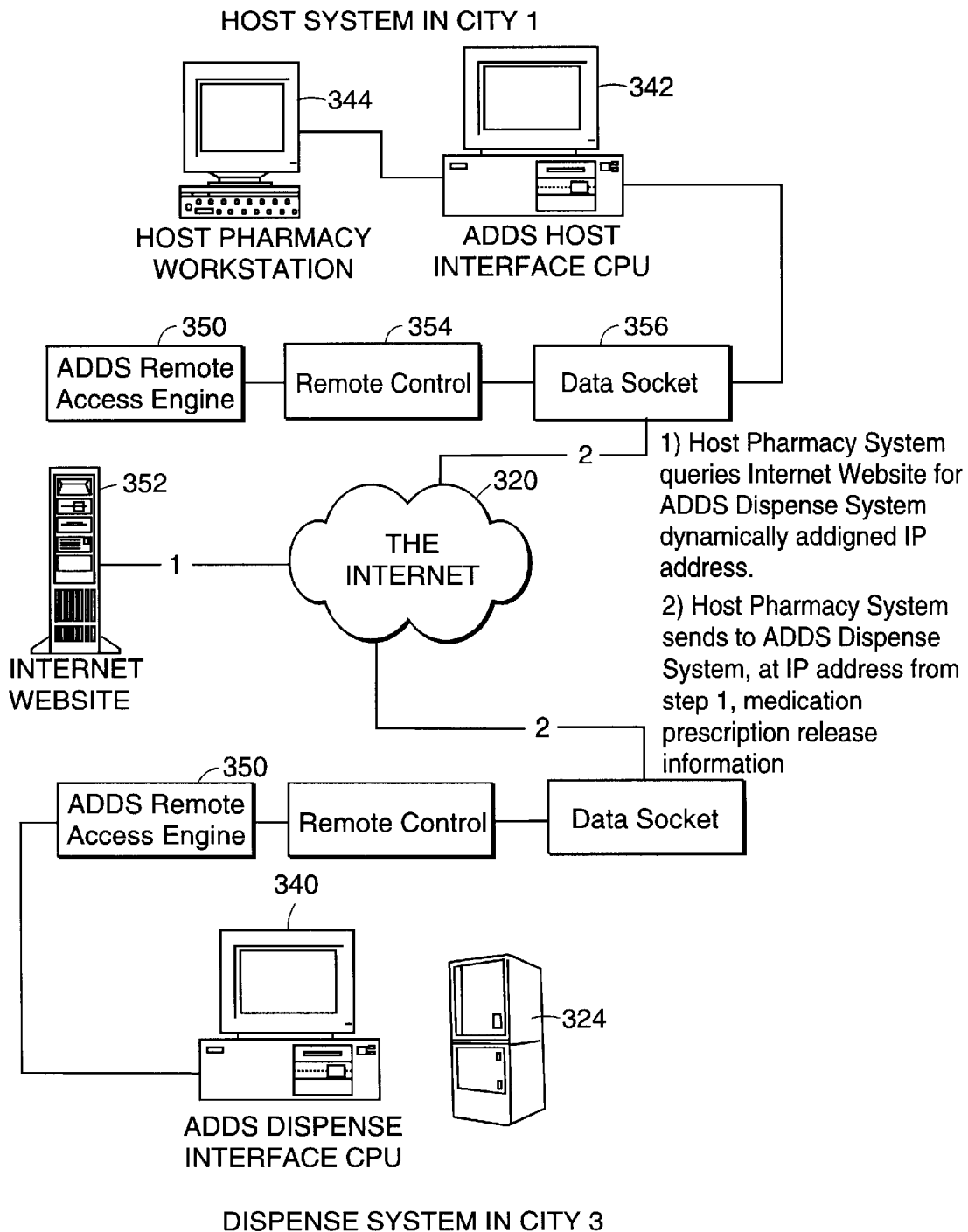

FIGS. 5A–5C schematically illustrate the sequence followed to transfer information between a host pharmacy system in one city and remote dispensing systems in a different city. As illustrated in FIG. 5A, a connection is first established between the host pharmacy system and a remote dispensing system using a remote access engine 350. Each location publishes the dynamically assigned EP address to an Internet website 352.

As illustrated in FIG. 5B, the dispense system in city 3 queries the Internet website 352 for the dynamically assigned IP address of the host pharmacy system. The dispense system then begins remote control 354 of the host pharmacy system to create a medication prescription.

As illustrated in FIG. 5C, the host pharmacy system queries the Internet website 352 for the dynamically assigned IP address of the dispense system using a data socket 356. The host pharmacy system then sends the medication prescription release information to the dispense system using the IP address given by the Internet website 352.

Figure 6A:
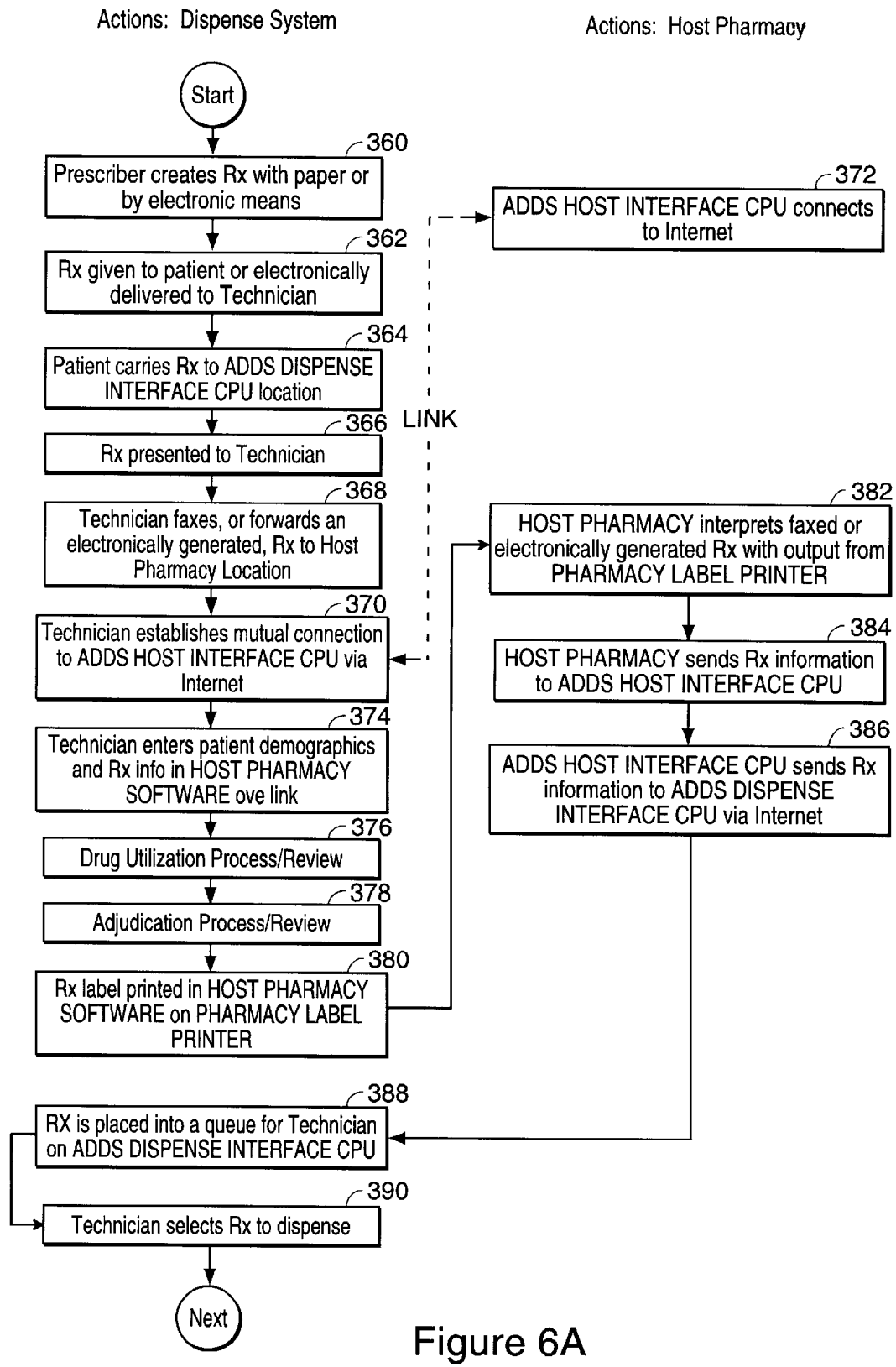
FIGS. 6A and 6B are flowcharts illustrating the process to dispense medications in accordance with the present invention.
Figure 6B:
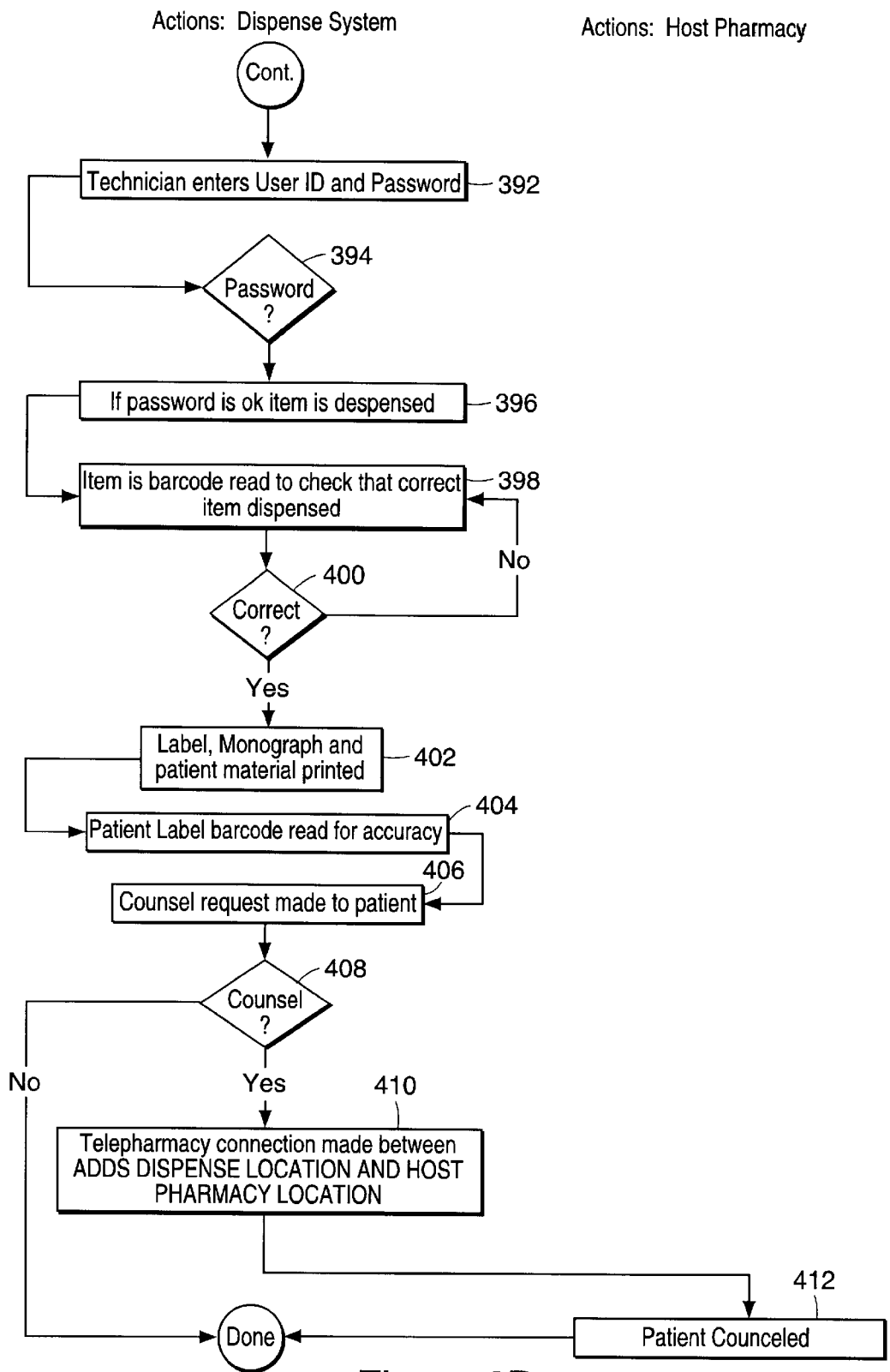

FIGS. 6A and 6B are flow charts illustrating the process to dispense medications using a remote controlled dispense system. The prescriber, for example, a physician creates a prescription on paper or via electronic means per step 360. The prescription is then given to the patient or electronically delivered to a technician who is co-located at a dispense interface CPU 340 per step 362. If the prescription was given to a patient, the patient carries the Rx to a dispense interface CPU 340 location per step 364. The prescription is presented to the technician in step 366. The technician then faxes, or forwards the electronically generated prescription to a host pharmacy location per step 368. The technician uses the Internet 320 to connect to the host interface CPU 342 per step 370.

The host interface CPU 342 also connects to the Internet 320 per step 372. The technician enters patient demographics and prescription information in a host pharmacy software over a link per step 374. A drug utilization review (DUR) process is then conducted by the pharmacist per step 376. This is followed by an adjudication process per step 378 if required. A prescription (Rx) label is printed in the host pharmacy software on the pharmacy label printer 348 per step 380. The host pharmacy then interprets the faxed or electronically generated prescription with the output from the pharmacy label printer per step 382. The host pharmacy then sends the prescription information to the host interface CPU 342 per step 384. The host interface CPU 342 sends the prescription information to the dispense interface CPU 340 via the Internet 320 per step 386. The prescription is then placed into a queue for the technician who is co-located with the dispense interface CPU 340 per step 388. The technician then selects the prescription to be dispensed per step 390. The technician enters their unique user ID per step 392. Upon being queried for a password, per step 394, the technician enters a valid password. If the password is accepted the item is dispensed from the RCD 324 per step 396. The item's barcode is read to check if the correct item has been dispensed per step 398. If the barcode is accurate, as decided per step 400, a label containing the monograph and patient material is printed per step 402. The patient label barcode is then read for accuracy per step 404. A counsel request is made to the patient per step 406. If a counsel is required per step 408, then a telepharmacy connection is made between the dispense location 340 and the host pharmacy location per step 410. Once the patient is counseled per step 412 the dispensing procedure is completed. If however, it is decided in step 408 that a counsel is not required then the procedure for dispensing the medication is completed then.

Figure 7:
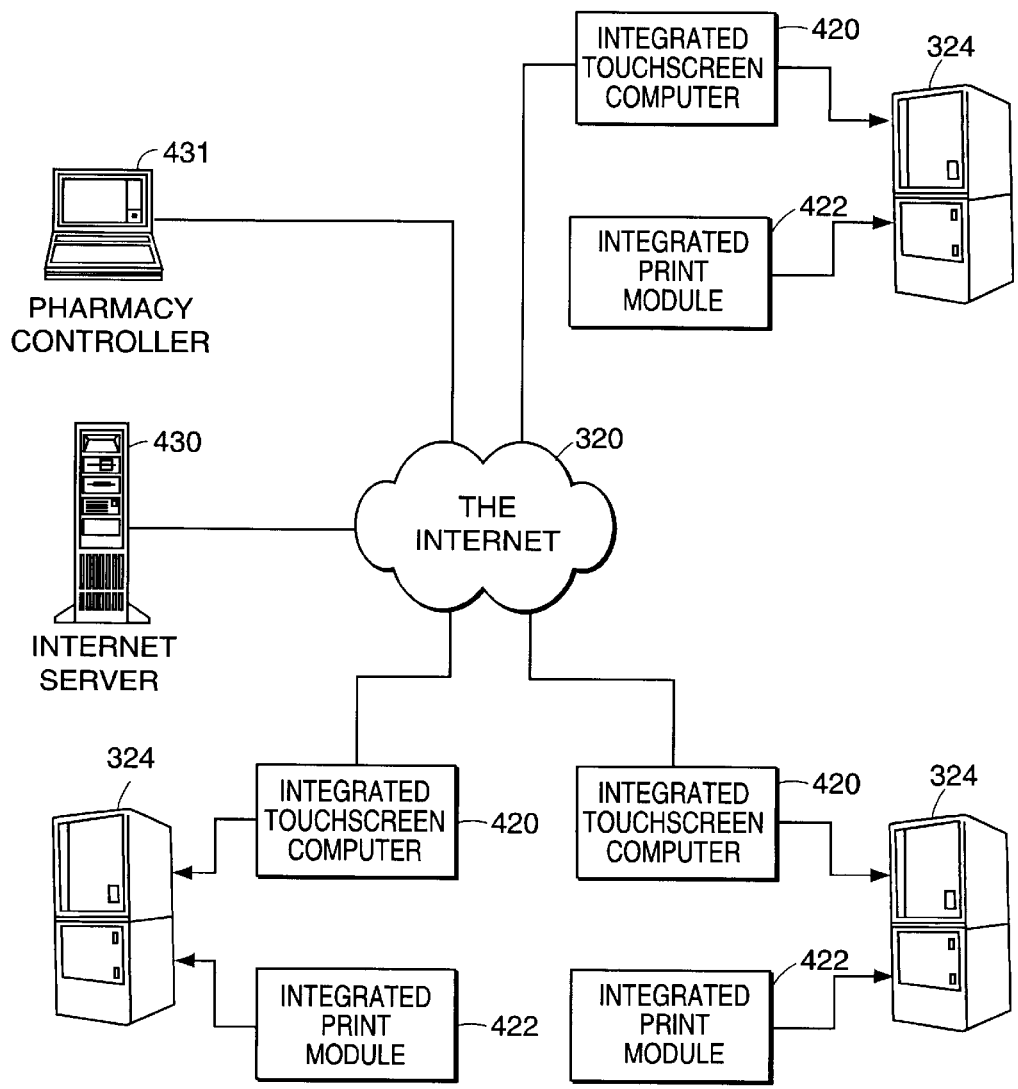
FIG. 7 is a schematic block diagram illustrating a drug dispensing system having an integrated touchscreen computer and print module in accordance with the present invention.

FIG. 7 illustrates a particular embodiment of a remote control dispenser 324 having an integrated touch screen 420 and a print module 422. This embodiment does away with the need for a workstation co-located with an RCD 324.

Figure 8A:
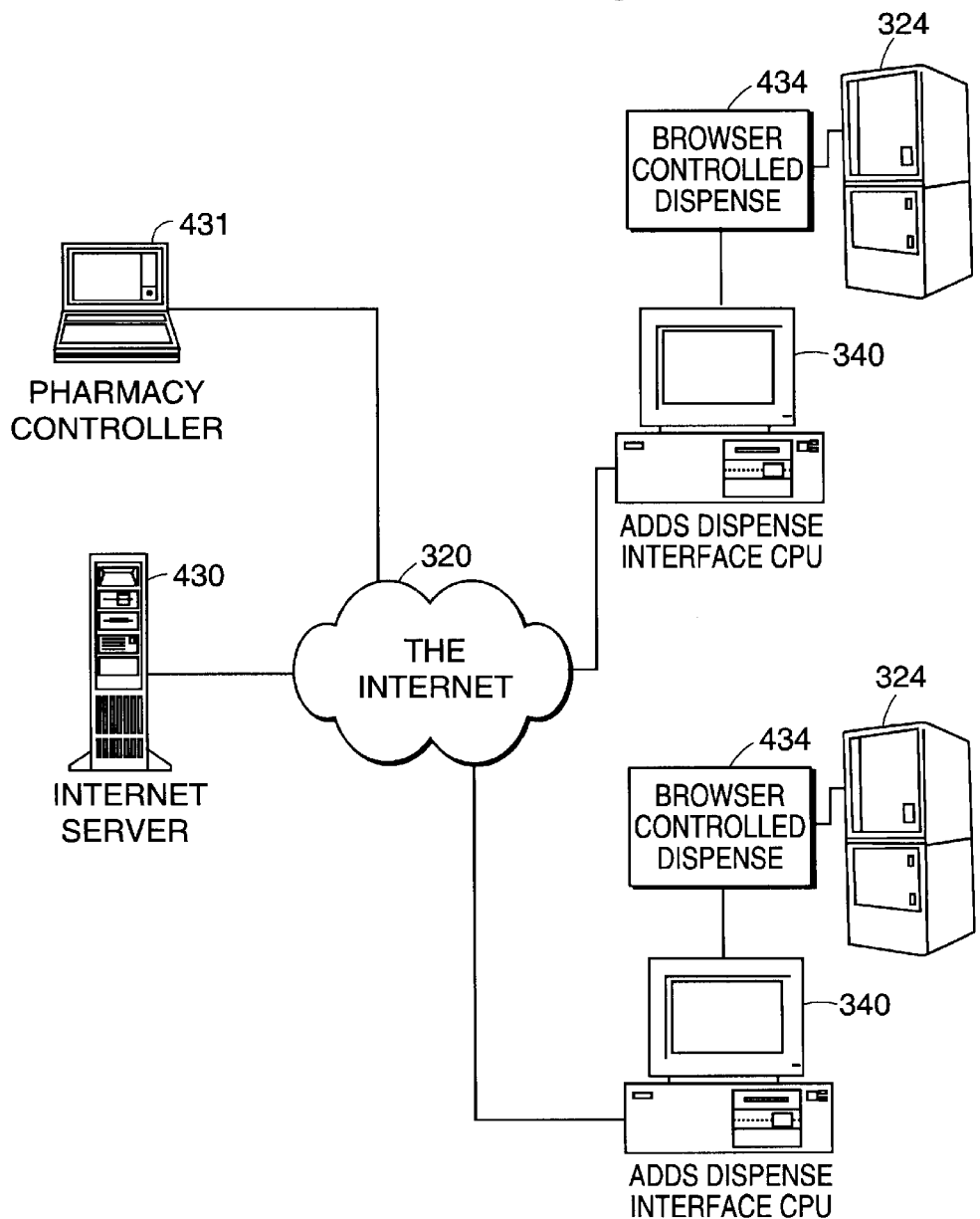
FIGS. 8A and 8B are schematic block diagrams illustrating a remote control dispensing system which uses a server to control drug dispensing in accordance with the present invention.
Figure 8B:
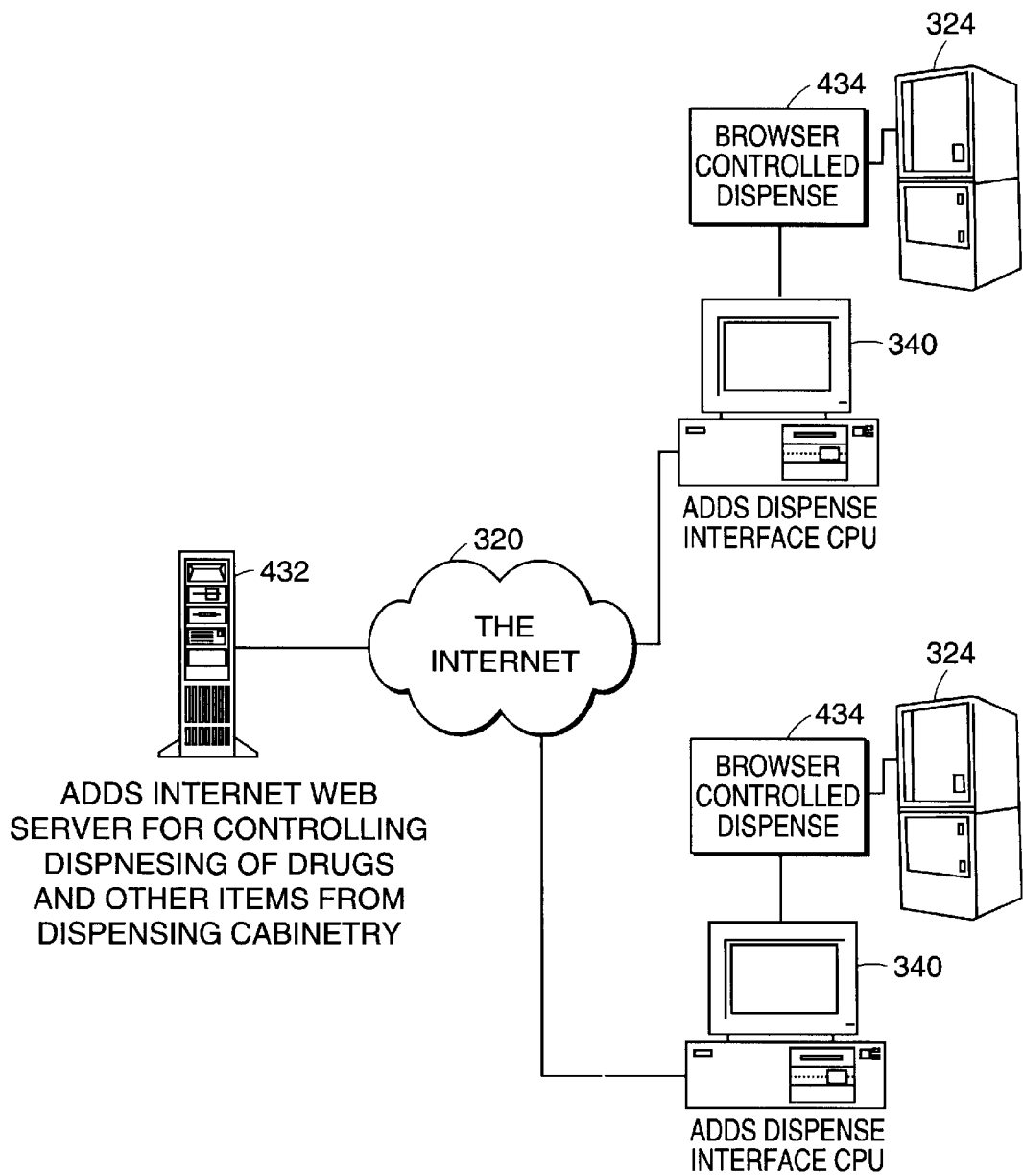

FIGS. 8A and 8B illustrate a particular embodiment of the remote control dispense system which relies on a web server such as an Internet server 430 as illustrated in FIG. 8A, or a customized web server 432 as illustrated in FIG. 8B. A browser 434 is used to control the dispensing of the medication or package from the RCD 324. The Internet server 430 and the web server 432 effectively function as the host interface CPU 342.

The drug dispensing method in accordance with the present invention includes at least one of the following different methods to dispense a drug from hardware such as the RCD 324 using a computer network such as the Internet. A first method includes having the web browser which causes a local executable to launch which communicates with the communications port (COMM PORT) of a workstation 340 and thereby the electronics in the RCD 324. This activates automatically in an unattended fashion, effectively like a batch file running.

A second method to dispense a drug from the RCD 324 using the Internet includes direct communications between the browser and the COMM PORT. An ADD-ON element is built for the browser that is downloaded each time a dispense signal is to occur, or only once (the first time) and it is called when needed.

A third method to dispense a drug from the RCD 324 hardware using the Internet is via a customized software application such as, for example, a JAVA APPLET downloaded as part of the permission to dispense. The applet activates the COMM PORT and causes the dispense cycle.

Another method to dispense a drug is to have a local executable which is "WebEnabled" by having built into it a hypertext transfer protocol (http) or file transfer protocol (ftp) service which frequently scans a table on the server 328 for the needed codes to dispense an item.

Another method to dispense a drug includes PCAnywhere. Both systems are connected to the Internet, one runs pcAnywhere HOST, the other pcAnywhere REMOTE. The remote, via the Internet 320, controls a local executable—the dispense software—just by entering the host IP address, or searches a sub-net for any connected system running HOST. The dispense protocol remains the same as described herein before.

It should be noted that the software the technician interacts with can exist on an attached and co-located external computer configuration, or as an integrated computer using TouchScreen components built directly into the RCD.

Referring to FIG. 9A, in this embodiment of the dispensing system an existing host pharmacy software system 470 with a co-located interface application server 476, and a remotely installed dispense location interact to provide pharmaceutical dispensing across a wide geographic region. This preferred embodiment uses the Internet 482 to communicate Rx dispense information. The host pharmacy software system 470, via the interface application server 476, sends Rx dispense information onto the dispense location workstation 486. At the dispense location workstation 486 the local user, for example, a technician, is presented with a queue of processed prescriptions received from the host pharmacy software system 470.

The dispense location workstation 486 contains local executable program(s) that manage the connection to the internet 482, internet data socket communications, data acceptance, inventory management, and visually prepares the Rx information received from the interface application server 476 in an easy to read queue for the local caregiver, typically a technician. In addition the dispense location workstation 486 communicates with the co-located Remote Control Dispenser (RCD) 490 to dispense packaged pharmaceuticals, a printer 472, such as a laser jet or color jet printer to provide patient and record keeping materials, as well as, a barcode scanner for doing quality checks during a dispense. The dispense location needs access to a telephone system to get a "dial tone", or a LAN based Internet connection, in order to receive and send communications.

The host pharmacy software 470 is maintained or run at the pharmacy control location. Typically these are small networks of pharmacy workstations where a retail or hospital pharmacy team interacts with insurers computers to create the order that leads to the filling of a drug to be handed to the patient.

The interface application server 476 is a computer that is co-located with the host pharmacy software system 470. It is used to collect information (the Rx data) for a dispense from the host pharmacy system and then forwards that information to the dispense location workstation 486 via the Internet 482.

Figure 9B:
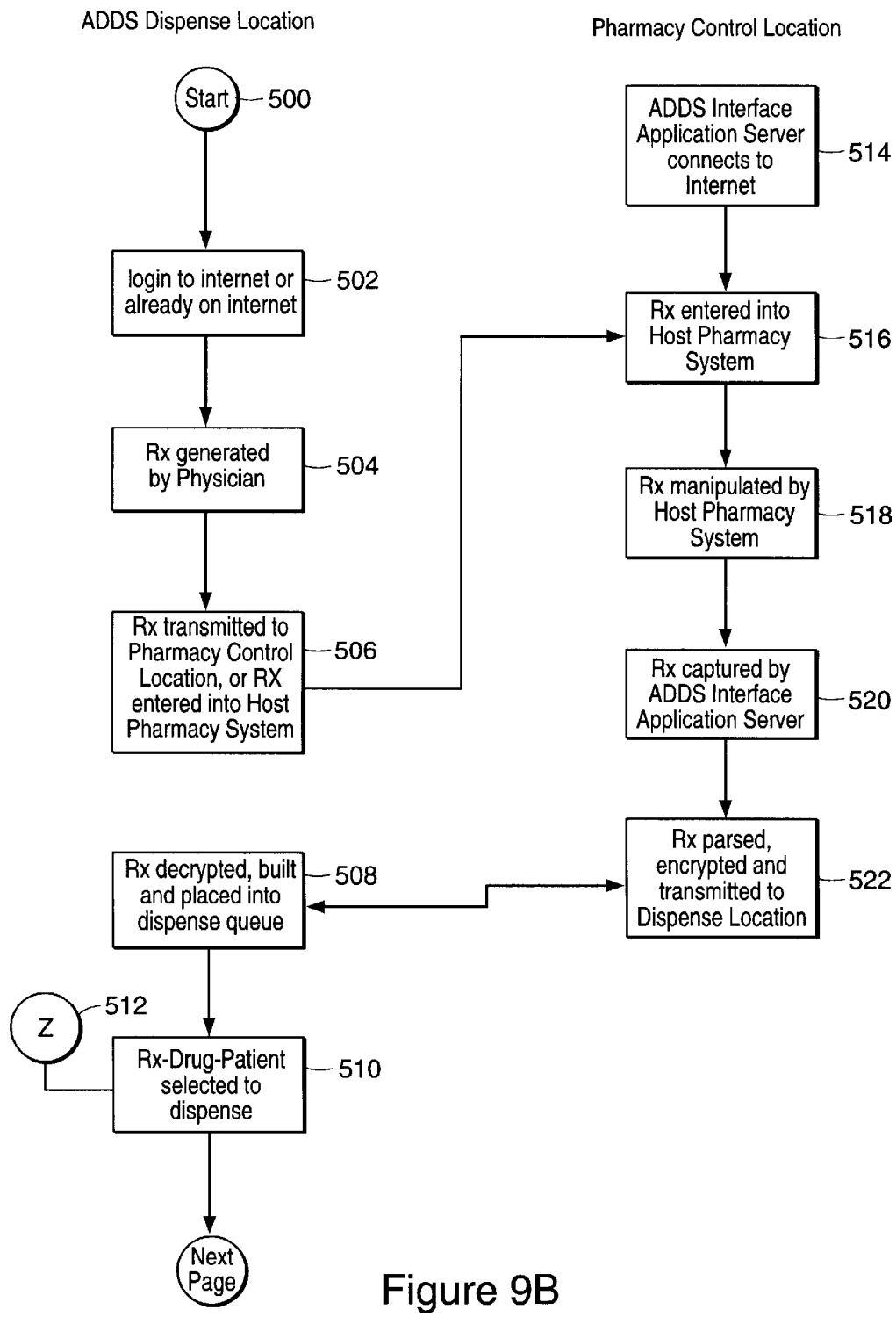
FIGS. 9B and 9C are flow charts illustrating the process to dispense medications using the preferred embodiment of the present invention illustrated in FIG. 9A.
Figure 9C:
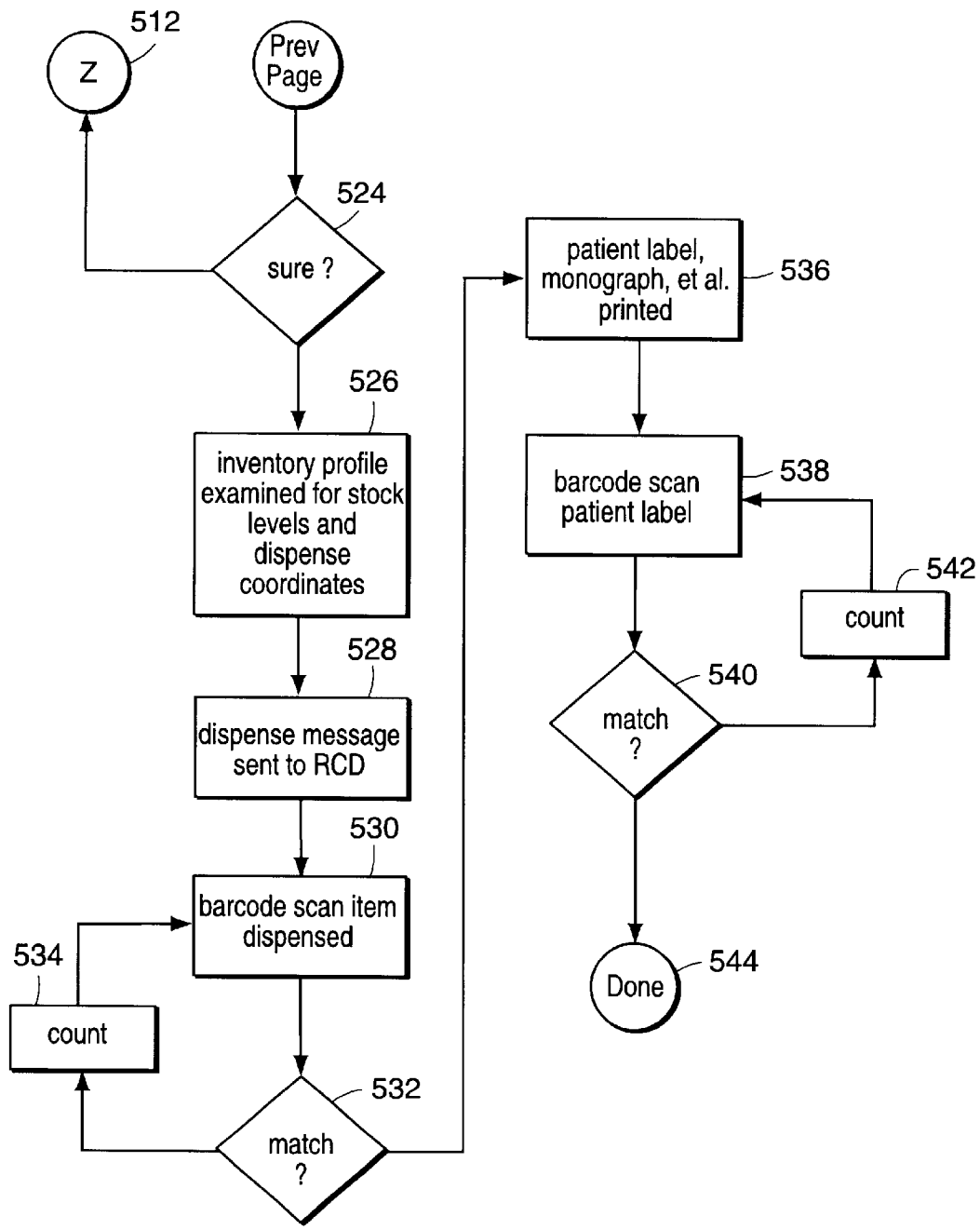

Referring to FIGS. 9B and 9C, a typical workflow of the embodiment illustrated in FIG. 9A includes the following sequence of steps. An Rx is generated by a Physician or caregiver using a paperless method such as a PDA or TouchScreen or by usual methods using pen and paper, fax and scanners in step 504. The Rx information typically contains the patient name, prescriber name and Drug Enforcement Agency identifiers, instructions for the administration of the drug, drug; name, and quantity to be given to the patient. The Rx is transmitted to different locations per step 506, for example, if the Rx is transmitted to a pharmacy control location via fax or an electronic means, the authorized dispenser, typically a pharmacist, interprets the transmitted information. Alternatively, if the Rx is transmitted to a dispense location electronically or physically delivered, a user, typically a technician can take authorized action.

Once entered into the host pharmacy system per step 516, the Rx is manipulated into the host pharmacy software system per step 518 either by an authorized dispenser interpreting the Rx information transmitted directly to his/her location and then manually or through an electronic interface transfers the Rx information into the host pharmacy software, or the technician has an option to transmit the information to, the authorized dispenser, pharmacist, for the pharmacist to manipulate as described hereinbefore or to remotely connect to the host pharmacy software via a variety of interfaces to transfer the Rx information into the host pharmacy software system either manually or via an electronic interface. The connection interfaces can be, but are not limited to, Symantec pcAnywhere directly, Symantec pcAnywhere via the: Internet, or by a co-located WAN connection provided with the host pharmacy software.

Once the information is transcribed or transferred into the host pharmacy software system a number of typical processes are applied to the Rx information. The processes can be a Drug Utilization Review; which entails scanning the drug to be dispensed against the patient profile contained within the host pharmacy software system to determine if any pharmaceutical contra-indications for dispensing exist. An example of a DUR can be a drug-to-drug interaction test, or a patient drug allergy test. A second typical process is an Adjudication process whereby the host pharmacy Software system communicates with a pharmacy benefit management computer to determine the patient's insurance coverage and payment amounts, if any.

The Rx information, having been processed by the host pharmacy software system can generally then be determined to be a valid Rx; which can be processed by the pharmacist. In a retail setting, the pharmacist then triggers patient drug labeling to be produced by the host pharmacy software system and takes a large bottle of medications from the shelf and counts and places into a smaller bottle, typically called a vial, the number of tablets, caplets, or milliliter's called for by the physician. The pharmacist then applies labeling and hands the drug to the patient. When the dispense is processed in conjunction with the remote dispensing system, the pharmacist or authorized dispenser triggers a patient drug label to be produced by the host pharmacy software system, however, instead of the label being processed by a co-located printer (laser jet or dot matrix) the output is directed to the interface application server. The interface application server accepts the Rx information as a printer stream per step 520, or through a direct electronic interface to the host pharmacy software system network constructs.

Per step 522, an application, such as, for example, Parse Engine, parses the output received by the host pharmacy software system.into discreet data elements. Once the parsing is completed, the data is then encrypted and is uniquely identified for transmission to the dispense location workstation via the Internet.

The information is received by the dispense location workstation, decrypted and is placed into a work in process queue that is accessed by local executable programs run by the technician per step 508.

The technician at the dispense location selects the Rx-Drug-Patient to be dispensed from a list of one or more possible to be displayed per step 510. The selections are shown as mouse selectable lines. Each line represents a different RX-Drug-Patient to be processed by the technician.

Upon selecting the Rx-Drug-Patient to dispense the technician at the dispense location is queried if this is in fact the RX-Drug-Patient per step 524. If the answer to the query is no, the technician is returned to the entire queue list as described above per step 512. If the answer to the query is in the affirmative, the local executable program resident on the dispense location workstation examines a local inventory file that contains data specific to the drug requested to be dispensed per step 526. The drug contains a profile which includes but is not limited to current stock level, suggested restock levels, and coordinate position within a single or plurality of RCD's.

The RCD receives a technician coordinate type communication from the locally resident executable. The X,Y coordinate represents a location within a single or plurality of RCD's where the requested pharmaceutical is stored for dispensing. The X,Y coordinate is determined by examining an inventory profile of the drug to be dispensed. Upon receiving the dispense signal from the dispense location workstation the RCD presents a drug to the technician per step 528.

As a result of the dispense occurring, the technician is presented with an additional screen which requires the input of barcode data embedded onto the label of the dispensed drug. A barcode reader co-located at the Dispense Location is used to read the barcode of the item dispensed from the RCD per step 530. The technician reads the barcode into the screen to be examined by the resident dispensing software.

The barcode of the item dispensed is read into the resident dispensing software and is compared with the value of the barcode expected from the drug inventory profile. If the values match per step 532 what the resident dispensing software is expecting, a patient education monograph, patient labeling, graphic representation of the drug expected, and picture of drug expected are generated per step 536 and delivered to the co-located printer. If the values do not match what the resident dispensing software is expecting, the user has three attempts with which to scan or enter the expected values per step 534. If three failed attempts are made, the transaction is terminated with warnings sent to appropriate parties like the authorized dispenser, technician, system operator, and pharmacy consultant via pager and email. Appropriate drug disposal and storage is maintained via training of the technician and an additional lock storage box within the RCD.

The technician at the dispense location is presented with one additional barcode on the patient label that is to be affixed to the item dispensed. The technician is required to perform one more barcode read by scanning the patient label after it is affixed to the item dispensed per step 538. The barcode of the item dispensed is read into the resident dispensing software and is compared with the a value of the barcode expected, the Rx number. If the values do not match what is expected, then the user has three attempts to scan the correct label before an error condition is reported per step 542. If the values do match per step 540, then the dispense is complete and the local technician is returned to the view of the queue show work in process, if any.

If the patient, who has been remotely administered medications has any questions an authorized pharmacist is available for consultation using a variety of telepharmacy systems, including, but not limited to, a telephone system audio visual connection 488, a networked audio visual connection, and an internet connected audio visual connection.

Referring to FIG. 10A, in another preferred embodiment of the present invention an existing host pharmacy software system 560 with a co-located interface application server 566, and a designed web server 574 work in-conjunction to provide a third location, the dispense location, with prescription information enough to identify and then dispense a pharmaceutical.

The dispense location uses a web browser, such as, for example, Microsoft Internet Explorer 5.0, instead of a locally installed executable. The web browser then interacts with data on a Web Server 574. The web server 574 gets its data from the interface application server 566 which is co-located with a customers Pharmacy software system 560.

The dispense location is where the RCD cabinet 582 is located, along with a personal computer 580, a printer 562 such as a laser jet printer, and a barcode scanner. This site has connectivity through a network or telephone system to the internet 576.

The pharmacy control location is where the host pharmacy software is maintained or run. Typically these are small networks of pharmacy workstations where a retail or hospital pharmacy team interacts with insurers computers to create the order that leads to the filling of a drug to be handed to the patient. The wholesalers have discovered a method to keep distribution by supplying retail outlets with pharmacy software that automatically places reorders with the wholesalers computers based upon use and an inventory threshold stockout level. An example of pharmacy software that can be used, but is not limited to, with the present invention is McKesson HBOC Pharmaserve software.

The interface application server 566 is a computer that is co-located with the pharmacy software system 560. It is used to collect information such as, for example, the Rx data for a dispense from the host pharmacy system and then forwards that information to the web server 574 in accordance with the present invention. The web server 574, runs ColdFusion™ with a Structured Query Language (SQL) 6.5+ database. The web server stores data sent to it, and displays that data in an easy to understand point and click format. The web server 574 is connected to the internet 576 at a static IP address using a Universal Resource Locator (URL) such as, for example, StarNetLite.COM. The web server 574 handles secure transmission of the data as well as the segmentation of data based upon a user login id/profile.

Figure 10B:
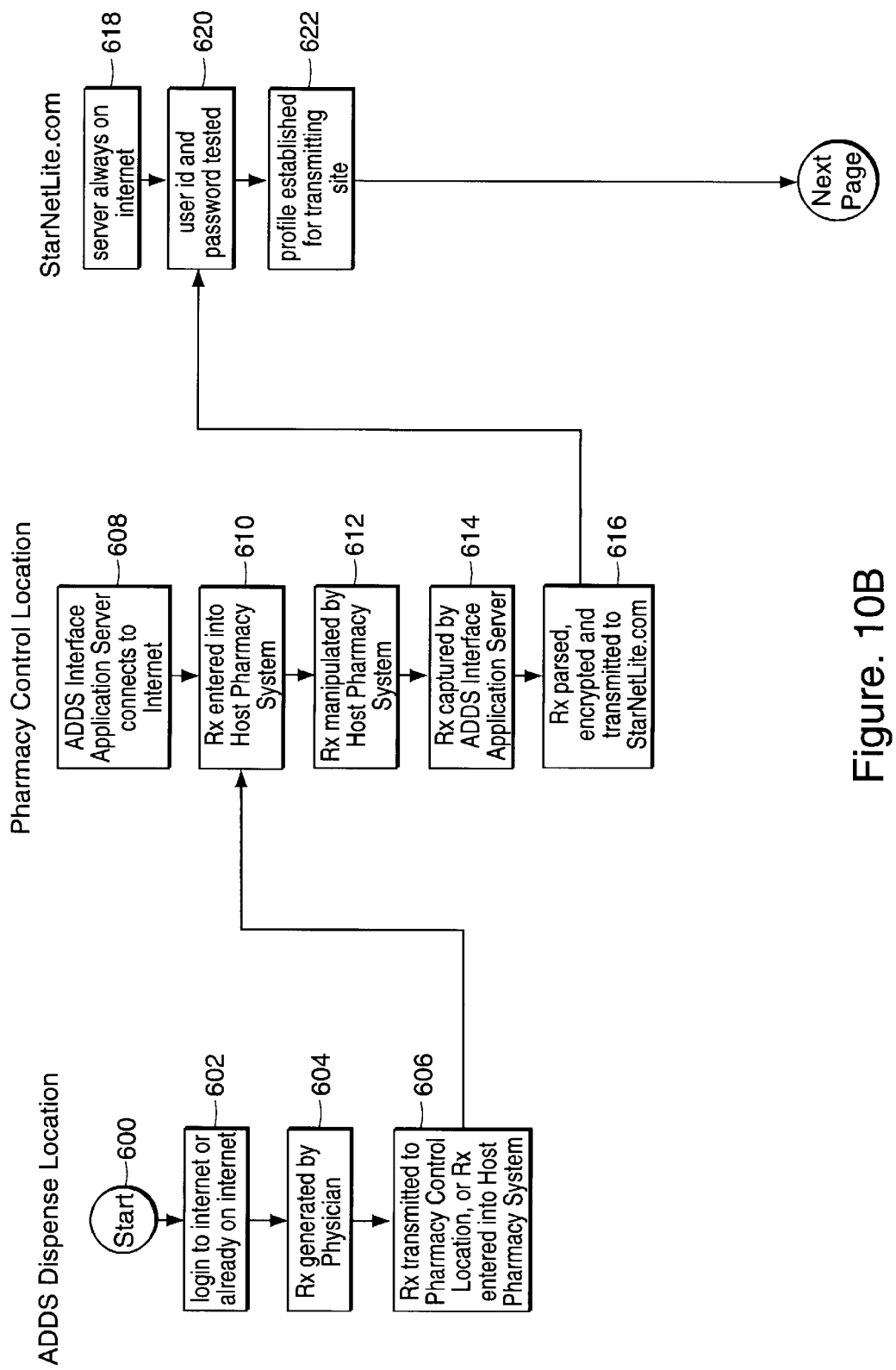
FIGS. 10B–10D are flow charts illustrating the process to dispense medications using the preferred embodiment of the present invention illustrated in FIG. 10A.
Figure 10C:
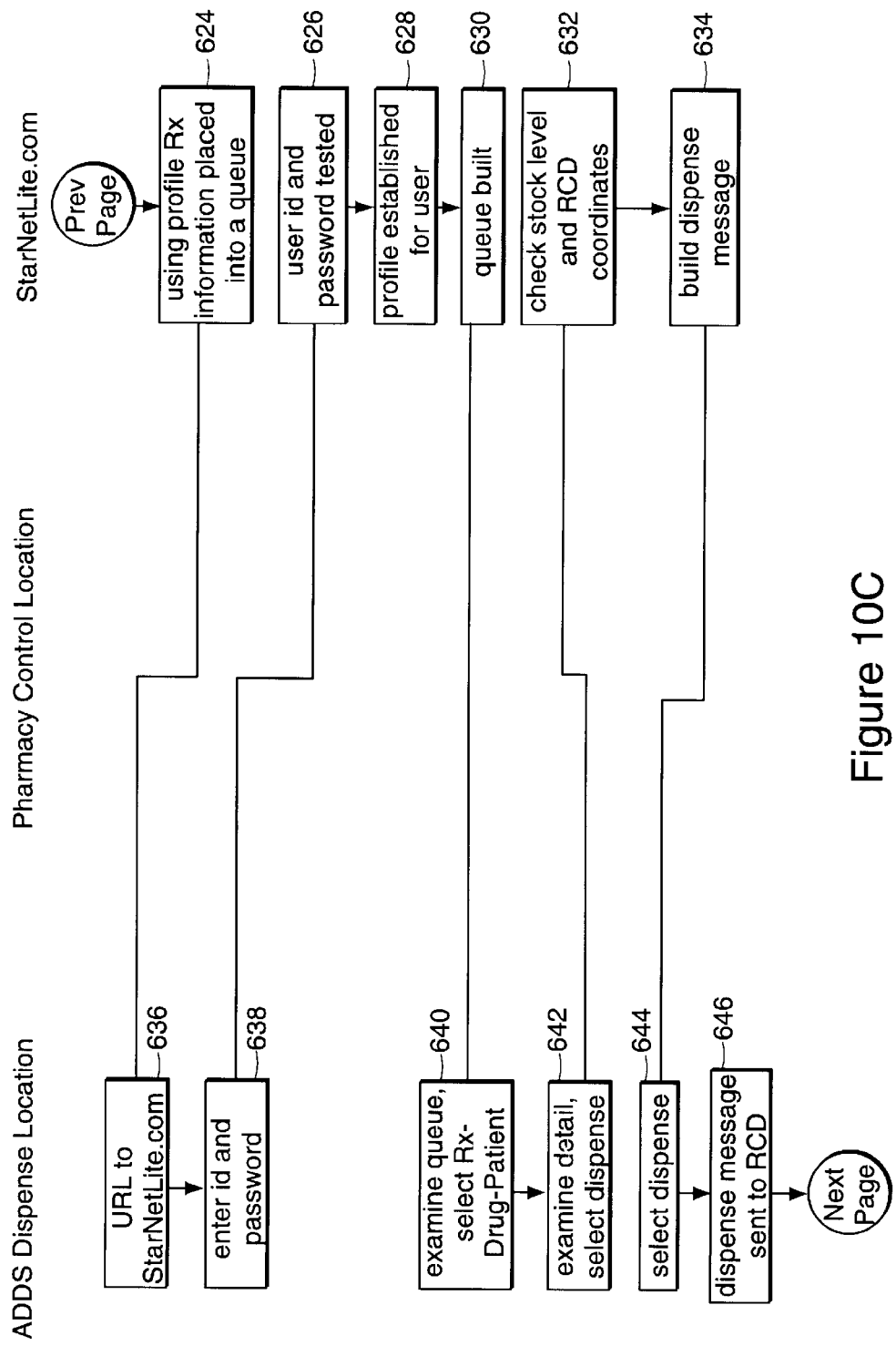
Figure 10D:
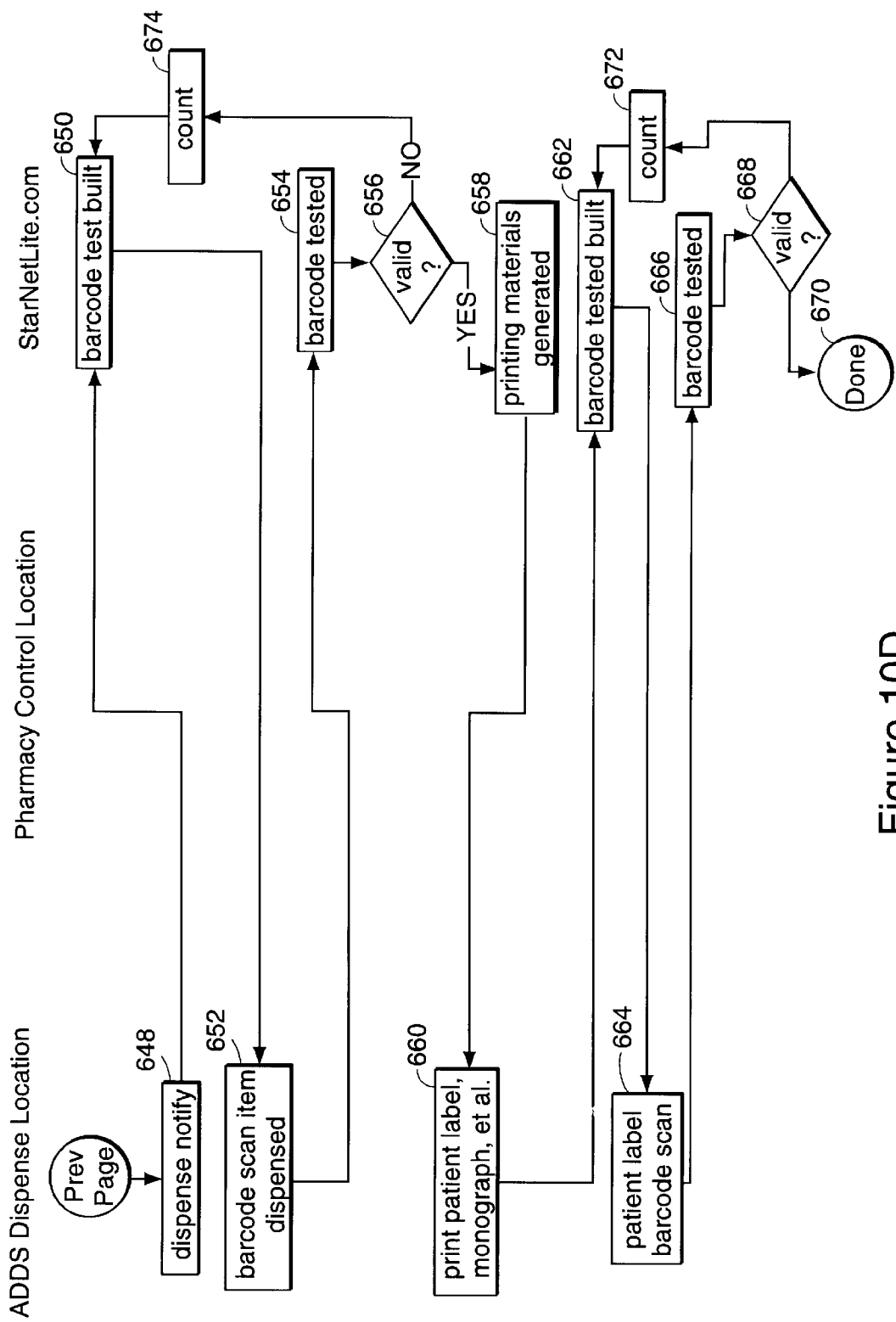

Referring to FIGS. 10B–10D, a typical workflow, illustrated as a flow chart, includes the following sequence of steps. Per step 604, an Rx is generated by a physician or caregiver using a paperless method such as a personal data assistant (PDA), such as, for example, a palm pilot, or TouchScreen or by usual methods using pen and paper, fax and scanners. The Rx information typically contains the patient name, prescriber name and Drug Enforcement Agency identifiers, instructions for the administration of the drug, drug name, and quantity to be given to the patient. Per step 606, the Rx can be transmitted to different locations. For example, if the Rx is transmitted to the web server 574 directly, then the image or Rx data is stored to an appropriate table on the web server for retrieval by a user authorized to dispense medications, typically a pharmacist. In the alternative, if the Rx is transmitted to a pharmacy control location via fax or other electronic means, the authorized dispenser, typically a pharmacist, interprets the transmitted information. If the Rx is transmitted to a dispense location electronically or is physically delivered, a user, typically a technician can take the authorized action upon the Rx.

Once the Rx is entered into the host pharmacy system per step 610, the Rx is manipulated into the host pharmacy software per step 612 using different methods. For example, an authorized dispenser reviews the web server 574 captured Rx information in a 10 browser, and then, transfers that Rx information manually or through an electronic interface into the host pharmacy software. Alternatively, an authorized dispenser interprets the Rx information transmitted directly to his/her location and then manually or through an electronic interface transfers the Rx information into the host pharmacy software. The technician has an option, to either transmit the information to the authorized dispenser, pharmacist, for the pharmacist to manipulate as described hereinbefore, or to remotely connect to the host pharmacy software via a variety of interfaces to transfer the Rx information into the host pharmacy software system either manually or via an electronic interface. The connection interfaces can be, but are not limited to, Symantec pcAnywhere directly, Symantec pcAnywhere via the Internet, and by a co-located wide area network (WAN) connection provided with the host pharmacy software.

Once the information is transcribed or transferred into the host pharmacy software system, a number of typical processes are applied to the Rx information. The processes can be, for example, a Drug Utilization Review (DUR) which entails scanning the drug to be dispensed against the patient profile contained within the host pharmacy software system to determine if any pharmaceutical contra-indications for dispensing exist. An example of a DUR can be a drug-to-drug Interaction test, or a patient drug allergy test. A second typical process is an Adjudication process whereby the host pharmacy Software system communicates with a pharmacy benefit management computer to determine the patients insurance coverage and payment amounts, if any.

The Rx information, having been processed by the host pharmacy software system can generally then be determined to be a valid Rx; which can be processed by the pharmacist. In a retail setting, the pharmacist then triggers patient drug labeling to be produced by the host pharmacy software system and takes a large bottle of medications from the shelf and counts and places into a smaller bottle, typically called a vial, the number of tablets, caplets, or milliliter's called for by the physician. The pharmacist then applies labeling and hands the drug to the patient. When the dispense is processed in conjunction with the web server, the pharmacist or authorized dispenser triggers a patient drug label to be produced by the host pharmacy software system, however, instead of the label being processed by a co-located printer (for example, a laser jet or dot matrix printer) the output is directed to the interface application server.

The interface application server accepts the Rx information as a printer stream per step 614, or through a direct electronic interface to the host pharmacy software system network constructs. An application, such as, for example, Parse Engine, parses the output received by the host pharmacy software system into discreet data elements per step 616. The parse engine, having completed parsing the data, then encrypts the data and uniquely identifies the data for transmission to the web server 574 via a network or dial-up Internet connection per step 616.

The information is received by the web server and placed into a work in process dispense queue/SQL database with flags identifying the dispense information as "belonging" to a particular dispense location per step 624. This is a method designed to permit many simultaneous dispense locations to use the same SQL database.

The dispense locations then have access to the data in the work in process table presented as an HTML document (web page). Only data designated as belonging to a dispense location is available to a dispense location.

The technician at the dispense location selects the Rx-Drug-Patient to be dispensed from a list of one or more possibilities to be displayed per steps 640, 642. The selections are shown as HTTP "hyperlinks".

Upon selecting the Rx-Drug-Patient to dispense, the technician at the dispense location is shown a dispense detail Page. The dispense detail page presents to the technician additional information about the Rx, not practically visible above. The technician has a choice of deleting the Rx-Drug-Patient selection, or the "GO BACK" to earlier step and select another, or to dispense the drug from the co-located Remote Control Dispenser (RCD)582. The Rx-Drug-Patient selection delete causes an early termination event which is communicated to the pharmacist via an email as an option, and is captured to the correct early termination database for review later or in real-time by the pharmacist or authorized dispenser. The "GO BACK:" step prompts the technician to return to the previous list of available dispenses in the work in process table represented by displaying them as a queue on a web page. The selection to dispense the drug from the co-located RCD continues the process by requesting final dispense authority from the web server.

Final dispense authority is received from the web server in the form of a single web page, HTML document, that expires quickly so that repeat requests for the same drug can not be made by reversing the browser using its imbedded back button. The web server 574 completes one more check to determine if the drug requested is still in the local RCD inventory and the location of the drug within the RCD per step 632. Each RCD contains an Identifier, for example, from 0 to 9 (10 total) and from 00–27, or 00–59 columns, depending upon the configuration. As part of the final dispense authorization the web server returns the exact position of the drug desired within a single or plurality of RCD's. The user clicks a button or link and a series of different options can occur. For example, a JAVA APPLET communicates with the RCD passing the RCD the data culled from the web server. In the alternative, a browser ADD-IN communicates with the RCD passing the RCD the data culled from the web server. In another embodiment, a local one-time use executable is downloaded that communicates with the RCD passing the RCD data culled from the web server. Alternatively, a local executable is launched which passes the needed variables and communicates with the RCD 582 passing the RCD data culled from the web server 574. In yet another embodiment, an alpha numeric page is sent to an integrated pager reception unit placed within the RCD, which passes the needed variables and communicates with the RCD passing the RCD data culled from the web server.

As a result of the dispense occurring, the technician is presented with an additional web page which requires the input of barcode data embedded onto the label of the dispensed drug. A barcode reader co-located at the dispense location is used to read the barcode of the item dispensed from the RCD per step 652. The technician reads the barcode into the browser and clicks a test hyperlink, or in some instances the barcode reader can interact with the browser directly and select the test hyperlink directly.

The barcode of the item dispensed is read into the browser and is compared with the value of the barcode expected. If the values match what the web server 574 is expecting, a patient education monograph, patient labeling, graphic representation of the drug expected, and picture of drug expected are generated and delivered to the technicians' browser for subsequent printing to a co-located printer per step 658. However, if the values do not match what the web server is expecting, the user has three attempts with which to scan or enter the expected values per step 674. If three failed attempts are made, the transaction is terminated with warnings sent to appropriate parties like the authorized dispenser, technician, system operator, and pharmacy consultant via pager and email. Appropriate drug disposal and storage is maintained via training of the technician and an additional lock storage box within the RCD.

The technician at the dispense location is presented with one additional barcode on the patient label that is to be affixed to the item dispenses. The technician is required to perform one more barcode read by scanning the patient label after it is affixed to the item dispensed per step 664. The barcode of the item dispensed is read into the browser and is compared with the a value of the barcode expected, the Rx number. If the values do not match what is expected, then the user has three attempts to scan the correct label before an error condition is reported per step 672. If the values do match per step 668, then the dispense is complete and the local technician is returned to the view of the queue show work in process, if any.

Figure 11A:
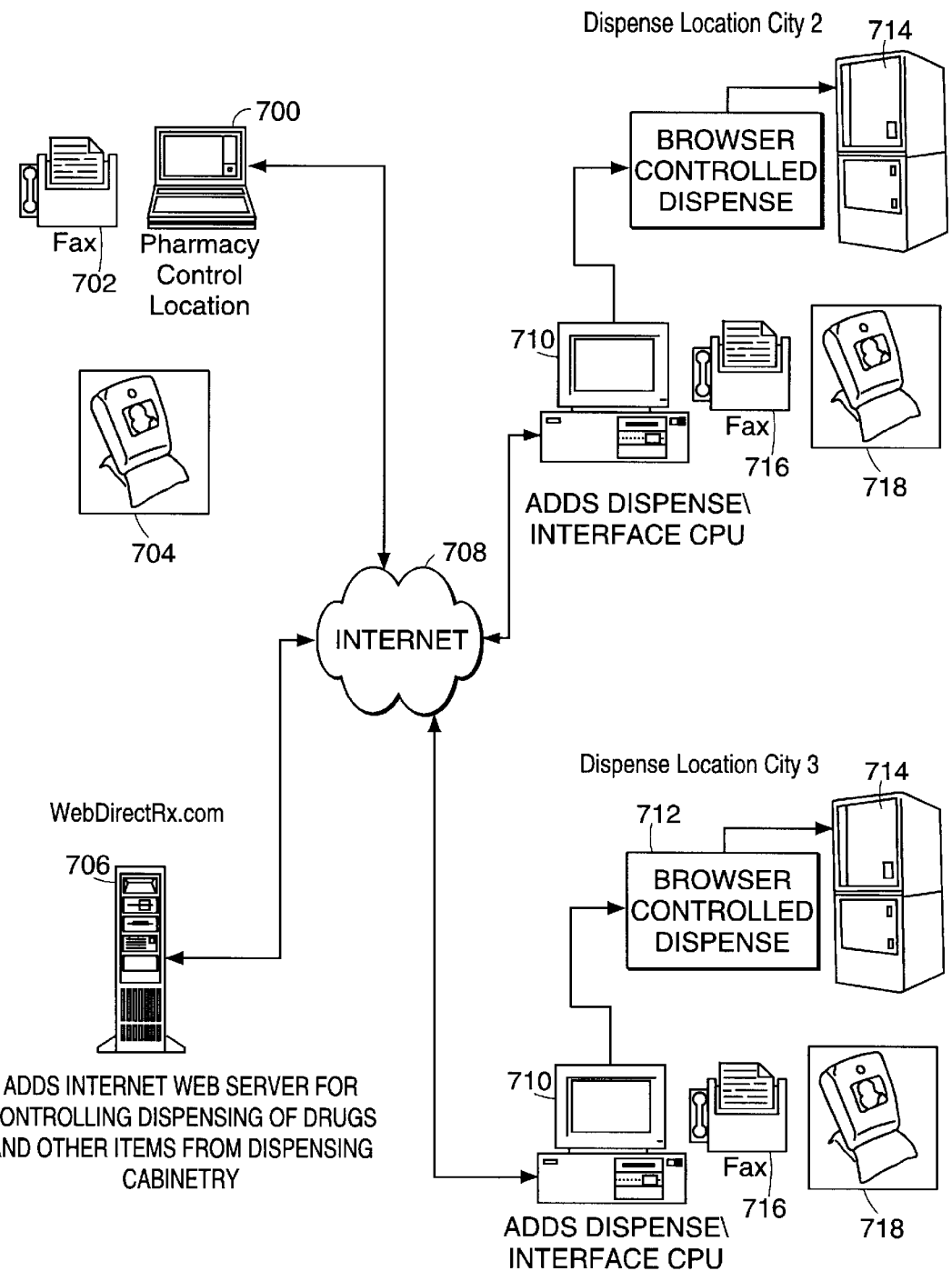
FIG. 11A is a schematic block diagram of a preferred embodiment of the remote control dispensing system using the internet network configuration.

Referring to FIG. 11A, in this embodiment of a dispense system the majority of the features and functions use a web server 706 on the Internet 708. Thus, no longer does a local EXE (executable program) reside on the computer at the dispense location (where the RCD 714 is co-located to dispense drugs). Instead the dispense location CPU 710 uses an Internet browser 712 to interact with the web server 706 to access patient information, drug selection, inventory control, and dispense permission.

Figure 11B:
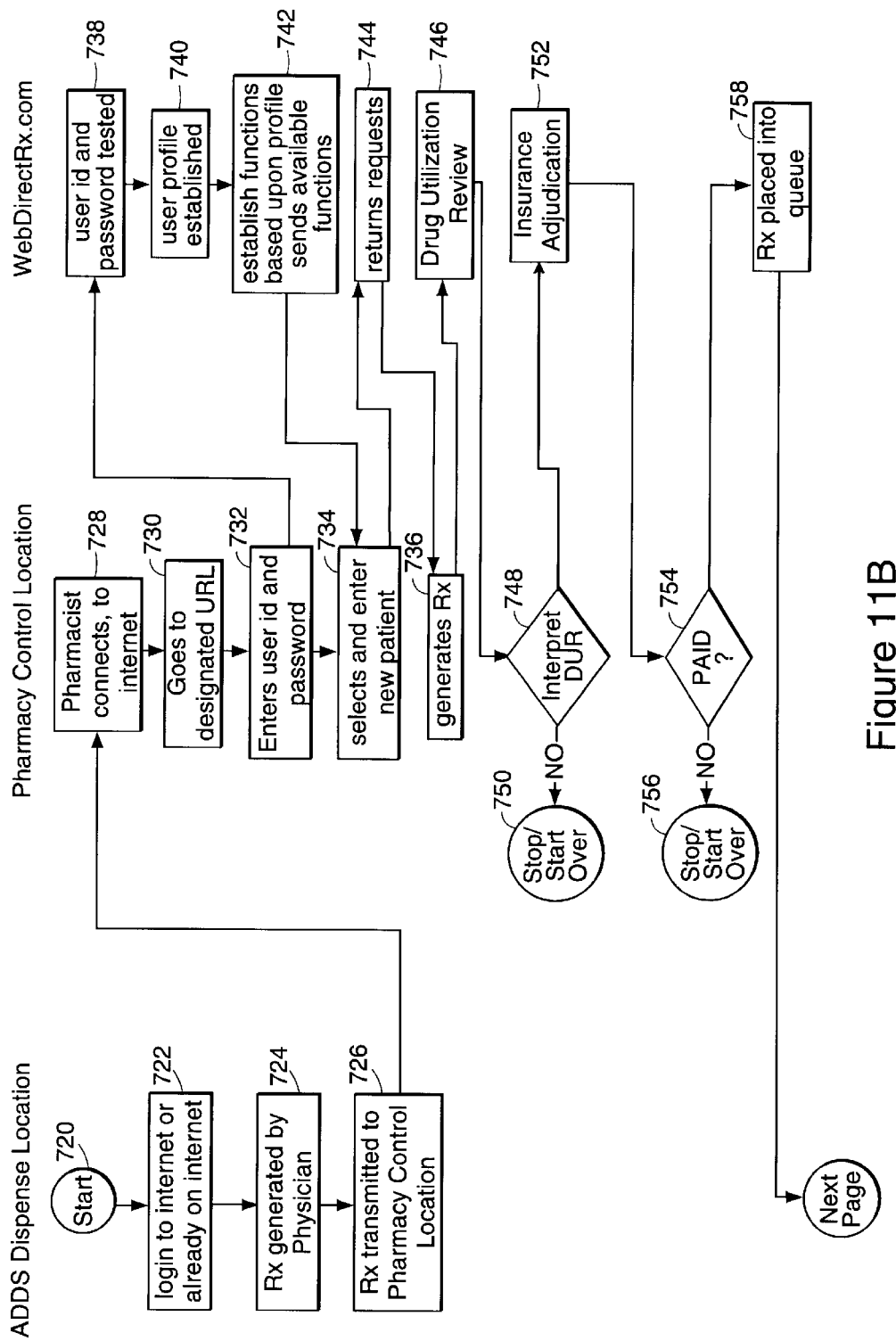
FIGS. 11B–11D are flowcharts illustrating the process to dispense medications using the preferred embodiment of the present invention illustrated in FIG. 11A.
Figure 11C:
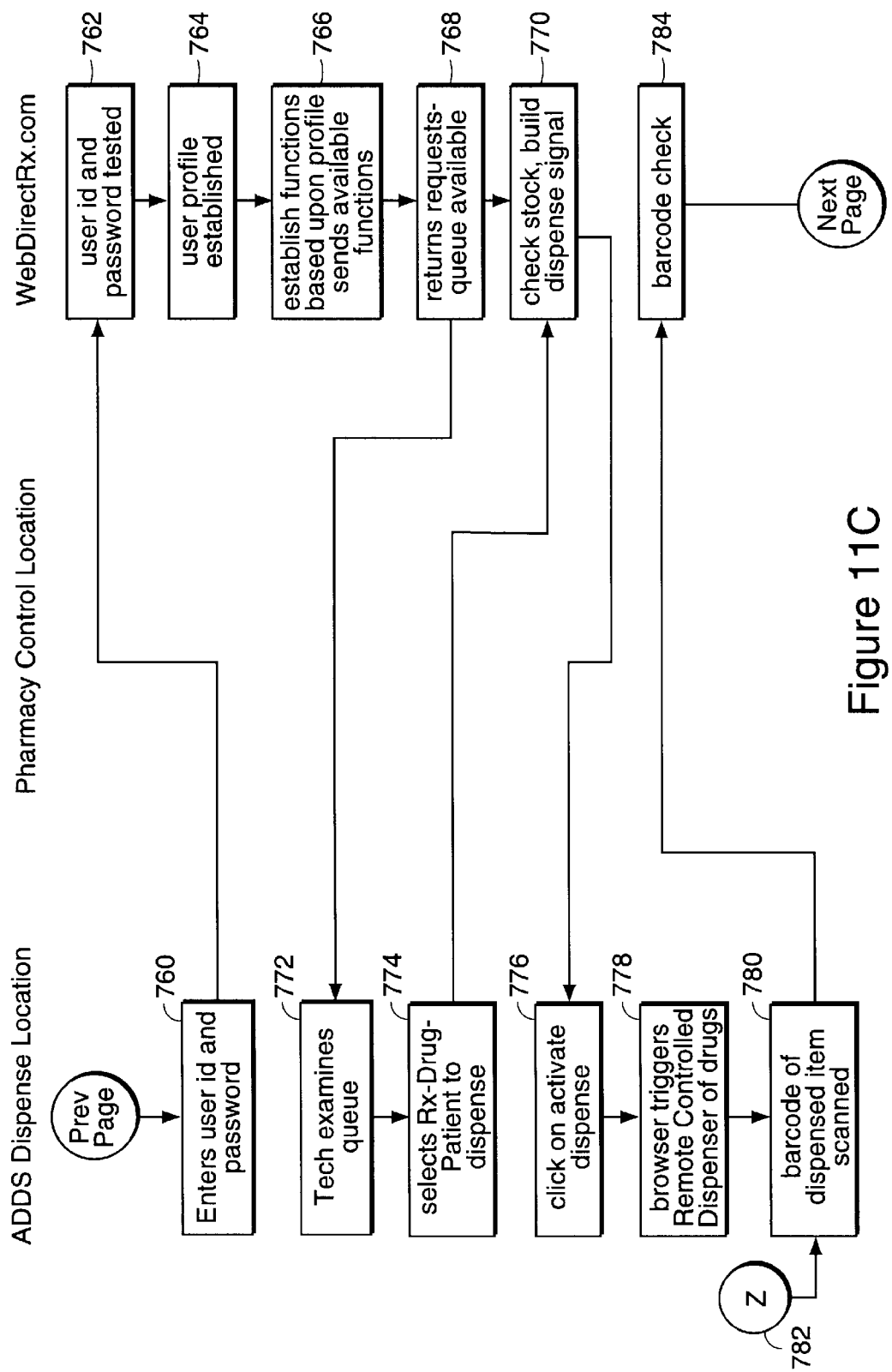
Figure 11D:
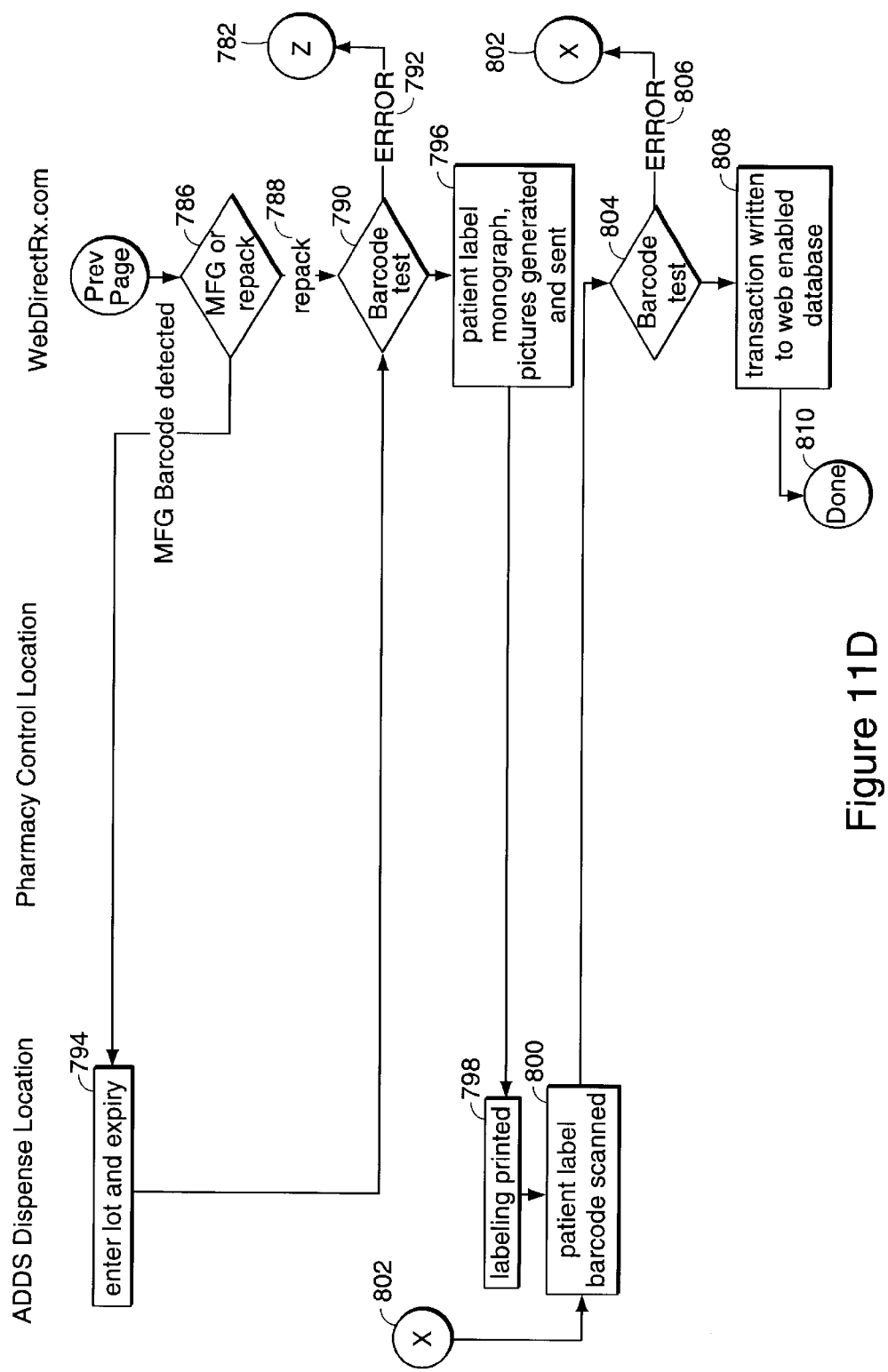

Referring to FIGS. 11B–11D, a flow chart of a typical workflow of the referred embodiment shown in FIG. 11A includes the following sequence of steps. An Rx is generated by a physician using a paperless method such as a personal data assistant (PDA), or by usual methods using pen and paper per step 724.

The Rx is transmitted to a pharmacy control location per step 726 whether by an electronic means for a PDA device, or fax for pen and paper method.

The pharmacy control location's pharmacists (Rph) or designated pharmacy technician, is logged onto the Internet, or logs onto the Internet using a local Internet Service Provider (ISP) per step 728. This device can be a PDA, a laptop, a cell phone with browser ability, or even a typical personal computer. Any device that is compatible with, but not limited to, HTML or XHTML or similar emerging protocol, can be used.

Using a device, for example, a laptop computer, the RPh or technician enters a URL (web address) such as, for example, WebDirectRx.com or gets this URL from her favorites List on the browser per step 730.

The RPh then enters her user id and password per step 732. This user name and password carries with it a profile. This, profile then permits different functionality on the web server 706 available to the person logging in. A RPh gets a functionality not available to others; like Rx generation, and the ability to see multiple dispensing queues across the network of dispensers.

If the patient is new, the RPh needs to enter patient demographics, insurance information, allergies, disease states, drug profile, et al., before beginning to generate an Rx per step 734.

The RPh then generates the Rx per step 736 by selecting the patient, drug, prescriber, SIG, tity, refills, ICD-9 (a disease code if known), etc.

The generated Rx is then run through a process called DUR (Drug Utilization Review) per step 746 to examine the drug for contra-indications against the patient profile. For example, allergies, and drug to drub; interactions are examined here. In this embodiment, the process is executed on the server 706. The RPH or technician then approves the results of the DUR per step 748 or cancels the Rx or picks a more appropriate therapy.

The RPH or technician then runs an Adjudication on the patient to determine if the patient is insured through a pharmacy benefit management company per step 752. This process returns a status of, for example, PAID per step 754, REJECTED, etc. A copay amount, among other items, is returned with a PAID claim.

The Rx is then placed into a queue per step 758 which the dispense location can see using its own browser. The dispense location caregiver, for example, a nurse, doctor, technician, also needs to be logged onto the Internet. This user/caregiver logs onto the web server at, for example, WebDirectRx.com with a user id and password per step 760. This user id and password carries with it a user profile per step 764. The user profile indicates that this person is a dispenser, and can only view the queue for his/her location per step 766. The user/caregiver sees his/her Rx—the one communicated to the RPh earlier and can now act upon that Rx as it has been approved per step 768.

The user/caregiver then clicks on the item to be dispensed. This triggers the web server to double check inventory per step 770 and acquire the location of the drug in the co-located RCD. When completed, the web server returns a page that the user can click on again to cause the computer to send a dispense signal to an RCD per step 776. The signals, as described hereinbefore, can be sent using different options, such as, but not limited to, Java Applet, browser add-ins, and launching local executables.

The RCD then dispenses the item. Whilst doing that, the web server 706 presents to the user a screen whereby the user can barcode scan the dispensed items' barcode per step 780. Upon entry of the barcode a test per step 790 is made to see if the item is a repackaged item or a manufacturers packaged item per step 786. If it is a manufacturers packaged item, then the web browser presents the user with places to enter a lot number and expiration date per step 794. The repackaged item has built into the barcode a lot number and expiry date. If the barcode of the item entered is what the web server, for example, WebDirectRx.com is expecting, then the web server presents the user/caregiver with a completed patient label, patient education monograph, receipts, and image of pill, tablet, capsule etc., that is then to be directed to a co-located laser jet printer per step 796. Once printed per step 798, the patient label, which contains a second barcode, is also scanned into a page presented to the user per step 800. The transaction details are written to a database on the web server, and the user/caregiver is returned to the queue view from where this process started initially.

If the patient, who has been remotely administered medications has any questions, an authorized pharmacist is available for consultation using a variety of telepharmacy systems. Including, but not limited to, a telephone service audio visual connection, a networked audio visual connection, and an Internet connected audio visual connection.

Figure 12A:
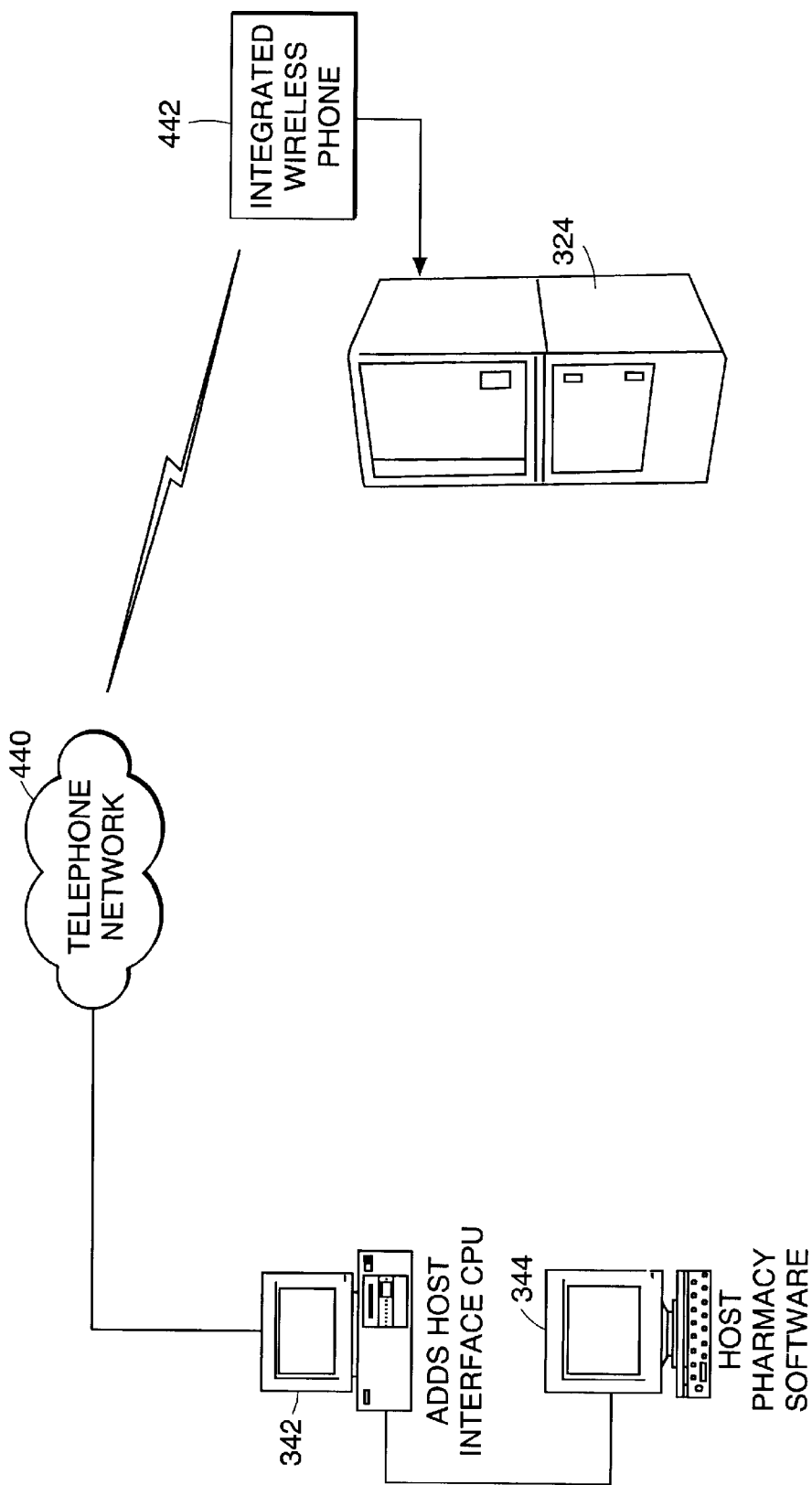
FIGS. 12A and 12B are schematic block diagrams illustrating the use of a telephone network in a drug dispensing; system in accordance with the present invention.
Figure 12B:
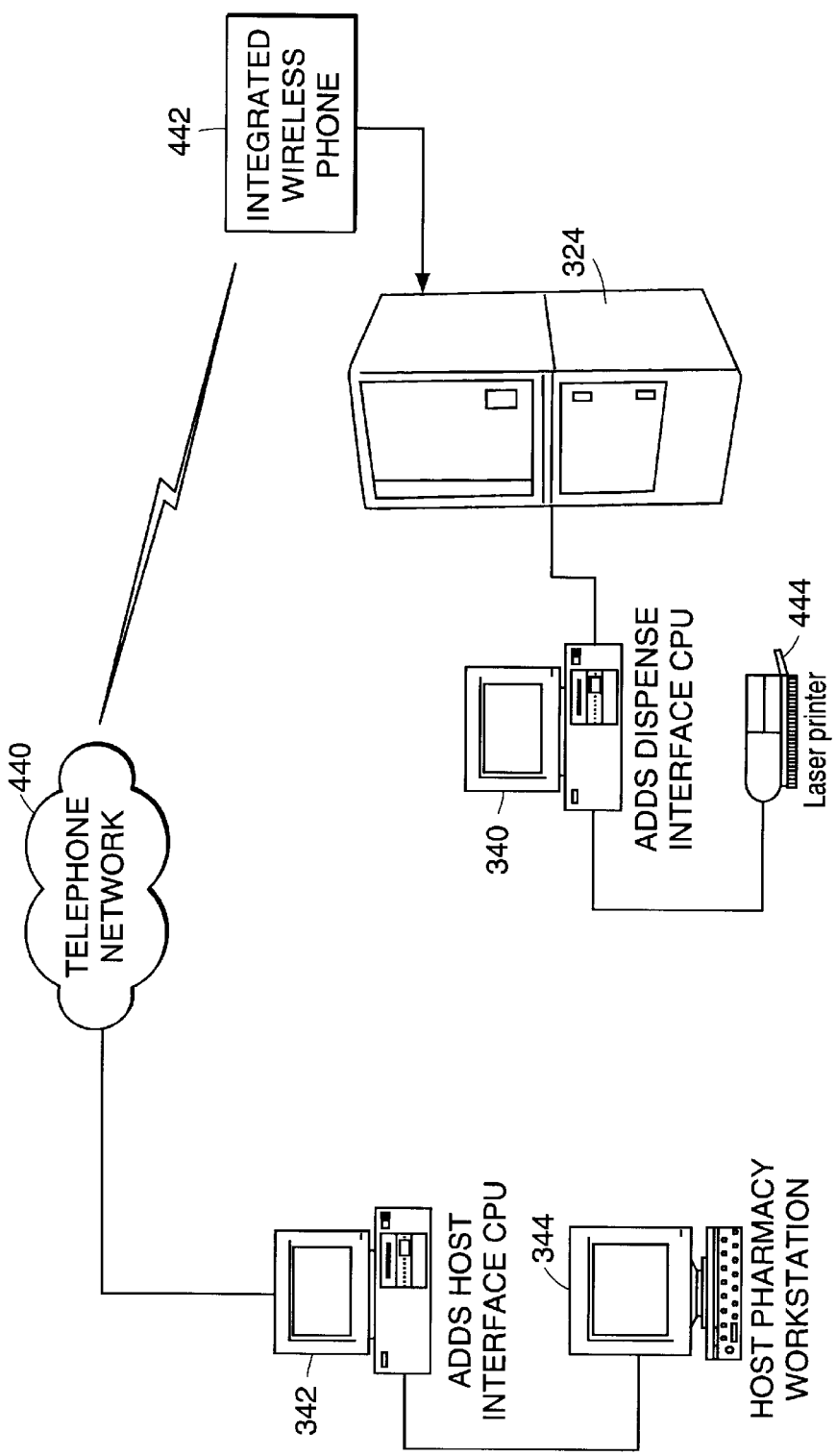

FIGS. 12A and 12B illustrate the use of a telephone network 440 in the drug dispensing system in accordance with the present invention. The telephone network 440 transfers information between the host interface CPU 342 and the RCD 324. A wireless phone 442 can be integrated with the RCD. The telephone network 440 takes the place of or is used in conjunction with the Internet as a mechanism to transfer information between the host pharmacy system represented by the host interface CPU 342 and the host pharmacy workstation 344 and the remote dispensing system represented by the RCD. The wireless phone device acts as the trigger mechanism to dispense pharmaceuticals or medical products out of the RCD. The wireless phone device can communicate with an integrated circuit within the RCD transferring the RCD information obtained during a wireless connection.

It should be noted that previous preferred embodiments are disclosed with respect to using a communications cable or link between a controlling CPU and the RCD to transfer a dispense message. The communications cable can be replaced with a wireless phone device thus, facilitating dispensing via a wireless connection.

FIG. 12B illustrates a dispense interface CPU 340 and a laser printer 444 co-located with the RCD 324. The remotely controlled dispense session can be managed entirely without land lines. The wireless phone connection can be integrated into the RCD or in the alternative, as an attachment to, the dispense CPU. The wireless phone connection serves as the connectivity media instead of the internet connection.

Further, as described hereinbefore, the software the technician interacts with can exist on an attached and co-located external computer configuration, or as an integrated computer using TouchScreen components built directly into the RCD.

Figure 13A:
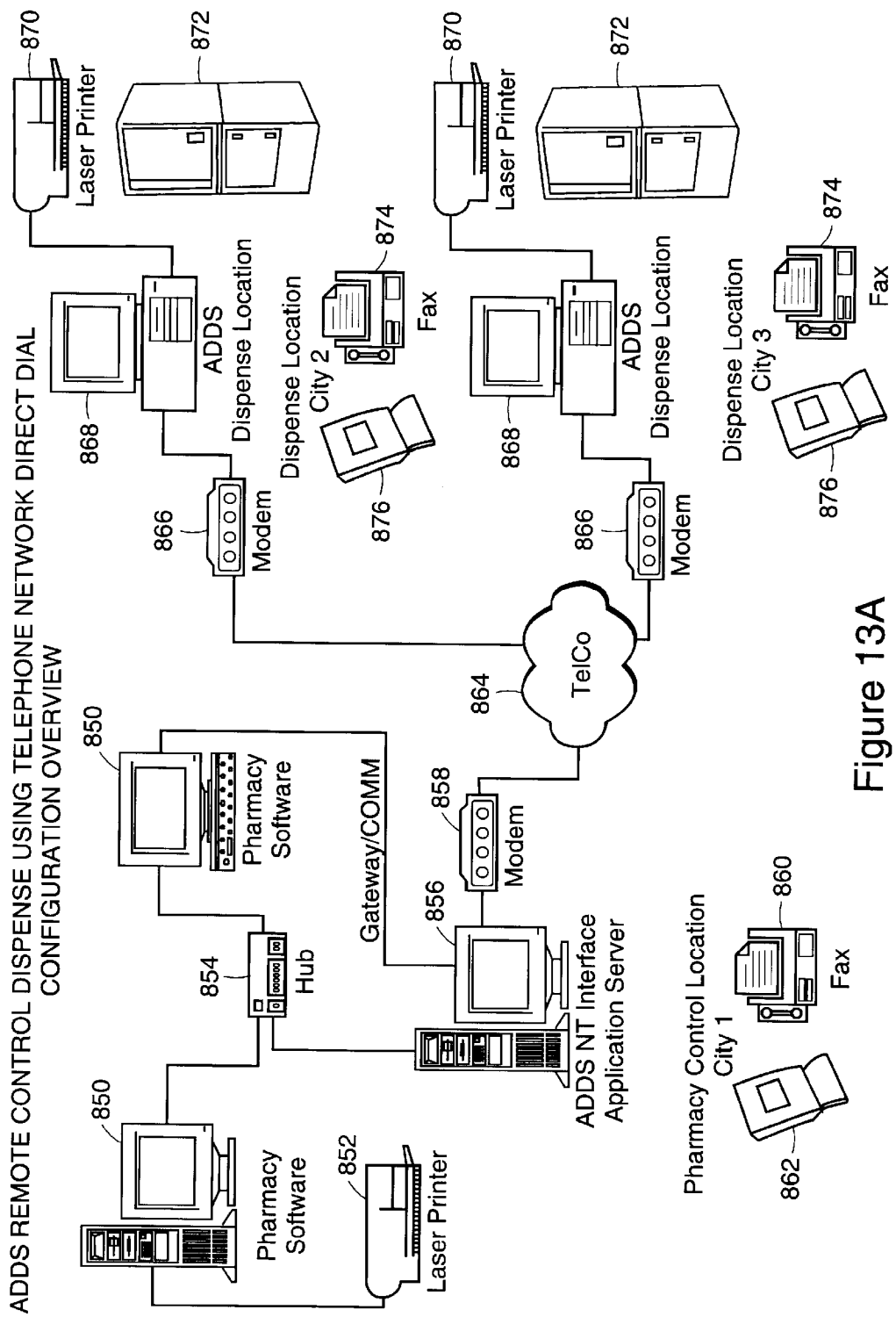
FIG. 13A is a schematic block diagram of a preferred embodiment of the remote control dispensing system using a telephone network direct dial configuration.

Referring to FIG. 13A, in this embodiment of a dispensing system an existing host pharmacy software system 850 with a co-located interface application server 856, and a remotely installed dispense location interact to provide pharmaceutical dispensing across a wide geographic region. This preferred embodiment uses the existing local telephone service available. The interface application server 856 and the dispense location workstation 868 connect and exchange Rx information directly with one another.

The dispense location workstation 868 contains local executable program(s) that manage the call pickup, data acceptance, inventory management, and visually prepares the Rx information received from the interface application server in an easy to read queue for the local caregiver, typically a technician. In addition, the dispense location workstation 868 communicates with the co-located Remote Control Dispenser (RCD) 872 to dispense pharmaceuticals, a printer 870, for example, a laser jet or color jet printer to provide patient and record keeping materials, as well as, a barcode scanner for doing quality checks during a dispense. The dispense location needs access to the telephone service 864 to get a "dial tone" in order to receive and send communications.

The pharmacy control location is where the host pharmacy software is maintained or run. Typically these are small networks of pharmacy workstations where a retail or hospital pharmacy team interacts with insurers computers to create the order that leads to the filling of a drug to be handed to the patient.

The interface application server 856 is a computer that is co-located with the host pharmacy software system. It is used to collect information (the Rx data) for a dispense from the host pharmacy system and then forwards that information to the dispense location workstation 868 via the telephone service, or the telephone network 864.

Figure 13B:
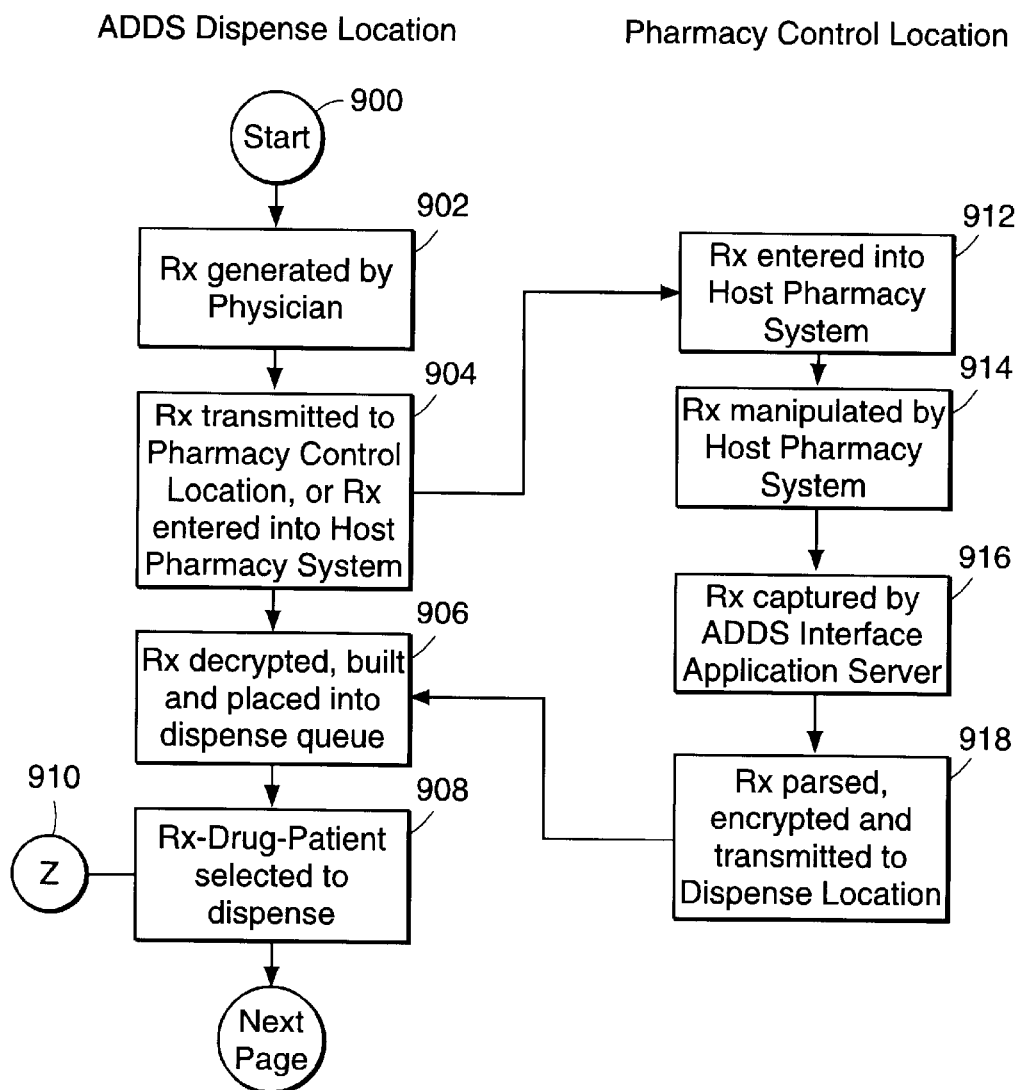
FIGS. 13B and 13C are flow charts illustrating the process to dispense medications using the preferred embodiments of the present invention illustrated in FIG. 13A.
Figure 13C:
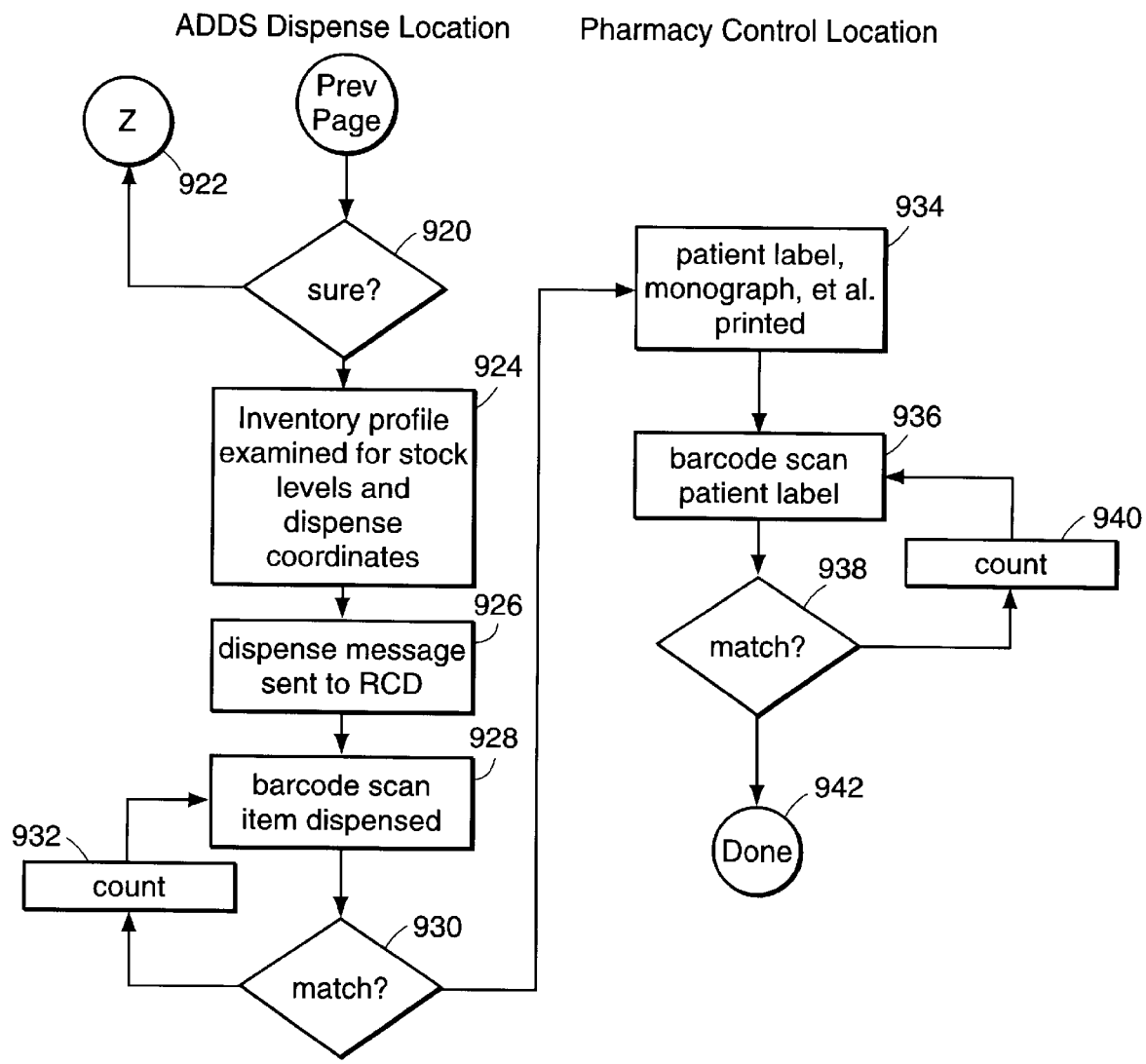

Referring to FIGS. 13B and 13C, a typical workflow includes the sequence of steps illustrated. An Rx is generated by a physician or caregiver using a paperless method such as a PDA or TouchScreen or by usual methods using pen and paper, fax and scanners per step 902. The Rx information typically contains the patient name, prescriber name and Drug Enforcement Agency identifiers, instructions for the administration of the drug, drug name, and quantity to be given to the patient.

The Rx is transmitted to different locations per step 904. If the Rx is transmitted to a phannacy control location via fax or an electronic means, the authorized dispenser, typically a pharmacist, interprets the transmitted information. If the Rx is transmitted to a dispense location electronically or physically delivered, a user, typically a technician can take authorized action.

The Rx is manipulated into the host pharmacy software system per step 914 either by an authorized dispenser who interprets the Rx information transmitted directly to his/her location and then manually or through am electronic interface transfers the Rx information into the host pharmacy software or by the technician who has an option to transmit the information to the authorized dispenser, pharmacist, for the pharmacist to manipulate or to remotely connect to the host pharmacy software via a variety of interfaces to transfer the Rx information into the host pharmacy software system either manually or via an electronic interface. The connection interfaces can be, but are not limited to, Symantec pcAnywhere directly, Symantec pcAnywhere via the Internet, by a co-located WAN connection provided with the host pharmacy software.

Once the information is transcribed or transferred into the host pharmacy software system a number of typical processes are applied to the Rx information. The processes can be a Drug Utilization Review or an Adjudication process as described hereinbefore.

The Rx information, having been processed by the host pharmacy software system can generally then be determined to be a valid Rx; which can be processed by the pharmacist.

In a retail setting the pharmacist then triggers patient drug labeling to be produced by the host pharmacy software system and takes a large bottle of medications from the shelf and counts and places into a smaller bottle, typically called a vial, the number of tablets, caplets, or milliliter's called for by the physician. The pharmacist then applies labeling and hands the drug to the patient.

When the dispense is processed in conjunction with telepharmacy systems, the pharmacist or authorized dispenser triggers a patient drug label to be produced by the host pharmacy software system 850, however, instead of the label being processed by a co-located printer 852 (laser jet or dot matrix) the output is directed to the interface application Server 856.

The interface application server accepts the Rx information as a printer stream per step 916, or through a direct electronic:interface to the host pharmacy software system network constructs. An application, Parse Engine (PE), parses the output received by the host pharmacy software system into discreet data elements. Once the parsing is completed, the data is encrypted and is uniquely identified for transmission to the dispense location workstation via telephone service per step 918.

The information is received by the dispense location workstation decrypted and placed into a work in process queue that is accessed by local executable programs run by the technician per step 906.

The technician at the dispense location selects the Rx-Drug-Patient to be dispensed from a list of one or more possible to be displayed per step 908. The selections are shown as mouse selectable lines. Each line represents a different RX-Drug-Patient to be processed by the technician. Upon selecting the Rx-Drug-Patient to dispense the technician at the dispense location is queried if this is in fact the RX-Drug-Patient per step 920.

If the answer to the query is no, the technician is returned to the entire queue list as described above per step 922. If the answer to the query is in the affirmative, the local executable program resident on the dispense location workstation examines a local inventory file that contains data specific to the drug requested to be dispensed per step 924. The drug contains a profile which includes, but is not limited to, current stock level, suggested restock levels, and coordinate position within a single or plurality of RCD's.

The Remote Controlled Dispenser (RCD) receives a X,Y coordinate type communication from the locally resident executable. The X,Y coordinate represents a location within a single or plurality of BCD's where the requested pharmaceutical is stored for dispensing. The X,Y coordinate is determined by examining an inventory profile of the drug to be dispensed. Upon receiving the dispense signal from the dispense location workstation the RCD presents a drug to the technician per step 926.

As a result of the dispense occurring, the technician is presented with an additional screen which requires the input of barcode data embedded onto the label of the dispensed drug. A barcode reader co-located at the dispense Location is used to read the barcode of the item dispensed from the RCD per step 928. The technician reads the barcode into the screen to be examined by the resident dispensing software.

The barcode of the item dispensed is read into the resident dispensing software and is compared with the value of the barcode expected from the drug inventory profile. If the values match what resident dispensing software is expecting per step 930, a patient education monograph, patient labeling, graphic representation of the drug expected, and picture of drug expected are generated and delivered to the co-located printer per step 934. If the values do not match what the resident dispensing software is expecting, the user has three attempts with which to scan or enter the expected values per step 932. If three failed attempts are made, the transaction is terminated with warnings sent to appropriate parties like the authorized dispenser, technician, system operator, and pharmacy consultant via pager and email. Appropriate drug disposal and storage is maintained via training of the technician and an additional lock storage box within the RCD.

The technician at the dispense location is presented with one additional barcode on the patient label that is to be affixed to the item dispensed. The technician is required to perform one more barcode read by scanning the patient label after it is affixed to the item dispensed per step 936. The barcode of the item dispensed is read into the resident dispensing software and is compared with the a value of the barcode expected, the Rx number. If the values do not match what is expected, then the user has three attempts to scan the correct label before an error condition is reported per step 940. If the values do match then the dispense is complete per step 942 and the local technician is returned to the view of the queue showing work in process, if any.

If the patient, who has been remotely administered medications has any questions an authorized Pharmacist is available for consultation using a variety of telepharmacy systems, including, but not limited, to a telephone service audio visual connection, a networked audio visual connection, and an internet connected audio visual connection.

Figure 14A:
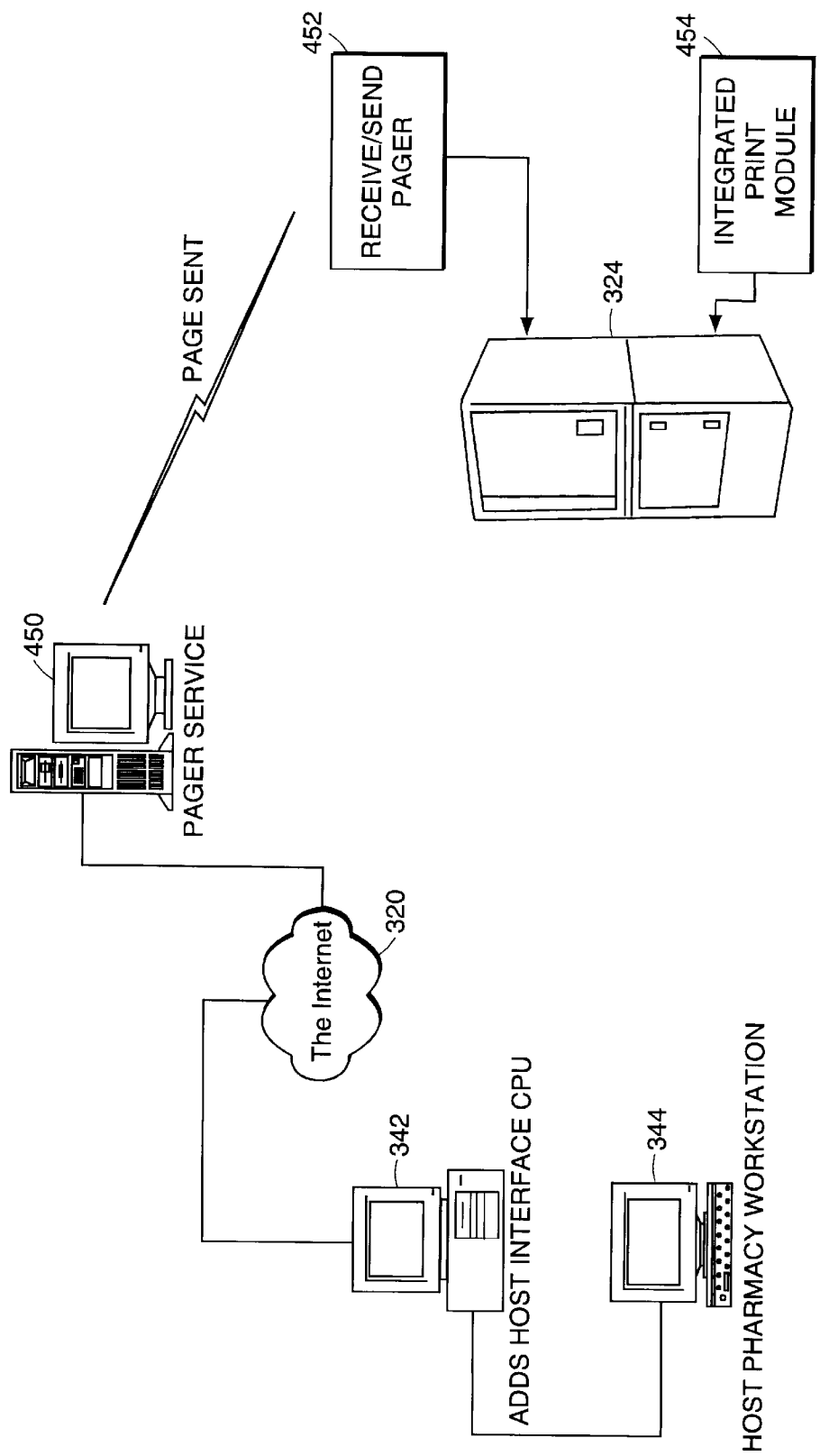
FIGS. 14A and 14B are schematic block diagrams illustrating the use of a pager service in a drug dispensing system in accordance with the present invention.
Figure 14B:
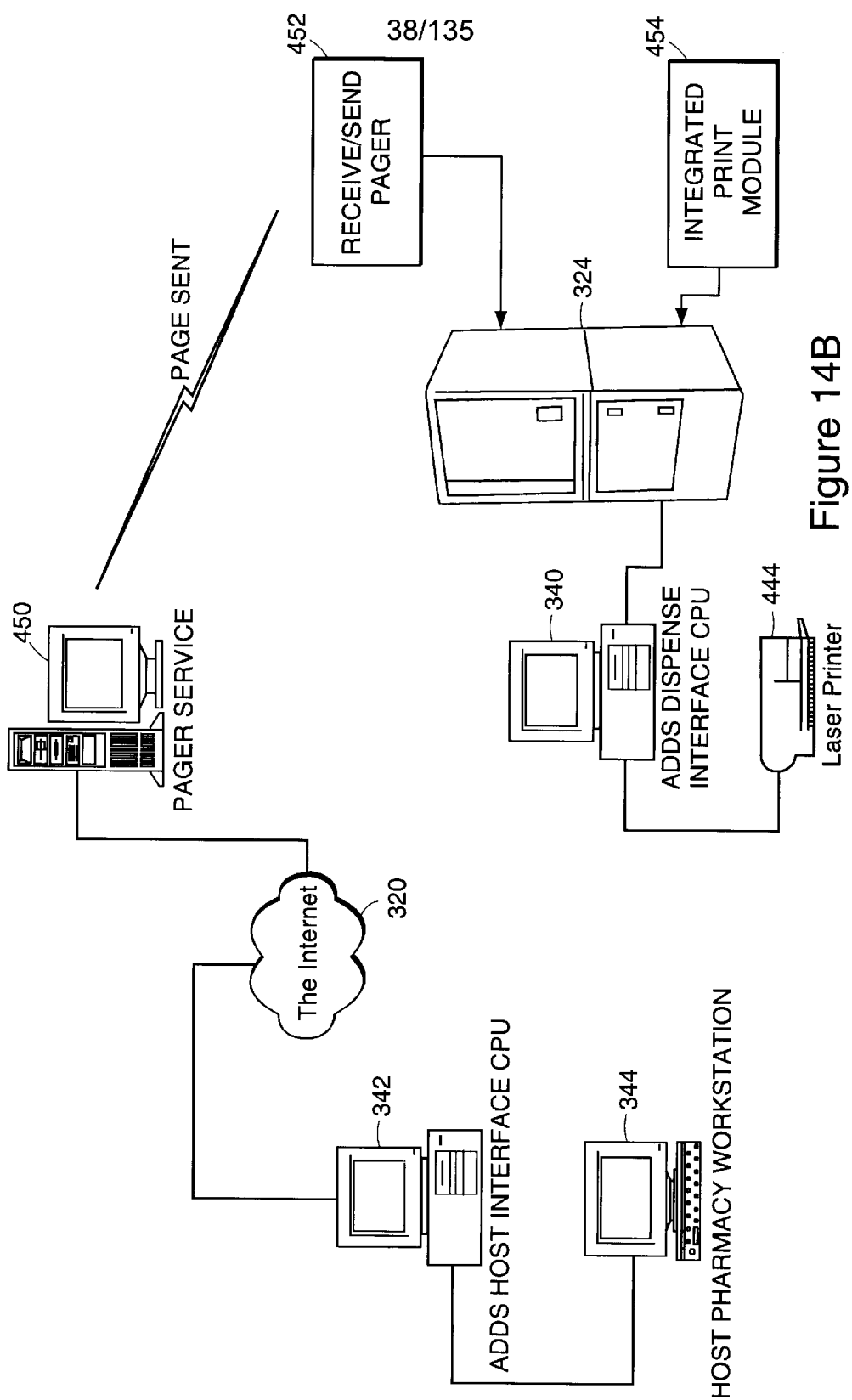

FIGS. 14A and 14B illustrate the use of a pager service 450 in combination with the Internet 320 to dispense medication from a remote location. The pager service 450 interacts with the Internet 320 to transfer information between the host pharmacy system represented by the host interface CPU 342 and the host pharmacy workstation 344 and the remote dispensing system 324. A receive/send pager 452 interfaces with the RCD 324 and transfers information regarding the dispensing of medication. A print module 454 can be integrated with the RCD. FIG. 14B illustrates an embodiment having a dispense interface CPU 340 and a laser printer 444 co-located with the RCD 324.

In a preferred embodiment, a pager service can forward dispense information via an alphanumeric page. A computer, such as, for example, but not limited to, an Aqcess Technologies Qbe Personal Computing Tablet, can be integrated with the RCD. In another preferred embodiment, the computing function can be accomplished using a combination of an external and integrated computer.

Figure 15A:
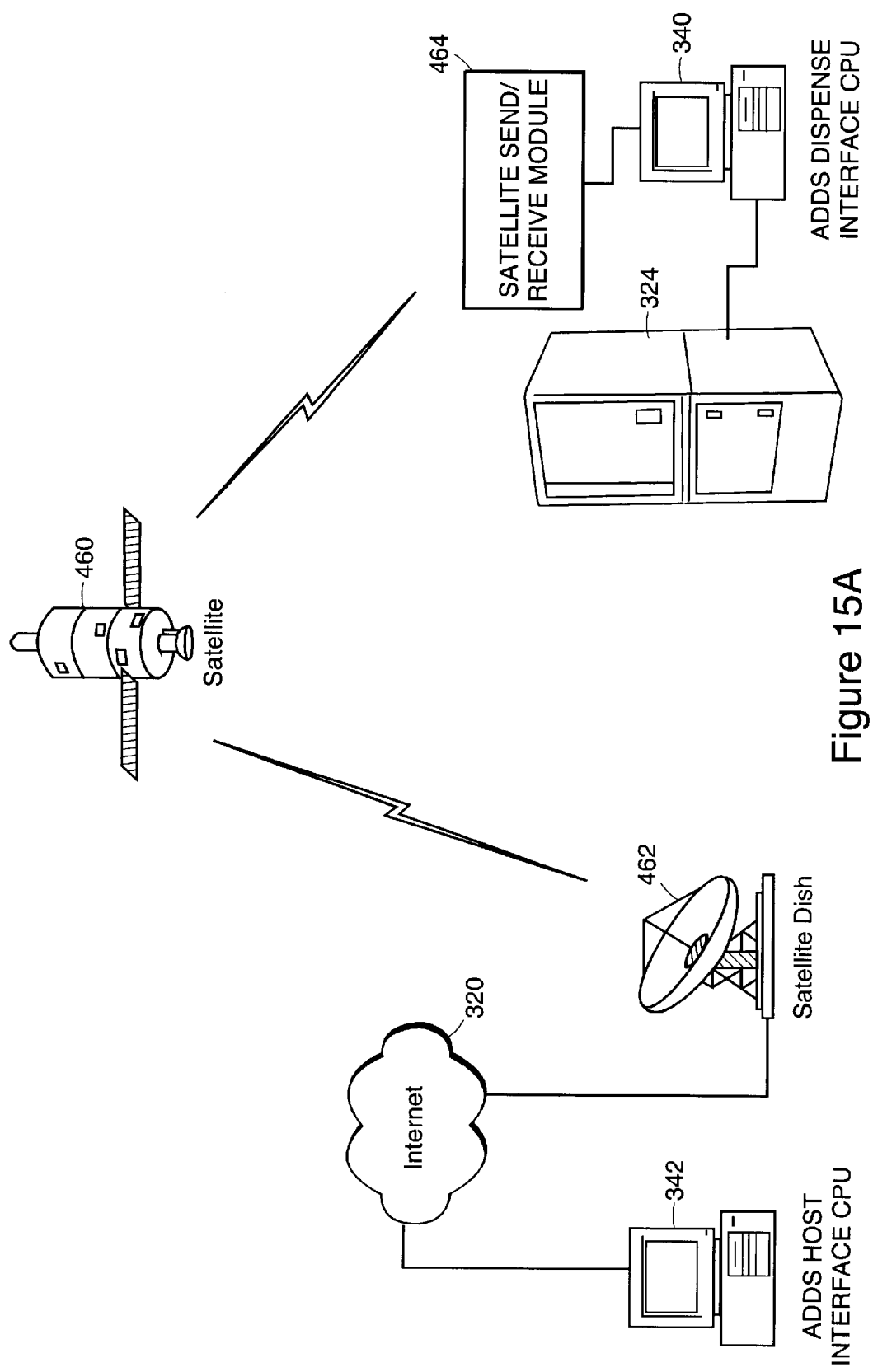
FIGS. 15A and 15B are schematic block diagrams illustrating the use of a satellite system to transfer information in a remote control drug dispensing system in accordance with the present invention.
Figure 15B:
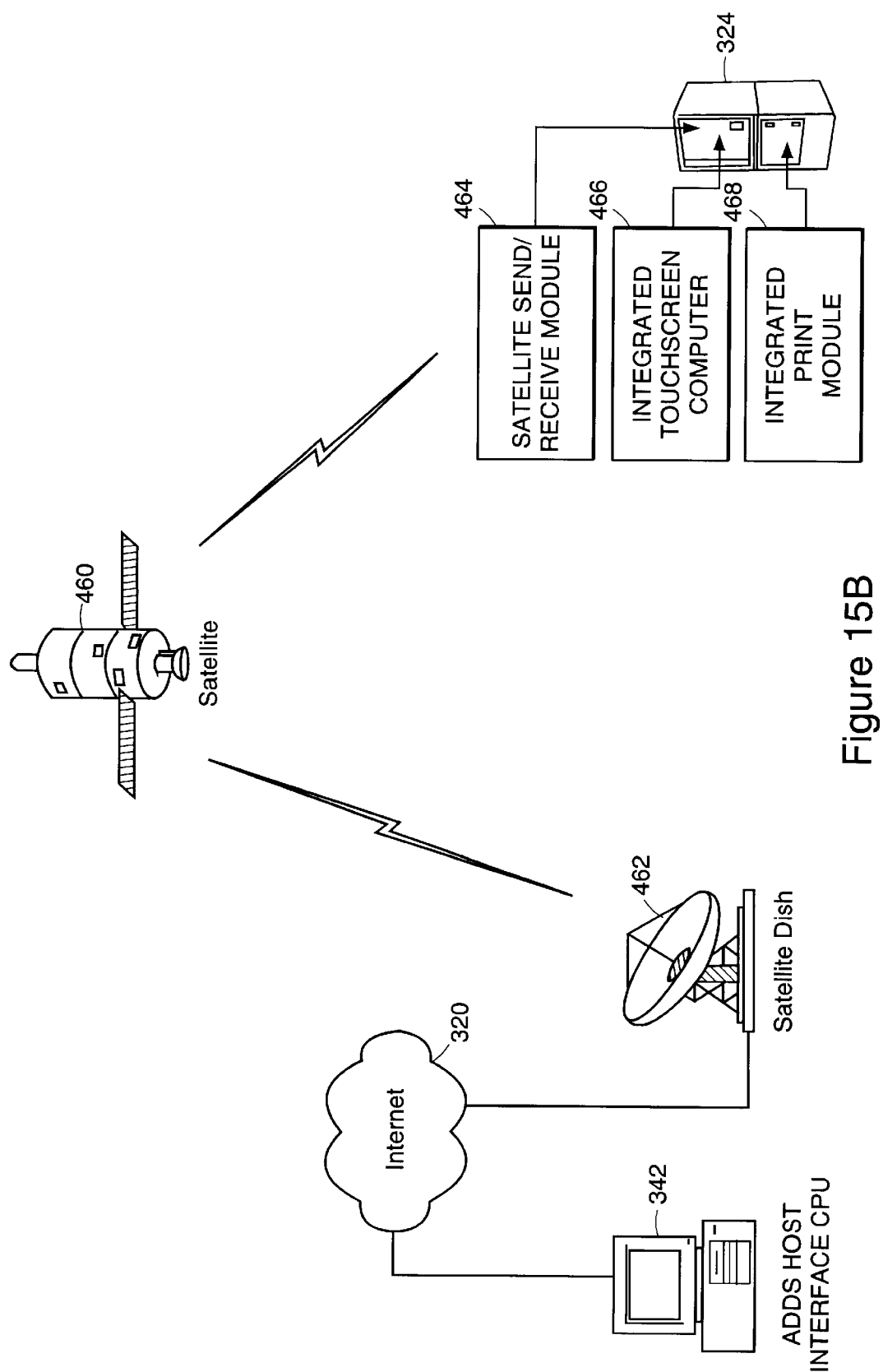

FIGS. 15A and 15B illustrate a preferred embodiment which uses a satellite system 460 to transfer information between a host pharmacy interface CPU 342 and a remote dispensing system or RCD 324. The Internet 320 transfers information from host interface CPU 342 to a satellite 460 via a satellite dish 462. The satellite in turn using a satellite send or receive module 464 transfers information to the dispense interface CPU 340 at a remote location from the host pharmacy system. The dispense interface CPU then directs the dispensing of medication from the RCID 324. As illustrated in FIG. 15B a touch screen computer 466 and a print module 468 can be integrated with the RCD which eliminates the need for a dispense interface CPU 340.

In a preferred embodiment, the remote dispensing location is sent Rx dispense information via a satellite network, such as, for example, the Iridium paging or telephone network. The dispensing workflow remains the same, only the connectivity to the RCD 324 changes.

According to another embodiment, a method of managing samples is a necessity in the highly regulated and cost control environment that exists in healthcare today. The current haphazard approach to sampling is both costly and inefficient for all parties concerned and provides little useful information to any party.

The Joint Commission on Accreditation of Healthcare Organizations (JCAHO) is citing healthcare institutions for failure to document and manage pharmaceutical samples. Drug cost control is a critical factor and formulary management, via the sampling process, is an important component in that overall process, especially in outpatient and independent practitioner settings.

The Joint Commission is citing hospitals and integrated delivery networks (IDNs) for failure to properly manage physician samples. The impact of a negative Joint Commission finding can be severe. Nonadherence with state and federal laws puts prescriber's licenses at risk, and violation of JCAHO-specified criteria in the drug sampling area can lead to a Type 1 citation and endanger the healthcare organization's accreditation status. Many insurance companies and government programs, such as Medicare/Medicaid require JCAHO accreditation before they will reimburse that institution for medical care of its patients.

JCAHO requires the institutions to have a policy on drug samples and requires a control system that tracks the receipt and distribution of each drug sample. Further, the samples have to be properly labeled for patient use (including any auxiliary cautionary statements and expiration dates). The pharmacy department has to include drug samples in its process for responding to drug recalls and in its monthly inspection routine. This is the reason for tracking lot numbers and expiration dates. Drugs need to be stored so that unauthorized individuals do not have access to them, such as, for example, by using a locked cabinetry or room. JCAHO also requires the institution to keep a drug sample receiving log that tracks date, drug name, strength, form, lot number, manufacturer, received amount, expiration date of drug, and location of storage. In addition, JCAHO also requires either a drug dispensing log or a drug sample dispensing database that includes the following information: date dispensed, patient name, drug name/strength/form, lot number, manufacturer, amount dispensed, directions for use, and physician name. The physician/pharmacist has to provide medication counseling per certain congressional regulations. This could be in the form of a drug monograph with the following information: name of medication, length of therapy, possible side effects of the medication, and expiration date and proper storage of the medication.

Uncontrolled sampling is driving up costs for physicians, patients and payers of all kinds. Drug companies need alternatives which give them information, reduce costs and retain access to prescribing physicians.

There are differing regulatory schemes in different jurisdictions that exist for drug samples and the dispensing thereof. The regulatory schemes address issues such as, for example, drug control license patient's chart or clinical record to include record of drugs dispensed; delegating authority to dispense drugs; storage of drugs; containers; labels; complimentary starter dose drug; information; inspection of locations; limitation on delegation; and receipt of complimentary starter dose drugs pharmacist. Further, the regulatory boards periodically inspect locations from which prescription drugs are dispensed.

Under some regulatory schemes, a prescriber who wishes to dispense prescription drugs obtains from a board a drug control license for each location in which the storage and dispensing of prescription drugs occur. A drug control license is not necessary if the dispensing occurs in the emergency department, emergency room, or trauma center of a hospital or if the dispensing involves only the issuance of complimentary starter dose drugs.

Per regulations, a dispensing prescriber can dispense prescription drugs only to his or her own patients. A dispensing prescriber has to include in a patient's chart or clinical record a complete record, including prescription drug names, dosages, and quantities, of all prescription drugs dispensed directly by the dispensing prescriber or indirectly under his or her delegatory authority. If prescription drugs are dispensed under the prescriber's, delegatory authority, the delegatee who dispenses the prescription drugs has to initial the patient's chart, clinical record, or log of prescription drugs dispensed. In a patient's chart or clinical record, a dispensing prescriber has to distinguish between prescription drugs dispensed to the patient and prescription drugs prescribed for the patient. A dispensing prescriber has to retain information required for not less than, for example, five years after the information is entered in the patient's chart or clinical record.

Regulations further include that a dispensing prescriber has to store prescription drugs under conditions that maintain their stability, integrity, and effectiveness and assure that the prescription drugs are free of contamination, deterioration, and adulteration. A dispensing prescriber has to store prescription drugs in a substantially constructed, securely lockable cabinet. Access to the cabinet: has to be limited to individuals authorized to dispense prescription drugs in compliance with the regulatory schemes.

Unless otherwise requested by a patient, a dispensing prescriber dispenses a prescription drug in a safety closure container that complies with the poison prevention packaging act, for example, of 1970, Public Law 91-601, 84 Stat. 1670.

Further, a dispensing prescriber has to dispense a drug in a container that bears a label containing all of the following information: the name and address of the location from which the prescription drug is dispensed, the patient's name and record number, the date the prescription drug was dispensed, the prescriber's name, the directions for use, the name and strength of the prescription drug, the quantity dispensed, the expiration date of the prescription drug, or the statement required per regulations.

Additionally, per the regulations, a dispensing prescriber who dispenses a complimentary starter dose drug to a patient has to give the patient at least all of the following information, either by dispensing the complimentary starter dose drug to the patient in a container that bears a label containing the information or by giving the patient a written document which may include, but is not limited to, a preprinted insert that comes with the complimentary starter dose drug, that contains the information: the name and strength of the complimentary starter dose drug, directions for the patient's use of the complimentary starter dose drug, and the expiration date of the complimentary starter dose drug.

Per some regulations, a supervising physician may delegate in writing to a pharmacist practicing in a hospital pharmacy with a hospital licensed the receipt of complimentary starter dose drugs other than controlled substances. When the delegated receipt of complimentary starter dose drugs occurs, both the pharmacist's name and the supervising physician's name has to be used, recorded, or other wise indicated in connection with each receipt. A pharmacist may dispense a prescription for complimentary starter dose drugs written or transmitted by other means of communication by a prescriber.

Per the regulations, "complimentary starter dose" means a prescription drug packaged, dispensed, and distributed in accordance with state and federal law that is provided to a dispensing prescriber free; of charge by a manufacturer or distributor and dispensed free of charge by the dispensing prescriber to his or her patients.

Referring to FIGS. 16A–27D, a preferred embodiment of the present invention includes a way to manage the sampling process and provide solutions to the persistent regulatory compliance issues and escalating pharmaceutical costs. The embodiment fully documents the sample process and addresses all the JCAHO standards. The preferred embodiment also plays a significant role in better formulary management via information captured through the sampling process. The cost savings realized through this process benefit all constituents of the healthcare industry—patients, providers, and payers. Following are two examples of the preferred embodiment's contribution to controlling drug costs.

Firstly, generic drug sampling can greatly reduce an overall pharmacy drug budget. A recent study, conducted by Scott & White Prescription Services, evaluated the cost savings achieved after implementation of a generic drug sampling program. Results showed savings per antibiotic prescription of over 10% of total prescription drug cost for antibiotics. Greater savings were shown for nonsteroidal anti-inflammatory medications. Drug sampling of nonsteroidal anti-inflammatories (NSAIDS) resulted in over 30% savings per prescription cost in this therapeutic category. Among the general conclusions of the study, generic drug sampling helped increase usage of generic medications and decrease average health plan cost per prescription, while allowing for opportunities to influence prescription habits.

Secondly, drug sampling can selectively reduce medication costs for economically disadvantaged. In a study conducted al the University of Arizona Department of Pharmacy Practice and Science, it was determined that Medicare managed care beneficiaries adopted predictable behaviors to cope with capped prescription drug benefits. The findings suggest that a considerable proportion of Medicare managed care enrollees take steps (i.e. obtain a medication sample, take less than the prescribed amount of medication, and using an over-the-counter product to replace the prescribed medication) to avoid facing the full financial impact of their prescription drug costs.

There are several benefits of the—preferred embodiment in accordance with the present invention. The benefits are gained by physicians and pharmaceutical companies. For example, the pharmaceutical companies can get specific information about the prescriber, demographics on the patient without identification, competitive usage factors and site specific information using the preferred embodiment.

Further, the distribution costs are lowered using the preferred embodiment of the present invention, enabling better use of the marketing representatives of the pharmaceutical companies. Lower wastage of samples due to strict controls over access and usage are realized with the preferred embodiment. Additionally, continued access to physicians is gained because the institution is able to meet accreditation standards. The preferred embodiment also provides the ability to get national rollout virtually overnight through information dissemination directly to users of sites employing the preferred embodiment. The preferred sample dispensing, is embodied by two components. A hardware component comprising uniquely designed cabinetry, and a touch screen software component.

In the preferred embodiment, the software, for example, is written for Microsoft Windows 98 and Microsoft Windows NT, using Visual Basic 6.0 and Visual C++, and runs on a typical Intel/Pentium based personal computer. Although disclosed with respect to being written for Microsoft Windows, the software may be written for any computer operating systems, for example, JAVA platforms, UNIX system, Windows CE, and IBM OS operating systems. The operating requirements, imposed upon the personal computer are minimal, permitting the purchase of less expensive, though proven, computer components. Printers such as, for example, a Laser Jet or Color Ink Jet printer which provides a patient specific education monograph and labels with each dispense are used with the computer. The laser jet printer can also be used to print reports locally. Typical components include, for example, but are not limited to, ASUS motherboards, Intel Pentium II CPU's, 3COM 3C90X network interface cards, digital hard drives of between four and six gigabytes capacity, internal or external 3COM US Robotics modems, and MicroTouch touch screens.

The software is used by a nurse, physician, or medical office staff, depending upon state laws and regulations. The functionality of the software breaks down into five main categories, namely, dispensing function, loading function, maintenance, reports, and communications.

All information transmitted, whether through the internet or a direct connection, is encrypted. An encryption program that is used, but not limited to, is for example, "Blowfish." In addition, the key bit exceeds 128-bits for sites located within the United States. Any sites located outside of the borders of the United States will use key bit encryption strength approved by the US government, such as for example, 56-bit key lengths. According to some public safety regulations a key of 128-bit meets or exceeds the level deemed necessary to transmit information over the internet or other electronic means.

All information generated by the users input is captured in a transaction database for transmittal via the internet, or direct modem dial out, to a server. Inventory is maintained perpetually with increases to the stocking level managed via the load process, and decreases in inventory managed by the dispense process. Inventory stock levels are also communicated to a server, with special attention to stockout threshold levels to trigger additional communications with clinic managers, chiefs of pharmacy, manufacturers, and any others involved in the sample dispensing value chain.

All information captured is aggregated in the server. The communications function of the samples dispensing software manages the aggregation process. At present time, throughout a 24 hour period, the communication module can deliver the days activity of an individual sample dispensing location to the server. This information is accumulated and is available for redistribution using a variety of ways and methods.

Distribution of each sample dispensing location's information occurs in at least one of two ways, depending upon the available information infrastructure. Where telephone access is available the sample dispensing locations can call, using an 800 number, a server, setup for receipt of up to 24 simultaneous connections. This type of server is commonly referred to as a Remote Access Server (RAS). The RAS can be set up with 24 ports or more capable of 56K connections using a T-1 data line. Additional simultaneous connections are available in groups of 24, 36, 128, or higher. If toll free access is not acceptable, the sample dispensing location can call a local Internet Service Provider access number, and then negotiate a session with the server also connected to the internet.

If modem access is not possible, then an existing hospital network running a protocol such as, for example, TCP/IP is used if that hospital can access the internet. The sample dispensing location is connected to the hospital network to transmit daily activity logs through the hospital network, out onto the internet, thence onto the server. The data is encrypted, and compressed so as to minimize the bandwidth necessary for each session. This reduction in bandwidth usage is important to many clinics, so that a drain on hospital networking resources is minimized, or as in the case of the information generated by the samples dispensing locations using modems is none.

Methods of redistribution of samples include, but are not limited to, email, fax, website, and a planned integrated voice response (IVR) system. The server aggregates the information into a series of larger databases, while keeping information accessible that is unique to an installation by using a unique key for each individual location. In this manner, access to the information can be attained as an aggregate of a market, or as an individual dispensing location, depending upon the need. For example, Microsoft SQL 6.5 acts as the main database repository engine.

In a particular, preferred embodiment, for the server processes, Allaire's ColdFusion™ web site database management and development solution can be used. Allaire is a web site development language and solution company with tools for data management over the Internet. Other database management and development solutions can be used. Each customer is offered a unique view of the aggregated data based upon the customers buying level.

Using password access, the preferred embodiment offers a user nearly real time sample dispensing information. In addition, based upon buying levels, daily, weekly, or monthly reports via email are provided.

In another preferred embodiment, a process that can be broken up into a series of questions that can be responded to using a telephone keypad is programmed using an IVR. A follow-on device can be provided for patients to interact with regard to their prescriptions. Medications used for treating various mental incapacities have a history of side effects ranging from mild to severe. These medications are typically quite expensive. In cases of severe side effects, the patient's entire prescription is destroyed and another new and different prescription is generated. The destroyed medications are a complete loss to the dispensing institution and the patients' insurer. Using samples, and an IVR system, a complete costly prescription is not given to a patient until the patient has completed a duration of free samples to determine if side effects are severe enough to warrant a different therapy approach.

A patient can query a prearranged IVR number to indicate that side effects are, or are not, present in his or her currently selected therapy regime. If the patient can tolerate the tested samples, then the NR can trigger the hospital pharmacy, an online pharmacy company like, for example, PlanetRx.com, or redirect the Rx to a mail order facility, a complete therapy cycle based upon the norms of the institution. Where an expensive prescription might have been wasted the patient can test a free sample of the medication before determining if a complete cycle of therapy would be effective without severe side effects.

A user, instead of dialing an IVR system, launches their favorite web browser using an Internet service such as, for example, AmericaOnLine or any other Internet access provider, and complete a series of simple questions about the sample of medicine, before being issued a complete therapy cycle. The therapy cycle can be redirected to many different locations, including, again the originating hospital outpatient pharmacy, a mail order house, etc.

FIGS. 16A through 22 illustrate embodiments of screens of the software component of the sample dispensing. The screens can be displayed by a monitor of a drug dispenser. In a preferred embodiment, the monitor is a touch screen. Therefore, it is possible for a user to interact with the dispenser by using the monitor and the screens shown in FIGS. 16A through 22 to provide commands to the dispenser 1500. To use the touchscreen monitor, the user must press the tip of a capacitive item, such as a finger against the screen. Non-capacitive items, such, as fingernails or pointed objects, will not work. In another embodiment, the user can also use a mouse or a keyboard to interact with the commands and options presented on the screens.

Figure 16A:
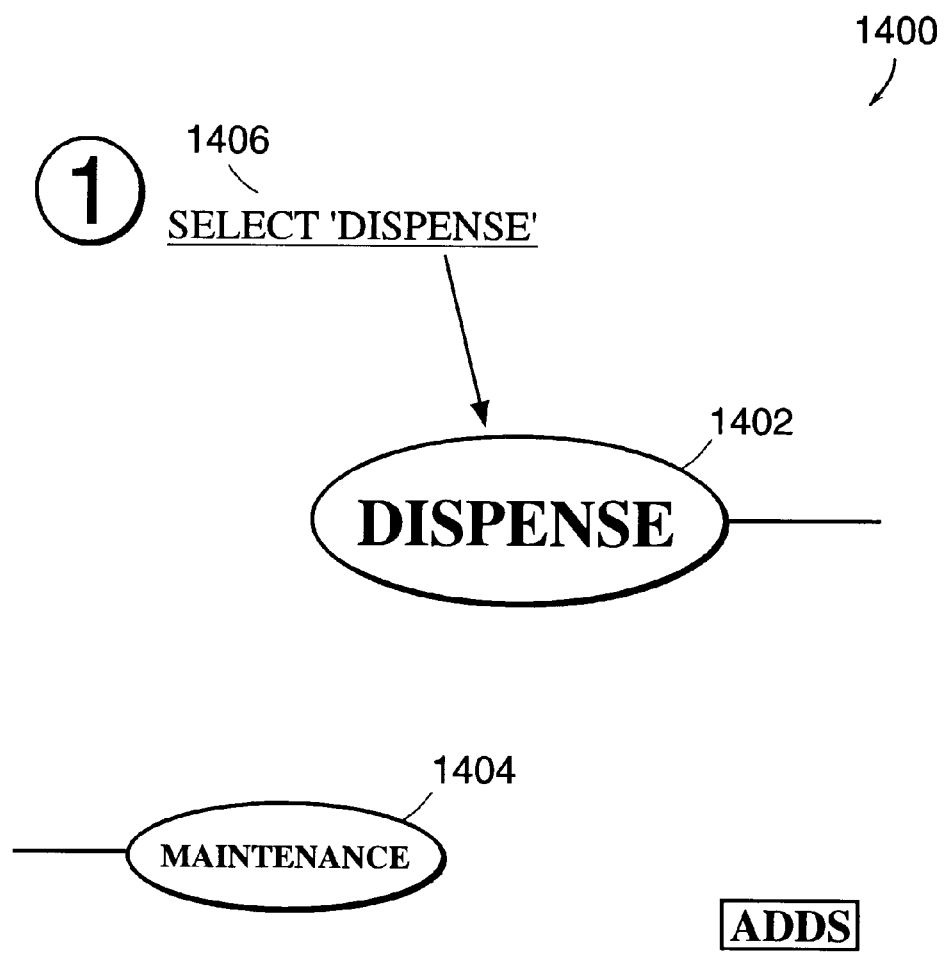
Figure 16B:
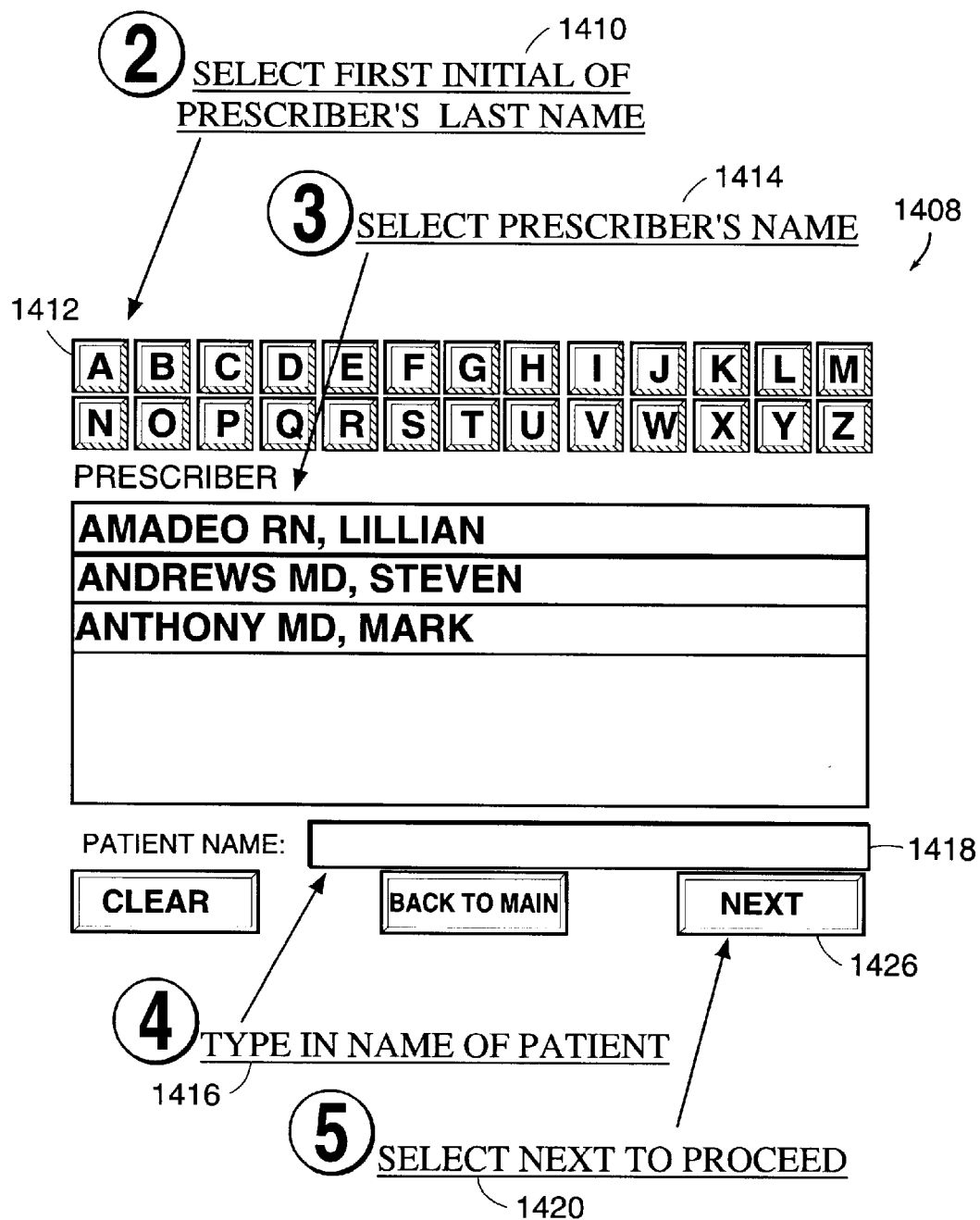

FIGS. 16A through 16E illustrate a method of dispensing drug samples from the sample dispenser 1500 and embodiments of screens associated with dispensing samples. FIG. 16A shows an introduction screen 1400 having a dispense command 1402 and a maintenance command 1404. To engage the dispenser to dispense drugs, the user can select the dispense command 1406. The user can then be presented with a subscriber name screen 1408, as shown in FIG. 16B. The user can select the first initial of the prescriber's last name 1410 using letter keys 1412. The user can then select the prescriber name 1414 from the screen 1408. Next, the user types in the patient name 1416 in a patient name area. The user can then proceed 1420 by selecting; a next command 1426.

Figure 16C:
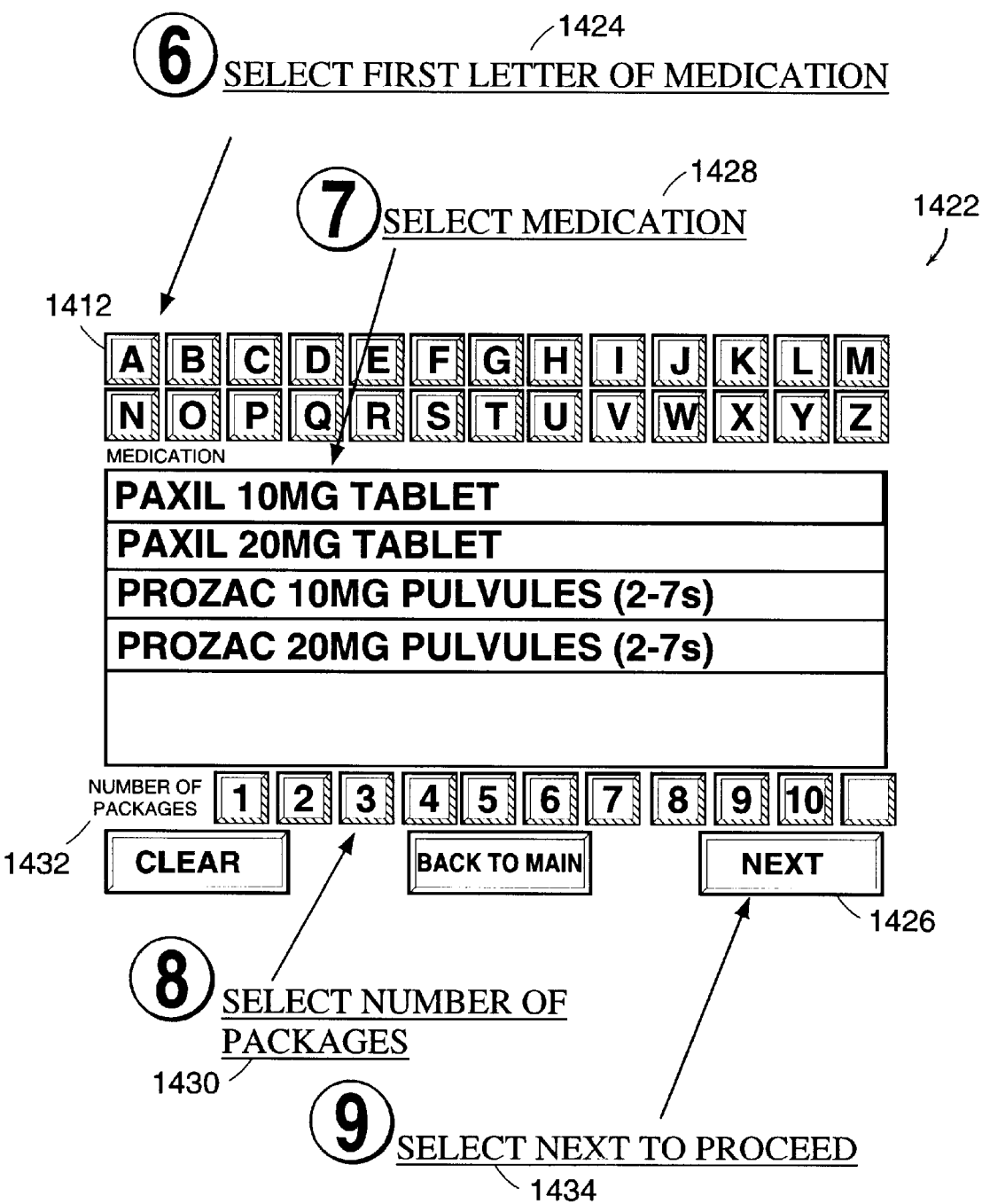

FIG. 16C shows a medication screen 1422 which can follow the subscriber name screen 1408. A user can select the first letter of a medication 1424 he wishes to receive using the letter buttons 1412 provided. A list of medications can then be listed on the screen 1422. The user can select the medication 1428 he requires by touching the portion of the screen corresponding to his drug choice. The user can select the number of packages he requires 1430 using the package quantity buttons 1432. The number of packages is not equivalent to the number of doses needed for a patient, since one package can have multiple doses of medication. The user can then proceed 1434 by selecting the next command 1426.

FIG. 16D shows a SIGS screen 1442 which can follow the medication screen 1422. The user can select one of the provided SIGS or use he space at the bottom to create a custom SIG 1436. The user can edit both the lot number and expiration date 1438 of the medication. The user can then proceed 1440 by selecting a next command 1426. The user can then be presented with a dispense summary screen 1442, shown in FIG. 16E. The user can then review all entries to make sure they are correct 1444. The user can also check the printer to ensure that paper is available 1444. The user can chose to give the same patient additional medications 1446, restart the process 1448 or select a finish command to print labels and monographs for the patient 1450.

Figure 17A:
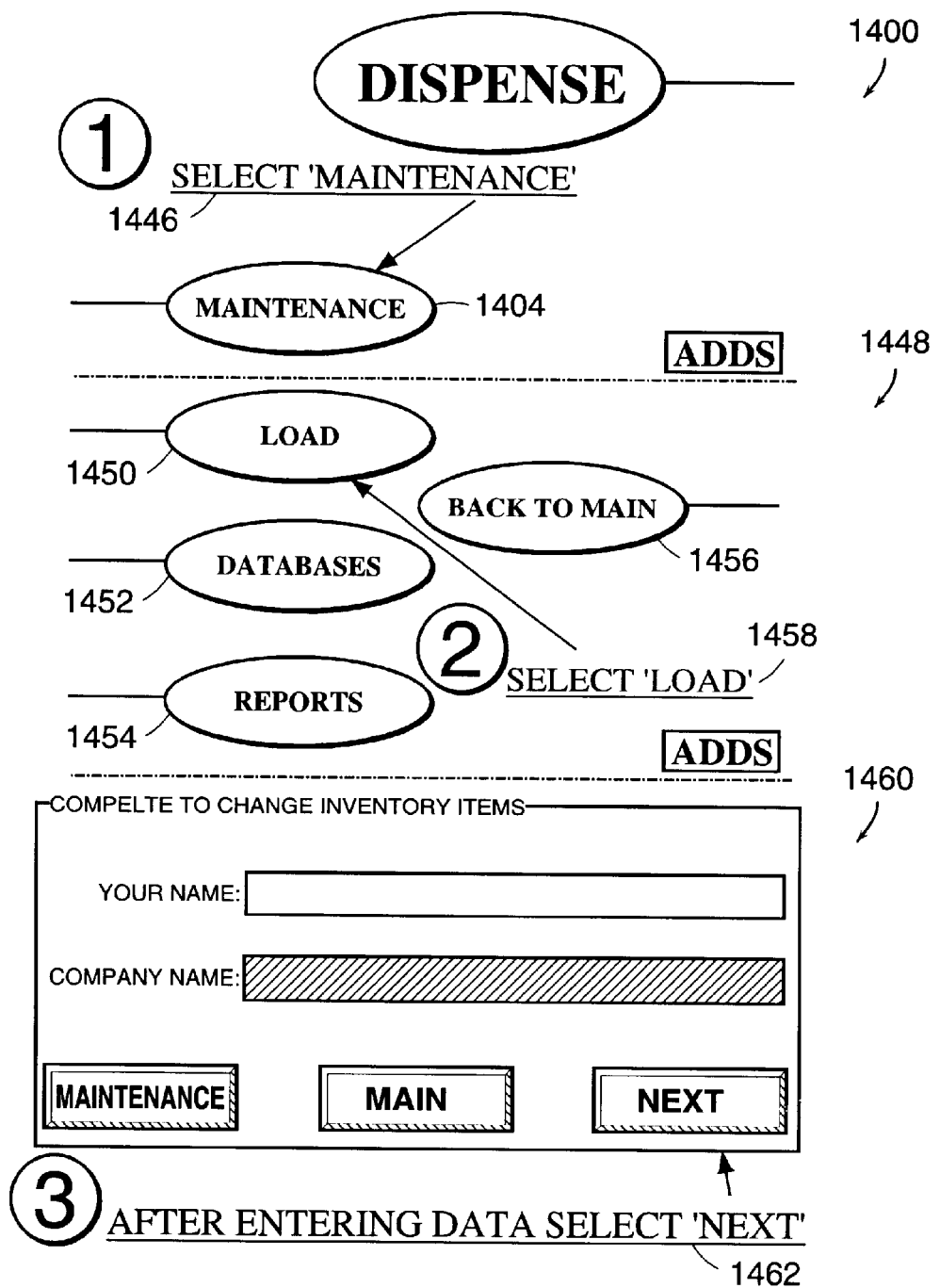
Figure 17B:
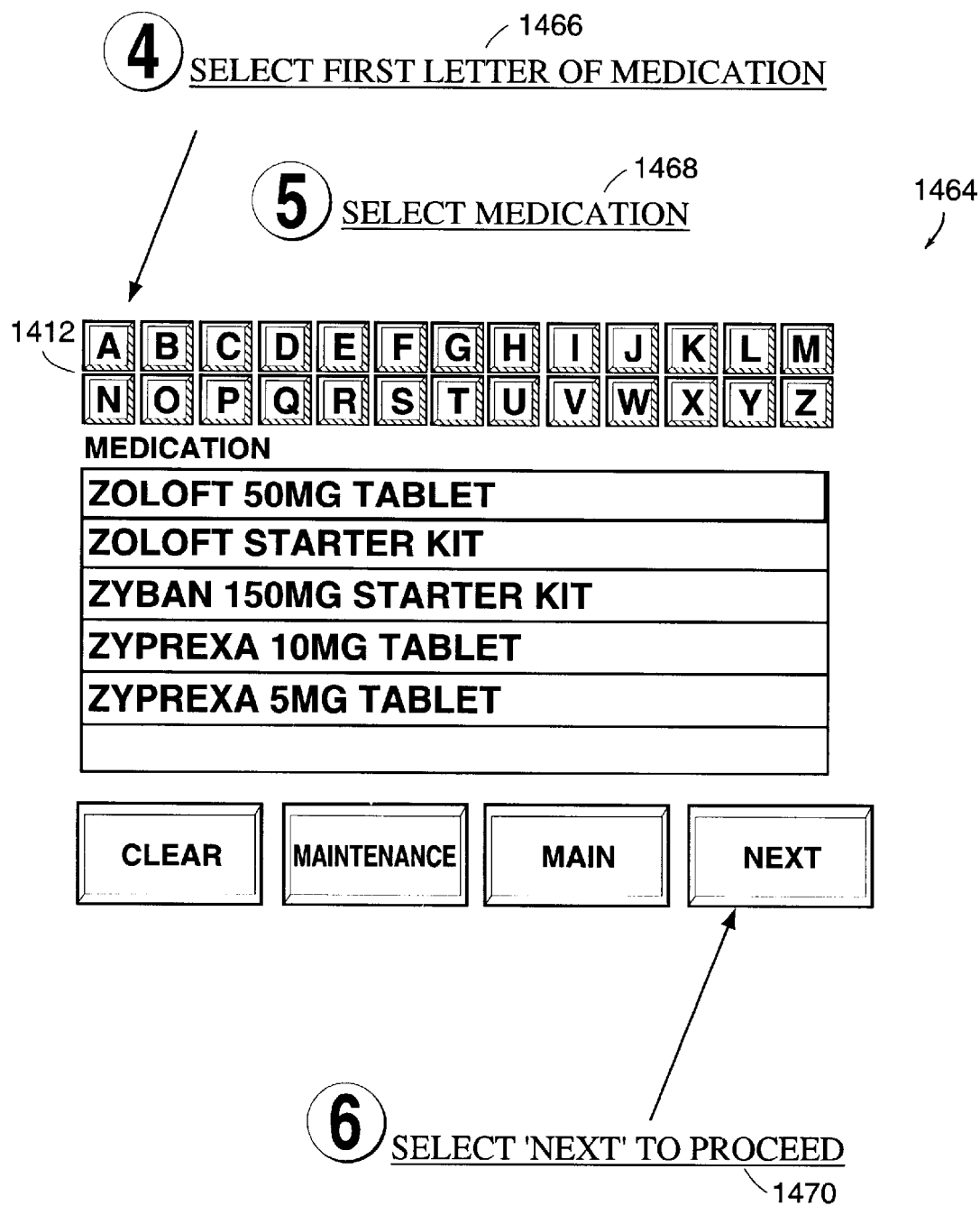

FIGS. 17A through 17C illustrate a method of loading medications into a dispenser. The user can first be presented with an introduction screen 1400 having a maintenance command 1404, shown in FIG. 17A. The user can select the maintenance command 1446 to proceed with the loading of medications. The user can then be presented with a menu screen 1448 having a load command 1450, a databases command 1452, a reports command 1454 and a return to introduction screen command 1458. The user can select the load command 1458 to proceed. The user can then be presented with a user identification screen 1460 where the user can enter his name and his company's name before proceeding. After the data has been entered, the user can select a next command 1462 to continue.

FIG. 17B illustrates a medication screen 1464, which follows the user identification screen 1460. The user can select the first letter of the medication to be loaded 1466 from the letter buttons 1412. The user can then be presented with a list of drugs having names starting with the chosen letter. The user can then select the medication to be loaded 1468 from the screen 1464. The user can proceed by selecting a next command 170, which brings him to a medication data screen 1472, shown in FIG. 17C. In the medication data screen 1472, the user can enter the lot number, the expiration date and the quantity of the medication added 1474 to the dispenser. The medication data screen 1472 includes a save command 1476 and a quit—no save command 1478. After entering the data and hitting the tab key to move through the screens, the user can check his entries and execute the save command if they are correct or execute a the quit—no save command if they are incorrect 1480.

Figure 18A:
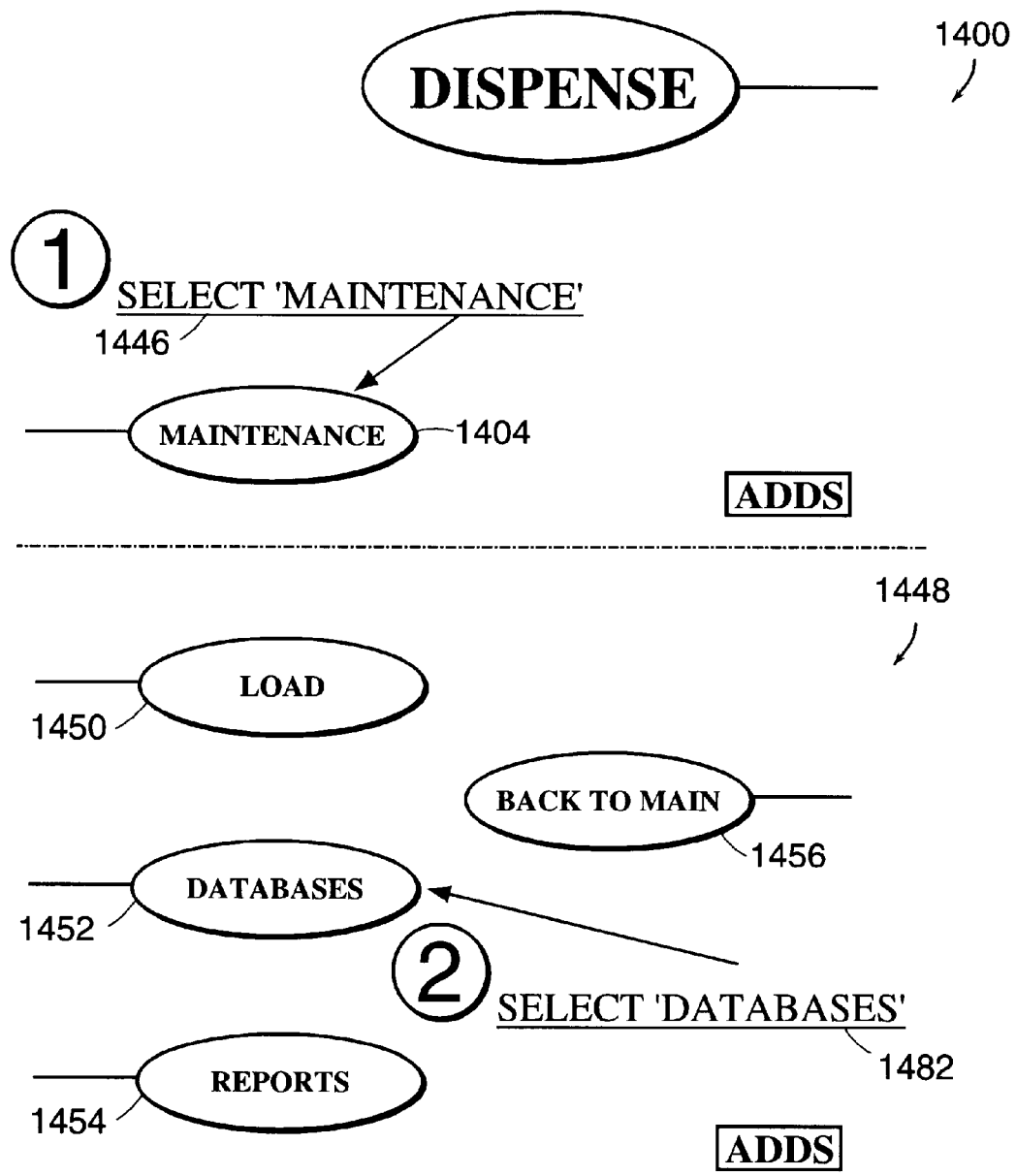
Figure 18B:
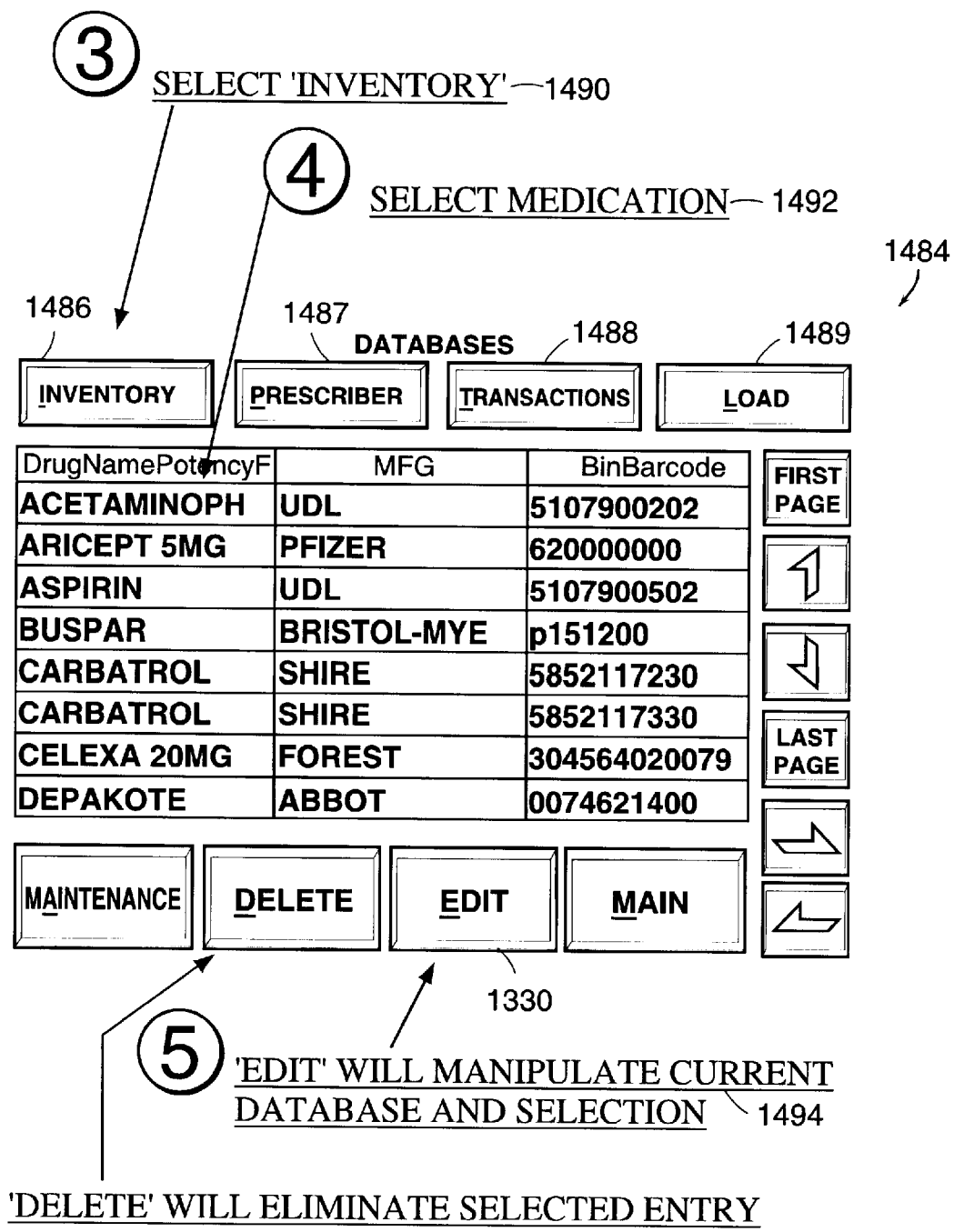

FIGS. 18A through 18D illustrate a method to view or edit inventory within the dispenser. The user can first be presented with an introduction screen 1400 having a maintenance command 1404, shown in FIG. 18A. The user can select the maintenance command 1446 to proceed with the loading of medications. The user can then be presented with a menu screen 1448 having a load command 1450, a databases command 1452, a reports command 1454 and a return to introduction screen command 1458. The user can select the databases command 1482 to proceed. A database screen 1484 can then be presented to the user as illustrated in FIG. 18B.

The database screen 1484 can include an inventory command 1486, a prescriber command 1487, a transactions command 1488 and a load command 1489. To view or edit inventory in the dispenser, a user can select the inventory command 1490 and select a medication 1492 shown on the screen 1484. The screen 1484 can present manufacturer and barcode information of the medications, in addition to medication names. The user can then manipulate the inventory database 1494 by either editing or deleting the database selection. When editing the database selection, an inventory database editor screen 1495 can appear, as shown in FIG. 18C. On this screen 1495, the user can edit items or add new items to the database 1496. To add new items to the database, the user can select the inventory command 1486, select the edit command 1330 and select a medication from the screen 1484. Any medication can be selected since it will immediately be changed. The user can then select the clear all fields command 1332, enter data into the blank fields shown on the screen 1495 and select the save command 1334.

The user can opt to get new GCN number and apply the new GCN number 1498 from the inventory database editor screen 1495. A GCN number is assigned to drugs that belong in the same class and can be used to create a monograph that the patient receives in the dispense process. If the use chooses to get and apply a new GNC, the user can be presented with a GCN screen 1300, shown in FIG. 18D. From this screen, the user can select a new GCN number by picking the actual medication or its closest therapeutic equivalent from the screen 1300. Whichever item is selected will have its GCN number added to the NEW GCN textbox 1306 on the inventory database editor screen 1495. The user can return to the inventory database editor screen 1308 and choose to save the new data or restore the previous data 1310.

Figure 19A:
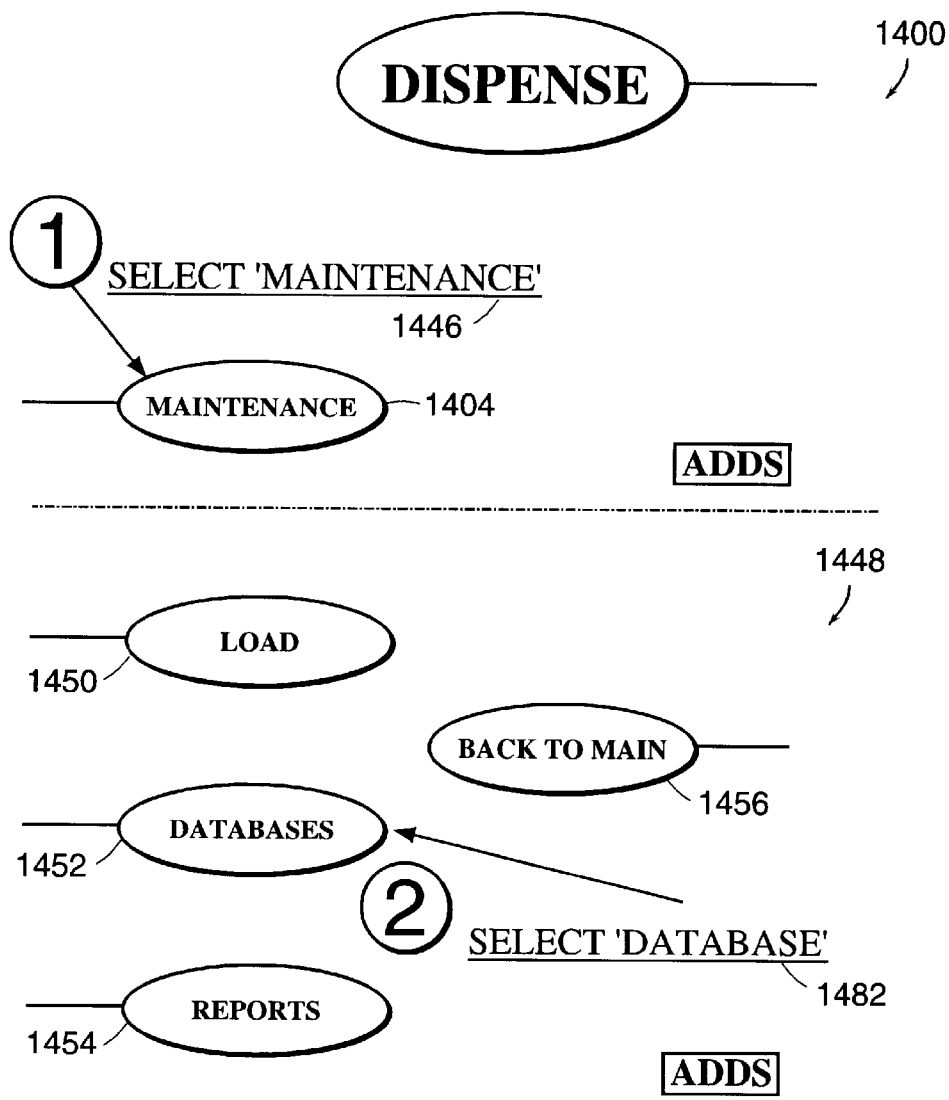
Figure 19B:
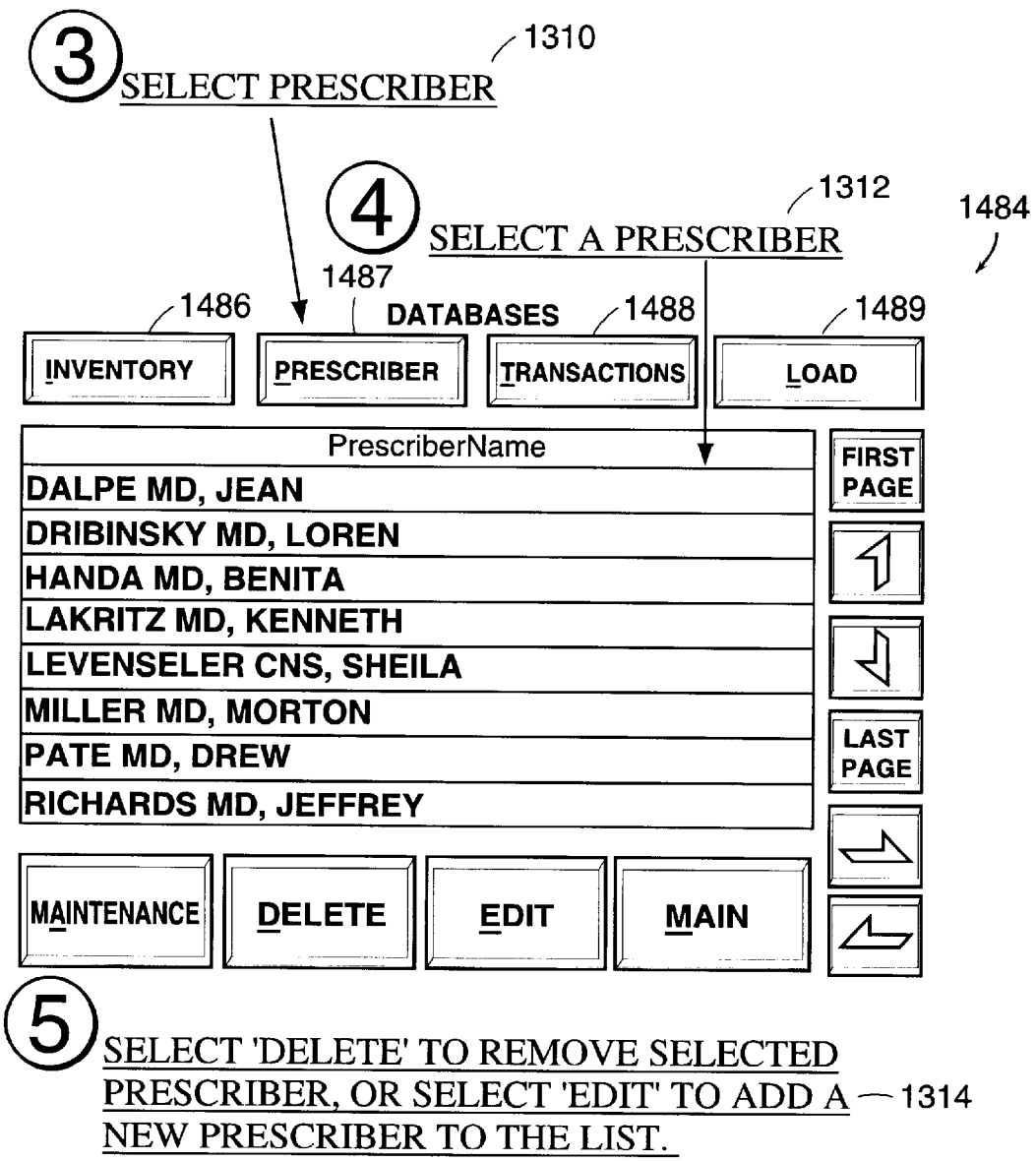

FIGS. 19A through 19C show a method to view or edit a prescriber within the database of the dispenser. The user can first be presented with an introduction screen 1400 having a maintenance command 1404, shown in FIG. 19A. The user can select the maintenance command 1446 to proceed with the loading of medications. The user can then be presented with a menu screen 1448 having a load command 1450, a databases command 1452, a reports command 1454 and a return to introduction screen command 1458. The user can select the databases command 1482 to proceed. A database screen 1484 can then be presented to the user as illustrated in FIG. 19B.

The database screen 1484 can include an inventory command 1486, a prescriber command 1487, a transactions command 1488 and a load command 1489. To view or edit a prescriber in a database interfaced with the dispenser, a user can select the prescriber command 1310 and select a prescriber 1312 shown on the screen 1484. The user can then remove the selected prescriber from the database or edit the prescriber information to add him to the database 1314. If the user chooses to add a new prescriber, he can be presented with a prescriber database editor screen 1316, shown in FIG. 19C. The user can enter a new prescriber name and return to the database screen 1318.

Figure 20A:
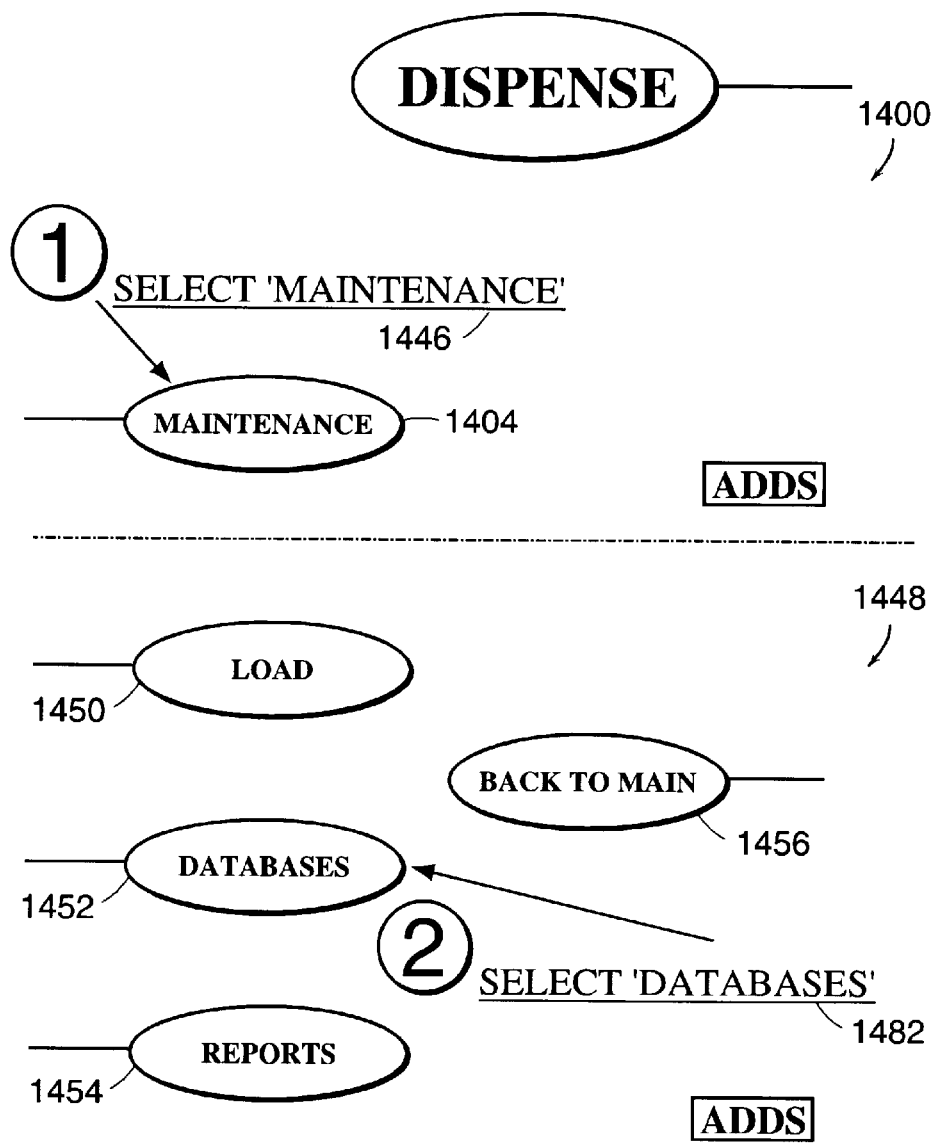
FIGS. 20A and 20B illustrate views of the display screen that a user interfaces with during a transaction process in accordance with a preferred embodiment of the present invention which includes dispensing of drug samples.
Figure 20B:
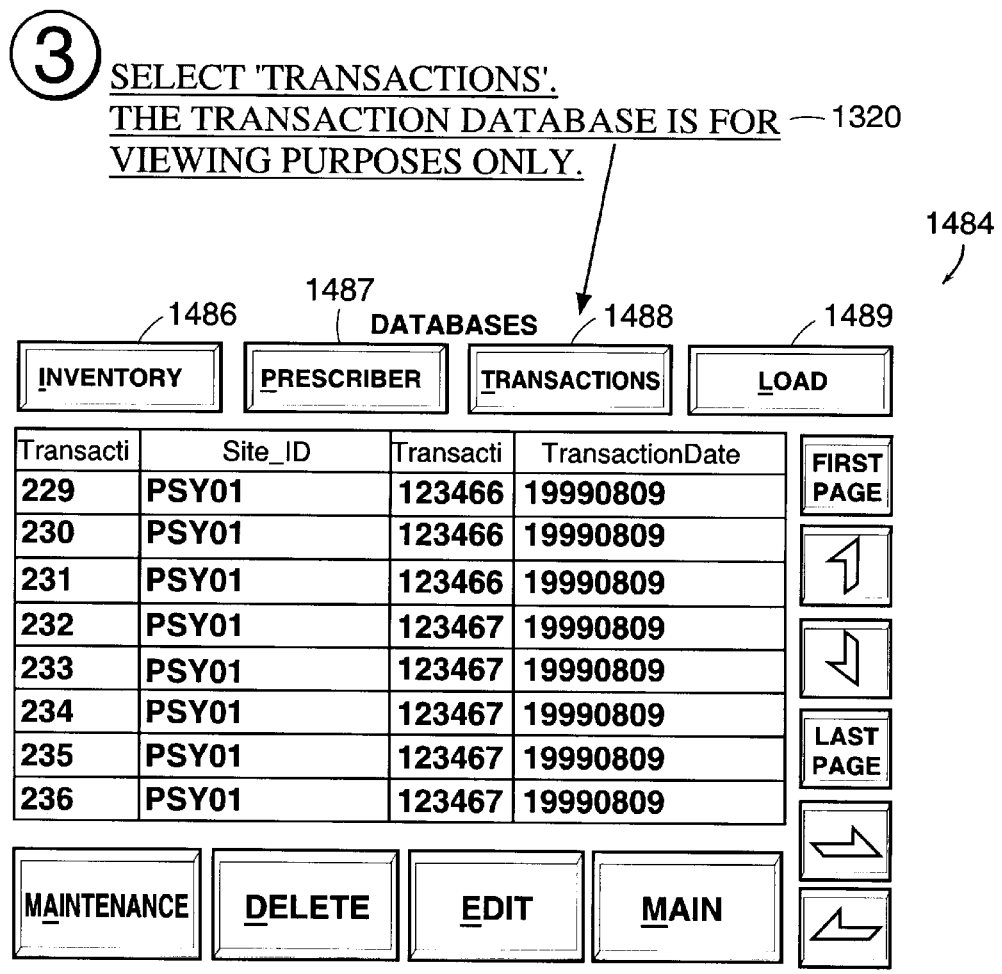

FIGS. 20A and 20B illustrate a method to view a transaction made with the dispenser. The user can first be presented with an introduction screen 1400 having a maintenance command 1404, shown in FIG. 20A. The user can select the maintenance command 1446 to proceed with the loading of medications. The user can then be presented with a menu screen 1448 having a load command 1450, a databases command 1452, a reports command 1454 and a return to introduction screen command 1458. The user can select the databases command 1482 to proceed. A database screen 1484 can then be presented to the user as illustrated in FIG. 20B.

The database screen 1484 can include an inventory command 1486, a prescriber command 1487, a transactions command 1488 and a load command 1489. To view the transactions made with the sample dispenser 1500, a user can select the transaction command 1320. The transaction database can be used for viewing purposes only. The user can view the transactions by transaction number or by transaction date, for example.

Figure 21:
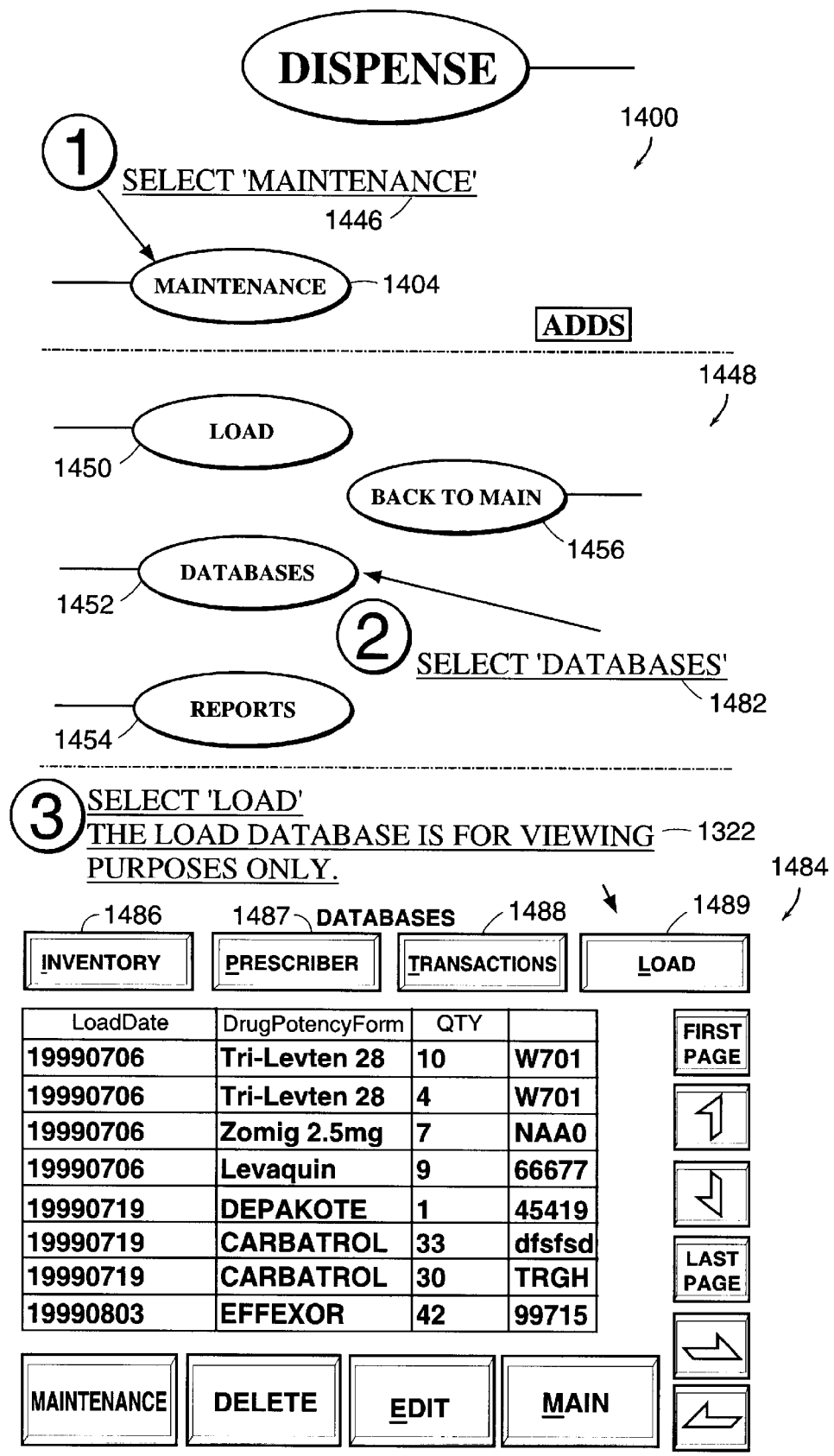
FIG. 21 illustrates views of the display screen that a user interfaces with during a history loading process in accordance with a preferred embodiment of the present invention which includes dispensing of drug samples.

FIG. 21 illustrates a method viewing the load history of the dispenser. The user can first be presented with an introduction screen 1400 having a maintenance command 1404. The user can select the maintenance command 1446 to proceed with the loading of medications. The user can then be presented with a menu screen 1448 having a load command 1450, a databases command 1452, a reports command 1454 and a return to introduction screen command 1458. The user can select the databases command 1482 to proceed. A database screen 1484 can then be presented to the user.

The database screen 1484 can include an inventory command 1486, a prescriber command 1487, a transactions command 1488 and a load command 1489. To view the database showing the medications loaded into the dispenser, a user can select the load command 1322. The database showing; the medications loaded can be used for viewing purposes only. The database screen 1484 can show various types of load data, including load date, drug potency, and quantity.

Figure 22:
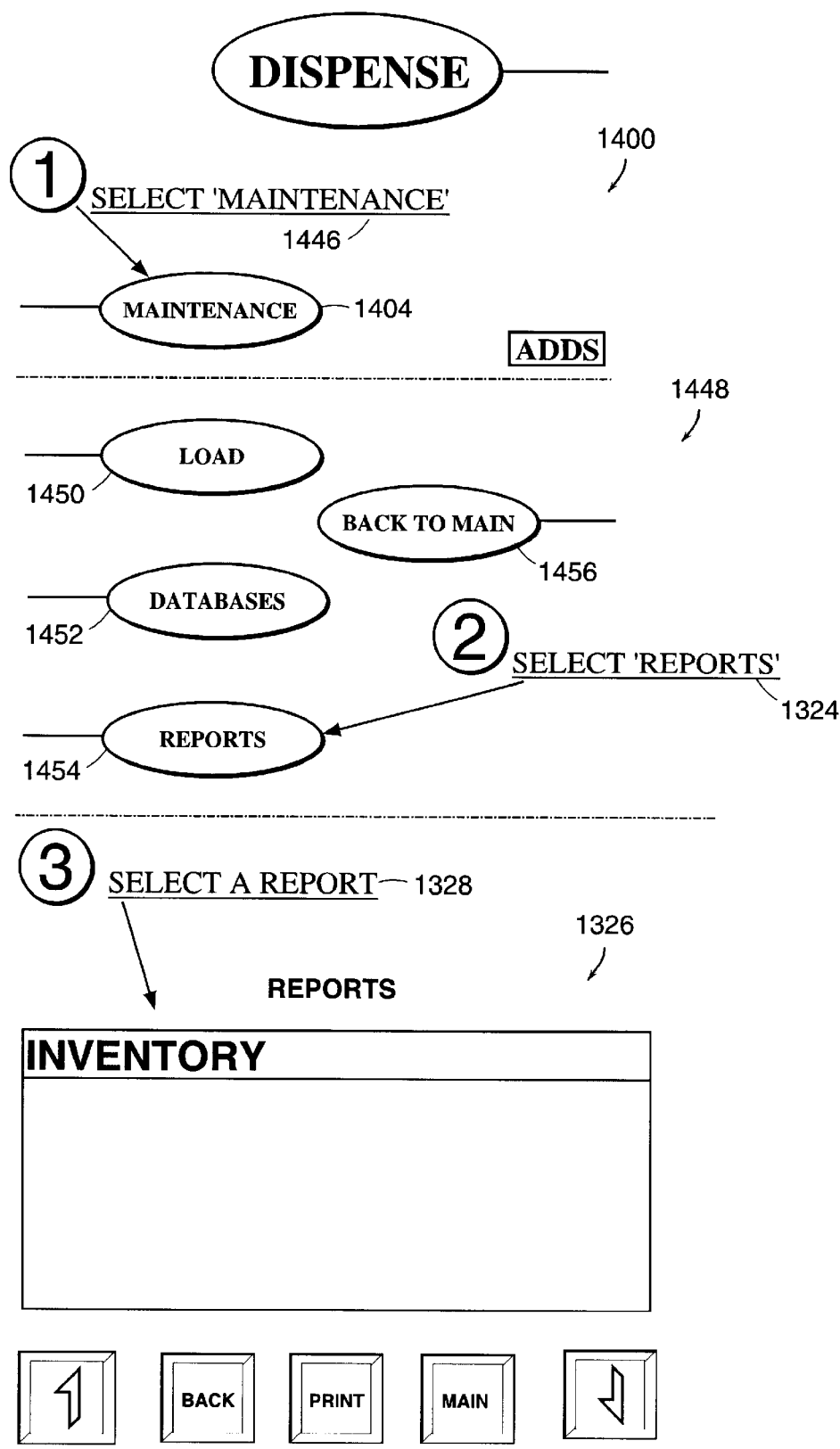
FIG. 22 illustrates views of the display screen that a user interfaces with during a report process in accordance with a preferred embodiment of the present invention which includes dispensing of drug samples.

FIG. 22 illustrates a method of viewing reports of the database of the dispenser. The user can first be presented with an introduction screen 1400 having a maintenance command 1404. The user can select the maintenance command 1446 to proceed with the viewing of reports. The user can then be presented with a menu screen 1448 having a load command 1450, a databases command 1452, a reports command 1454 and a return to introduction screen command 1458. The user can select the reports command 1324 to proceed. A reports screen 1326 can then be presented to the user. The user can then select a report 1328 from the screen 1326 that lie wishes to view. For example, an inventory report can be chosen and viewed by the user.

Figure 23A:
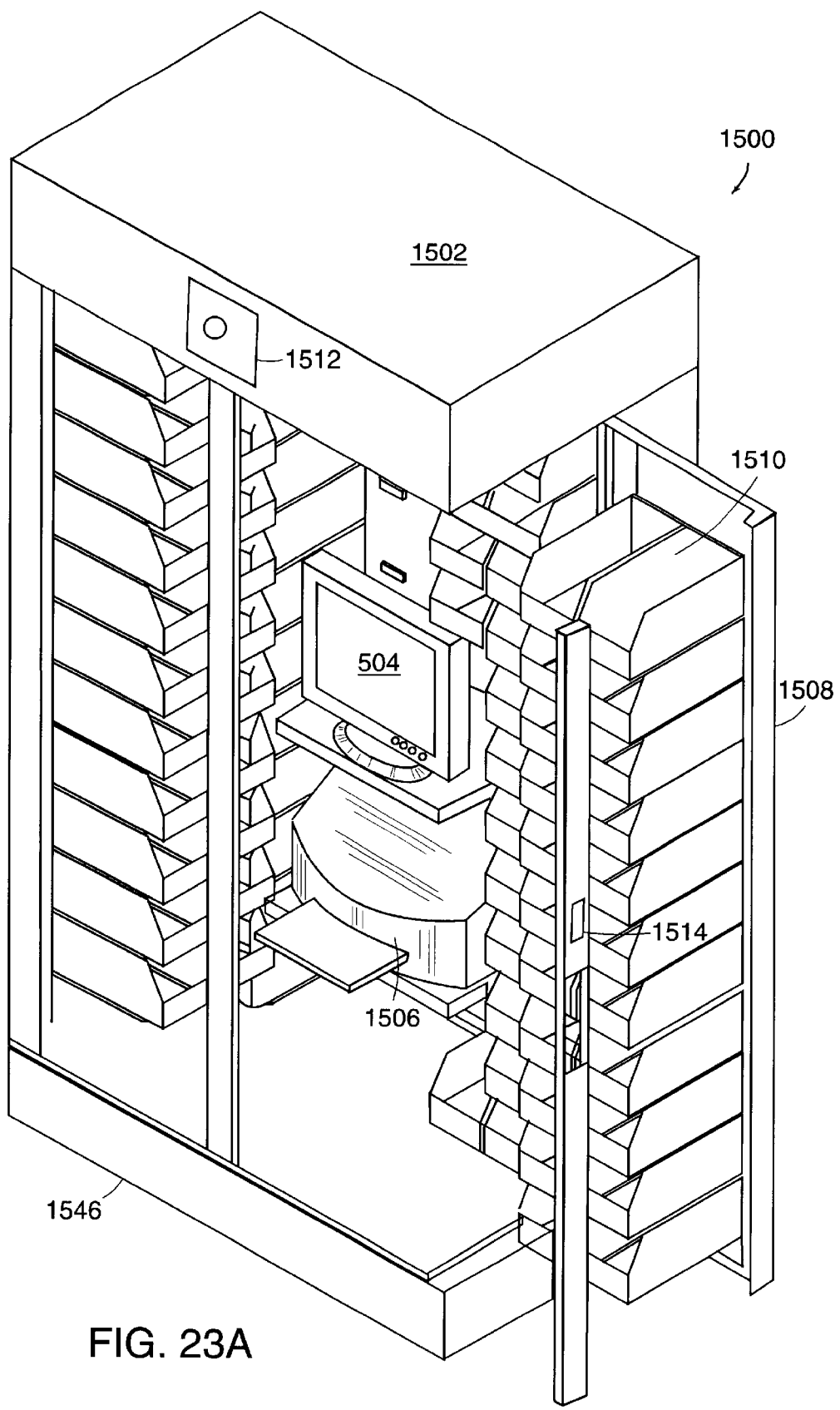
FIGS. 23A and 23B illustrate views of the drug sample dispenser in accordance with the present invention.
Figure 23B:
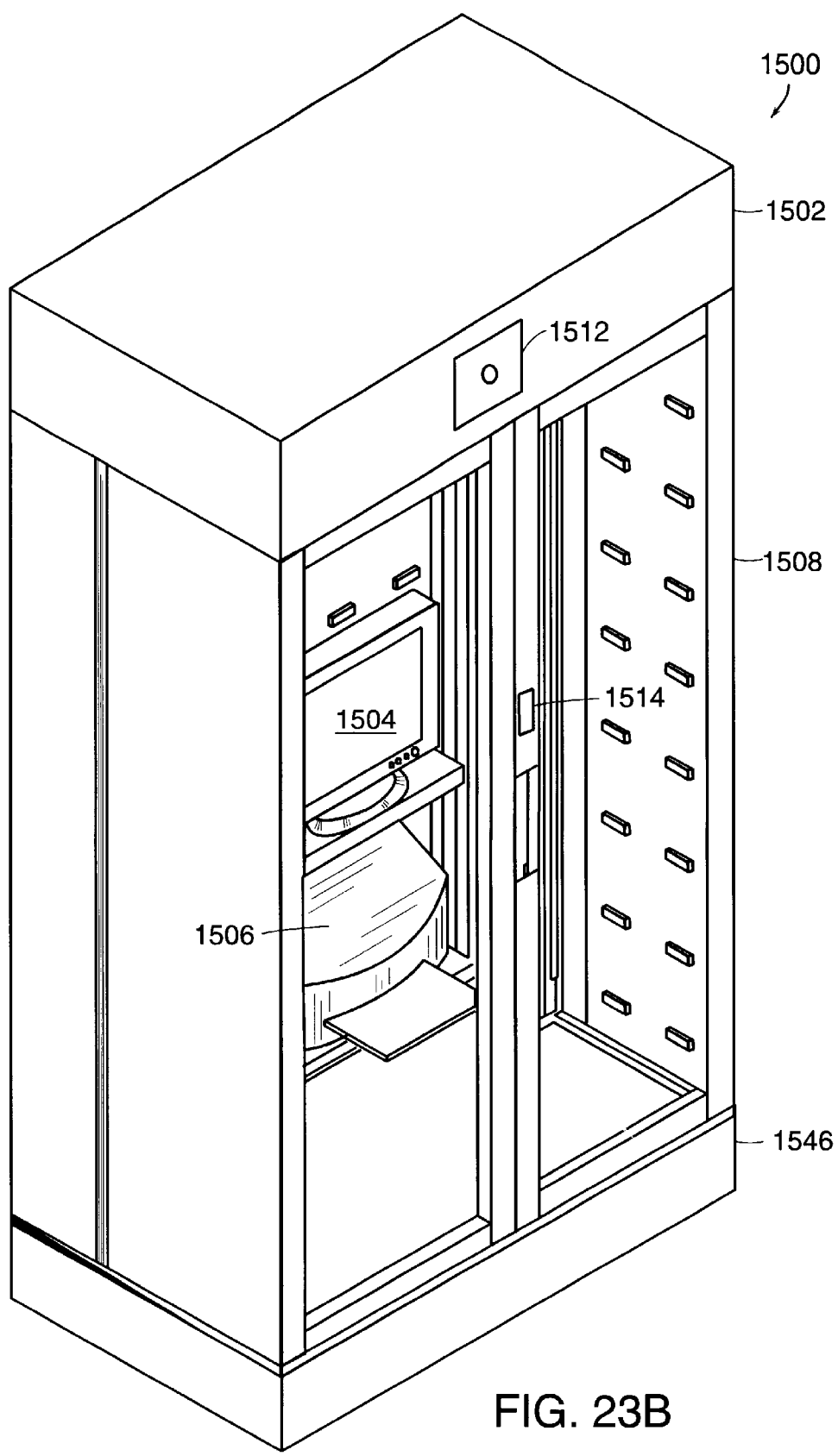

FIGS. 23A and 23B show a preferred embodiment of a sample dispenser 1500 the hardware system of sample dispensing. The dispenser 1500 can have a computer 1560 located within a computer housing 150.2, a monitor 1504, a printer 1506 and a control system 1518 located within a control system housing 1546. The dispenser 1500 can also have doors 1508 holding a plurality of bins 1510, a camera 1512 and a user identification system 1514. FIG. 23A shows a door 1508 of the dispenser 1500 in an open position. FIG. 16B shows a door 1508 of the dispenser 1500 in a closed position.

Figure 24A:
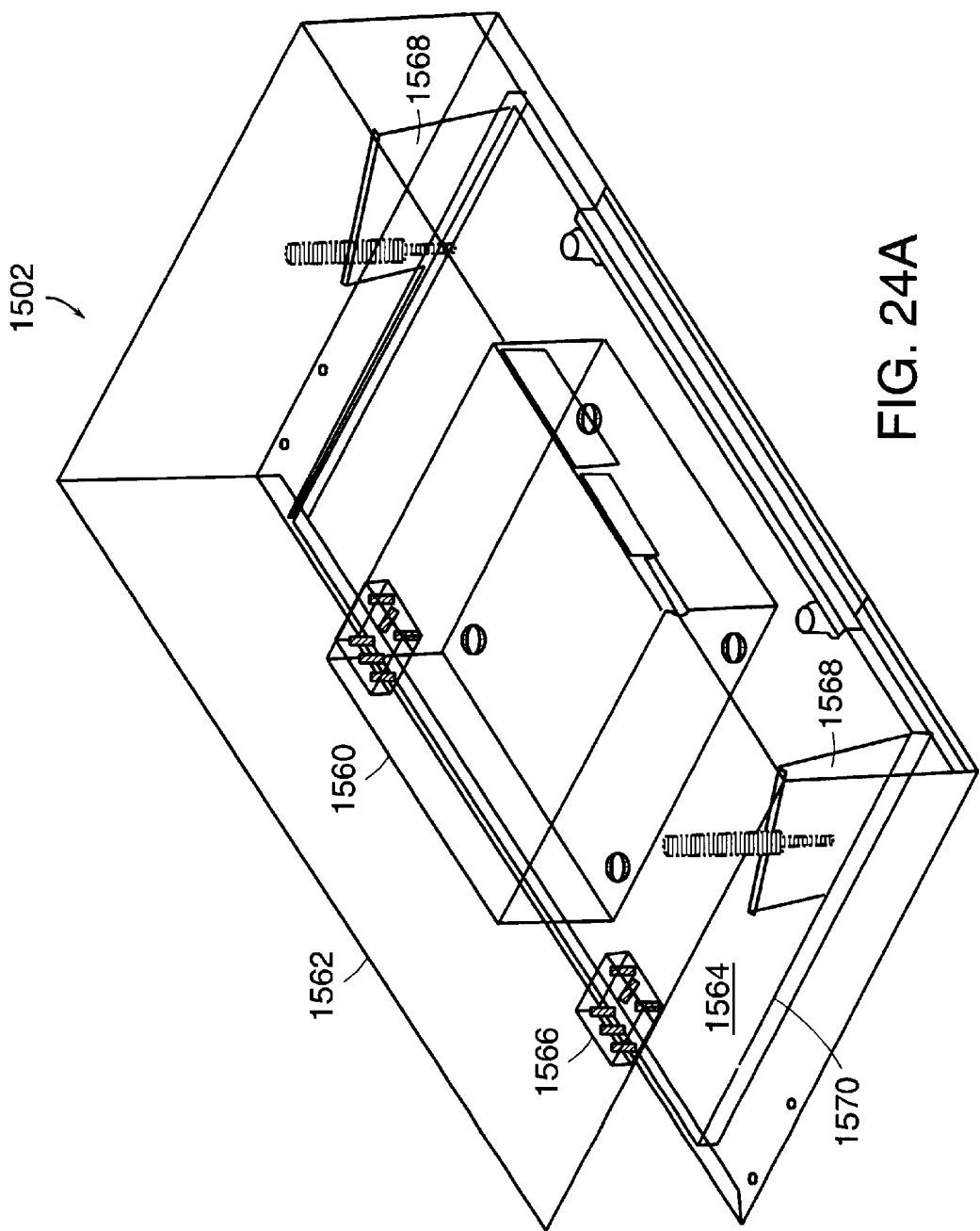
FIGS. 24A and 24B illustrate views of a computer chassis located within the dispenser illustrated in FIGS. 23A and 23B.
Figure 24B:
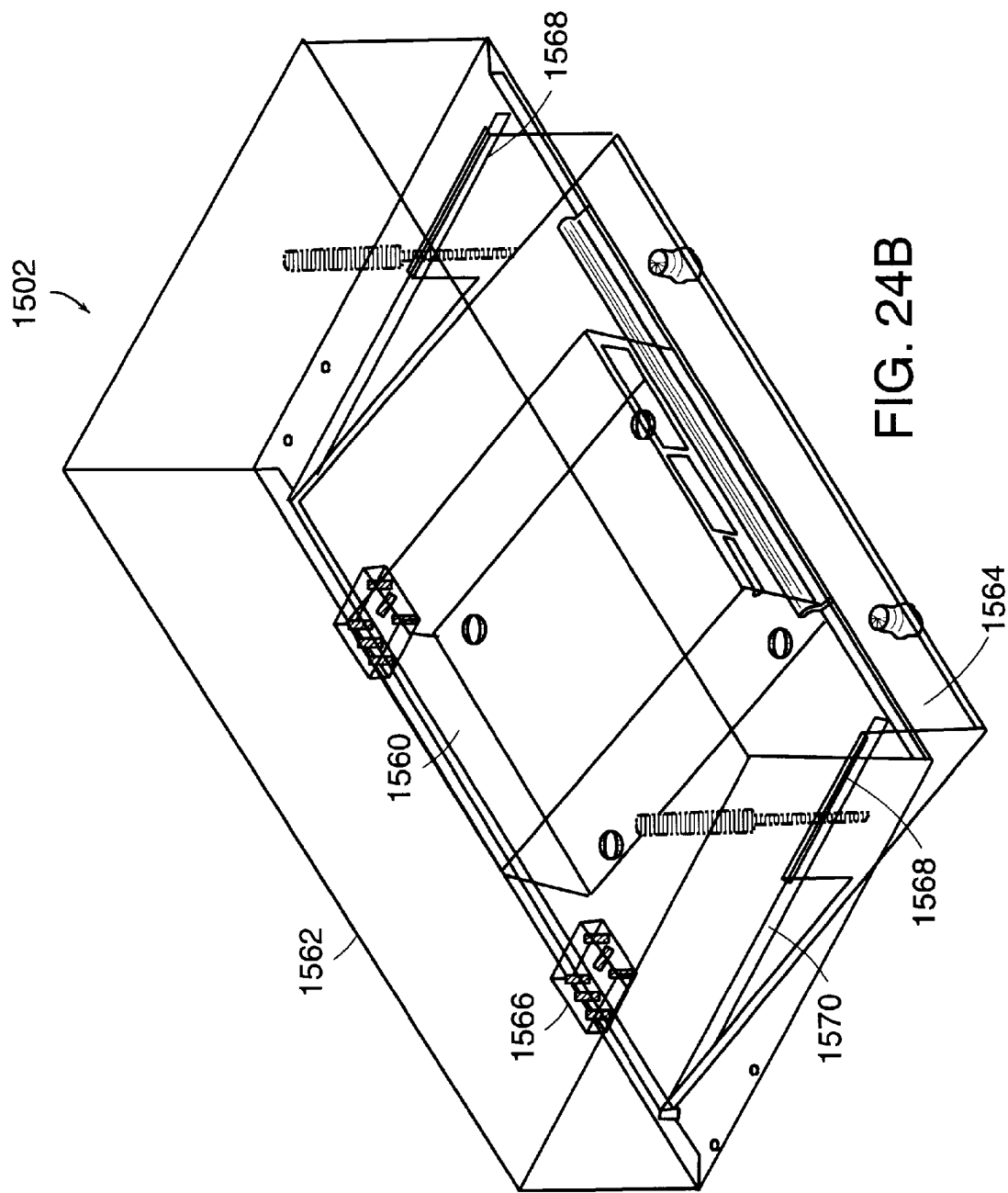

FIGS. 24A and 24B illustrate an embodiment of the computer housing 1502 in an open and a closed position, respectively. The computer housing 1502 can be opened and closed in order to allow restricted access to the computer for rebooting or servicing. The computer housing 1502 can have a stationary portion 1562 and a moveable portion 1564. The stationary 1562 and moveable 1564, portions can be attached by at least one hinge 1566. In a preferred embodiment, two hinges 1566 connect the stationary 1562 and moveable 1564 portions of the housing 1502. The moveable portion 1564 of the housing 1502 can include side rails 1568 and the stationary portion 1562 of the housing 1502 can have side walls 1570. The rails 1568 and walls 1570 can limit the motion of the moveable portion 1564 and the computer 1560 as the moveable portion 1564 is opened by a user. When the moveable portion 1564 is opened, the side rails 1568 can engage side walls 1570 of the stationary portion 1562 of the housing 1502, thereby preventing further rotation of the moveable portion 1564 of the housing 1502. Opening the computer housing 1502 can allow user access to the computer 1560.

Figure 25:
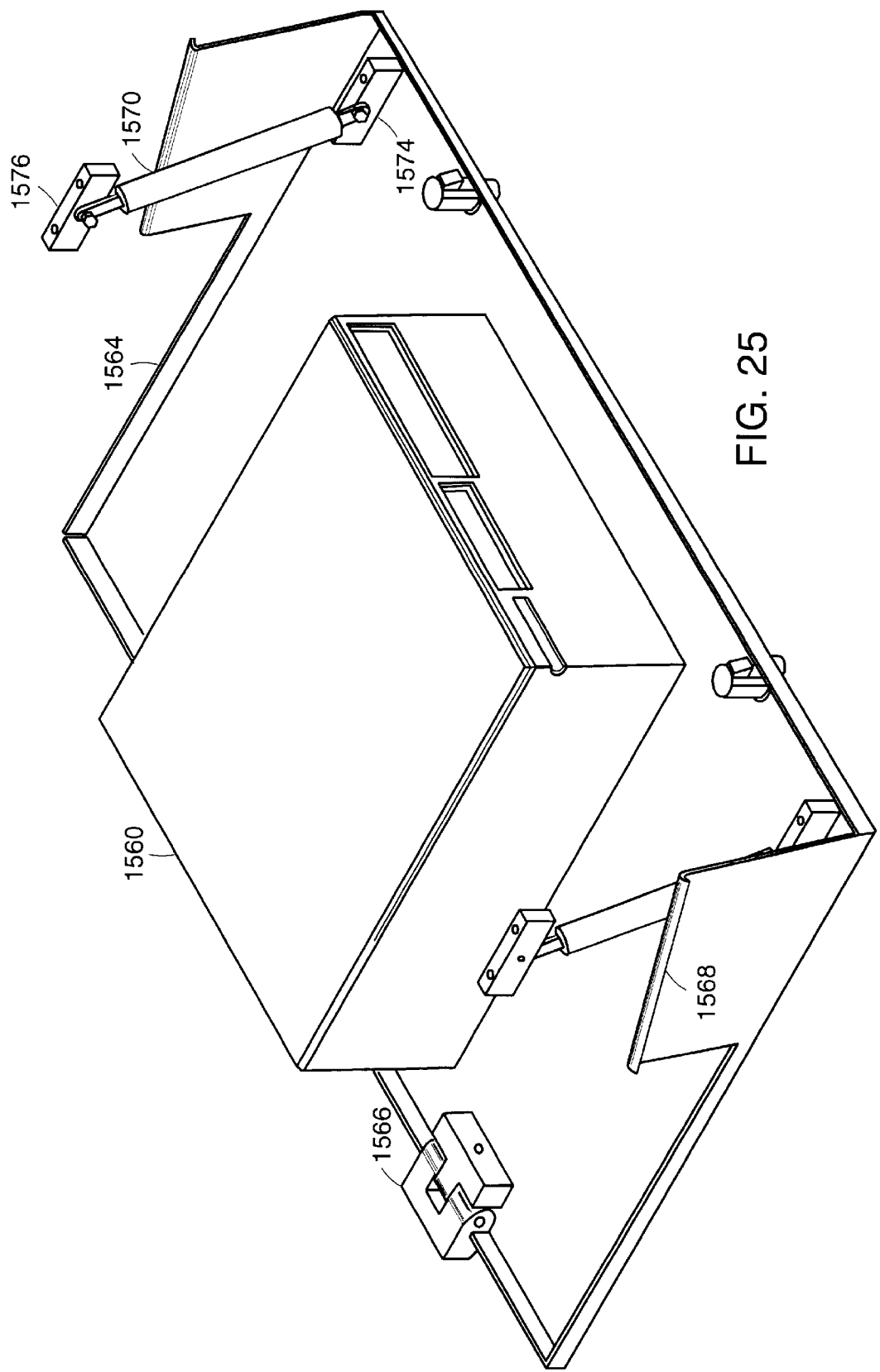
FIG. 25 illustrates a view of a computer mounted on the chassis located within the dispenser illustrated in FIGS. 23A and 23B.

FIG. 25 shows a computer 1560 mounted on a moveable portion 1564 of a housing 1502. In one embodiment, the housing 1502 can have pistons 1570 or dampeners mounted between the moveable portion 1564 and the stationary portion 1562. In the embodiment shown, the pistons 1570 can be mounted between movable portion brackets 1574 and stationary portion brackets 1576. The pistons 1570 can help to control the speed at which the moveable portion 1564 travels when the computer housing 1502 is opened.

The computer housing 1502 can have a computer 560 which can include a motherboard, a CPU, a network interface card, a hard drive and a modem. In a preferred embodiment, the computer housing 1502 can include an Asus motherboard, an Intel Pentium™ II CPU, a 3Com 3C90X network interface card, a Western Digital hard drive and a 3Com U.S. Robotics modem. The hard drive can have between a 4 and 6 gigabyte capacity, for example. The modem can be either an internal or an external modem. The monitor 1504, in a preferred embodiment, is a touch screen such as, for example, a MicroTouch screen which allows users to enter commands into the computer. The computer can also include a keyboard to allow commands to be entered into the computer. The printer 1506 can be a laser jet or a color ink jet, for example.

A camera 1512 can be mounted to the dispenser 1500, as shown in FIGS. 23A and 23B, and can be used to create a photographic record of all users of the sample dispenser 1500. Such a record can be used for security at the sample dispenser 1500 and to discourage tampering at the dispenser 1500. The camera 1512 can be triggered by some predetermined event to automatically take a picture of the area surrounding the dispenser. In one embodiment, a proximity sensor can be electronically coupled to the camera 1512 and can cause the camera 1512 to snap a picture based upon some external event. For example, if a user were to move within a certain distance of the dispenser 1500, the proximity sensor detects such a motion and causes the camera 1512 to automatically capture an image of an area surrounding the dispenser 1500. In another embodiment, the camera 1512 can be coupled with the user identification system 1514 such that engaging the system 1514 causes the camera 1512 to take a picture. For example, if a user were to attempt to use the identification system 1514, either successfully or unsuccessfully, such an attempt triggers the camera 1512 to snap a photograph. In another embodiment, the camera 1512 can be connected with the doors 1508 of the dispenser 1500 such that opening the doors 1508 causes the camera 1512 to snap a picture of an area surrounding the dispenser 1500. The camera 1512 can have a control system which can be a computer. The computer which controls the camera 1512 can be separate from the computer which controls the dispenser 1500 or integrated with it.

The sample dispenser 1500 can also have a user identification system 1514 to protect against unauthorized access. The user identification system 1514 can be used as a security device to permit authorized user access to the medications dispensed by the dispenser. In this system 1514, a user would be required to provide some paper form of identification to the system 1514 before the doors 1508 of the dispenser 1500 could be opened. The user identification system 1514 can be used in conjunction with a locking mechanism to provide security for the dispenser 1500. In one embodiment, the user identification system 1514 operates by identifying a fingerprint of a user. In a preferred embodiment, the user identification system 1514 operates by identifying a thumb print of a user. To access the dispenser 1500, a user places a finger or a thumb against the user identification system 1514. If the user's fingerprint was recognized by the user identification system 1514, a locking mechanism in the dispenser 1500 is released and the doors 1508 opened. If the user's fingerprint was not recognized by the user identification system 1514, the locking mechanism in the dispenser is not be released, thereby preventing access to the samples in the dispenser 1500. The user identification system 1514 can have a control system which can be a computer. The computer which controls the user identification system 1514 can be separate from the computer which controls the dispenser 1500 or integrated with it. It should be noted that the user identification system can include, but is not limited to, hospital identification cards, credit card, debit card, other identification paperwork, keyword or password access using a keypad.

The sample dispenser 1500 can also have doors 1508. The doors 1508 can house a plurality of bins 1510 which can be used to contain or organize samples within the dispenser 1500. Each door 1508 can be connected to the dispenser by a hinge 1516.

Figure 26A:
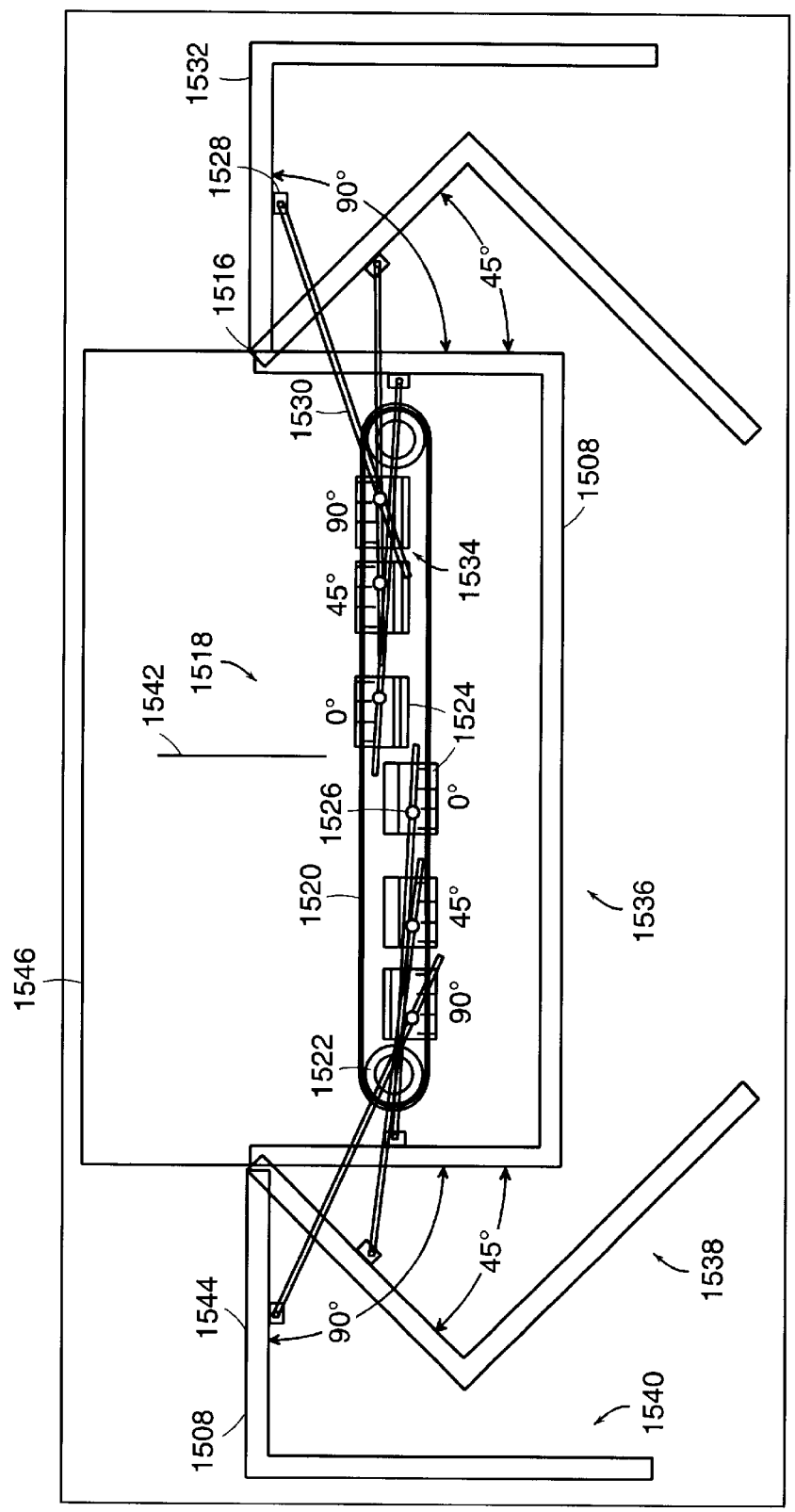
FIGS. 26A and 26B illustrate views of a motion control system located within the dispenser illustrated in FIGS. 23A and 23B.

FIG. 26A shows a control system 1518 for the doors 1508. The control system 1518 can include a belt 1520 having at least one block 1524 attached therein and having a set of rollers 1522 to control the motion of the belt 1520. In one embodiment, the blocks 1524 are bolted to the belt 1520. In another embodiment, the belt 520 is a chain drive. In one embodiment, the rollers 1522 can be gears. The rollers 1522 can be connected to a control system which can control the motion of the rollers 1522, thereby providing automatic opening and closing of the doors 1508. The control system can include a computer.

Each door 1508 can be connected to a first end 1532 of a rod 1530 at a pivot 1528 on the door 1508. A second end 1534 of each rod 1530 can be attached to a pivot 1526 on each block 1524. The rods 1530 connect the doors 1508 to the motion control system 1518. The pivots 1528 on the doors 1508 allow the doors 1508 to rotate about their hinges 1516 without impingement from the rods 1530. Similarly, the pivots 1526 on the blocks 1526 allow the rods 1530 to follow the rotational motion of the doors 1508 without impinging this motion.

FIG. 26A also shows the control system 1518 in various stages of operation. The control system 1518 can control the positioning of the doors 1508. In a first stage 1536, the doors 1508 are in a closed position, with a side door portion 1544 forming a zero degree angle with a centerline 1542. The blocks 1524 are located on the belt 1520 near the centerline 1542 of the control system 1518. The belt 1520 causes the rods 1530 to create a force on each door 1508 directed toward the centerline 1542, thereby holding the doors 1508 in a closed position. In a second silage 1538, the doors 1508 are half-opened, with a side door portion 1544 forming a forty-five degree angle with the centerline 1542. In this position 1538, each block 1524 is forced to move away from the centerline 1542 of the system 1518 by the belt 1520, in an opening motion, or forced to move toward the centerline 1542 of the system 1518 by the belt 1520, in a closing motion. In an opening motion, the belt 1520 causes each rod 1530 to create a force against each respective door 1508, directed away from the centerline 1542, thereby forcing the doors 1508 in a partially open position. In a closing motion, the belt 1520 can cause each rod 1530 to create a force on each respective door 1508, directed toward the centerline 1542, thereby forcing the doors 1508 in a partially open position. In a third stage 1540, the doors are filly opened, with a side door portion 1544 forming a ninety degree angle with a centerline 1542. In this position 1540, each block 1524, again, has been forced to move away from the centerline 1542 of the system 1518 by the belt 1520. The motion of the belt 1520 to this position 1540 further causes each rod 530 to create a force against each respective door 1508, directed away from the centerline 1542, thereby, forcing the doors 1508 into a fully open position.

The motion system 1518 can be operated automatically. Such operations can provide security for the dispenser 1500 and can limit user access to the device 1500. When operated, the control system 1518 can cause the doors 1508 to expand or contract to an open or closed position, respectively. Automatic operation of the control system 1518 can be triggered by some predefined event. For example, in one embodiment, the doors 1508 can be programmed to be opened by the motion control system 1518 only when the user provides positive identification. Also, the doors 1508 can be programmed to automatically close after a set time period has elapsed. In another embodiment, the doors 1508 can also be caused to close when the user moves away from a proximity sensor located on the dispenser 1500. For automatic operation of the control system 1518, the system 1518 can be controlled by a computer. The computer which controls the system 1518 can be separate from the computer which controls the dispenser 1500 or integrated with it.

The sample dispenser 1500 can also include a barcode reader, or an electronic reader in an alternate embodiment. The samples held by the plurality of bins 1510 can include barcodes. The inclusion of a barcode reader on the sample dispenser 1500 can allow a user to quickly and accurately create a record of the samples removed from the sample dispenser 1500 and the dates and times of removal, for example.

Figure 26B:
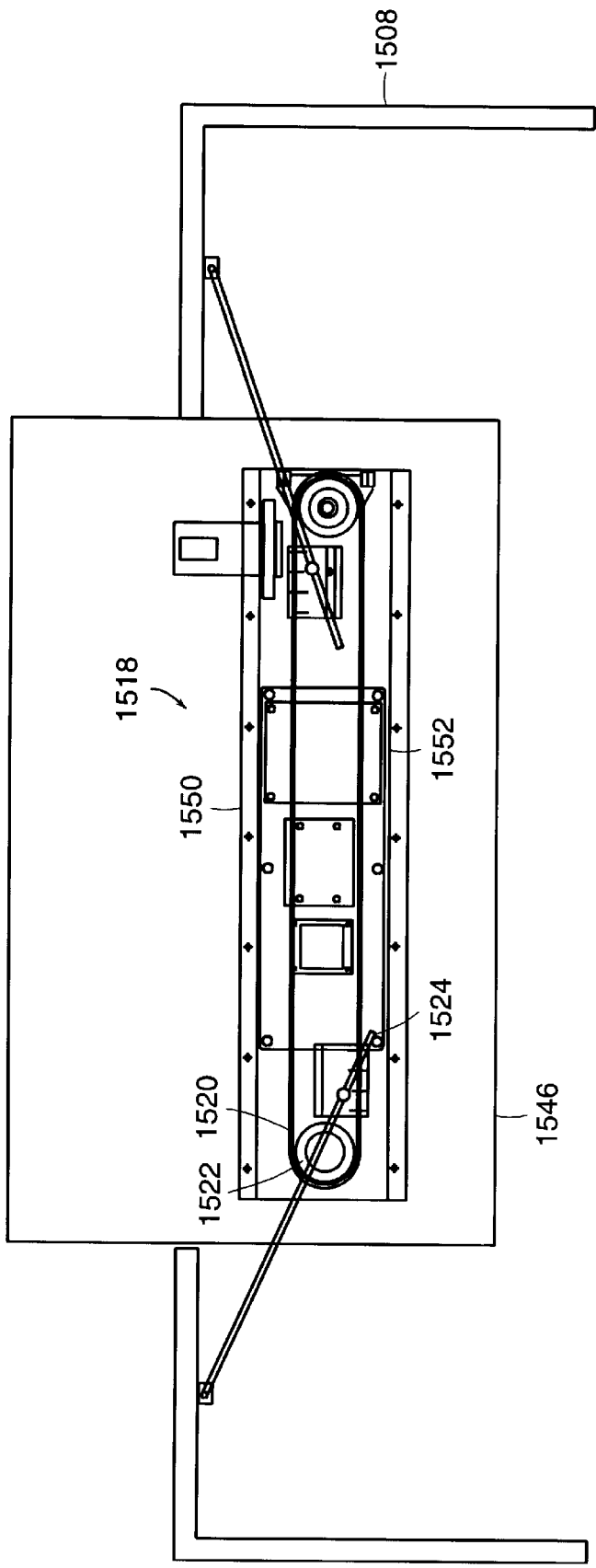
Figure 27B:
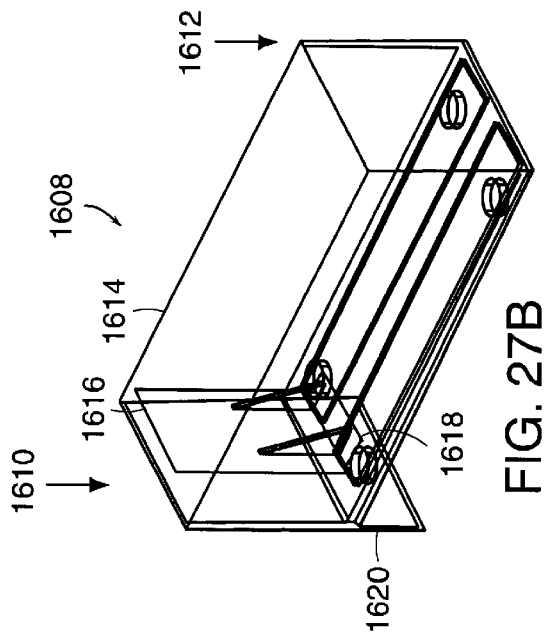
FIGS. 27A–27D illustrate views of an embodiment of a bin located within the dispenser illustrated in FIGS. 23A and 23B.
Figure 27D:
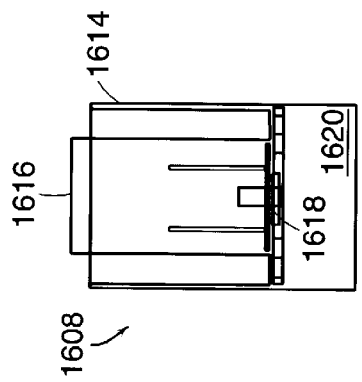
Figure 27A:
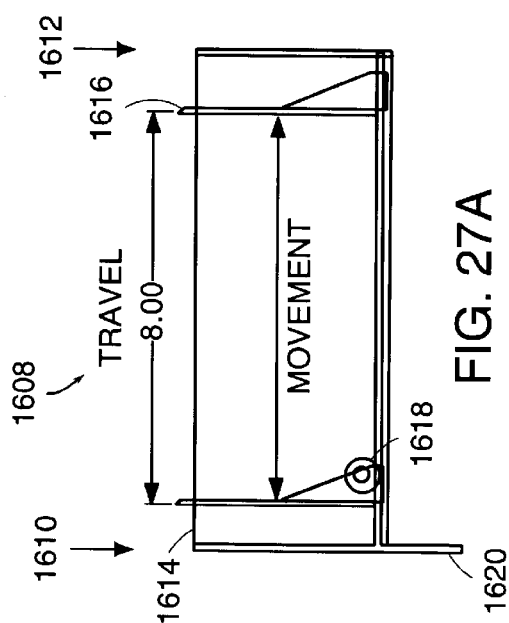
Figure 27C:
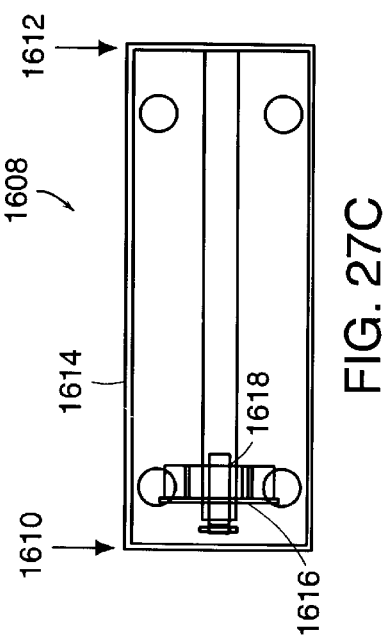

FIG. 26B illustrates a detailed, overhead view of the control system 1518 shown in FIG. 26A. The control system 1518 can have a housing 1550 to which the belt 1520, rollers 1522 and blocks 1524 are mounted. The housing 1550 can also hold and secure these components 1520, 1522 and 1524 to the motion control system housing 1546. The housing 1550 can have flanged portions 1552 which allow for attachment of the housing 1550 to the control system housing 1546. The control system 1518 can also have a shank 1554 attached to the housing 1550. Each block 1524 can have a groove formed therein such that the groove in each block 1524 mates with the shank 1554. The blocks 1524 can be mounted on the shank 1554 such that the blocks 1524 can slide along the length of the shank 1554. In a preferred embodiment, the shank 1554 is a raised steel rod.

FIGS. 27A through 27D illustrate an embodiment of a bin 1608 for a sample dispenser 1500. The bins 1608 can be used to store and organize drugs within the dispenser 1500. In the embodiment shown, the bin 1608 have a housing 1614 with a front end 1610 and a back end 1612. The housing 1614 includes a handle 1620, a pushing device 1616 and a continuous torsion spring 1618. The handle 1620 is used to aid in removing the bin 1608 10 from the dispenser 1500. When the bin 1608 is empty, the pushing device 1616 is forced to the front end 1610 of the bin 1608 by the continuous torsion spring 1618. A user can then load medicines or drug packages into the bin 1608 by moving the pushing device 1616 to the back end 1612 of the bin 1608. Such motion provides storage space for the medicine and extend the continuous torsion spring 1618. As drug packages are removed from the bin 1608, the pushing device 1616 is forced toward the front end 1610 of the bin 1608 by the contracting continuous torsion spring 1618. In this embodiment, the user can know immediately whether a bin 1608 is empty or full. Incrementing a second drug package to the front end 1610 of the bin 1608 when a first drug package is removed ensures that a package will always be readily available. Such a unit can save the user time in guessing whether a bin is entirely empty or contains a package "hidden" in the back of a bin.

In another preferred embodiment, a drug dispenser dispense non-prescription, over-the-counter drugs to patients who can positively identify themselves to the drug dispenser system. FIGS. 28 through 34 illustrate embodiments of user interactive touch screens which can be used with such a system. The screens can provide a way for a user to interact with the software at the non-prescription dispenser.

Figure 28:
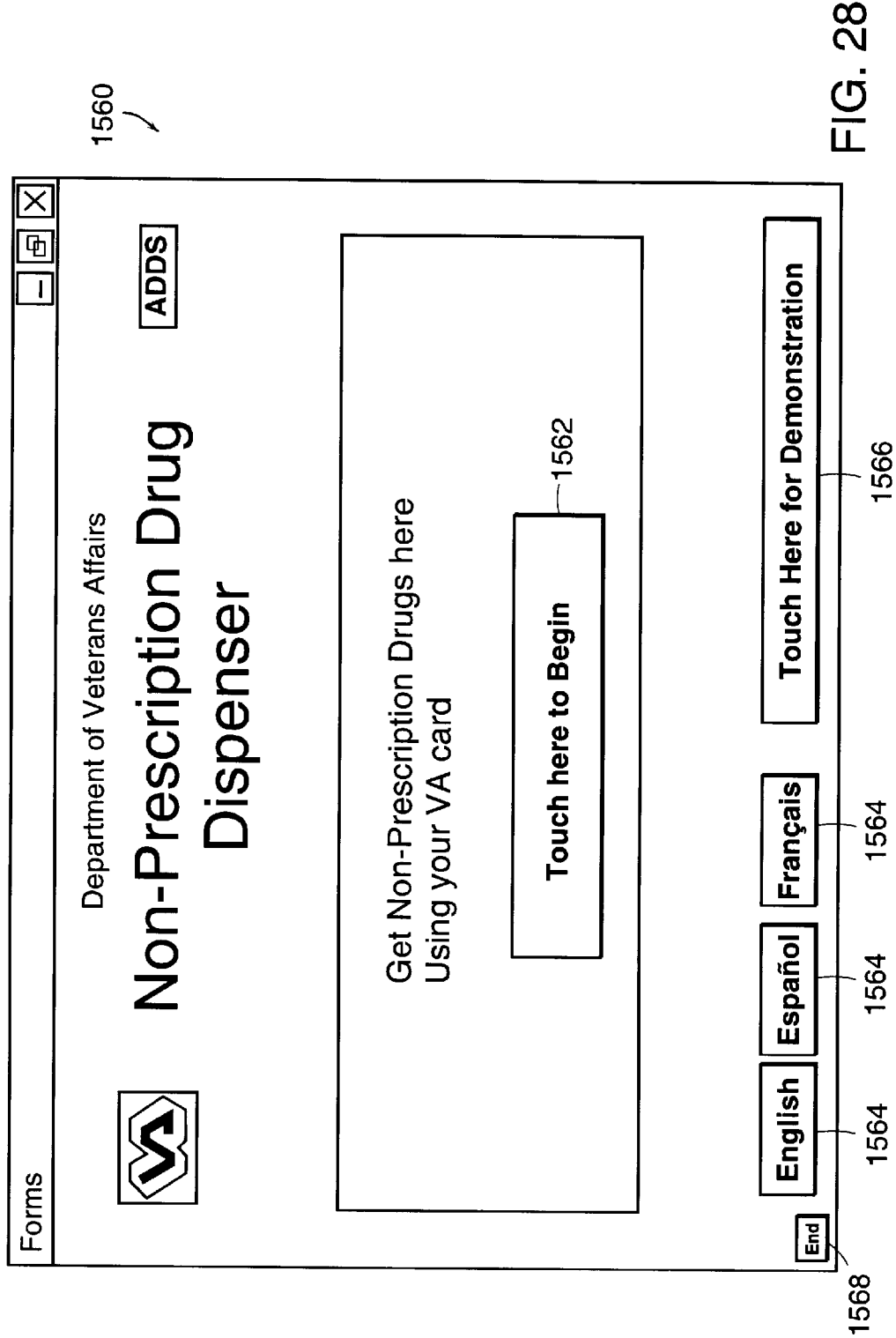
FIG. 28 illustrates a view of an introductory display screen that a user interfaces with to dispense a non-prescription drug in accordance with a preferred embodiment of the present invention.

FIG. 28 shows an introduction screen 1560 for a touch screen monitor of a non-prescription drug dispenser. The introduction screen 1560 can include a start command 1562, language option command 1564 and a demonstration command 1566. The start command 1562 can allow a user to progress through subsequent screens and choose the non-prescription drugs they wish to receive. The language option command 1564 allow a user the choice of language for subsequent display screens. The demonstration command 1566 can provide a demonstration of how the drug dispenser works. The introduction screen 1560, and all subsequent screens, can include an end command 1568 which allows a user to exit the screens at any point.

Figure 29:
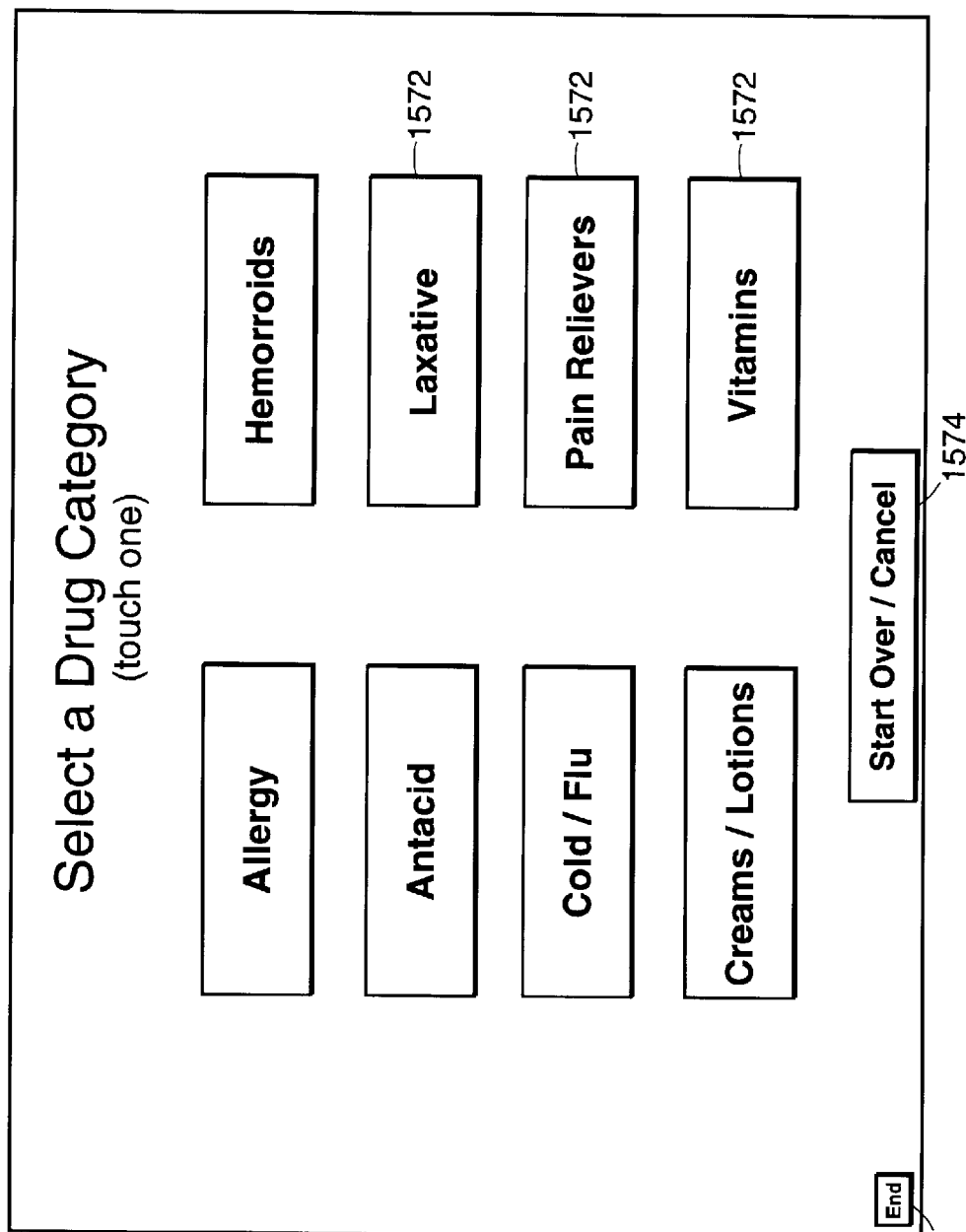
FIG. 29 illustrates a view of a display screen showing in particular a drug category selection screen that a user interfaces with to dispense a non-prescription drug in accordance with a preferred embodiment of the present invention.

FIG. 29 illustrates a drug category selection screen 1570 having drug category selections 1572 and a reset command 1574. The drug category selections 1572 allows a user to select the drug categories from which they would like to receive products. The drug categories can include medications for allergies, antacids, cold/flu, creams/lotions, hemorrhoids, laxatives, pain relievers and vitamins, for example. The reset command 1574 allows the user to start over or cancel his selection, if the wrong selection had been made.

Figure 30:
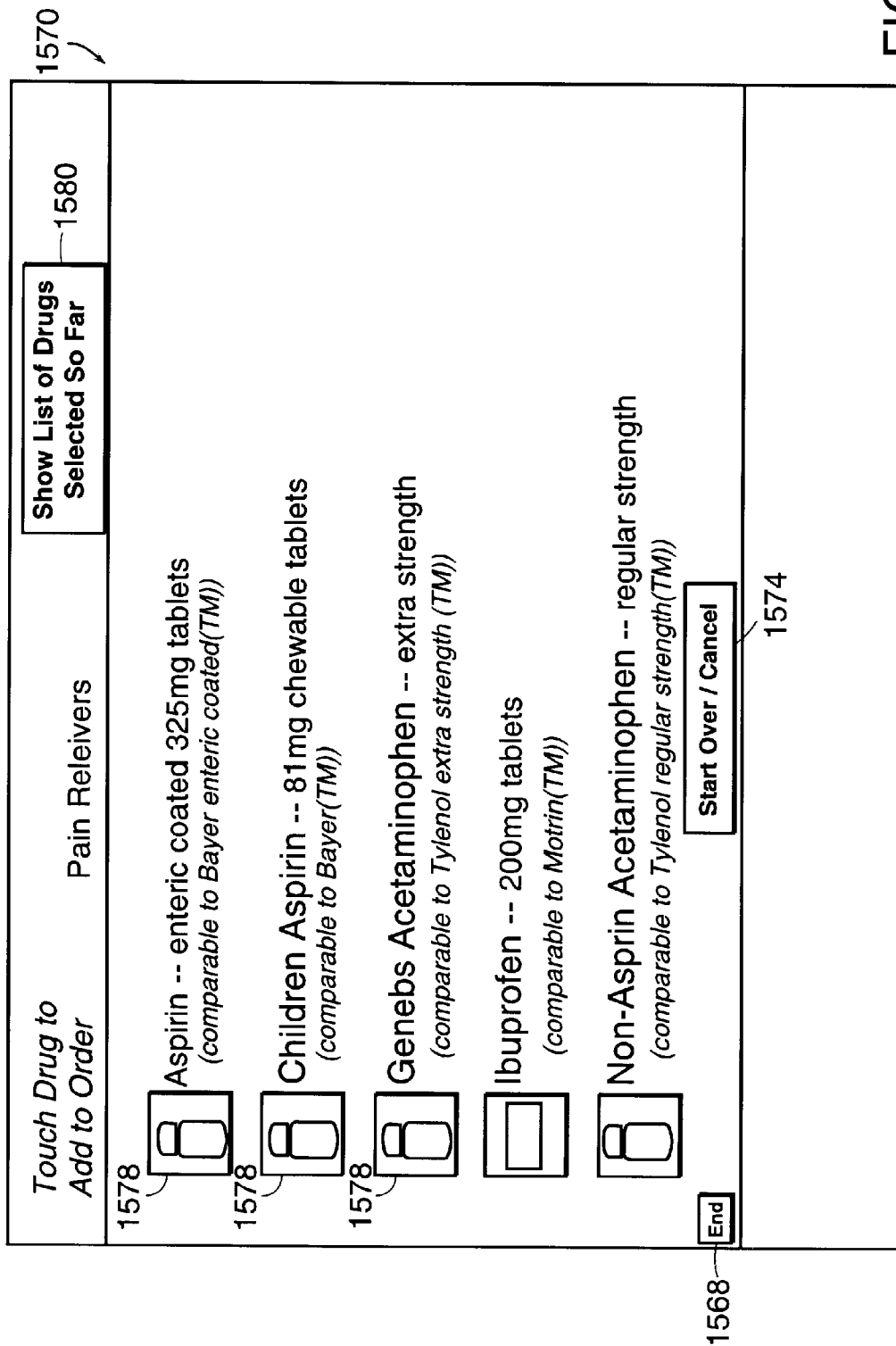
FIG. 30 illustrates a view of a display screen showing in particular a drug availability screen that a user interfaces with to dispense a non-prescription drug in accordance with a preferred embodiment of the present invention.

FIG. 30 illustrates a drug availability screen 1576 showing the availability of different dugs within a selected category. If a user selected Pain Relievers as a drug category, the screen shown in FIG. 30 can provide the user with a list of the types of pain relievers available. For example, under the pain relievers category, a user can choose from aspirin, children's aspirin, acetaminophen, ibuprofen or non-aspirin acetaminophen. The user can choose the drugs he wishes to receive, using the drug selection commands 1578. Each drug selection command 1528 can be associated with a particular drug. The drug availability screen 1576 can also have a drug list command 1580 which, when activated, can show the user a list of all of the drugs he has selected.

Figure 31:
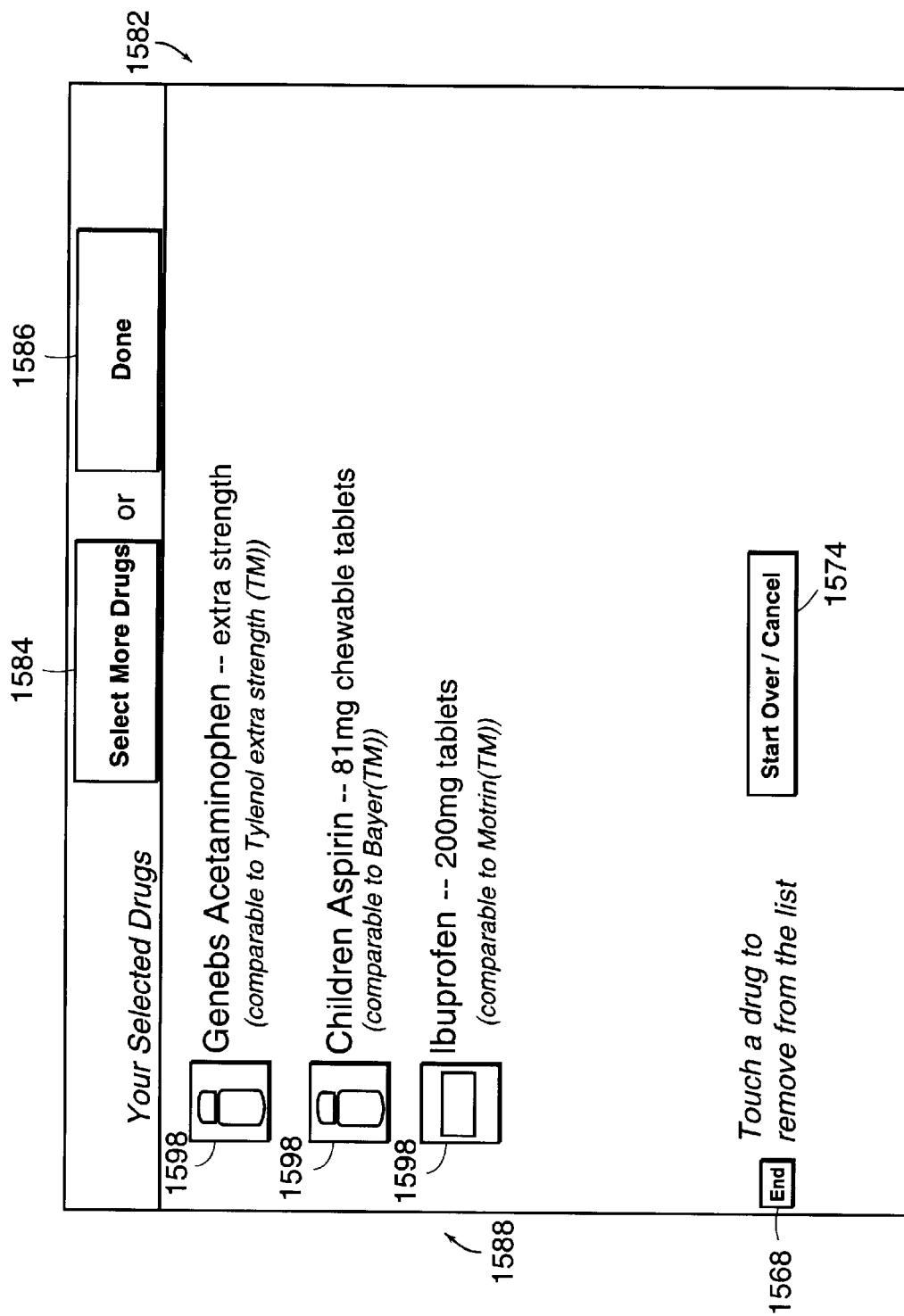
FIG. 31 illustrates a view of a display screen showing in particular a drug list screen that a user interfaces with to dispense a non-prescription drug in accordance with a preferred embodiment of the present invention.

FIG. 31 shows a drug list screen 1582 which lists the user's selection of drugs 1588. The drug list screen 1582 can include drug selection commands 1598 which allow a user to delete certain drug choices from the list. In one embodiment, to delete a drug choice, a user can touch a drug selection commands 1598 corresponding to the drug to be removed from the list. The drug list screen 1582 also shows a "continue" command 1584 and a "done" command 1586. The "continue" command 1584 allows the user to make further drug selections. The "done" command 1586 allows the user to exit the drug selection screens and receive the drugs he has chosen.

Figure 32:
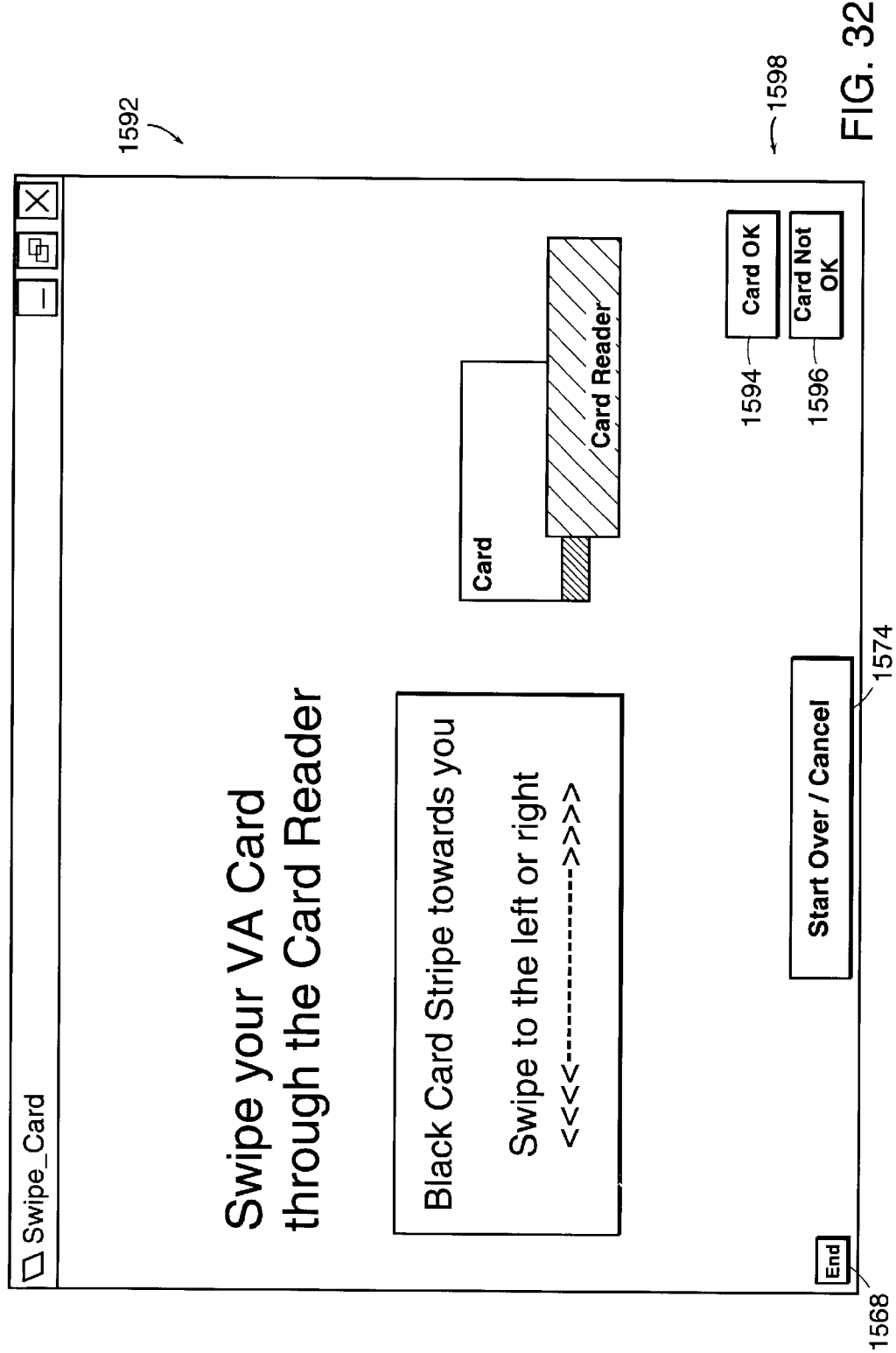
FIG. 32 illustrates a view of a display screen showing in particular a user identification screen that a user interfaces with to dispense a non-prescription drug in accordance with a preferred embodiment of the present invention.

FIG. 32 illustrates a user identification screen 1590. This screen 1590 instructs the user to identify himself to the drug dispensing system, in order for the drugs to be dispensed. In one embodiment, the user can be instructed to swipe his Veteran's Administration card through a card reader. The information on the user's card can then be compared to information within the system's database to determine the user's eligibility to receive the requested drugs. The user identification screen 1590 can also include user identification indicator buttons 1592. The buttons 1592 can include a positive identification button 1594, which indicates the user's identification as valid, or a negative identification button 1596, which indicates the user's identification as invalid.

Figure 33:
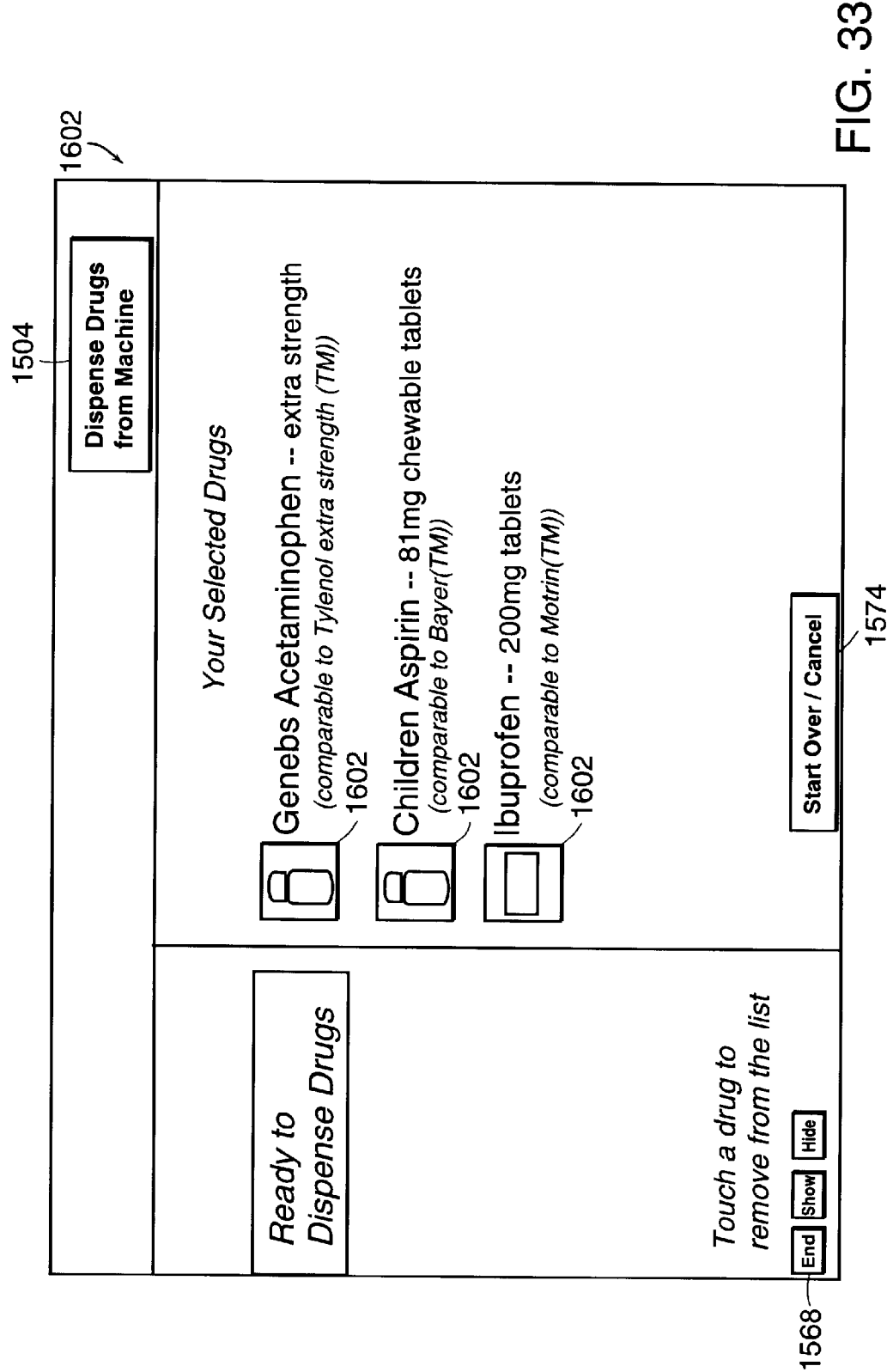
FIG. 33 illustrates a view of a display screen showing in particular a ready-to-dispense screen that a user interfaces with to dispense a non-prescription drug in accordance with a preferred embodiment of the present invention.

FIG. 33 shows a ready-to-dispense screen 1600 which can indicate the drugs the user has selected and will be dispensed. The ready-to-dispense screen 1600 can also include drug selection commands 1602 which allow a user to delete certain drug choices from the list. In one embodiment, to delete a drug choice, a user can touch a portion of the touch screen corresponding to a drug selection command 1602 which, in turn, corresponds to the drug to be removed from the list. The ready-to-dispense screen 1600 can also have a drug dispense command 1604. When a user is satisfied with his drug request, he can touch this button to begin the drug dispensing procedure.

FIG. 34 shows an ending screen 1606. The ending screen 1606 can provide instructions to the user involving picking up drugs from the dispenser tray and taking information from the printer. The ending screen 34 can also indicate to the user that the request is being processed and delivered.

Figure 35:
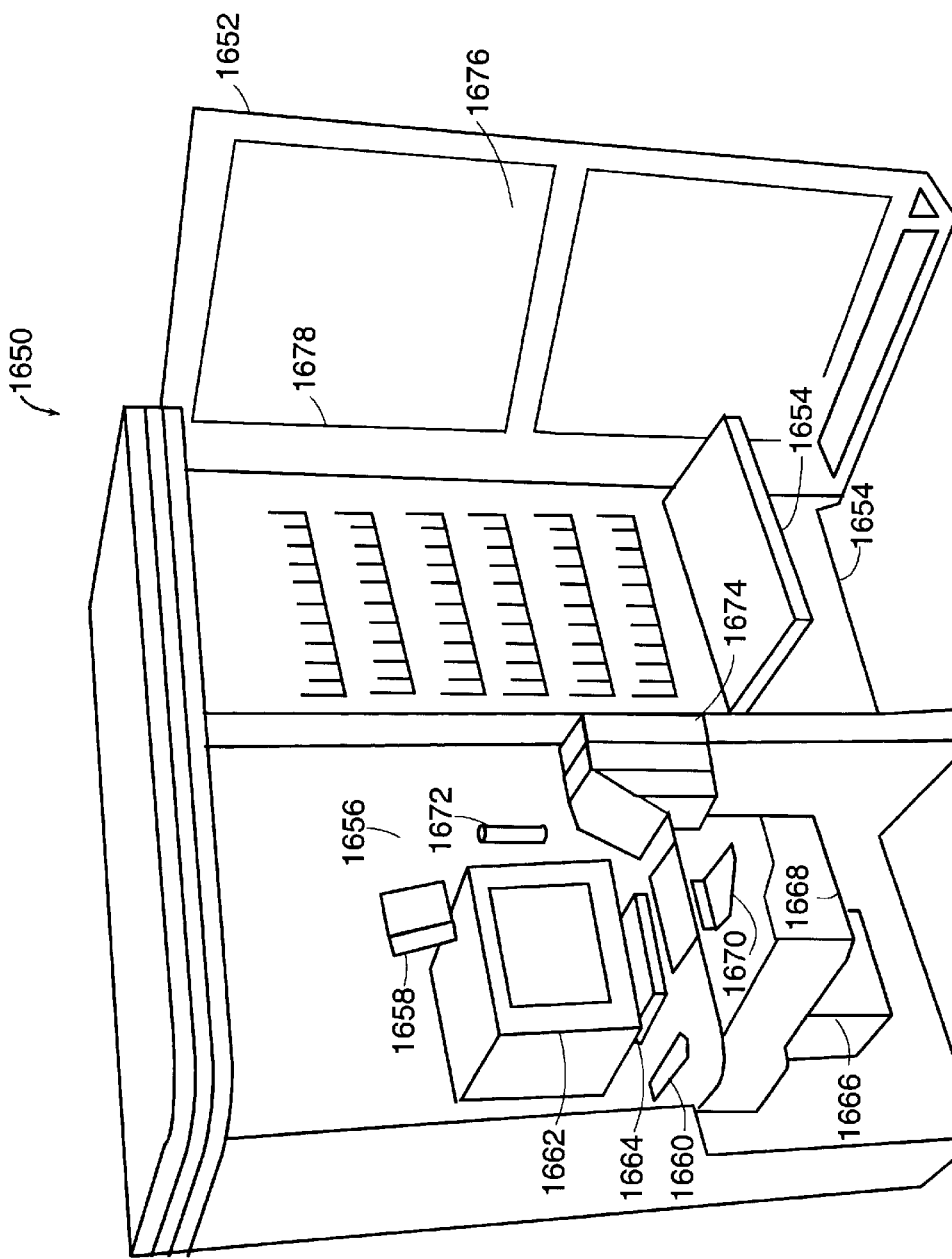
FIG. 35 illustrates a detailed view of the preferred embodiment of the non-prescription drug dispenser in accordance with the present invention.
Figure 36:
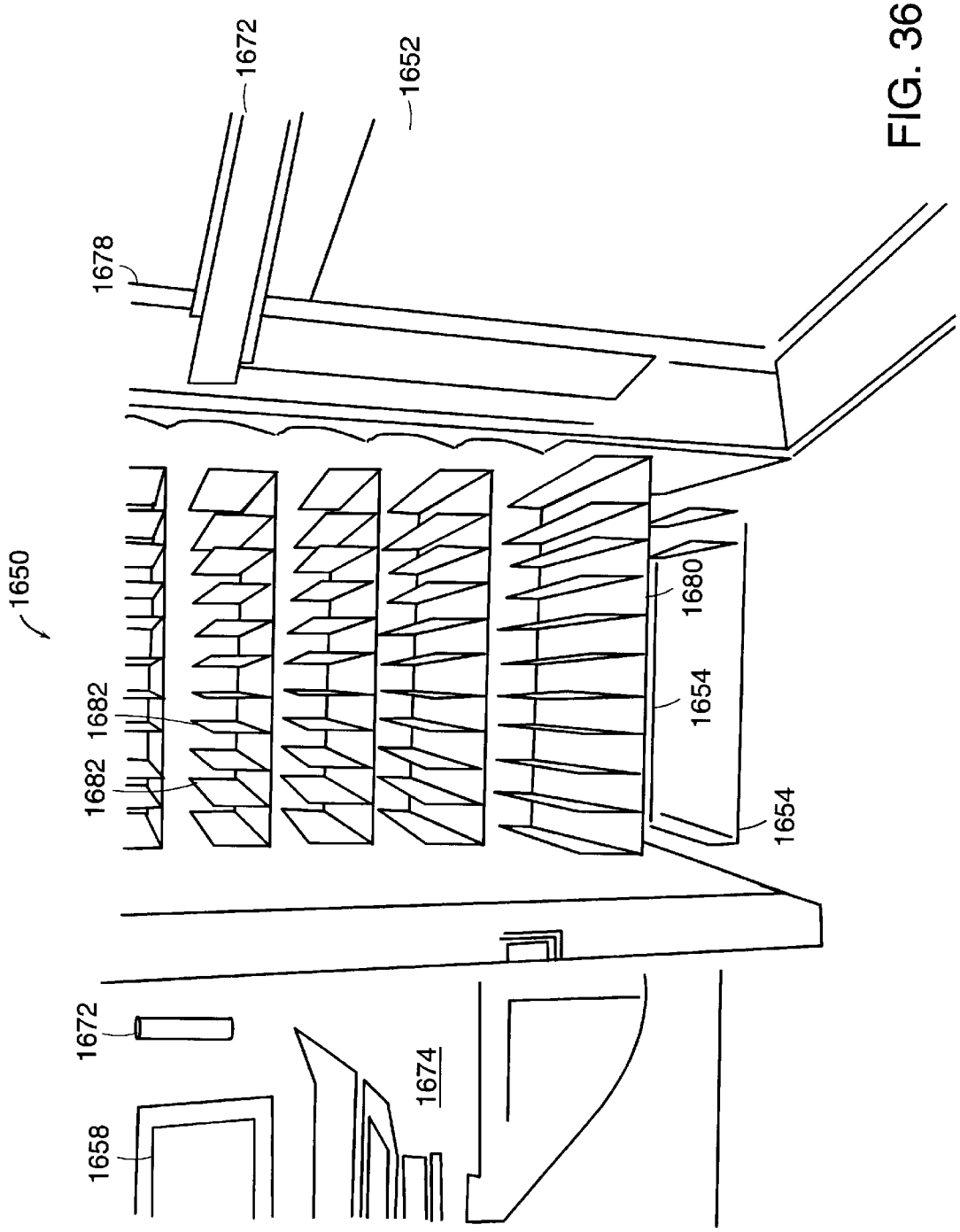
FIG. 36 illustrates a view of an embodiment of the helix trays of the non-prescription drug dispenser in accordance with the present invention.

FIGS. 35 and 36 illustrate an embodiment of an over-the-counter (OTC) medication dispenser 1650. The OTC medication dispenser 1650 can have a housing 1684 which includes a door 1652, drug storage trays 1654, a labeling device 1656, electronics 1658, a user identification system 1660, a computer 1666, a security monitoring device 1668, a magnetic card reader 1672 and a pickup location 1674. The computer 1666 can include a display 1662 and a printer 1664 having a paper pickup location 1674. The display 1662 can be a touch screen display. The display screen can display materials such as, for example, advertisement material pertinent to the nonprescription drugs or related educational material. The door 1652 is shown in an open position to better illustrate the drug storage trays 1654 of the medication dispenser 1650.

Both the user identification system 1660 and the magnetic card reader 1672 can be used to either permit or prevent a user's access to the medication dispenser 1650. The user identification system 1660 can be a fingerprint reader and, preferably, is a thumb print reader. However, other user identification systems can be incorporated, such as, for example, but not limited to, credit card, debit card, and smart card reader systems. The user identification system 1660 can compare the user's fingerprint data against fingerprint data contained in a database interfaced with the dispenser 1650.

The magnetic card reader 1672 can read information from a user's medication dispenser card, such as a Veteran's Administration card, and compare the information to that within a database interfaced with the dispenser 1650. In either the user identification system 1660 or the magnetic card reader 1672, if the user's information is present in the database, the user will be allowed to proceed and can receive his requested medication. Conversely, if the user's information is not located in the database, the user will not be able to proceed within the system or receive any medication. A dispenser 1650 can include either the user identification system 1660 or the magnetic card reader 1672, or both, depending upon the level of security required by the customer. For example, a dispenser 1650 located in a doctor's office can require a different level of security than a dispenser 1650 located in a methadone clinic. For customer's requiring a high level of security, the dispenser 1650 can include both the user identification system 1660 and the magnetic card reader 1672.

The electronics 1658 can include a camera, speakers or a microphone. The speakers or microphone can allow for user interaction with the computer 1666 with the presence of a voice recognition system. The camera can be connected to the security monitoring device 1668. The security monitoring device 1.668 can detect tampering of the dispenser 1650. In one embodiment, the security monitoring device 1668 can be an infrared detector. In another embodiment, the security monitoring device 1668 can be a vibration recorder. If the dispenser 1650 was tampered, the security monitoring device could cause the camera to create a photographic record of the area surrounding the dispenser 1650, for example. In one embodiment, the photographic record could be a digital image which could then be transferred to a monitoring station, byway of modem technology, for example.

The drug storage trays 1654, as shown in FIG. 36, can include a dispensing device. In a preferred embodiment, the dispensing device can include helix coils 1680. In a preferred embodiment, the helix coils 1680 are motor driven and allow the dispensing of medications to a user. When a user selects a medication to be dispensed from the dispenser 1650, the helix coil 1680 corresponding to the chosen medication can be forced to rotate, thereby causing the medication to move toward the door 1652 of the dispenser 1650 and into a collection tray 1676 located on the door 1652. The drug storage trays 1654 can also include dividers 1682. The dividers 1682 can be adjustable within the trays 1654 such that the trays 1654 can accommodate medication packages of varying sizes or shapes. The rotation of the helix coils 1680 can be controlled by some control system, such as a computer for example.

Figure 37:
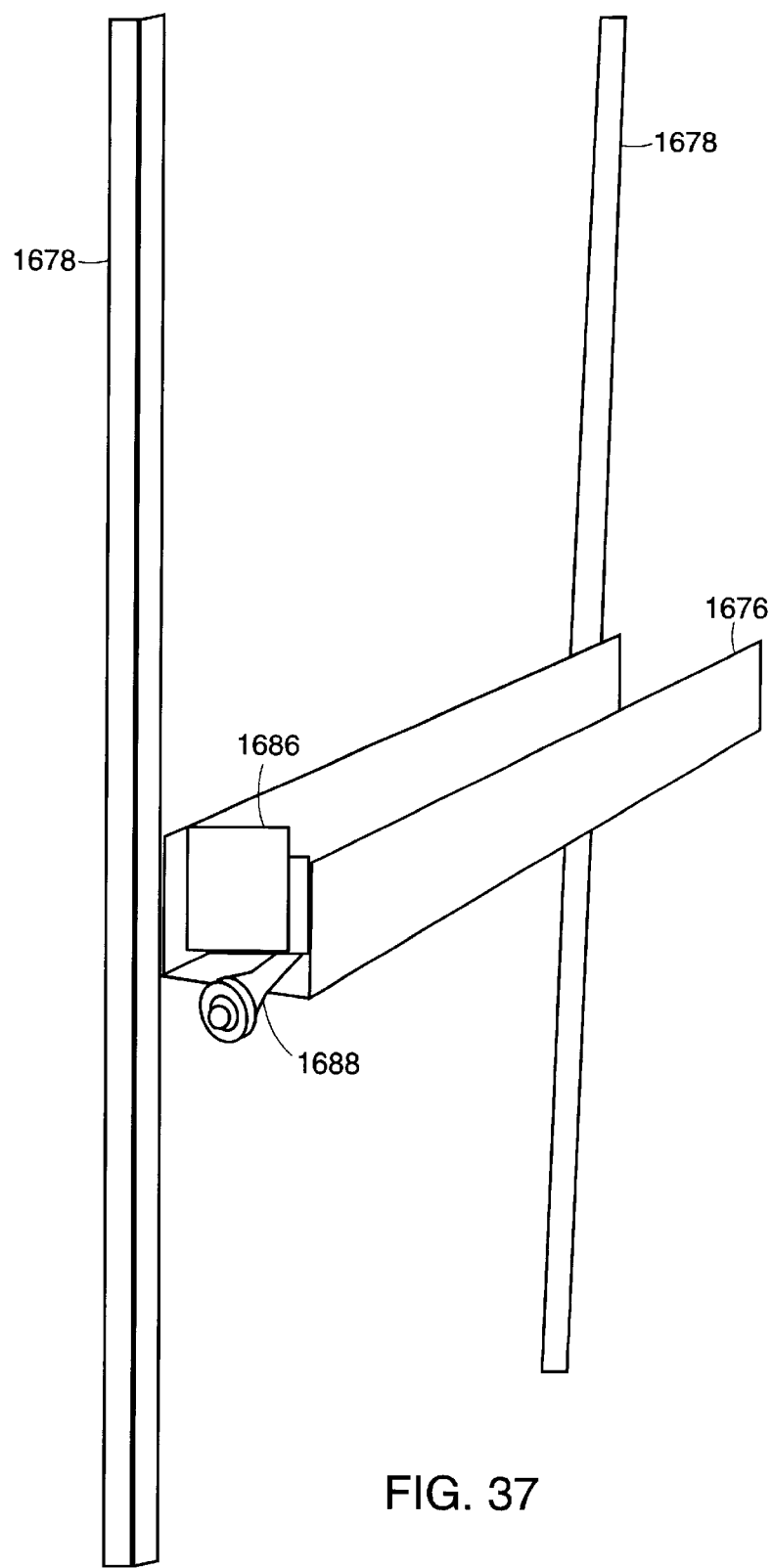
FIG. 37 illustrates a view of the details of an embodiment of a door installed in a preferred embodiment of the non-prescription drug dispenser in accordance with the present invention.

The door 1652 can be used to secure the drug storage trays 1654 and the medications within the housing 1684 of the OTC medication dispenser 1650. The door 1652 can include lifting mechanisms 1678, which are shown without the door 1652 in FIG. 37. The door 1652 can also include a collection tray 1676, a pushing device 1686 and a pushing device control 1688.

In a preferred embodiment, the lifting mechanisms 1678 are S-rail lifting screws. The S-rail lifting screws can be threaded through the collection tray 1676 and can rotate about a central axis, either in a clockwise or a counterclockwise direction, thereby causing the collection tray 1686 to translate in an upward or downward direction. The S-rail lift screws can also be Teflon coated to provide for smooth translation of the collection tray 1676.

The collection tray 1676 can be used to collect medicine packages from the drug storage trays 1654 and deliver the packages to the labeling device 1656. By allowing for the collection tray 1676 to translate upwards and downwards, the tray 1676 can collect medicine packages from drug storage trays 1654 located along the entire height of the dispenser 1650. Positioning the collection tray 1676 at a particular drug storage tray 1654 from which a package is being dispensed prevents the medicine in the package from being damaged by an impact after being dispensed. The positioning at the collection tray 1676 can be controlled by a control system, such as a computer, for example.

The collection tray 1676 can include a pushing device 1686 which can be used to move medical samples from the collection tray 1676 into the labeling device 1656. The pushing device 1686 can include a pushing device controller 1688 which controls the positioning of the pushing device 1686. In one embodiment, the pushing device controller 1688 is an S-rail screw. In another embodiment, a conveyor can be used as the pushing device controller 1688. The pushing device controller 1688 can be driven by a control system, such as a computer, for example.

When a user wishes to retrieve drugs from the OTC medication dispenser 1650, he can first be prompted to provide his identification, either by utilizing the user identification system 1660 or the magnetic card reader 1672, or both and can then enter his medication choices into the computer 1666. In another embodiment, the user can first be prompted to enter his drug choices and then be required to provide his identification to the dispenser 1650. Next, the collection tray 1676 can be forced to move, in either an upward or downward direction, to the drug storage trays 1654 which contain the requested medication. The helix coils 1680 can then be forced to rotate in the drug storage trays 1654 so as to advance the selected medication into the collection tray 1676. The collection tray 1676 can then be caused to move upwards or downwards to the labeling device 1656. The pushing device 1686 of the collection tray 1676 can then be caused to push the medication from the collection tray 1676 into the labeling device 1656. In the labeling device 1656, the drug can be identified by a barcode reader which can read the medication's barcode. The labeling device 1656 can also apply a label to the medication. The labeling device 1656 can then transfer the medication to the pickup location 1674. In a preferred embodiment, the labeling device 1656 can transfer the medication to the pickup location 1674 by a conveyance mechanism, such as an S-rail or a conveyor. In a preferred embodiment, the pickup location 1674 can have a cover which can be automated. When the medications arrive at the pickup location 1674, as requested by the user, the cover can open. Once the user removes the requested medications, the cover can automatically close and secure itself to the pickup location 1674.

Without limiting the generality of the claimed invention, those skilled in the art can appreciate that the components of the dispensing system—physical and program code—can be physically split and operated from different locations, connected together by a computer network. Further, components of the system can be divided and owned and operated by multiple entities, connected by a computer network if applicable.

It will be apparent to those of ordinary skill in the art that methods involved in the remote dispensing of pharmaceuticals or other medical products can be embodied in a computer program product that includes a computer usable medium. For example, such a computer usable medium can include a readable memory device, such as a hard drive device, a CD-ROM, a DVD-ROM, or a computer diskette, having computer readable program code segments stored thereon. The computer readable medium can also include a communications or transmission medium, such as a bus or a communications link, either optical, wired, or wireless, having program code segments carried thereon as digital or analog data signals.

Figure 38:
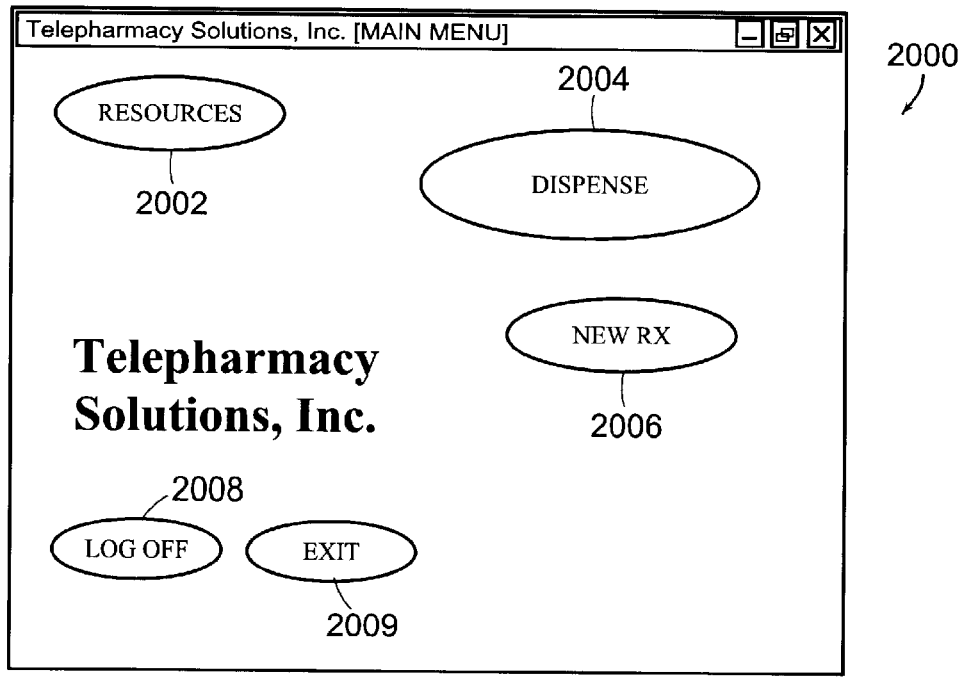
FIG. 38 illustrates a view of a display screen of a user interface showing a main screen used to dispense a prescription medical product in accordance with a preferred embodiment of the present invention.

FIG. 38 illustrates a view 2000 of a display screen of a user interface showing a main screen used to dispense a prescription medical product in accordance with a preferred embodiment of the present invention. The system is fully integrated with a pharmacy software system and if located at a medical facility, for example, a hospital can be integrated with the facilities software platforms and systems. The system enables the dispensing of starter prescription doses and initial fills at the point of care medical facility or at a remote dispensing site and captures mail order refills in a preferred embodiment. The preferred embodiment provides communication user interfaces to both local area networks (LANS) and wide area networks. A pharmacy workstation can be equipped with modems such as a 56 kps modem, for example, for telecommunication connections and 10/100 MB Ethernet Network Interface cards. The communication user interfaces support remote dispensing of medical products, real time, third party claims adjudication, remote diagnostics and maintenance. The first interface screen accessed by a user is the main screen 2000 which provides a user interface such as, for example, a touch screen that may offer gray scale images or a color touch screen having ergonomic, easy to use interfaces such as buttons. These interfaces include a resources button 2002, a dispense button 2004, a new RX button 2006, a log off button 2008 and an exit button 2009.

Figure 39:
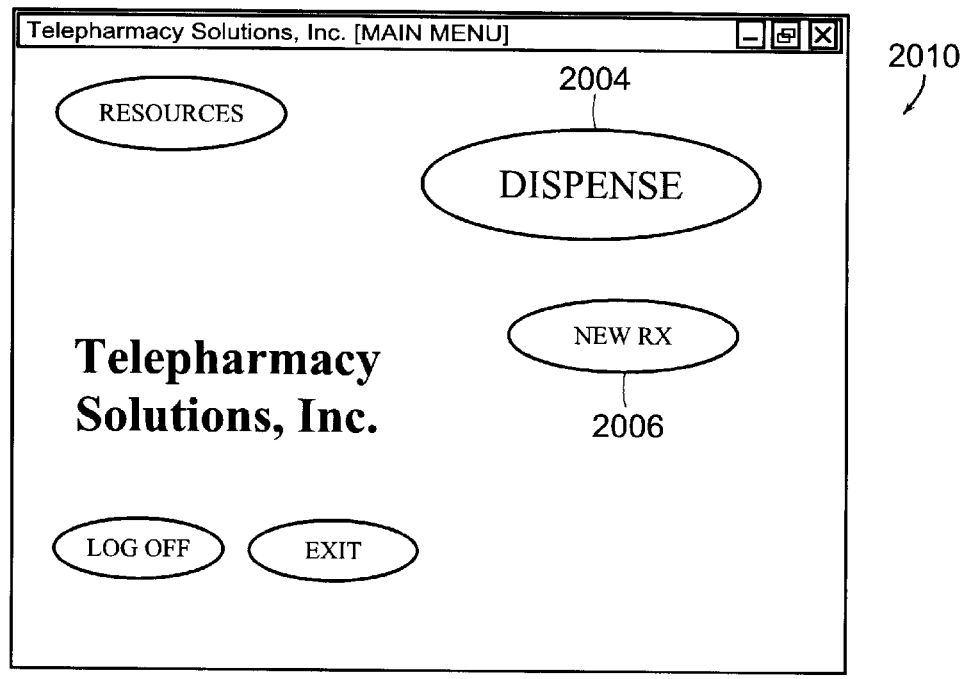
FIG. 39 illustrates a view of a display screen of a user interface illustrating use of a dispense function interface such as a button in accordance with a preferred embodiment of the present invention.

FIG. 39 illustrates a view 2010 of a display screen of a user interface illustrating use of a dispense function interface such as a button in accordance with a preferred embodiment of the present invention. A user activates the dispense button 2004 by touching the dispense button 2004. Where there is a medical product waiting to be dispensed the dispense interface button 2004 flashes with the number of medical products waiting in the queue. Clicking on the dispense button, 2004 allows access to the dispense screen.

Figure 40:
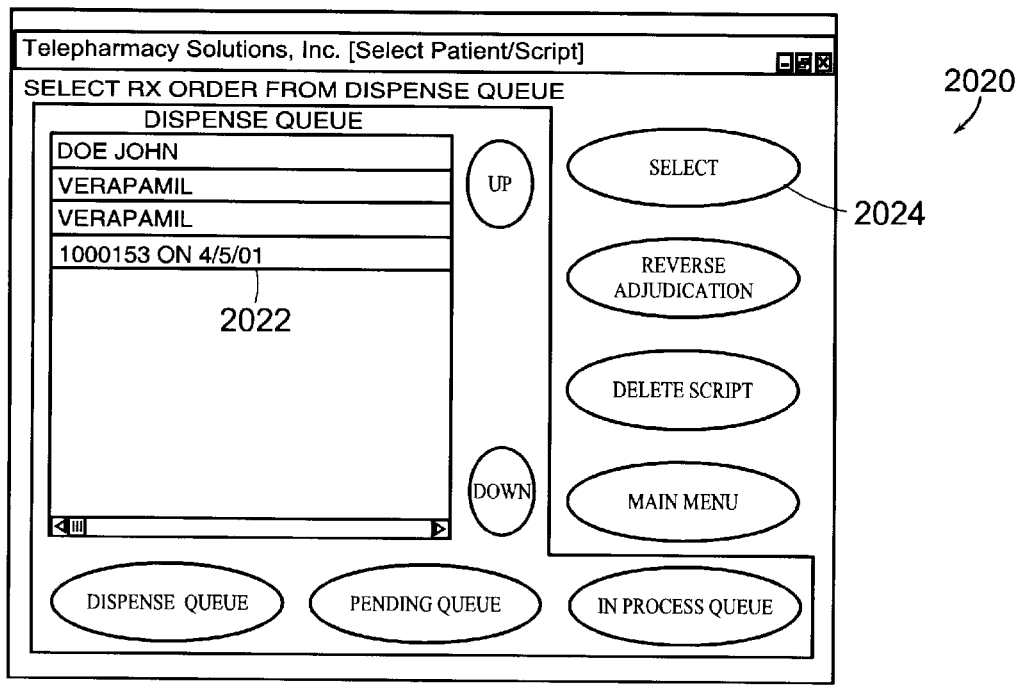
FIG. 40 illustrates a view of a display screen of a user interface illustrating a dispense queue in accordance with a preferred embodiment of the present invention.

FIG. 40 illustrates a view 2020 of a display screen of a user interface illustrating a dispense queue in accordance with a preferred embodiment of the present invention. The dispense queue screen has a list 2022 of medical products available for dispensing. The product to be dispensed is selected by clicking on the product or touching the screen to highlight it. A subsequent interface, the select button, 2024, for example, can be touched to select the product.

Figure 41:
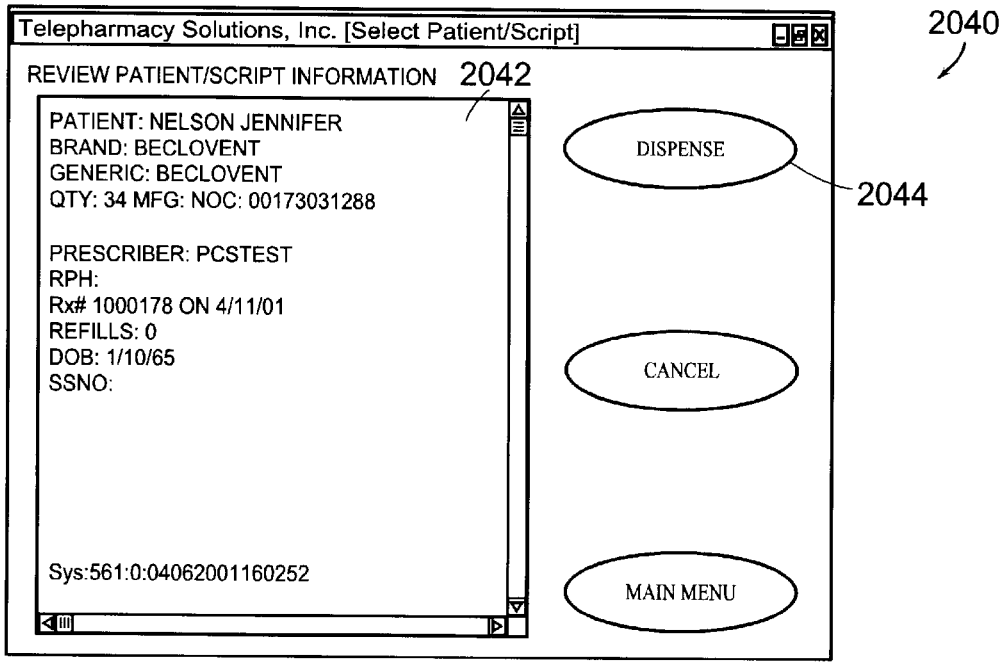
FIG. 41 illustrates a view of a display screen of a user interface showing a review of patient script information in accordance with a preferred embodiment of the present invention.

FIG. 41 illustrates a view 2040 of a display screen of a user interface showing a review 2040 of patient script information in accordance with a preferred embodiment of the present invention. The dispense screen provides all of the patient specific information 2042 for review. After reviewing the patient information for accuracy, the user can click on or touch the dispense button 2044.

Figure 42:
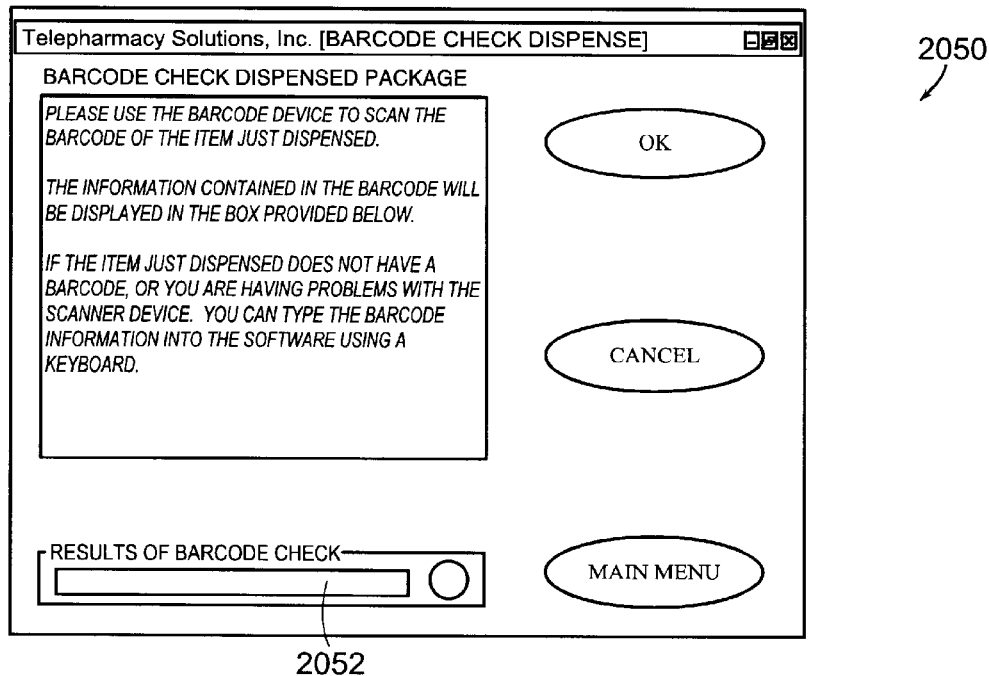
FIG. 42 illustrates a view of a display screen of a user interface showing the prompt for scanning a barcode on a medical product in accordance with a preferred embodiment of the present invention.

FIG. 42 illustrates a view 2050 of a display screen of a user interface showing the prompt for scanning a barcode on a medical product in accordance with a preferred embodiment of the present invention. The remote control dispensing system unit releases the medication to be dispensed to the user. The user is prompted to scan the barcode on the medication to identify the dispensed product as part of a verification method. This verification ensures that the product dispensed from the RCD system matches the prescription for the patient.

Figure 43:
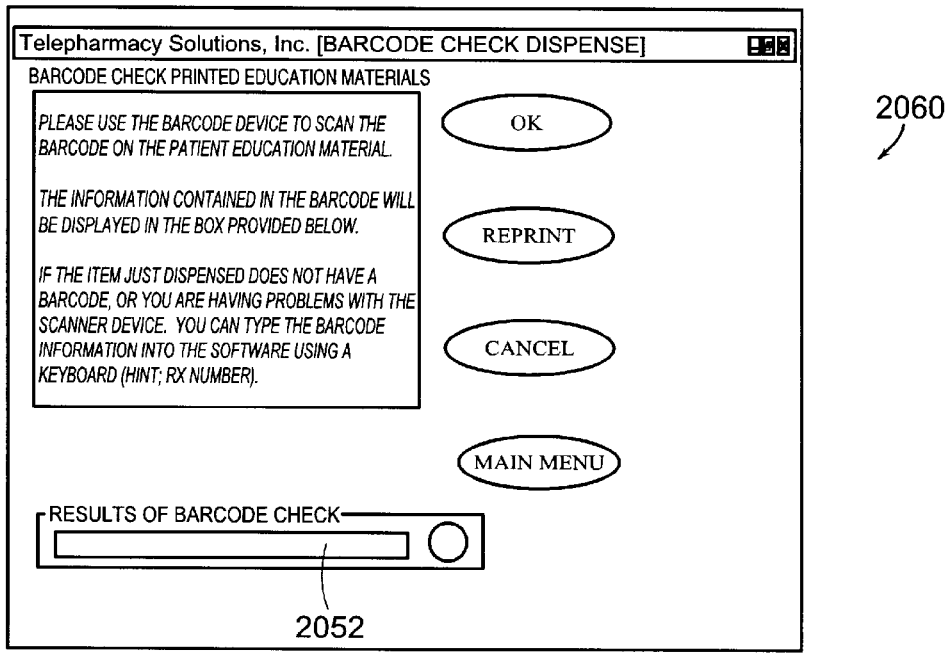
FIG. 43 illustrates a view of a display screen of a user interface showing the barcode check information in accordance with a preferred embodiment of the present invention.

FIG. 43 illustrates a view 2060 of a display screen of a user interface showing the barcode check information in accordance with a preferred embodiment of the present invention. As discussed hereinbefore, each medication or medical product dispensed has a barcode identifier label. Using a scanner, the barcode identifier is scanned and the barcode data appears in the field labeled "Results of Barcode Check" 2052. The proper completion of the printed label scan check returns the user to the main screen described with respect to FIG. 38.

Figure 44:
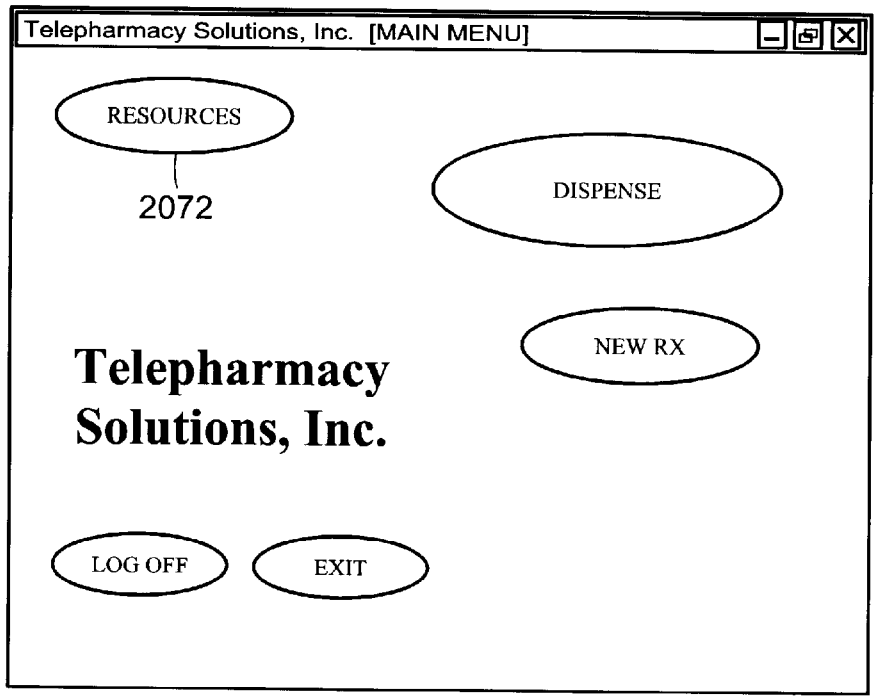
FIG. 44 illustrates a view of a display screen of a user interface showing the access of the resources function by interacting with the "Resources" button in accordance with a preferred embodiment of the present invention.

FIG. 44 illustrates a view 2070 of a display screen of a user interface showing the access of the resources function by interacting with the resources button 2072 in accordance with a preferred embodiment of the present invention. All non-dispensing functionality is provided by the resource interface and executable instructions provided with respect to the resources interface. Interaction with the resources button 2072, for example, by touch or clicking on it using a computer mouse provides access to view the resources screen which is analogous to access to inventory management.

Figure 45:
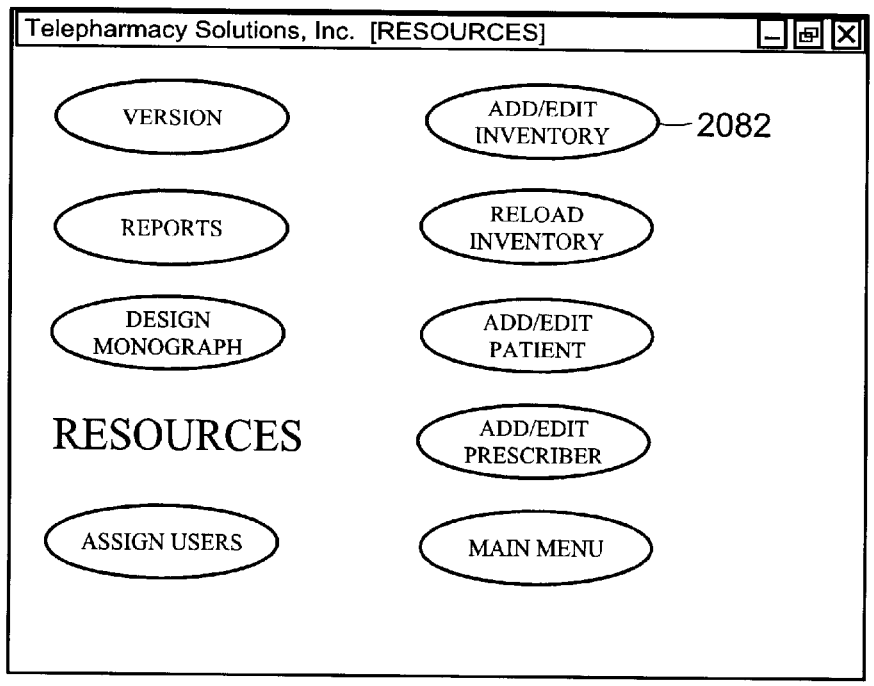
FIG. 45 illustrates a view of a display screen of a user interface showing the details of the resources function in accordance with a preferred embodiment of the present invention.

FIG. 45 illustrates a view 2080 of a display screen of a user interface showing the details of the "Resources" function in accordance with a preferred embodiment of the present invention. The resources screen 2080 has a user interface button 2082 to add/edit inventory.

Figure 46:
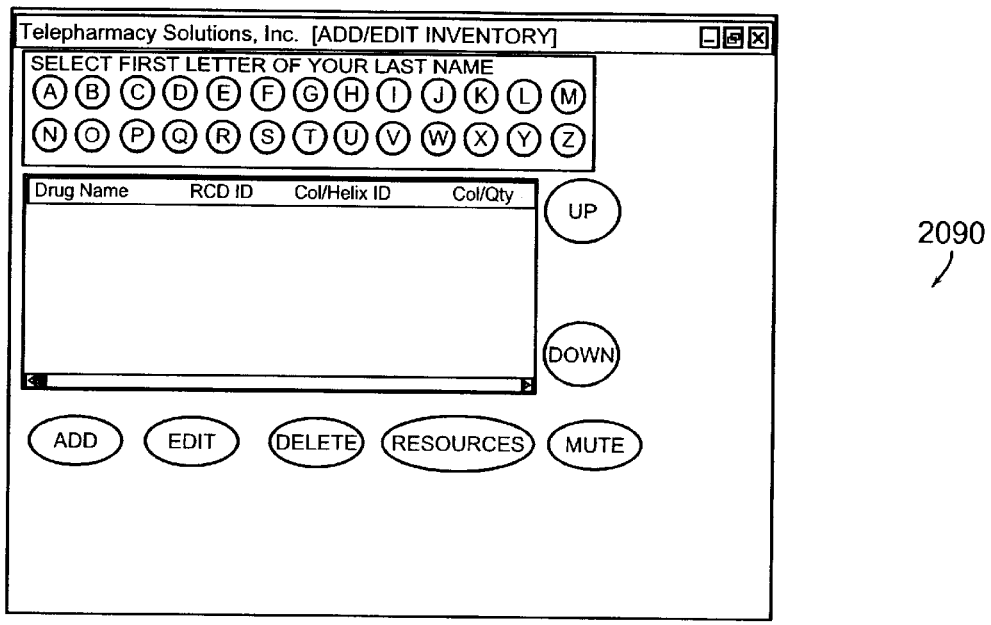
FIG. 46 illustrates a view of a display screen of a user interface showing the method of selecting the drug that needs to be accessed and edited in accordance with a preferred embodiment of the present invention.

FIG. 46 illustrates a view 2090 of a display screen of a user interface showing the method of selecting the medical product, for example, a drug that needs to be accessed and edited in accordance with a preferred embodiment of the present invention. For ease of accessing the drug a first letter of the drug to be edited can be selected from the interface buttons 2092 a–z indicative of the alphabet.

Figure 47A:
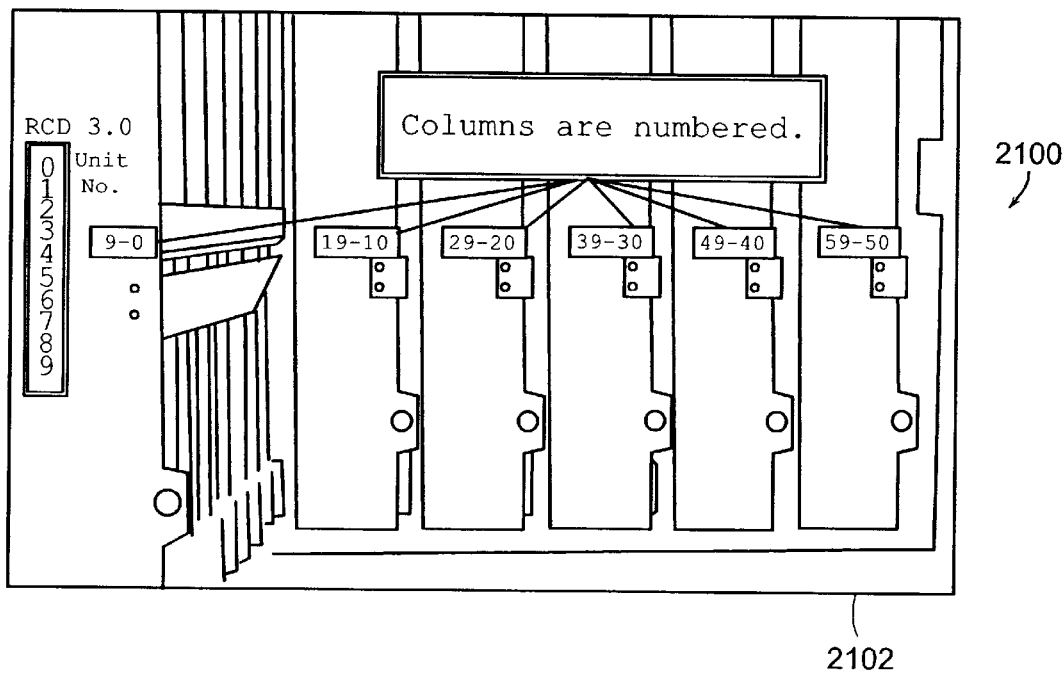
FIGS. 47A and 47B illustrate a preferred embodiment of a remote control dispensing system, the resources of which are being managed by the user interface described with respect to FIG. 45 and FIG. 46 in accordance with the present invention.
Figure 47B:
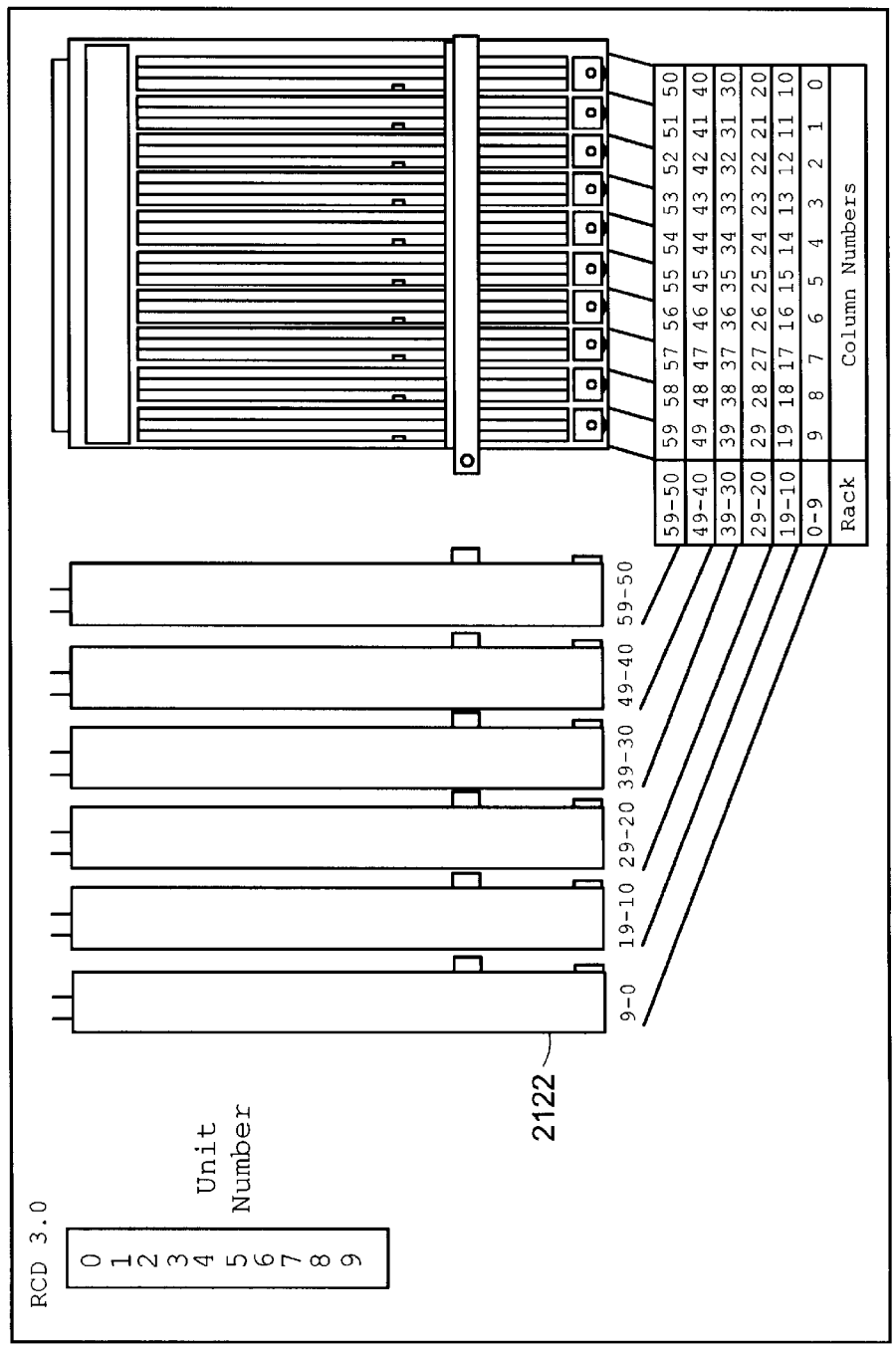

FIGS. 47A and 47B illustrate a preferred embodiment of a remote control dispensing system, the resources of which are being managed by the user interface described with respect to FIG. 45 and FIG. 46 in accordance with the present invention. The RCD 2010 can have a total of 60 columns 2102, for example. When the medical products are loaded, the bottles, for example, are loaded horizontally with the cap first to ensure that they are dispensed properly during the dispensing process. The columns can be numbered and the name of the medical products can be attached to columns to assist with a loading or reloading process. FIG. 47B illustrates a schematic 2120 that can be attached to the inside of the dispenser door. The RCD, in a preferred embodiment, has helixes placed in multiple slots, such as 30 slots. A helix clips on to a plastic cam, which in turn clips on to the rotor of a small electronic motor attached to the back of the dispense drawer. The terminus or small end of the helix sits roughly in the 12 o'clock position when at rest. Helixes come in multiple sizes, with larger sizes holding larger medical products when loading the RCD, the medical products are placed between the coils of the helix starting with the space in front. In a preferred embodiment the item is made to lean forward to ensure that the item falls correctly during the dispense process.

In a preferred embodiment, some items must be put into clear plastic containers so they discharge properly. The dividers between the slots are anchored to the drawer by a nut at the top and back of the dispense drawer. There is one nut per drawer. Should an item not fit into a standard sized slot, the dividers between the slots can be adjusted. This can be accomplished by first unclipping the neighboring motor from the slot next to the one needing adjustment. Removing the motor provides better access to the nut to be loosened.

After the nut has been removed, the divider can be moved. After the desired width is selected, the flanges are clipped on the bottom of the divider into the slots on the bottom of the dispense drawer, and the nut is tightened. Note that the motor removed from the drawer cannot be used for dispensing.

In the preferred embodiment if a drug does not fit into a modified slot in the RCD, it can be stored in the storage drawer (bottom drawer) and entered into the inventory. The dispense door still opens, but the drug has to be manually retrieved from the storage drawer.

Figure 48:
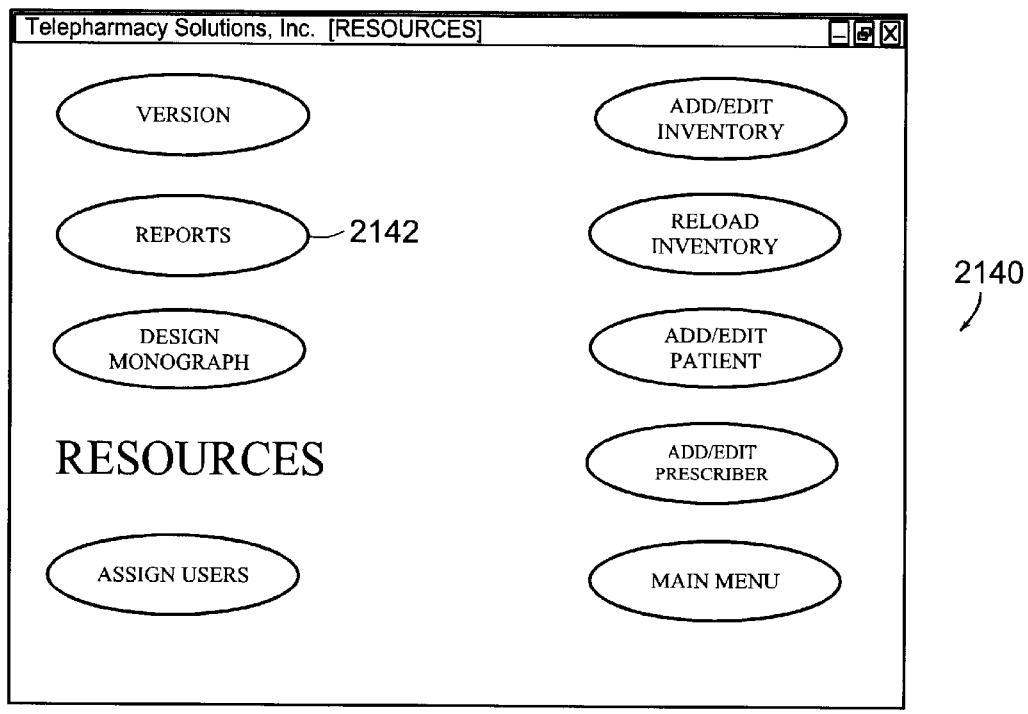
FIG. 48 illustrates a view of a display screen of a user interface showing the access of the reporting function by the use of the "reports" button in accordance with a preferred embodiment of the present invention.

FIG. 48 illustrates a view 2140 of a display screen of a user interface showing the access of the reporting function by the use of the reports button 2142 in accordance with a preferred embodiment of the present invention. To navigate to the reports menu the user thus touches or clicks on the resources button in the main screen as shown in FIG. 38 which provides access to all non-dispensing functionality and then clicks or touches the interface button "Reports" 2142.

Figure 49:
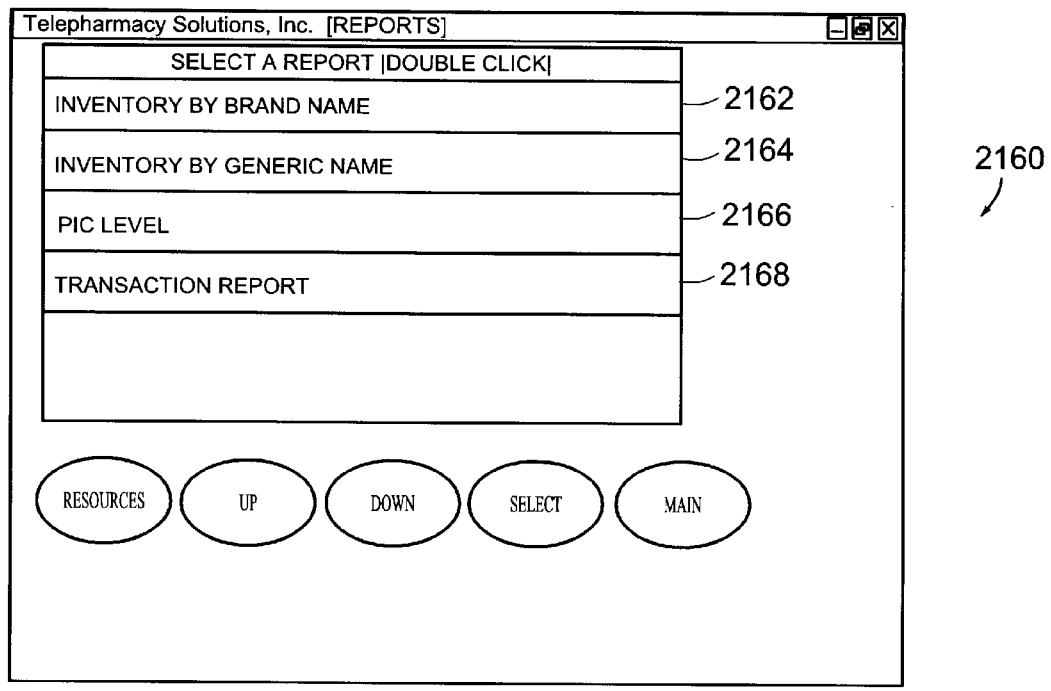
FIG. 49 illustrates a view of a display screen of a user interface showing the selections of reports available in accordance with a preferred embodiment of the present invention.

FIG. 49 illustrates a view 2160 of a display screen of a user interface showing the selections of reports available in accordance with a preferred embodiment of the present invention. A type of report is selected by double clicking or touching it. In a preferred embodiment, the system provides four types of reports. The first report being inventory by brand name report 2162. This report provides information by brand name on the current number of drug packages in the RCD unit as well as the location of the drugs in the RCD unit (column/helix). The second report is inventory by generic name report 2164. This report provides information by generic name on the current number of drug packages in the RCD unit as well as the location of the drugs in the RCD unit (column/helix). The next report is called the PIC level report 2166. This report provides documentation of drugs that are at or below the set PIC level. The last report, but not limited to, is the transaction report 2168. This report provides documentation on all transactions completed by the drug dispensing software.

Figure 50:
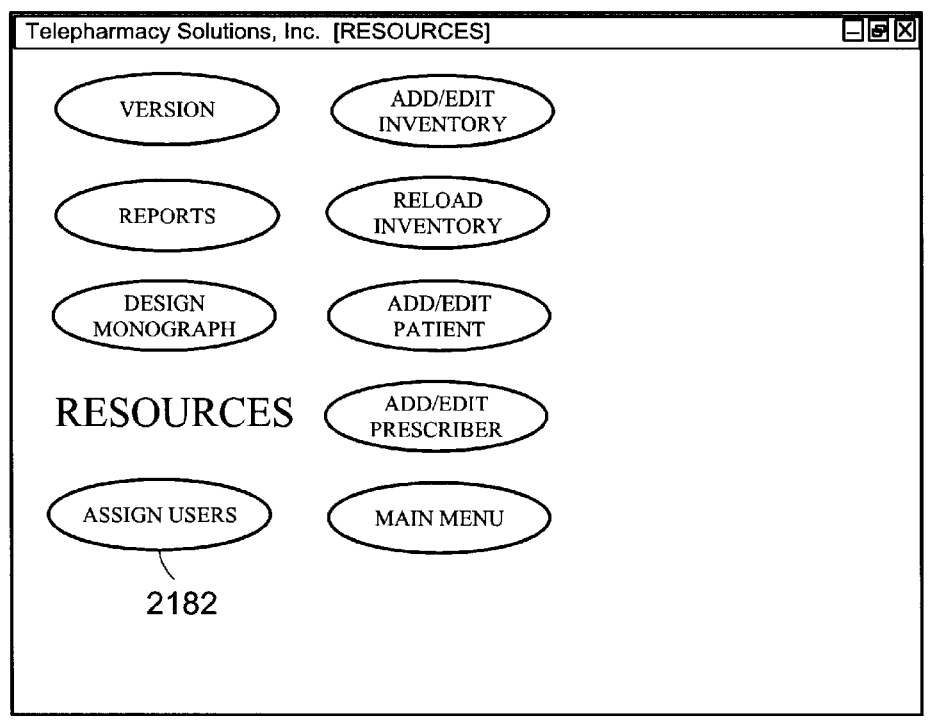
FIG. 50 illustrates a view of a display screen of a user interface showing the access to an "Assign User" functionality by the use of a particular button in accordance with a preferred embodiment of the present invention.

FIG. 50 illustrates a view 2180 of a display screen of a user interface showing the access to an "Assign User" functionality by the use of a particular button in accordance with a preferred embodiment of the present invention. The assign users button 2182 is accessed after touching or clicking the resources button on the main screen. Each user has a user name, user ID and password. User access to the executable instructions is limited to four levels: password control, dispense authority, inventory control and schedule for dispensing. The individual with password control determines user access.

Figure 51:
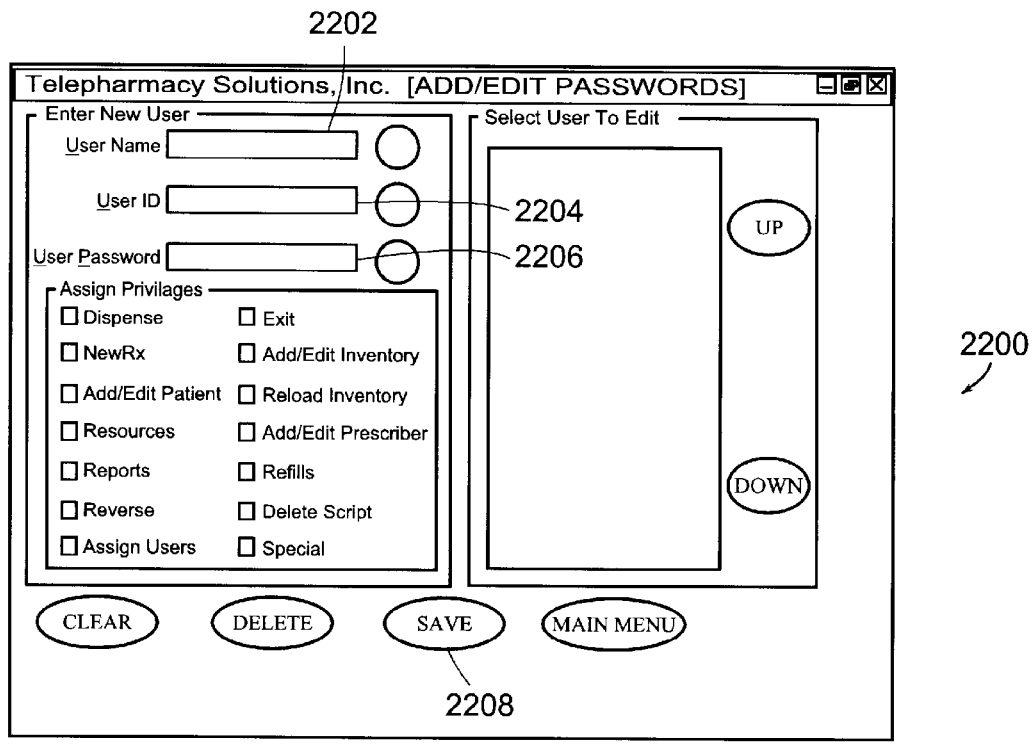
FIG. 51 illustrates a view of a display screen of a user interface showing the method used to add a new user to the system in accordance with a preferred embodiment of the present invention.

FIG. 51 illustrates a view 2200 of a display screen of a user interface showing the method used to add a new user to the system in accordance with a preferred embodiment of the present invention. The responsibility to add a new user and enter the pertinent information rests with the password administrator. At the display screen 2200 the user creates their own User ID by typing in a unique configuration of numbers and letters in the User ID field 2204 and then the password in field 2206. In the field corresponding to the user name 2202 the actual name of the user is entered. In a subsequent step the user's permission level is checked and by activating the save button interface the information is saved.

Figure 52:
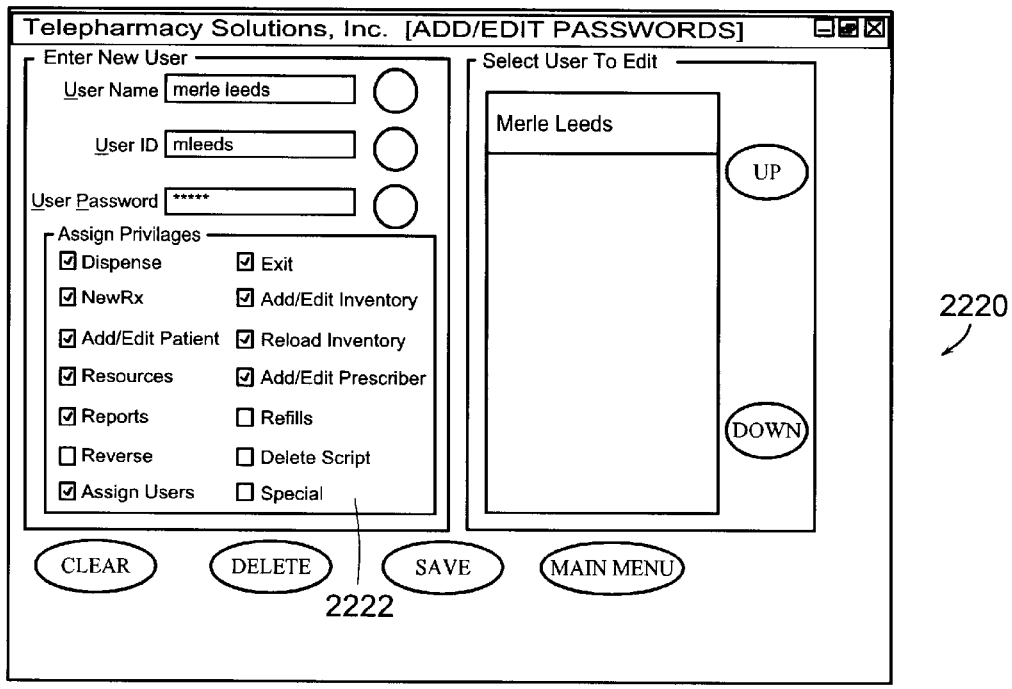
FIG. 52 illustrates a view of a display screen of a user interface showing the method to edit user privileges in accordance with a preferred embodiment of the present invention.

FIG. 52 illustrates a view 2220 of a display screen of a user interface showing the method to edit user privileges in accordance with a preferred embodiment of the present invention. To edit user privileges 2222 the name of the user to be edited is activated by touching the screen or clicking to highlight the name. Then the privileges are either checks or unchecked by the checks in boxes next to the appropriate privileges. The password administrator has the responsibility to assign privileges.

Figure 53:
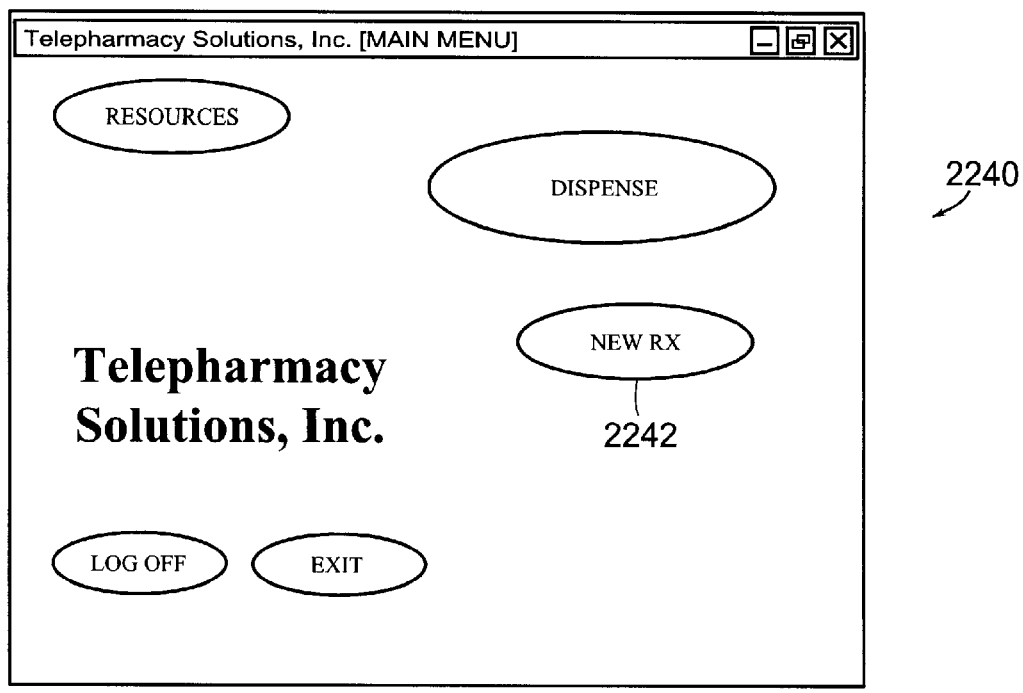
FIG. 53 illustrates a view of a display screen of a user interface showing the use of the "New Rx" interface button in accordance with a preferred embodiment of the present invention.

FIG. 53 illustrates a view 2240 of a display screen of a user interface showing the use a method to create a new medical product prescription (Rx) using the "New Rx" interface button in accordance with a preferred embodiment of the present invention. The user begins from the display screen 2240 by selecting the "New Rx" interface button 2242 either by touching the interface or clicking on New Rx button 2242.

Figure 54:
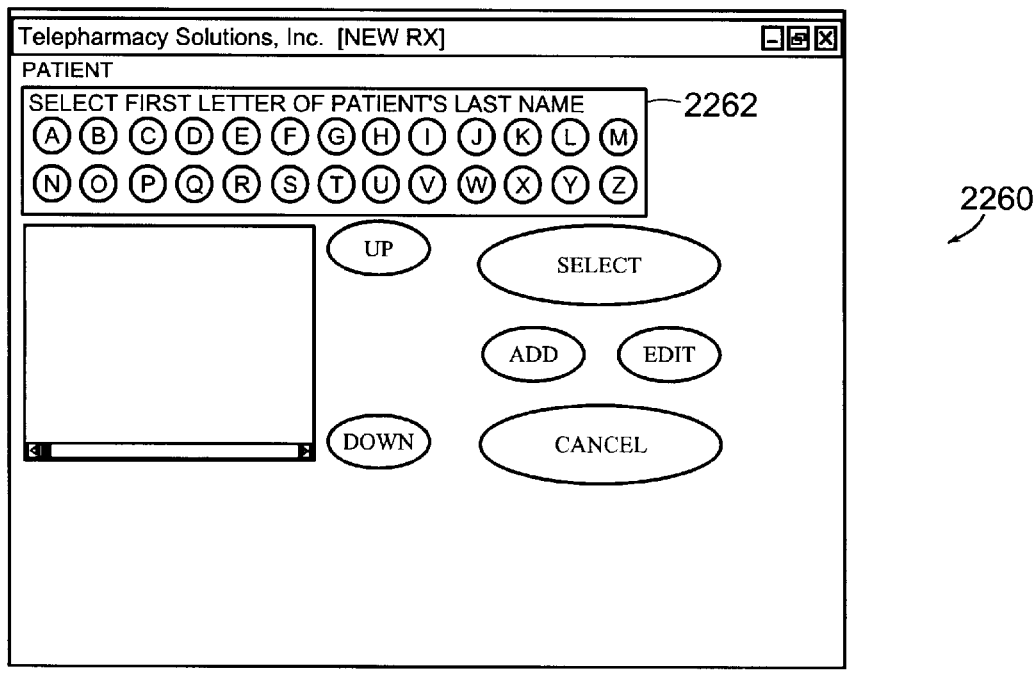
FIG. 54 illustrates a view of a display screen of a user interface showing the method used to select the patient in the "New Rx" option in accordance with a preferred embodiment of the present invention.

FIG. 54 illustrates a view 2260 of a display screen of a user interface showing the method used to select the patient in the "New Rx" option in accordance with a preferred embodiment of the present invention. The patient is selected by accessing the interface 2262 that provides an alphabet panel by, for example, touching or clicking on the first letter of a patient's last name.

Figure 55:
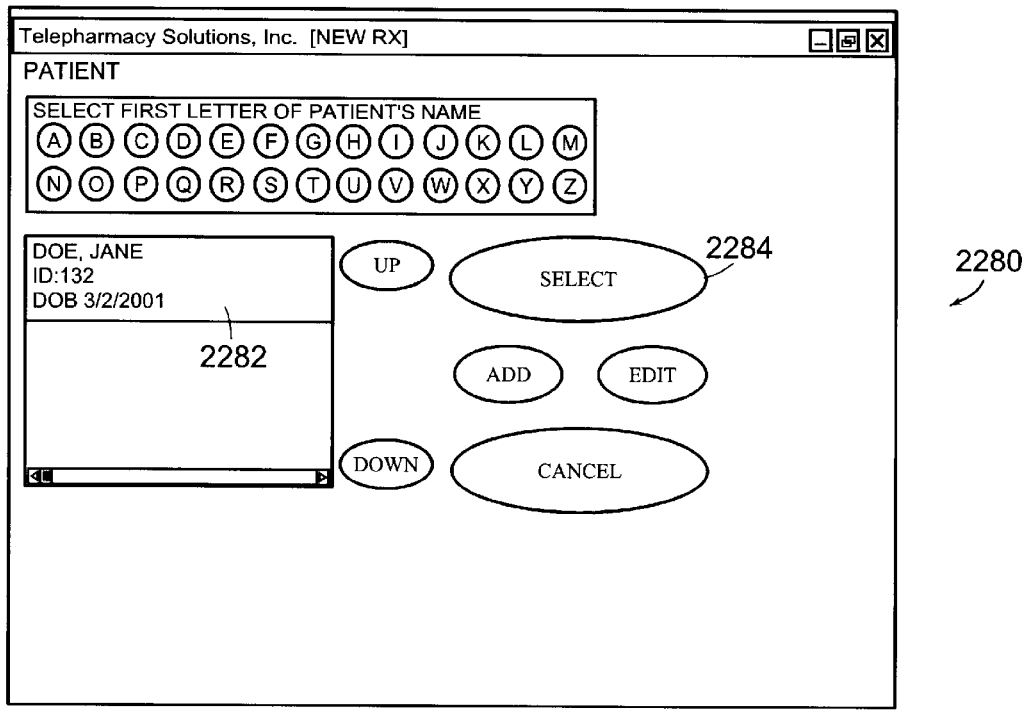
FIG. 55 illustrates a view of a display screen of a user interface showing the next step in the method to select the patient in accordance with a preferred embodiment of the present invention.

FIG. 55 illustrates a sequential view 2280 of a display screen of a user interface showing the next step in the method to select the patient in accordance with a preferred embodiment of the present invention. The patient's name is highlighted 2282 by clicking or touching the patient's name that is listed under the particular alphabet. The name is selected by interfacing by touch or via the mouse click with the select button 2284.

Figure 56:
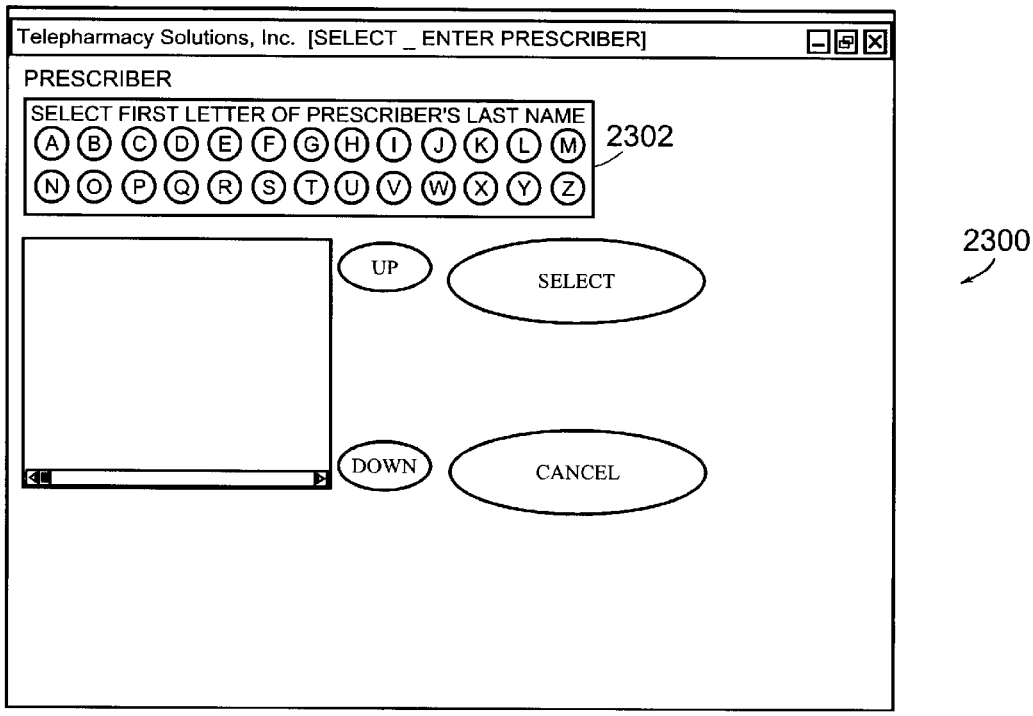
FIG. 56 illustrates a view of a display screen of a user interface showing a method to select a prescriber in accordance with a preferred embodiment of the present invention.

FIG. 56 illustrates a view 2300 of a display screen of a user interface showing a method to select a prescriber in accordance with a preferred embodiment of the present invention. Similar to the method to select the patient, a first letter of the last name of the prescriber is selected from an alphabet panel 2302.

Figure 57:
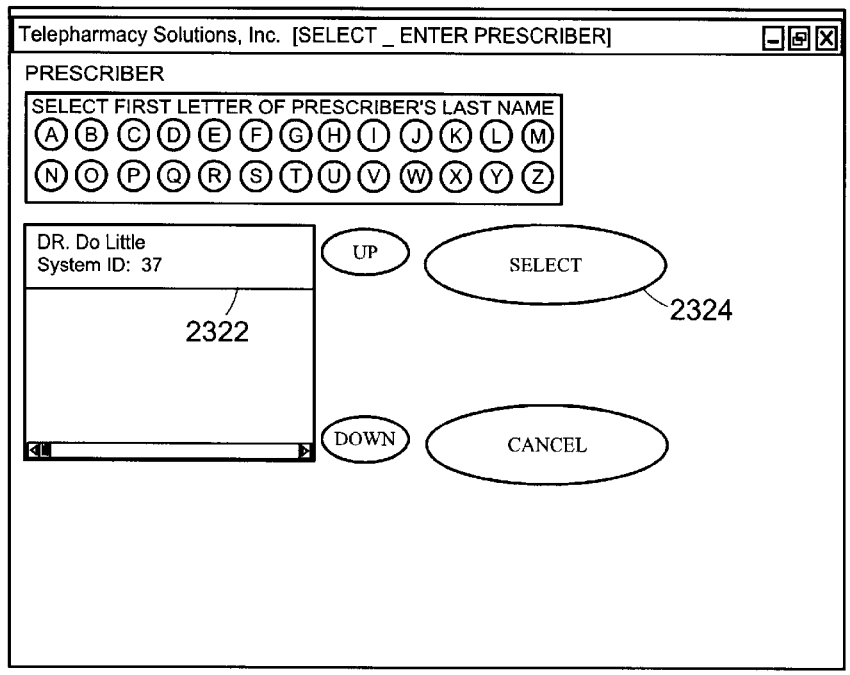
FIG. 57 illustrates a view of a display screen of a user interface showing a subsequent step in the method used to select the prescriber in accordance with a preferred embodiment of the present invention.

FIG. 57 illustrates a view 2320 of a display screen of a user interface showing a subsequent step in the method used to select the prescriber in accordance with a preferred embodiment of the present invention. The prescriber is selected by clicking or touching on the prescriber's name 2322 and then selecting the prescriber by clicking or touching the screen.

Figure 58:
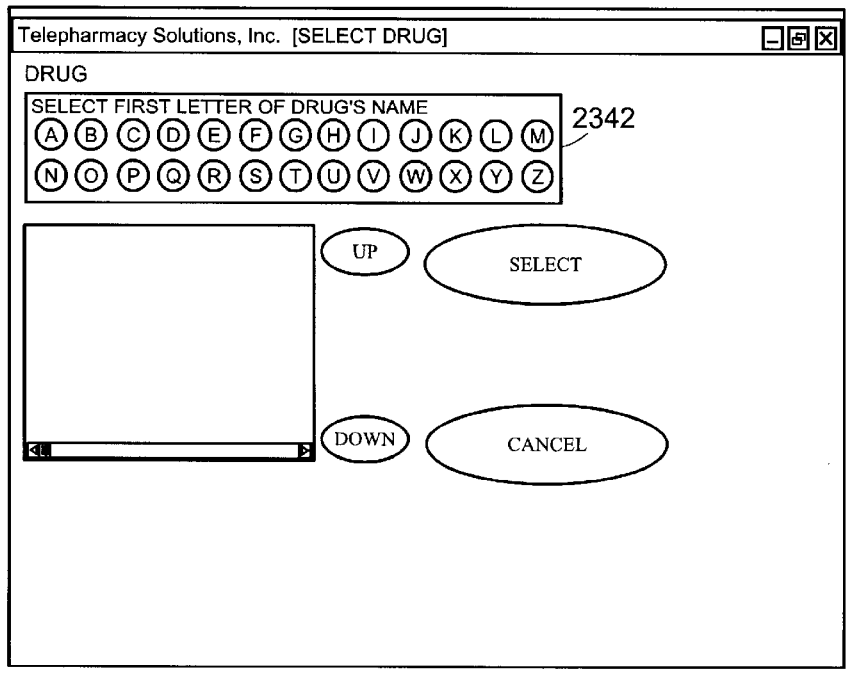
FIG. 58 and FIG. 59 illustrate views of a display screen of a user interface showing steps in a method to select a drug in accordance with a preferred embodiment of the present invention.
Figure 59:
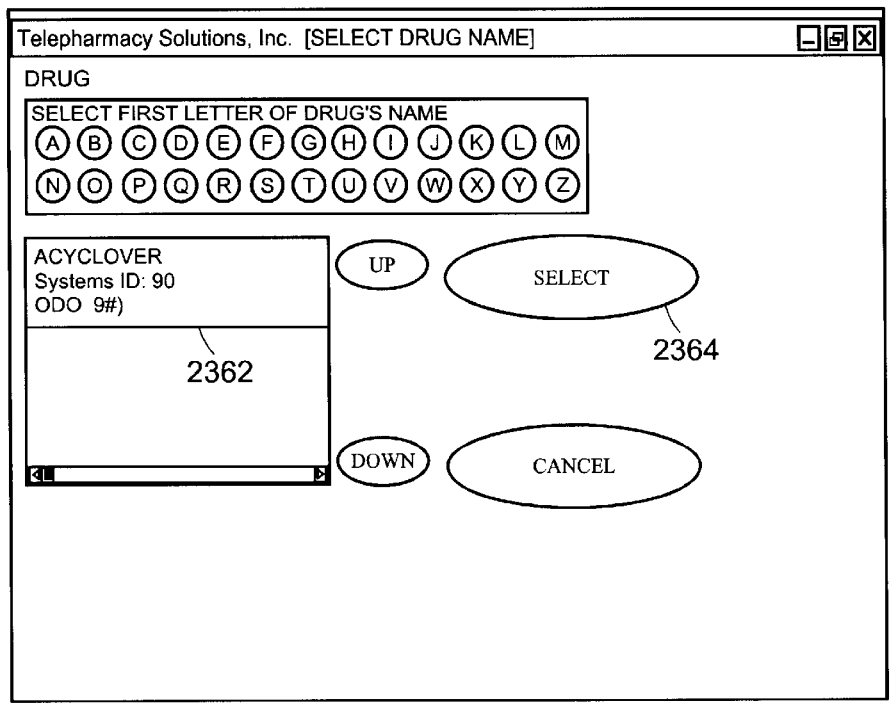

FIG. 58 and FIG. 59 illustrate views 2340, 2360 of a display screen of a user interface showing steps in a method to select a drug in accordance with a preferred embodiment of the present invention. The first letter of the drug name is selected from the interface button 2342 that is alphabetized. As discussed herein the interface buttons are accessed by touch or a click of a mouse. The drug name is then selected by highlighting the drug 2362 and then touching or clicking on the select button 2364.

Figure 60:
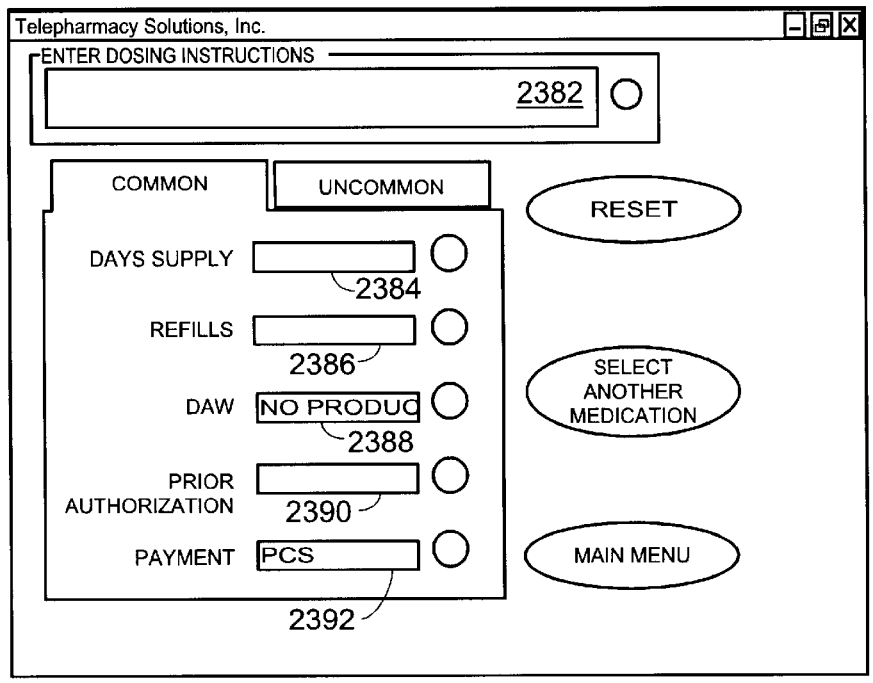
FIG. 60 illustrates a view of a display screen of a user interface showing the information fields that can be edited pertaining to a drug in accordance with a preferred embodiment of the present invention.

FIG. 60 illustrates a view 2380 of a display screen of a user interface showing the information fields than can be edited pertaining to a drug in accordance with a preferred embodiment of the present invention. Dosage information can be entered in field 2382, followed by filling the fields for day's supply 2384, refill 2386, DAW 2388, authorization 2390 and payment 2392.

Figure 61:
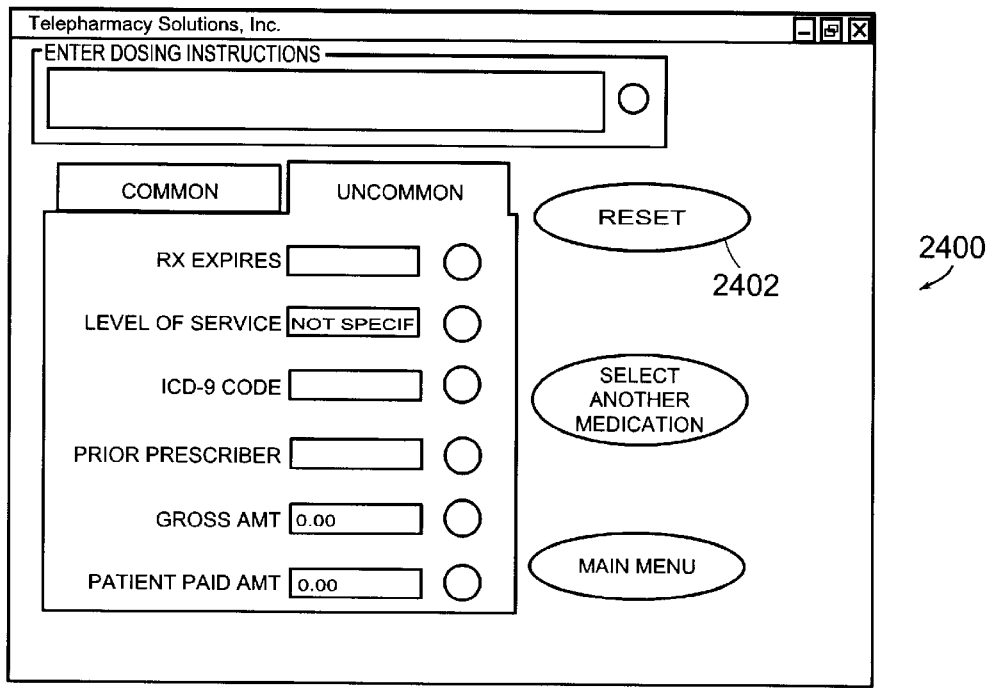
FIG. 61 illustrates a view of a display screen of a user interface showing the required fields that need to be entered in accordance with a preferred embodiment of the present invention.

FIG. 61 illustrates a view 2400 of a display screen of a user interface showing the required fields that need to be entered in accordance with a preferred embodiment of the present invention. The data boxes required such as script expiration, level of service and such need to be filled and then the finish interface button 2402 has to be accessed via touch or a click. The dispense button on the main screen flashes a message indicating a dispense along with the number of prescriptions available.

Figure 62:
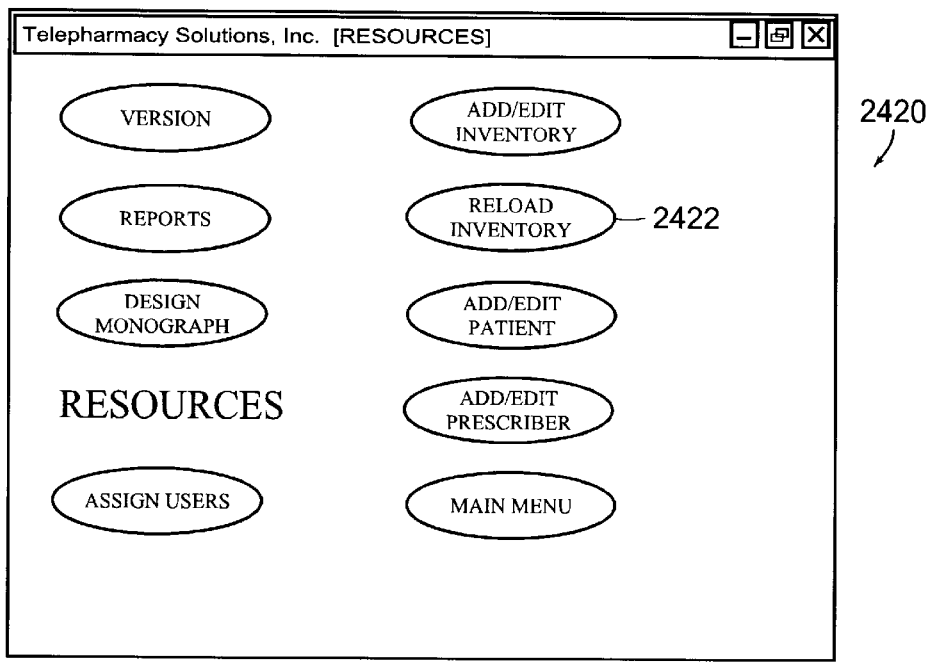
FIG. 62 illustrates a view of a display screen of a user interface showing the reload inventory function interface, in particular a button, in accordance with a preferred embodiment of the present invention.

FIG. 62 illustrates a view 2420 of a display screen of a user interface showing a reload inventory function interface, in particular a button, in accordance with a preferred embodiment of the present invention. The reload functionality is also accessed by accessing the resources button on the main screen as reloading is a non-dispensing function. Then the reload inventory button 2422 is touched or clicked.

Figure 63:
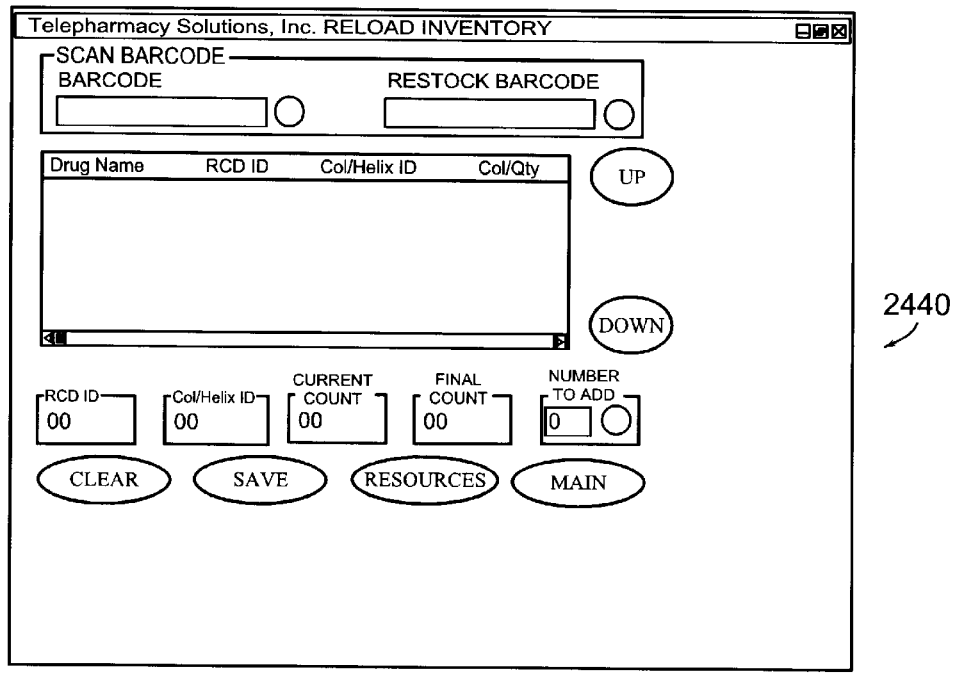
FIG. 63 illustrates a view of a display screen of a user interface showing a prompts to scan a barcode of a medical product to be reloaded into inventory in accordance with a preferred embodiment of the present invention.

FIG. 63 illustrates a view 2440 of a display screen of a user interface showing the prompts to scan a barcode of a medical product to be reloaded into inventory in accordance with a preferred embodiment of the present invention. The barcode on the medical product is required to be scanned prior to be reloaded into inventory.

Figure 64:
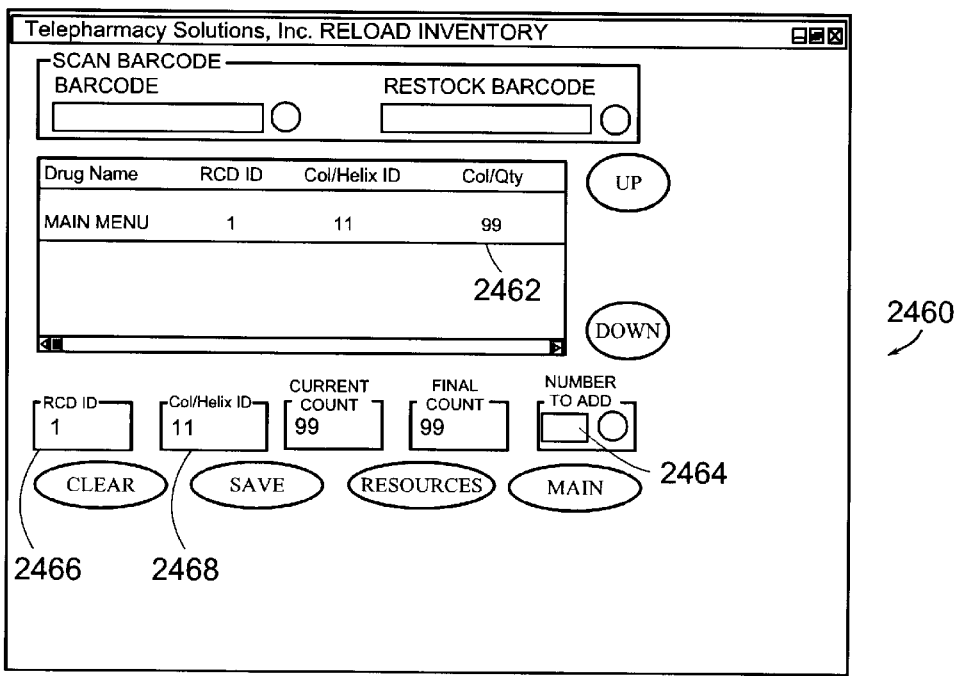
FIG. 64 illustrates a view of a display screen of a user interface showing the selection of the drug and the related information in accordance with a preferred embodiment of the present invention.

FIG. 64 illustrates a view 2460 of a display screen of a user interface showing the selection of the drug and the related information in accordance with a preferred embodiment of the present invention. The drug to be reloaded is selected by accessing the drug name 2462 via touching the interface or clicking on it. The number of packages to be placed in inventory is added to the Number to Add box 2464. The RCD ID 2466 and the col/helix ID box 2468 provide the physical location to restock the product.

Figure 65:
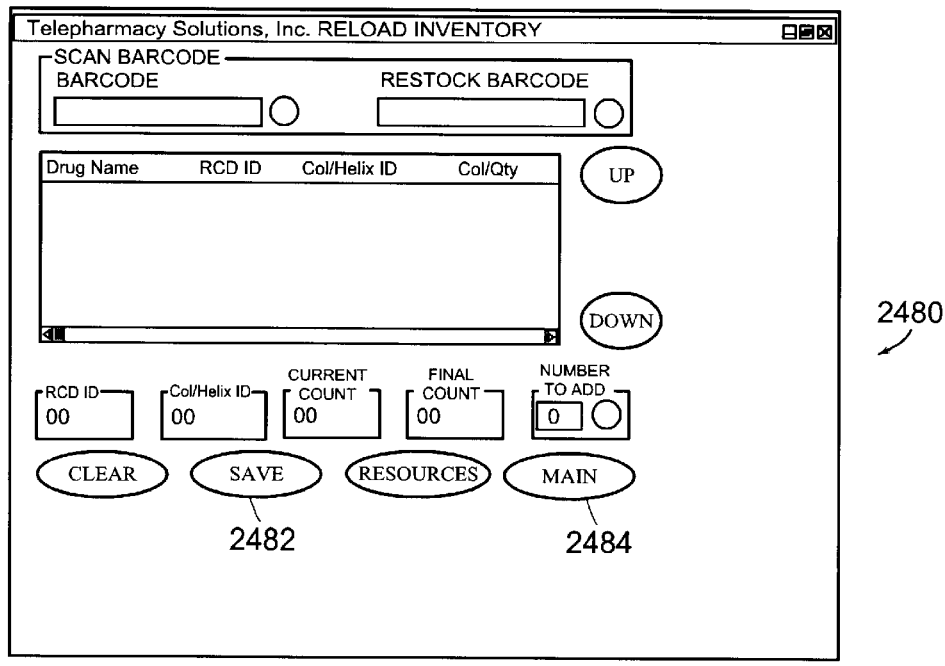
FIG. 65 illustrates a view of a display screen of a user interface showing the use of the save interface (button) after restocking a particular medical product in accordance with a preferred embodiment of the present invention.

FIG. 65 illustrates a view 2480 of a display screen of a user interface showing the use of the save interface (button) after restocking a particular medical product in accordance with a preferred embodiment of the present invention. After restocking the product, for example, the drug save button 2482 is accessed by touching the interface button. The screen clears and this process is repeated until the process of restocking is complete. By touching or clicking on the main button 2484 the user returns to the main screen.

Figure 66:
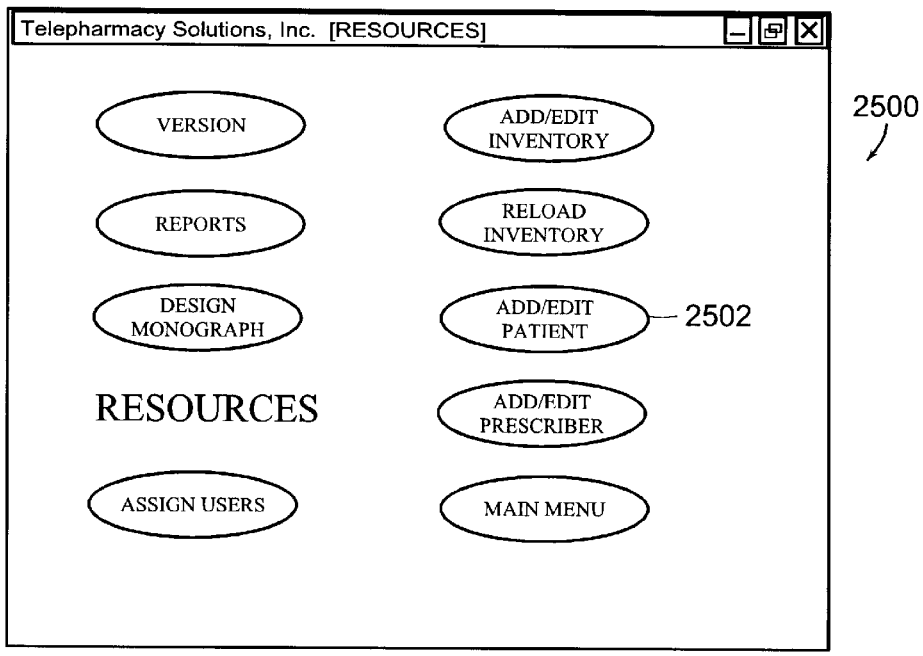
FIG. 66 illustrates a view of a display screen of a user interface showing the use of the add/edit patient interface button in accordance with a preferred embodiment of the present invention.

FIG. 66 illustrates a view 2500 of a display screen of a user interface showing the use of the add/edit patient interface button in accordance with a preferred embodiment of the present invention. The system to dispense pharmaceuticals also provides for adding or editing the list of patients. This functionality is accessed via the resources button in the main screen described with respect to FIG. 38. Once the resources screen 2500 appears, the add/edit patient button 2502 can be touched or clicked to begin the process of revising the patient list.

Figure 67:
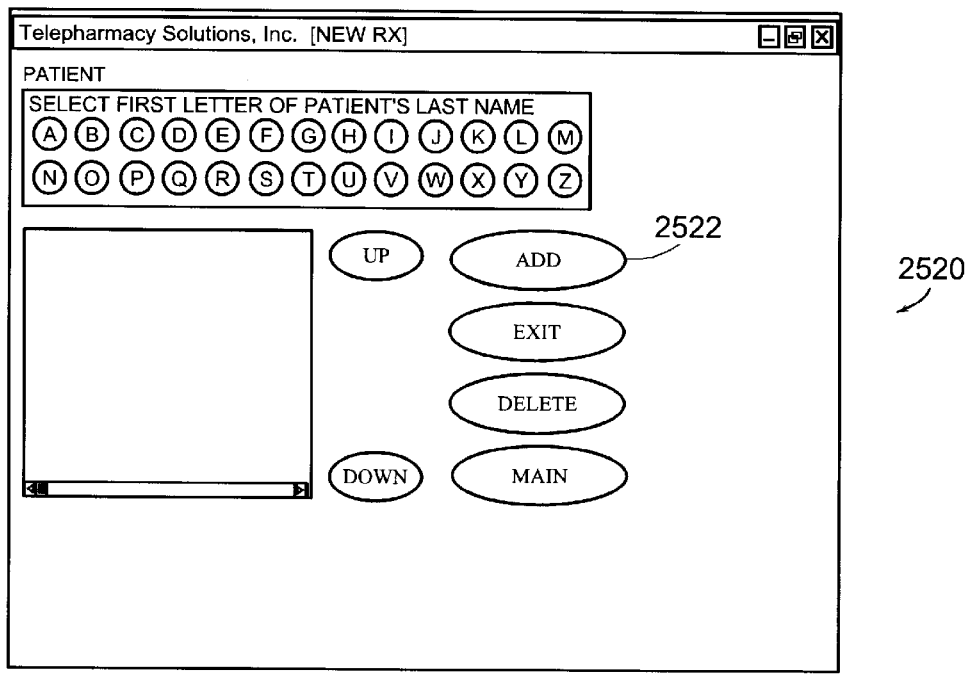
FIG. 67 illustrates a view of a display screen of a user interface showing the subsequent step in the method to add the patient in accordance with a preferred embodiment of the present invention.

FIG. 67 illustrates a view 2520 of a display screen of a user interface showing the subsequent step in the method to add a patient in accordance with a preferred embodiment of the present invention. The ADD button 2522 is used by touching or clicking on as the next step.

Figure 68:
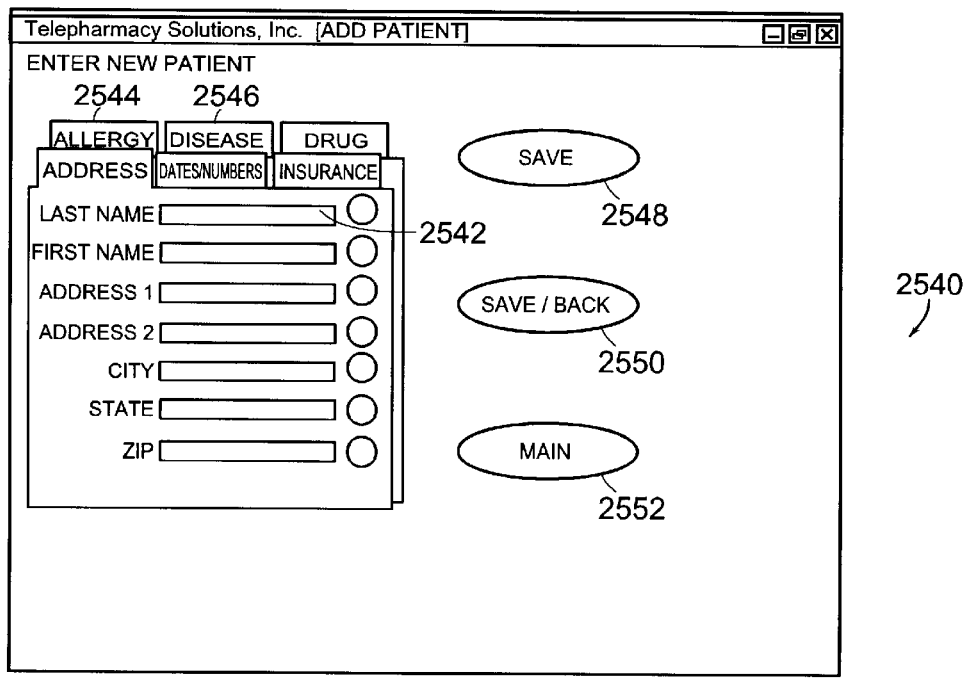
FIG. 68 illustrates a view of a display screen of a user interface showing a plurality of fields that need to be filled to add a patient in accordance with a preferred embodiment of the present invention.

FIG. 68 illustrates a view 2540 of a display screen of a user interface showing a plurality of fields that need to be filled to effectively add a patient in accordance with a preferred embodiment of the present invention. Data in all the applicable fields or data boxes need to be entered, for example, last name 2542. The pages are changed by clicking or touching the tabs such as Allergy 2544, Disease 2546 etc. Upon completion of the process to enter all pertinent patient information the Save button 2548 is interfaced to save the patient information. The save/back button 2550 is interfaced to save patient information and clear the form for the next patient. The main button 2552 is used to access the main screen.

Figure 69:
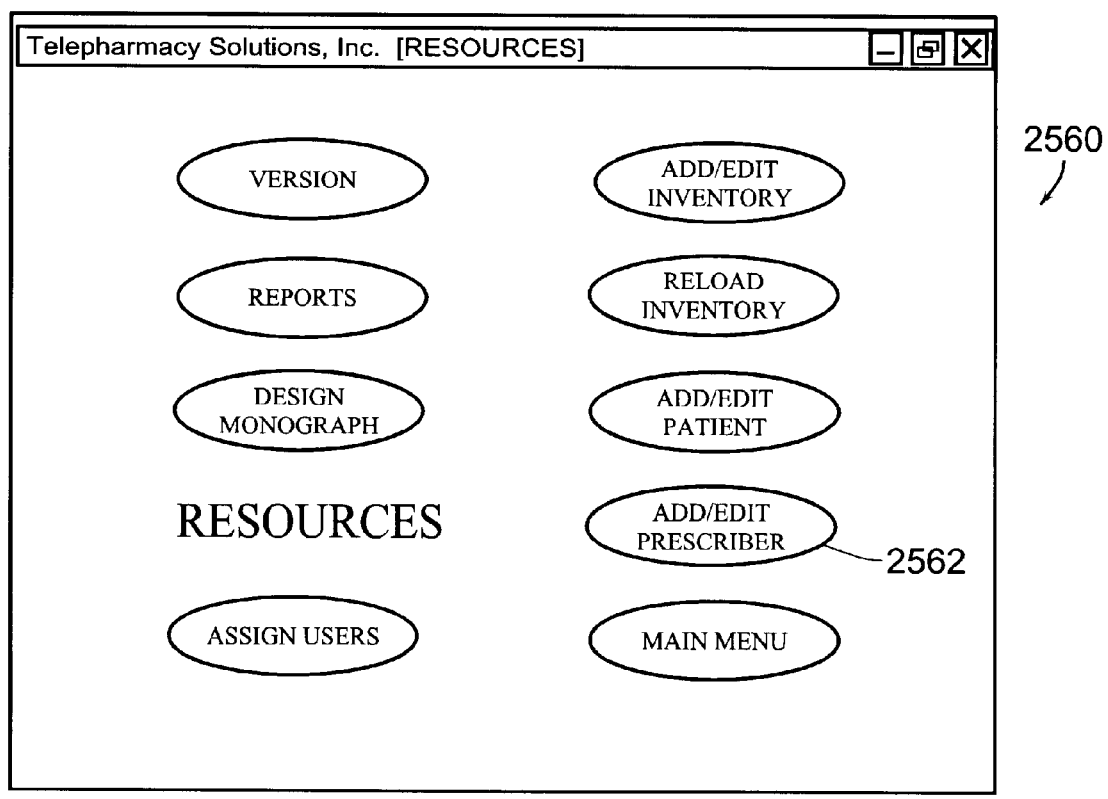
FIG. 69 illustrates a view of a display screen of a user interface showing the use of the add/edit prescriber interface button in accordance with a preferred embodiment of the present invention.

FIG. 69 illustrates a view 2560 of a display screen of a user interface showing the use of the add/edit prescriber interface button in accordance with a preferred embodiment of the present invention. The resources screen 2560 is again accessed via the resources button on the main screen. The add/edit prescriber button 2562 is interfaced with via touch or clicking on.

Figure 70:
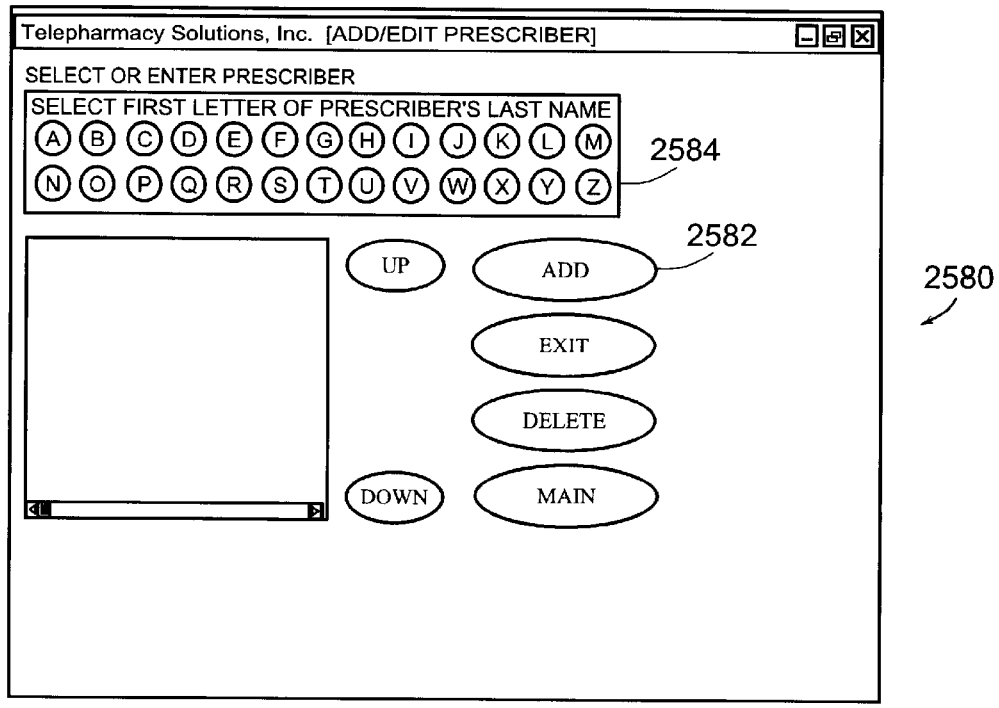
FIG. 70 illustrates a view of a display screen of a user interface showing a subsequent step in the method to add a prescriber in accordance with a preferred embodiment of the present invention.

FIG. 70 illustrates a view 2580 of a display screen of a user interface showing a subsequent step in the method to add a prescriber in accordance with a preferred embodiment of the present invention. To add a prescriber the add button 2582 is touched or clicked. The prescriber's last name is accessed from the alphabetized interface buttons grouped in the interface 2584.

Figure 71:
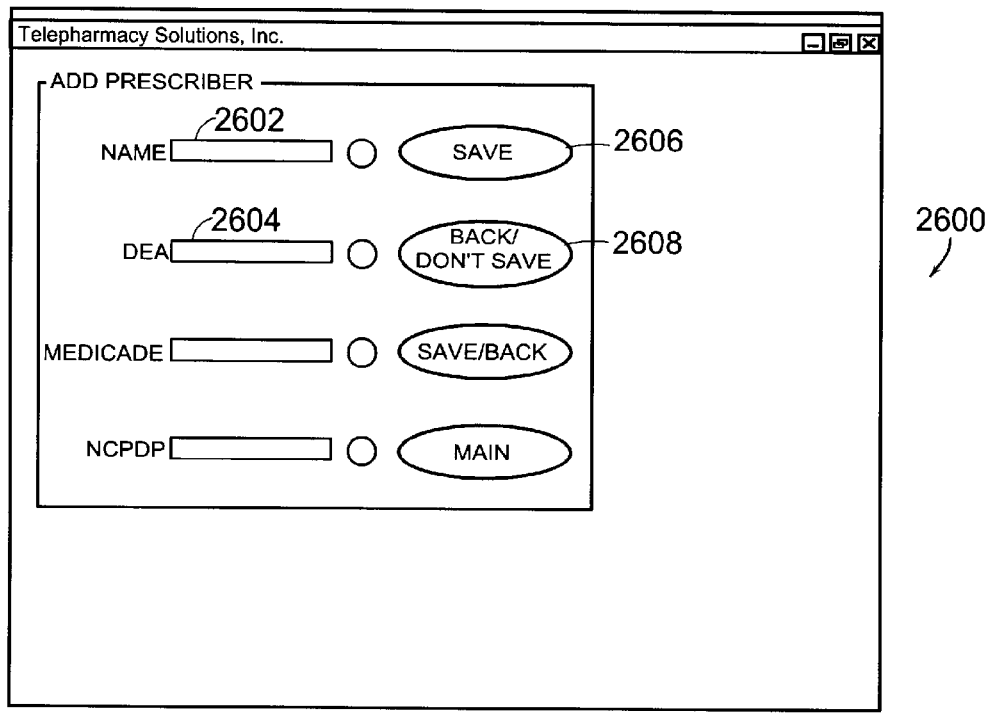
FIG. 71 illustrates a view of a display screen of a user interface showing the fields that are required to be filled to add a prescriber in accordance with a preferred embodiment of the present invention.

FIG. 71 illustrates a view 2600 of a display screen of a user interface showing the fields that are required to be filled to add the prescriber in accordance with a preferred embodiment of the present invention. The data box fields such as, for example, name 2602, DEA 2604, related to the particular prescriber need to be entered. The save button 2606 is used to save prescriber information. The back/don't save button 2608 returns the user to the previous screen without saving information. The save/back button 2610 saves the information and returns the user to the previous screen.

Figure 72:
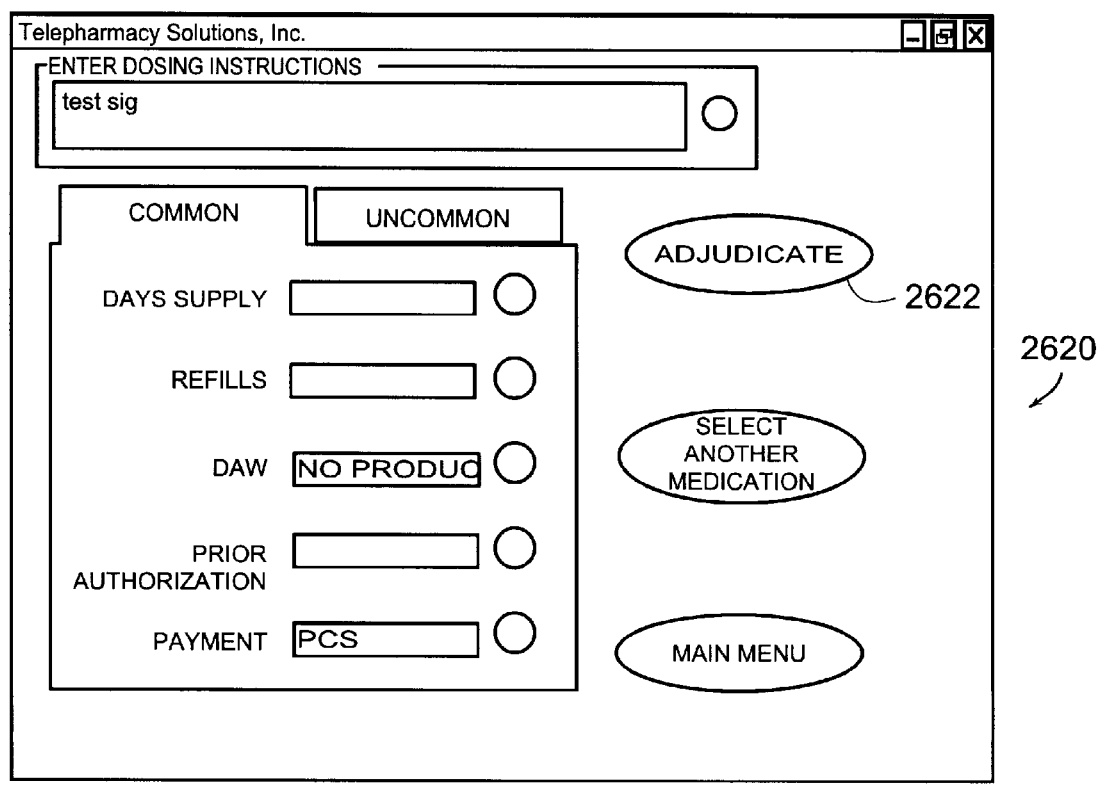
FIG. 72 illustrates a view of a display screen of a user interface showing the start of an adjudication method in accordance with a preferred embodiment of the present invention.

FIG. 72 illustrates a view 2620 of a display screen of a user interface showing the start of an adjudication method in accordance with a preferred embodiment of the present invention. The adjudication method starts after the instructions from the new Rx method described hereinbefore in FIGS. 53–61. After creating a new Rx (prescription) and entering in a patient specific dosing instructions and filling out the required data fields the adjudication button 2622 is used by touching or clicking.

Figure 73:
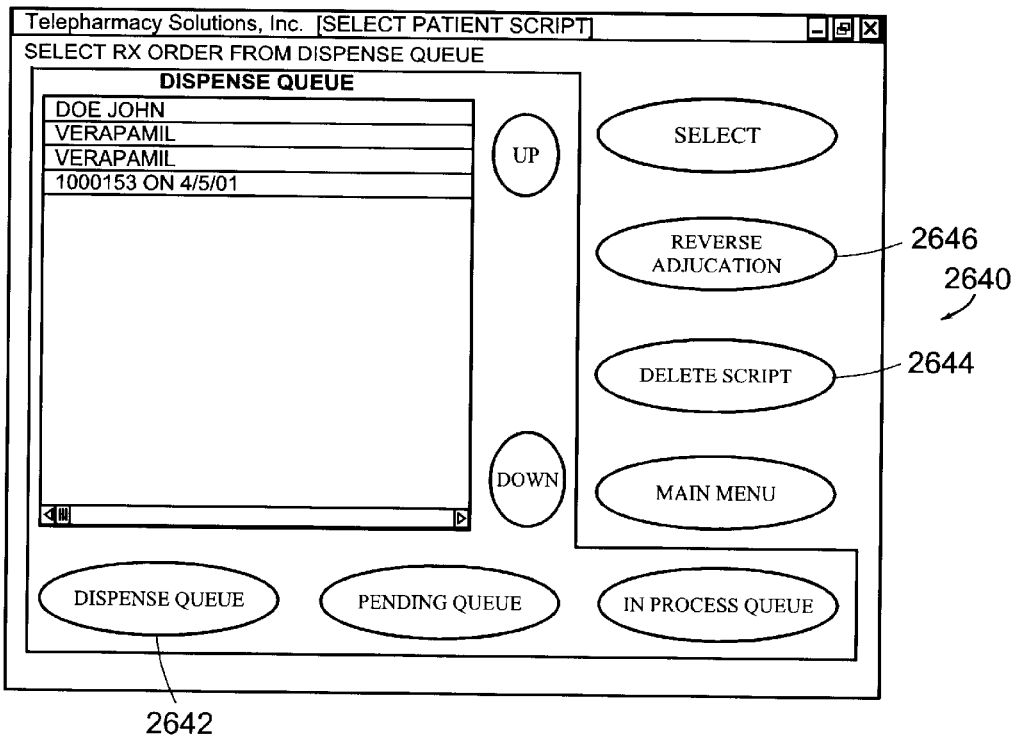
FIG. 73 illustrates a view of a display screen of a user interface showing a dispense queue in the adjudication method in accordance with a preferred embodiment of the present invention.

FIG. 73 illustrates a view 2640 of a display screen of a user interface showing a dispense queue in the adjudication method in accordance with a preferred embodiment of the present invention. At the main screen when a claim is returned, text flashing in the largest button tells a user whether the claim has been paid (dispensed) or rejected (ending). A number after the caption such as, for example, DISPENSE1, indicates how many products are in each queue. The dispense queue screen 2640 is a queue-viewing page. Scripts can be dispensed, deleted or reversed from this screen by using the respective buttons 2642, 2644, 2646.

Figure 74:
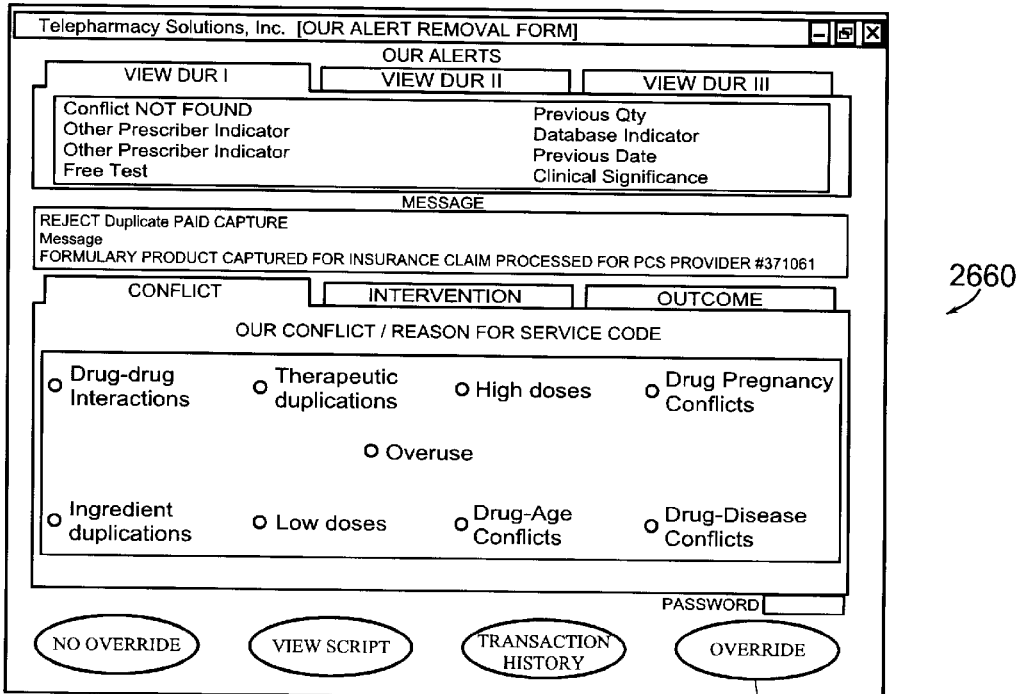
FIG. 74 illustrates a view of a display screen of a user interface showing drug utilization review (DUR) alerts in an adjudication method in accordance with a preferred embodiment of the present invention.

FIG. 74 illustrates a view 2660 of a display screen of a user interface showing drug utilization review (DUR) alerts in an adjudication method in accordance with a preferred embodiment of the present invention. If the claim has been paid, but with DUR alerts a screen similar to display screen 2660 is displayed to the user after selecting "Dispense". The pharmacist is then called into the process. After viewing the alerts the pharmacist can choose the appropriate options and if so inclined enters a password and selects the override function by touching the override button 2662.

Figures 75, 76:
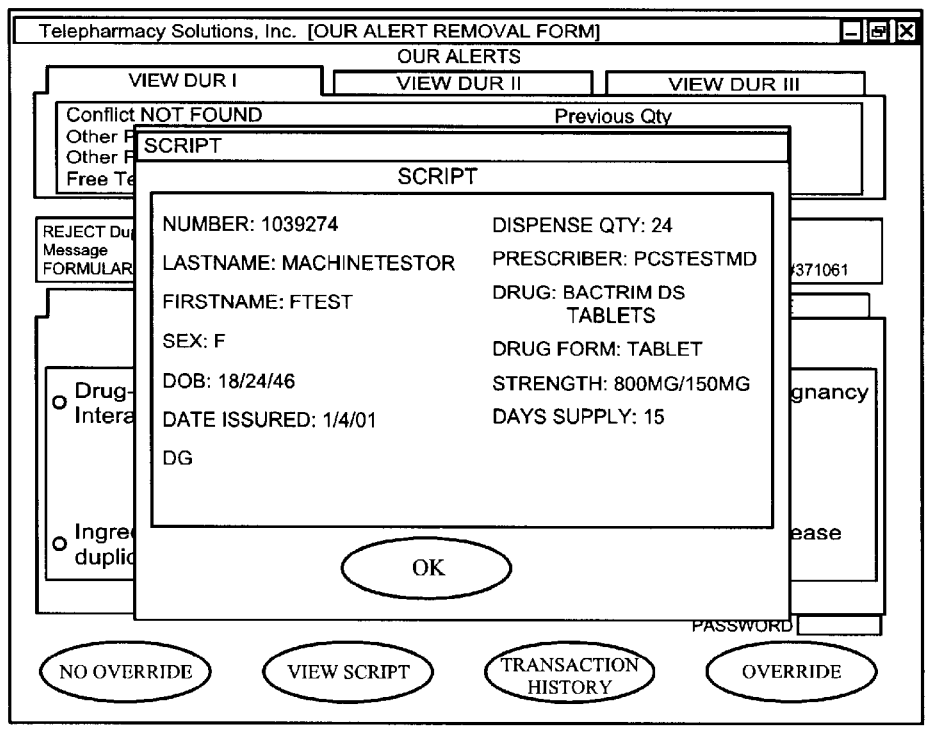
FIG. 75 illustrates a view of a display screen of a user interface showing script information in the DUR alert described with respect to FIG. 74 in accordance with a preferred embodiment of the present invention.
FIG. 76 illustrates a view of a display screen of a user interface showing the patient transaction history in an adjudication method in accordance with a preferred embodiment of the present invention.

FIG. 75 illustrates a view 2680 of a display screen of a user interface showing script information in the DUR alert described with respect to FIG. 74 in accordance with a preferred embodiment of the present invention. This is a viewing screen.

FIG. 76 illustrates a view 2700 of a display screen of a user interface showing the patient transaction history in an adjudication method in accordance with a preferred embodiment of the present invention. This screen is another viewing screen.

Figure 77:
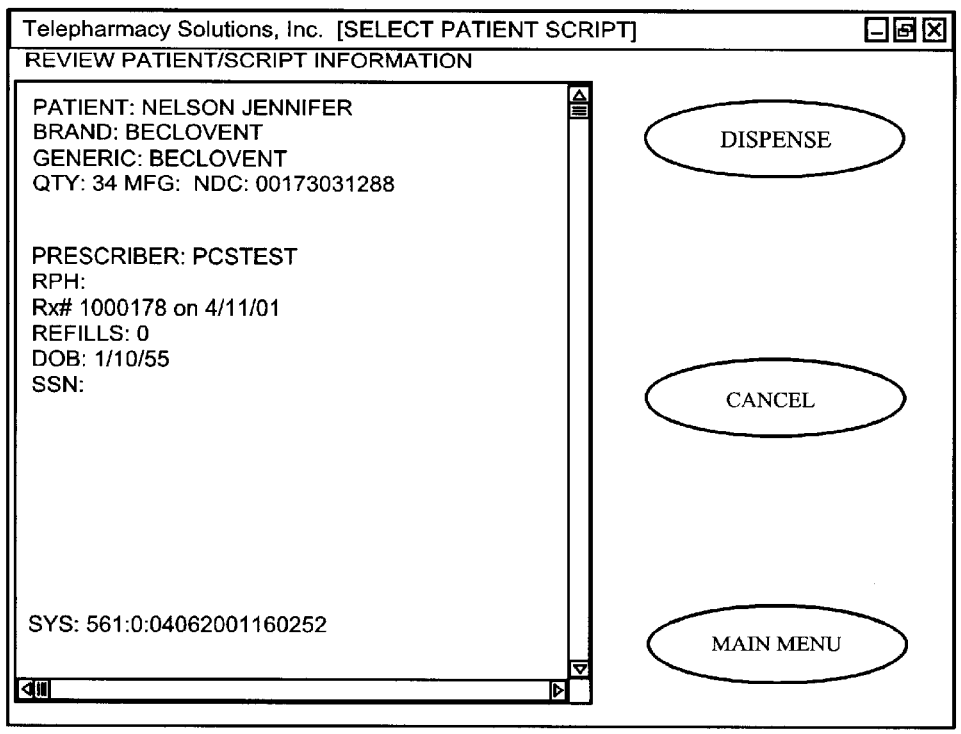
FIG. 77 illustrates a view of a display screen of a user interface showing the patient script information to be reviewed after an override or a returned claim during the adjudication process in accordance with a preferred embodiment of the present invention.

FIG. 77 illustrates a view 2720 of a display screen of a user interface showing the patient script information to be reviewed after an override or a returned claim during the adjudication process in accordance with a preferred embodiment of the present invention. After an override or if the claim is returned without an alert or rejection, a screen similar to the view 2720 is displayed for the user.

Figure 78:
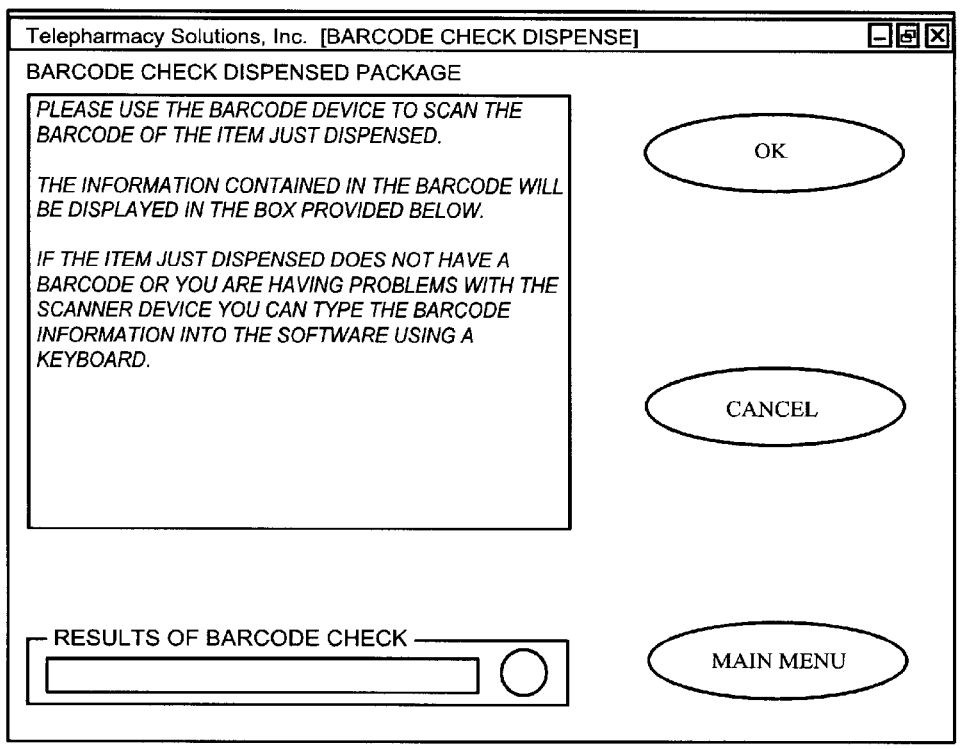
FIG. 78 illustrates a view of a display screen of a user interface showing the final portion of the dispense process that includes the scanning of barcodes as part of the adjudication process in accordance with a preferred embodiment of the present invention.

FIG. 78 illustrates a view 2740 of a display screen of a user interface showing the final process that includes the scanning of barcodes as part of the adjudication process in accordance with a preferred embodiment of the present invention. This is a safety check step in the adjudication and dispense process.

Figure 79:
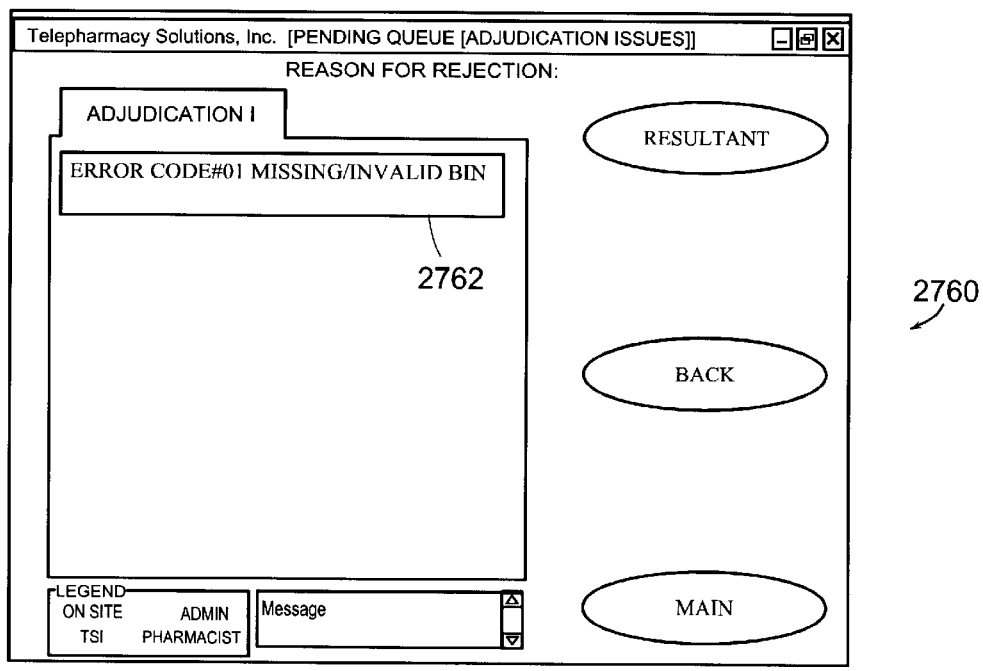
FIG. 79 illustrates a view of a display screen of a user interface showing the reason for rejection as part of the adjudication process in accordance with a preferred embodiment of the present invention.

FIG. 79 illustrates a view 2760 of a display screen of a user interface showing a reason for rejection as part of the adjudication process in accordance with a preferred embodiment of the present invention. If the adjudication claim has generated a reject then in the main screen a pending message is generated in a button. After selecting the pending queue in the queue-viewing screen and selecting a script from the list box, a screen such as view 2760 is displayed to the user. This screen can display multiple reject reasons such as up to 20 reasons one of which is shown in the field 2762. Extra tabs and text boxes are dynamically constructed and displayed on need. The reasons are color-coded. Yellow indicates an onsite issue, green a TSI issue which can be resolved on-site, blue an administrative concern and pink requiring the intervention of the pharmacist.

Figure 80:
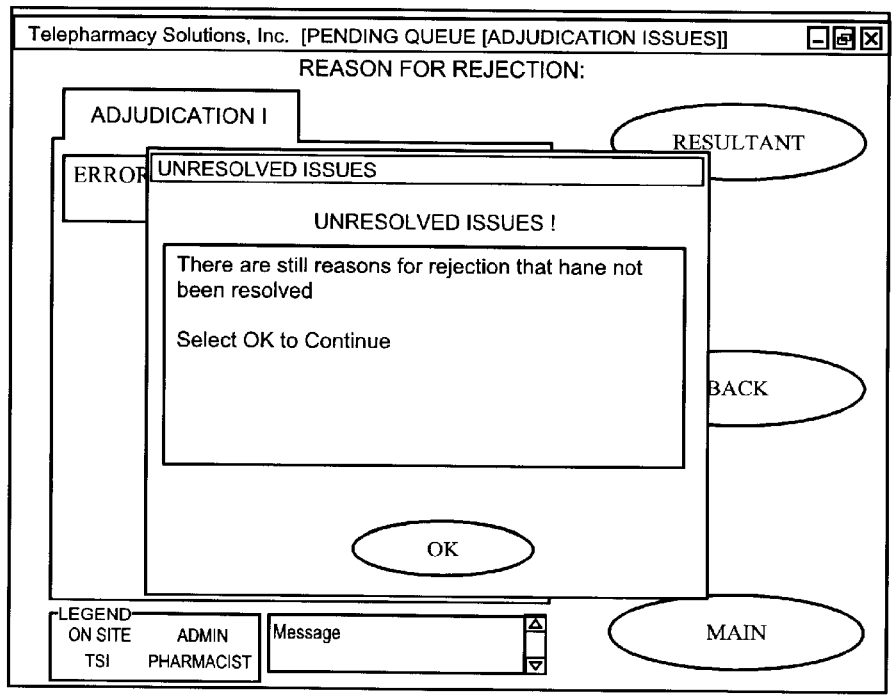
FIG. 80 illustrates a view of a display screen of a user interface showing a subsequent step indicating unresolved issues as part of the adjudication process in accordance with a preferred embodiment of the present invention.

FIG. 80 illustrates a view 2780 of a display screen of a user interface showing a subsequent step indicating unresolved issues as part of the adjudication process in accordance with a preferred embodiment of the present invention. If the user tries to resubmit the claim without first addressing all outstanding rejection issues, they are prohibited from proceeding and the display screen 2780 appears.

Figure 81:
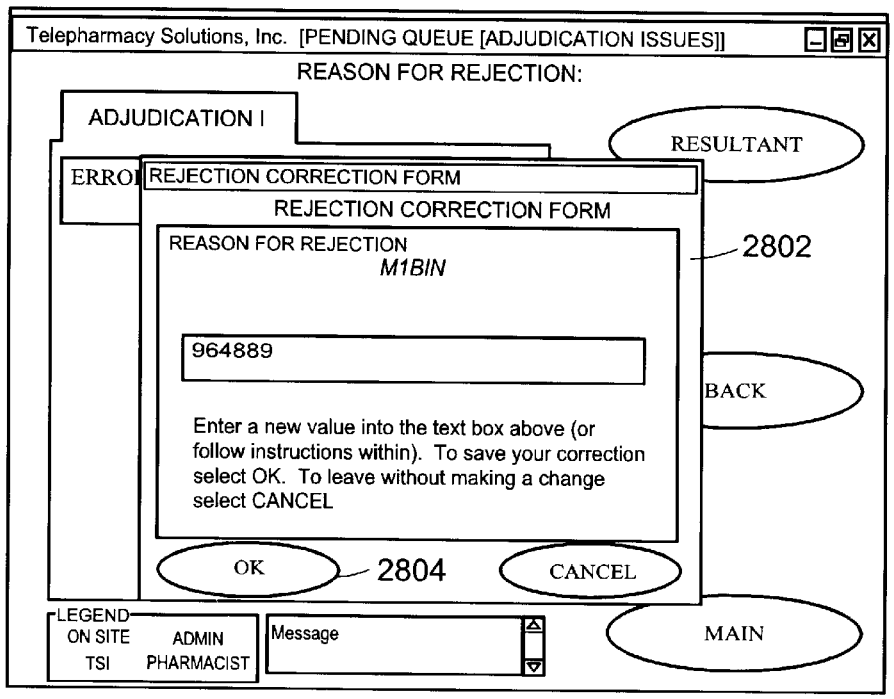
FIG. 81 illustrates a view of a display screen of a user interface showing a rejection correction form as part of the adjudication process in accordance with a preferred embodiment of the present invention.

FIG. 81 illustrates a view 2800 of a display screen of a user interface showing a rejection correction form as part of the adjudication process in accordance with a preferred embodiment of the present invention. When the reject message is selected a rejection correction form 2802 is displayed. The current value is displayed in the text field. The user has the option of revising the form 2802 and trying to resubmit the claim. If the claim is repeatedly rejected the user needs to contact the administrator depending on the nature of the reason for rejection.

Figure 82:
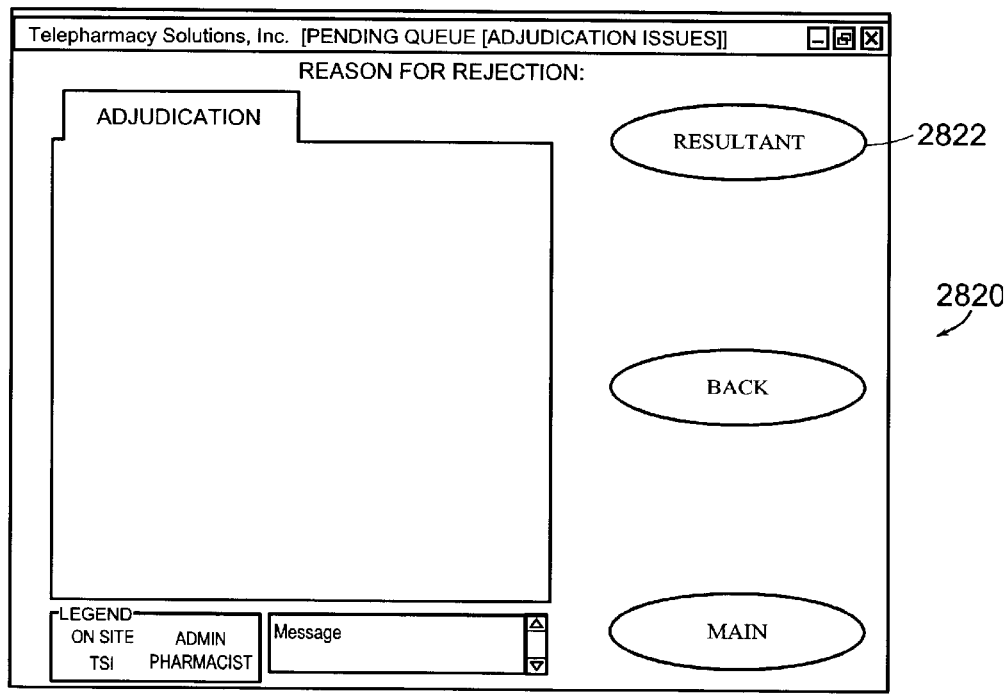
FIG. 82 illustrates a view of a display screen of a user interface showing a claim pending adjudication after being resubmitted as part of the adjudication method in accordance with a preferred embodiment of the present invention.

FIG. 82 illustrates a view 2820 of a display screen of a user interface showing a claim pending adjudication after being resubmitted as part of the adjudication method in accordance with a preferred embodiment of the present invention. After selecting the interface button "OK" 2804 in the previous screen 2800, the reason for rejection is removed from the screen. If there were twenty reject reasons the same process is repeated until they are all examined. The claim is then ready to be reexamined and resubmitted by interfacing and touching button 2822.

Figure 83:
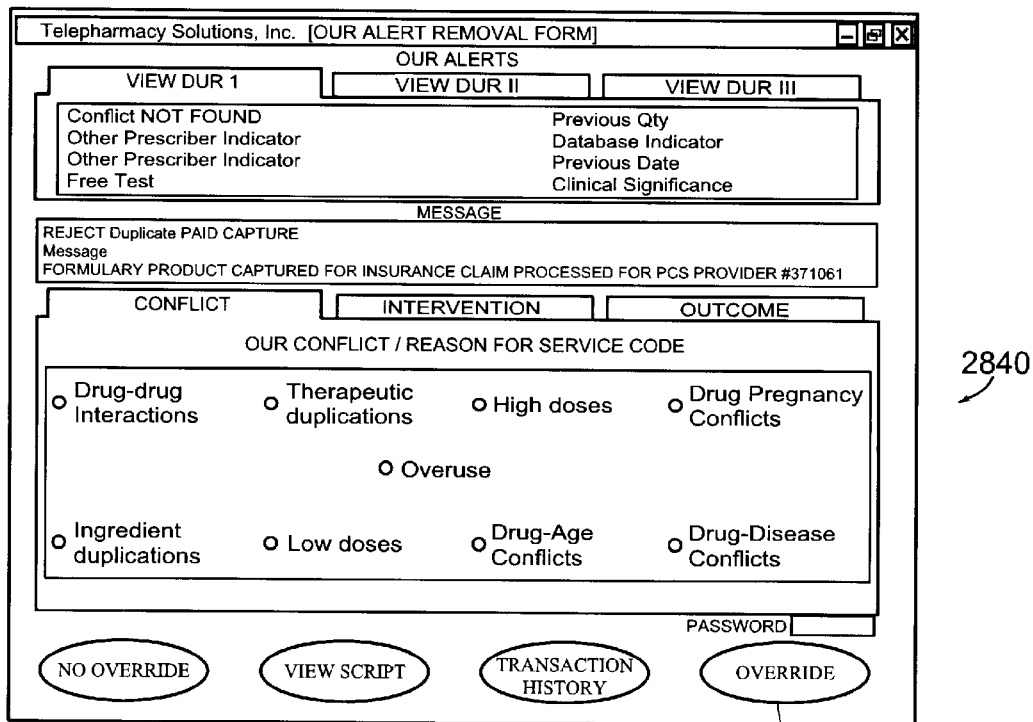
FIG. 83 illustrates a view of a display screen of a user interface showing a DUR alert removal form as part of the adjudication method in accordance with a preferred embodiment of the present invention.

FIG. 83 illustrates a view 2840 of a display screen of a user interface showing a DUR alert removal form as part of the adjudication method in accordance with a preferred embodiment of the present invention. Typically on-site staff, and administrators can handle a majority of errors, however, any drug related reject causes a screen such as screen 2840 to be displayed. Intervention and outcome fields can only be entered once on a resubmitted claim. Therefore, if more than one DUR reject reason exists, all is overridden if one of them is. It should be noted that a screen similar to display screen 2840 is displayed if a paid claim has DUR alerts.

Figure 84:
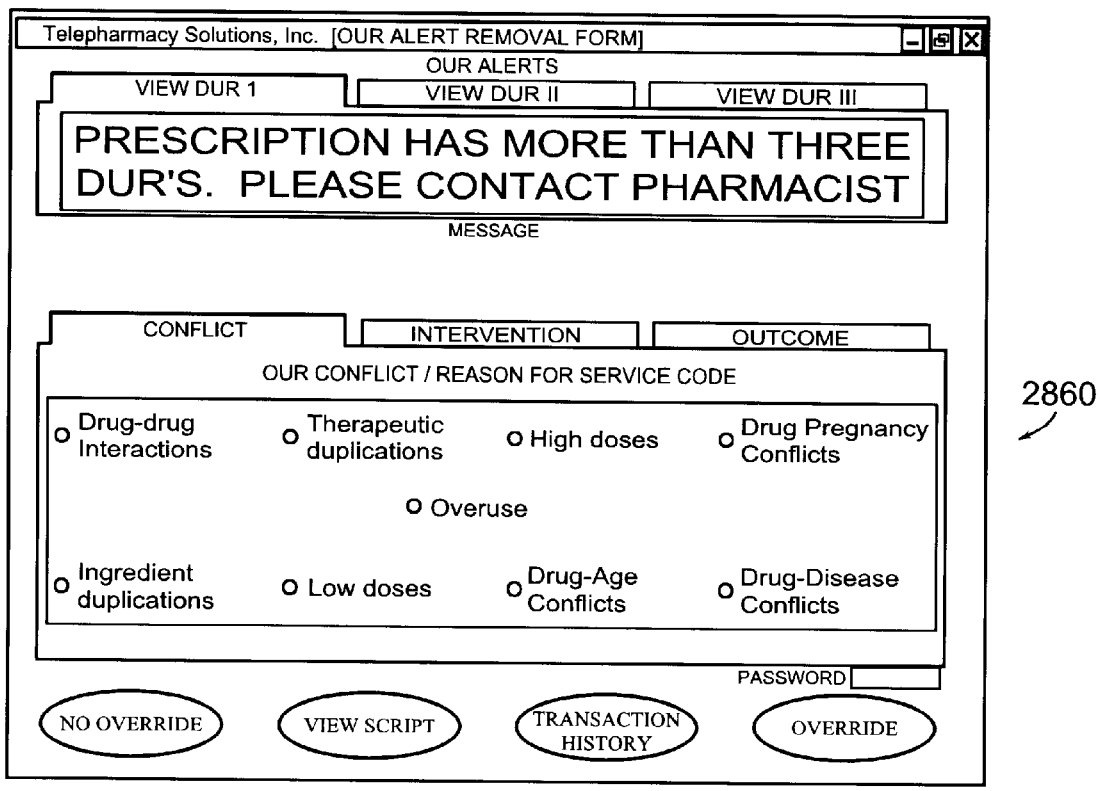
FIG. 84 illustrates a view of a display screen of a user interface showing a returned claim as a result of the adjudication process in accordance with a preferred embodiment of the present invention.

FIG. 84 illustrates a view 2860 of a display screen of a user interface showing a returned claim as a result of the adjudication process in accordance with a preferred embodiment of the present invention. If the returned claim has more than three errors a screen similar to screen 2860 is displayed to the user.

FIG. 85 illustrates a view 2880 of a display screen of a user interface showing an access users screen for dispensing, tracking and returning of particular classes of drugs such as, for example, narcotics in accordance with a preferred embodiment of the present invention. On the assign users screen an access level field 2882 is additionally displayed to further control the dispensing of classes of drugs. The number 0–99 can be entered in the field 2882.

Figure 86:
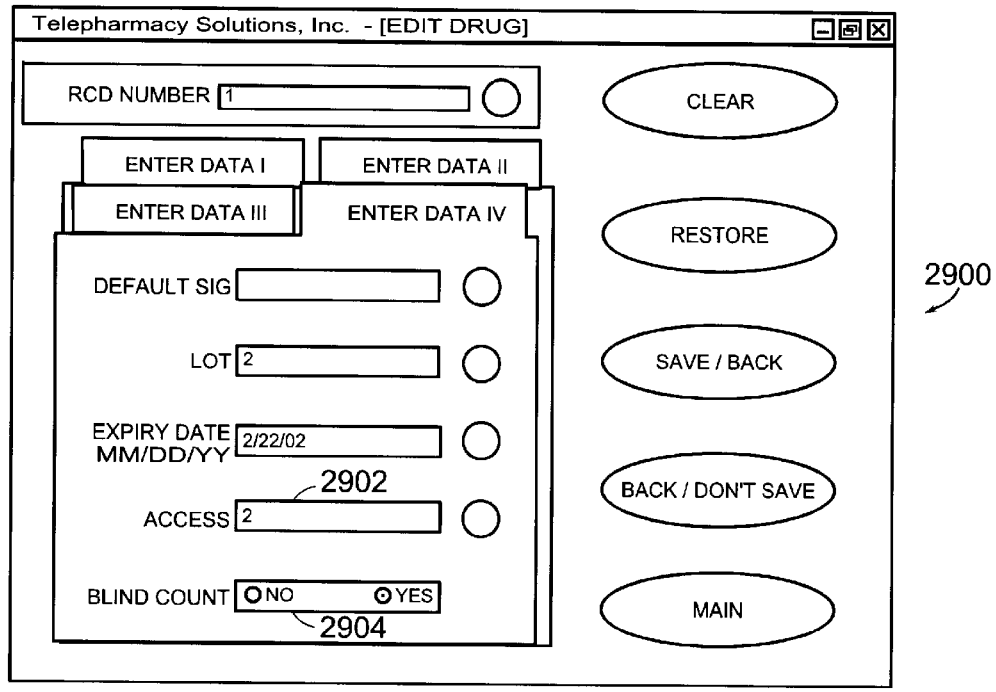
FIG. 86 illustrates a view of a display screen of a user interface showing an access level field for adding and editing medical products into a system for dispensing medical products in accordance with a preferred embodiment of the present invention.

FIG. 86 illustrates a view 2900 of a display screen of a user interface showing an access level field for adding and editing medical products into a system for dispensing medical products in accordance with a preferred embodiment of the present invention. The access level field 2902 is added to add and edit drug or medical product screens to better control certain classes of drugs such as narcotics. In the example, since this drug is set to "2", any user with an access level of 2 or higher can dispense the medical product. Other users get an access denied message. In the blind count field 2904 when "Yes" is selected, upon dispensing the medical product, the user is asked to count the amount currently on hand in inventory. If the number differs from that within the database they are asked again to make certain if the count differs. A warning is immediately printed and the fact that there is a discrepancy is recorded and can be reviewed in a discrepancy report.

Figure 87:
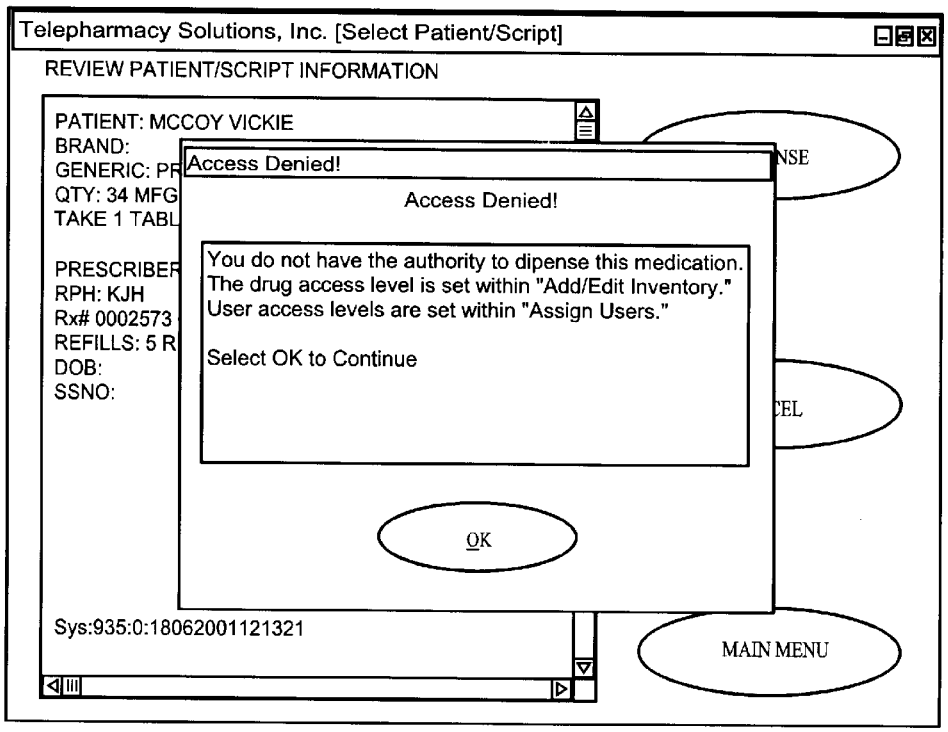
FIG. 87 illustrates a view of a display screen of a user interface showing the denial of access to dispense a medical product in accordance with a preferred embodiment of the present invention.

FIG. 87 illustrates a view 2920 of a display screen of a user interface showing the denial of access to dispense a medical product in accordance with a preferred embodiment of the present invention. The screen 2920 is displayed if the user does not have the proper access level and attempts an access.

Figure 88:
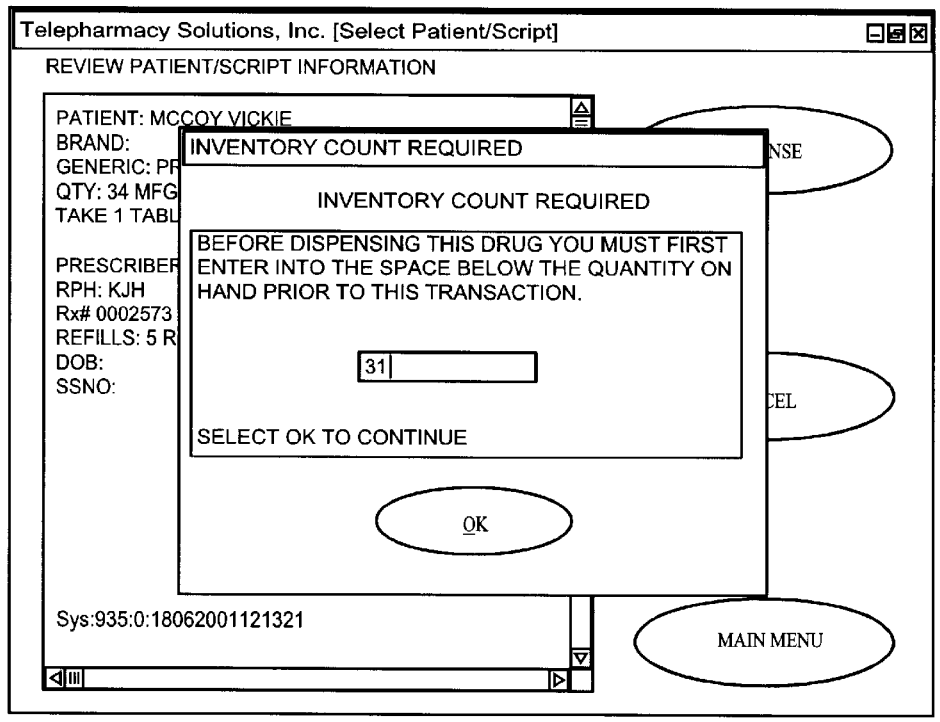
FIG. 88 illustrates a view of a display screen of a user interface showing an inventory count required field for an access level field in accordance with a preferred embodiment of the present invention.

FIG. 88 illustrates a view 2940 of a display screen of a user interface showing an inventory count required field for an access level in accordance with a preferred embodiment of the present invention. If the user has a proper access level, but the drug or medical product is set to force a blind count the screen 2940 is displayed. A number such as 31 is entered by the user, which differs than the amount listed in the inventory.

Figure 89:
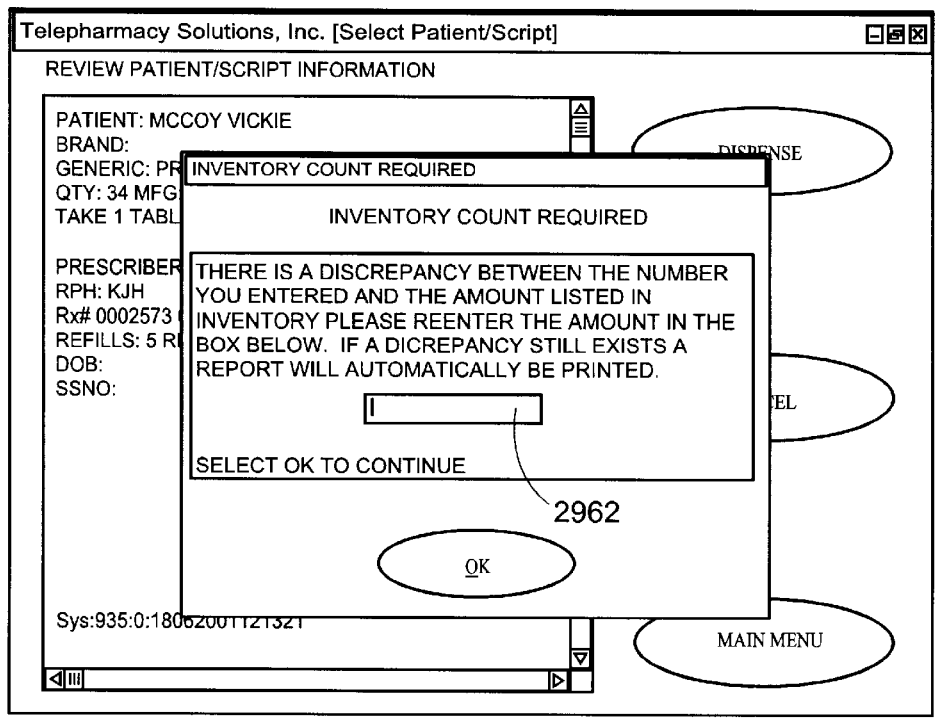
FIG. 89 illustrates a view of a display screen of a user interface showing a response to an incorrect entry made into an inventory count for an access level field in accordance with a preferred embodiment of the present invention.

FIG. 89 illustrates a subsequent view 2960 of a display screen of a user interface showing a response to an incorrect entry made into an inventory count for an access level field in accordance with a preferred embodiment of the present invention. Because in the previous screen 2940 a number 31 was inputted and is different from the inventory count, the user is prompted again to verify the entry. If the amount entered is still wrong in field 2962, a warning is sent to the printer with pertinent information.

Figures 90, 91:
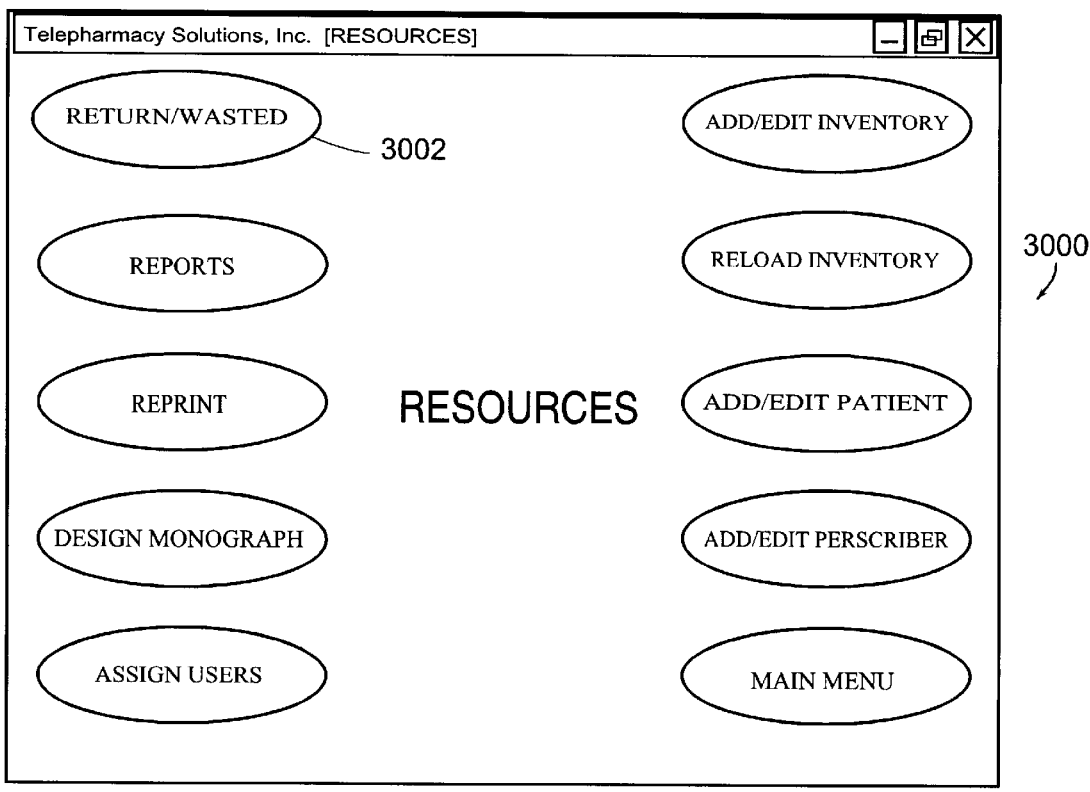
FIG. 90 illustrates a view of a display screen of a user interface showing a discrepancy report generated in response to denial of access in accordance with a preferred embodiment of the present invention.
FIG. 91 illustrates a view of a display screen of a user interface showing a "return/wasted" interface button in accordance with a preferred embodiment of the present invention.

FIG. 90 illustrates a view 2980 of a display screen of a user interface showing a discrepancy report generated in response to a denial of access in accordance with a preferred embodiment of the present invention. It delineates information pertaining to the drug, the user, date/time information, quantity counted and quantity on hand in the inventory.

FIG. 91 illustrates a view 3000 of a display screen of a user interface showing a return/wasted interface button 3002 in accordance with a preferred embodiment of the present invention. This button 3002 appears in the resource screen and is important for tracking certain classes of drugs such as, for example, regulated medication such as narcotics.

FIG. 92 illustrates a view 3020 of a display screen of a user interface showing return/wasted information generated in accordance with a preferred embodiment of the present invention. A transaction 3022 can be selected on the return/waste display screen and then selected using the interface button 3024.

FIG. 93 illustrates a view 3040 of a display screen of a user interface showing the details of the selected transactions for an access level user in accordance with a preferred embodiment of the present invention. The selected transactions are displayed on the left half 3042 of the screen. The current quantity dispensed appears in the field 3044. The user enters the amount returned or wasted, and then the actual amount dispensed. A witness can then enter their user ID in field 3046 and password in field 3048 to save the changes. This form allows for the complete return of a drug. The entire amount to return is entered in field 3050, "0" into amount wasted field 3052 and "0" into actual quantity dispensed. A record of the transaction is made, albeit for a quantity of zero.

Figure 94B:
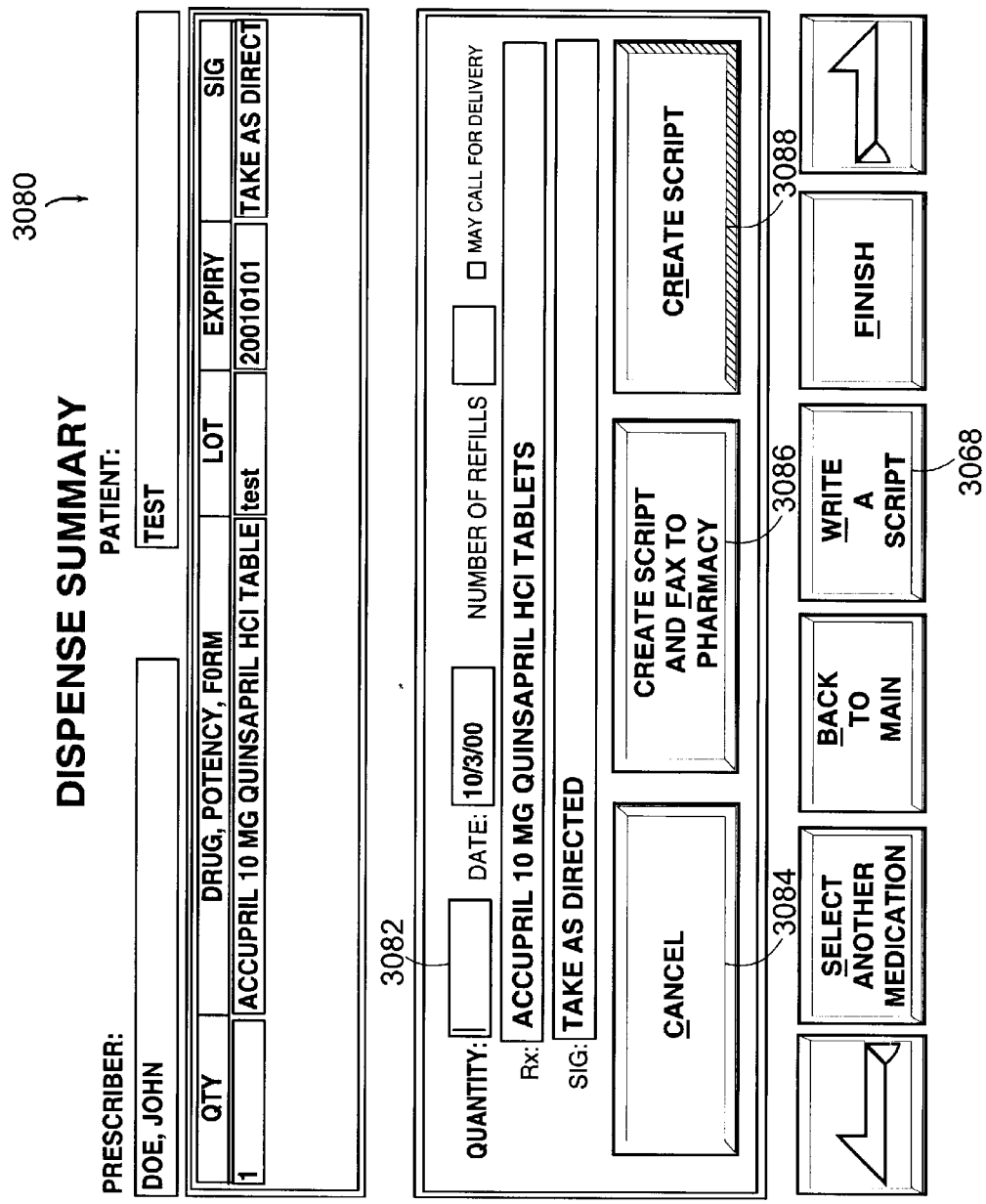

FIGS. 94A–94D illustrate display screens in a user interface that is used in a system for dispensing samples of medical products showing displays for dispense summaries in accordance with a preferred embodiment of the present invention. As described herein with respect to FIGS. 16A–27D a method for dispensing and managing samples of medical products are described. The following figures describe an alternate preferred embodiment for dispensing and managing samples of medical products. This alternate preferred embodiment documents the sample process and addresses all the JCAHO standards. The drug sampling sequence of executable instructions can be used by a system enclosed in a special cabinet or a stand alone processor. In a preferred embodiment the executable instructions are provided for a touch screen monitor. In another preferred embodiment, the monitor also responds to mouse and keyboard commands. Further, in a preferred embodiment, in order to input text into a text box, it has to be in focus. A text box receives focus automatically, or by the user pressing or clicking on the appropriate box interface. Upon coming into focus, the interface box or field may change color, for example, the text box is yellow when it has focus. Message boxes are used to prevent improper or inadequate entries. The sequence described with respect to FIGS. 16A–16D remain the first steps that are performed in the method for dispensing medical product samples. FIG. 94A provides a dispense summary display screen. All entries need to be verified for accuracy. The interface 3062 allows the selection of additional medications for a patient. The interface 3064 allows the user to select back to the main screen. The finish interface 3066 selection allows the printing of labels and monographs for a patient. If the write a script field 3068 is selected, some of the other buttons are disabled multiple samples and scripts can be created for the same patient by selecting add another medication interface 3062.

FIG. 94B describes further details of the dispense summary once write a script interface 3068 is selected. Three new buttons appear while four buttons disappear. The quality field 3082 has to be filled. The selections that can then be made include cancel, create script and fax to pharmacy or create script. In a preferred embodiment the processor does not fax a script to the pharmacy. Instead it transfers the data over the sites' intranet to a base computer. The base computer acts as a server and stores the data into a directory. Another set of executable instructions polls the directory, when a file is found it is either printed or faxed. The fields number of refills and may call for delivery are optional fields.

Figure 94C:
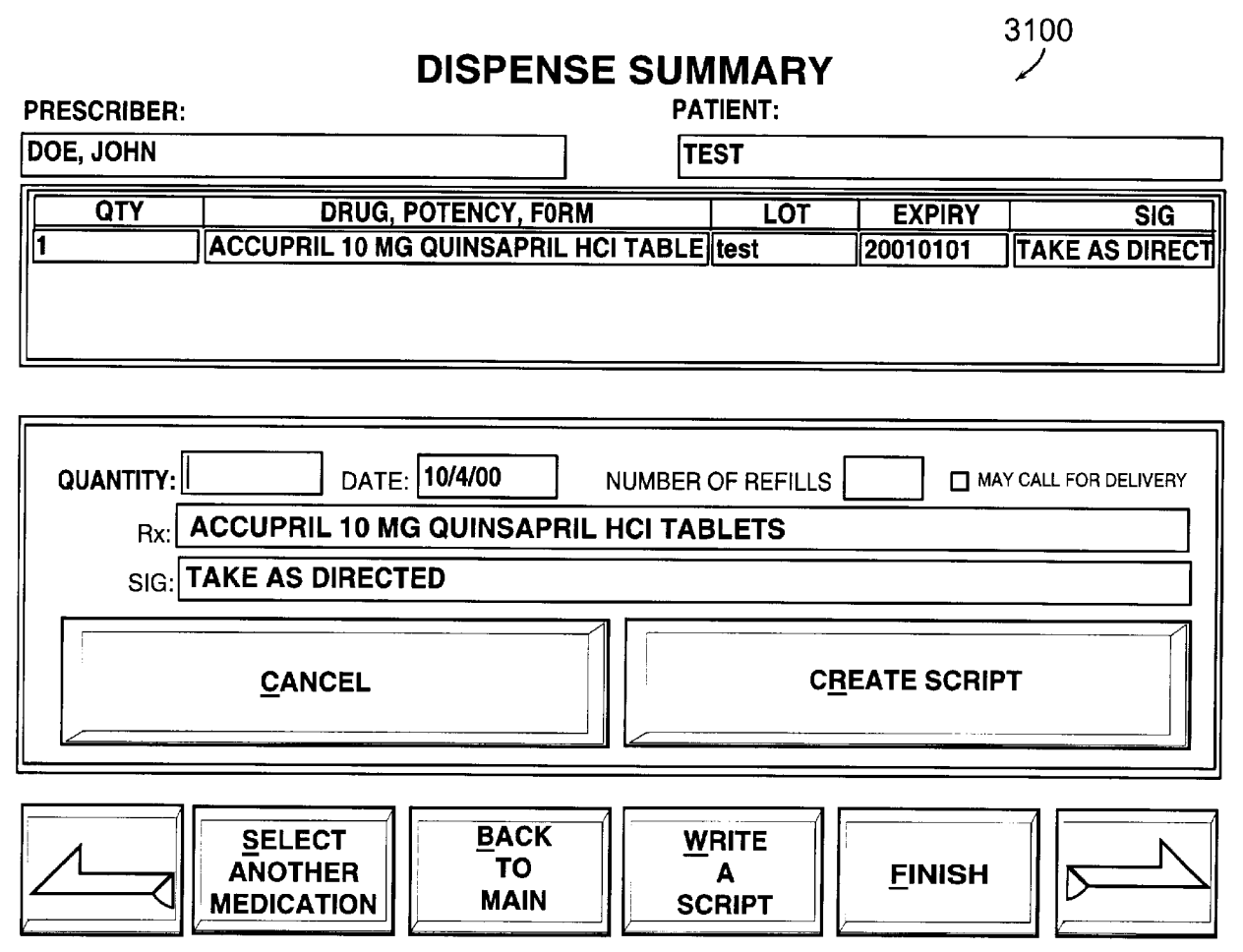
Figure 94D:
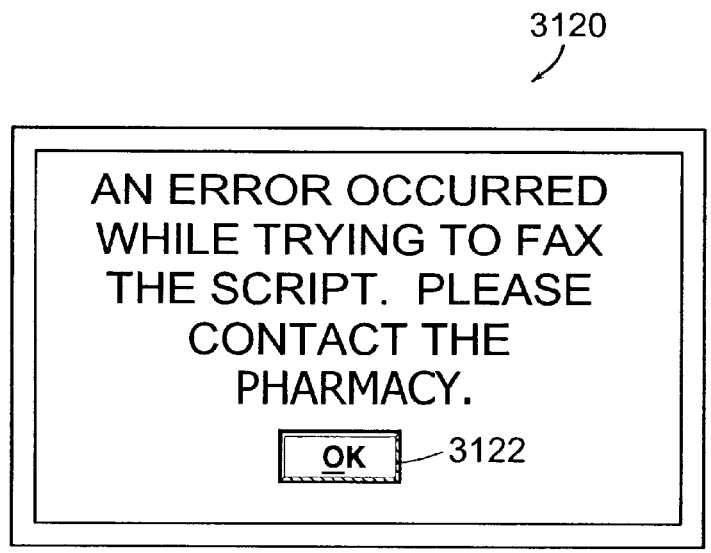

FIG. 94C illustrates another preferred embodiment of a subsequent dispense summary screen analogous to the description in FIG. 94B. In FIG. 94D, the screen display 3120 is displayed when a fax to the pharmacy fails. After a pre-determined time period, for example, approximately sixty second, the image 3120 disappears and the main screen appears. Selecting the OK button 3122 removes the image 3120 immediately and displays the main screen.

FIGS. 95A–95G illustrate display screens in a user interface that is used in a system for dispensing samples of medical products showing the methods of entering medical products to an inventory in accordance with a preferred embodiment of the present invention. The method of entering or adding to inventory begins with selecting the maintenance interface button 3142 in the main screen, followed by selecting the databases interface button 3162 on the touch screen 3160 displayed.

When a medical product is first loaded into the system database, the add method is used, however if additional quantities of the product are added at a later date, the load method is used. The inventory interface button 3182 is touched for selection and an item can be removed from the inventory by the interfacing with the delete button 3184 or added to inventory by interfacing with the add interface button 3182.

Figure 95A:
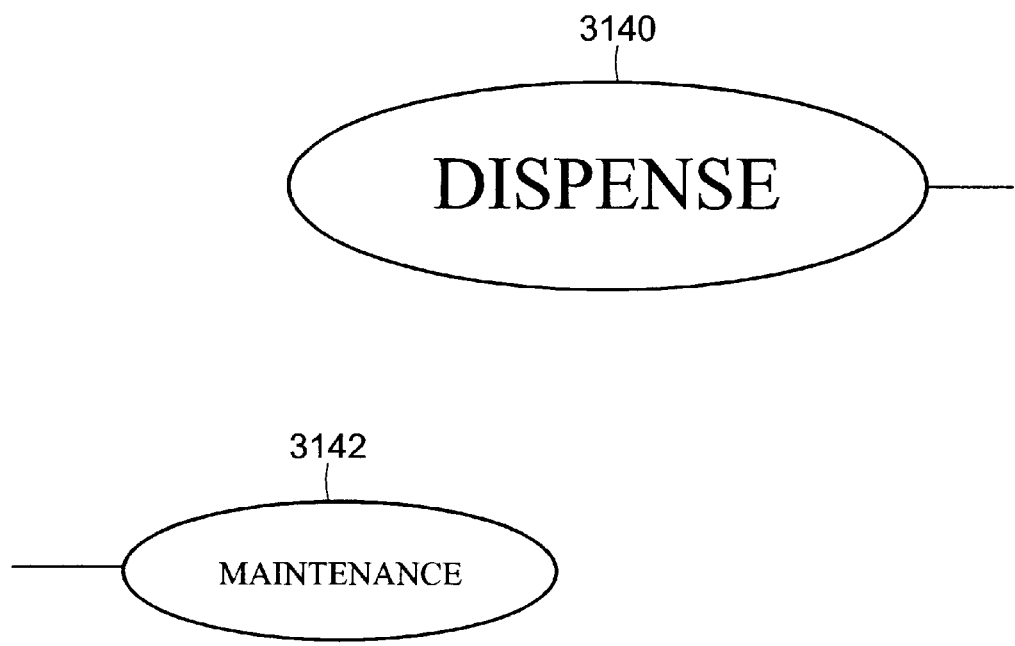
Figure 95B:
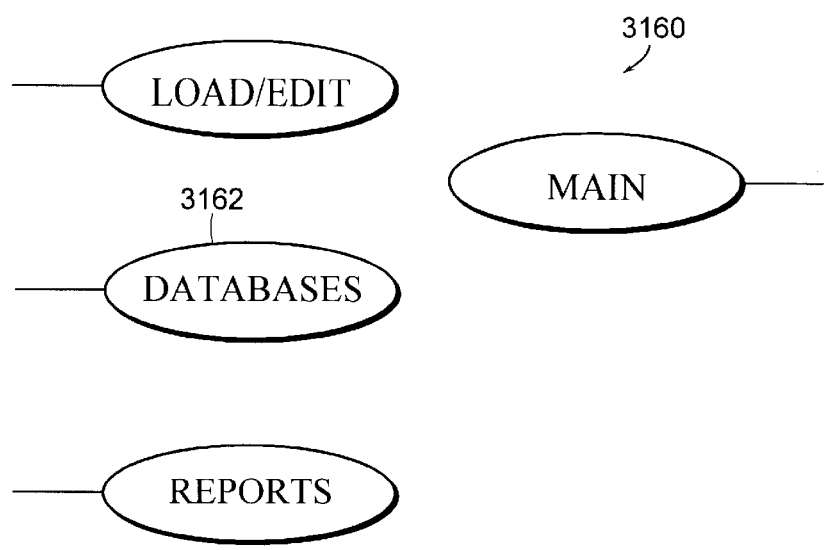
Figure 95C:
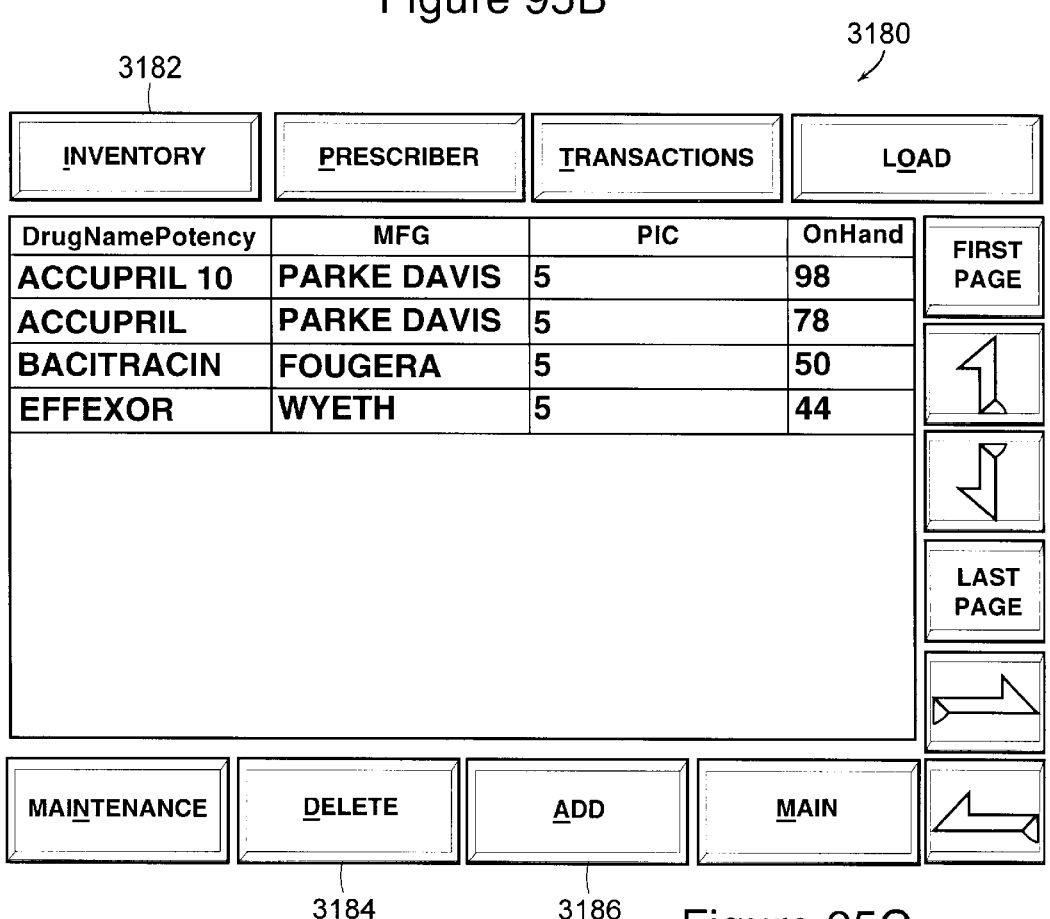
Figures 95D, 95E:
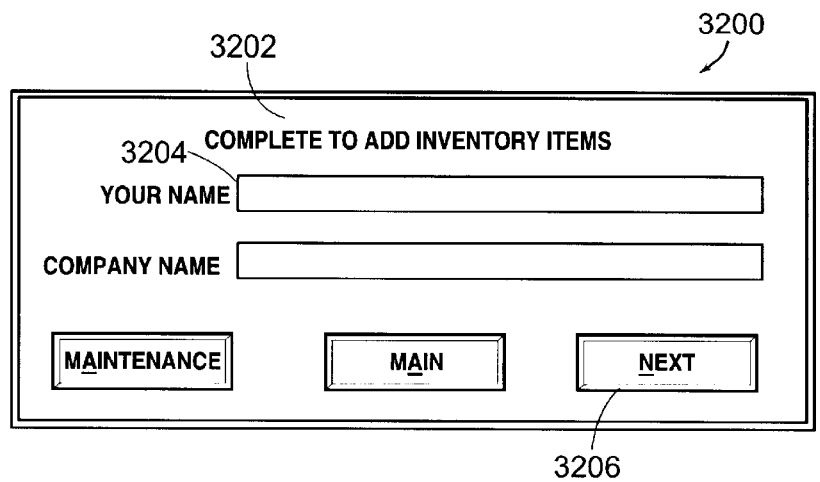
Figure 95F:
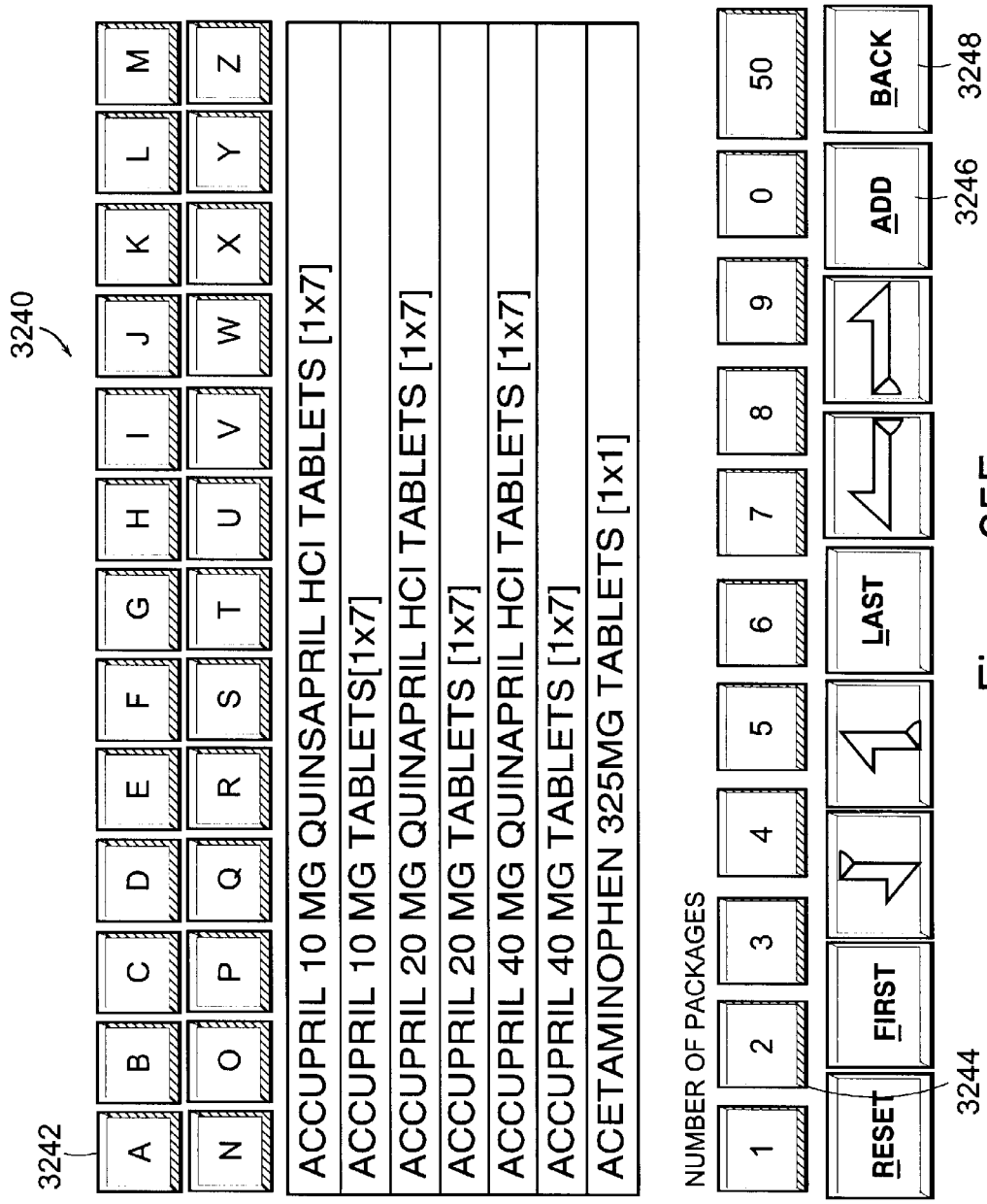
Figure 96A:
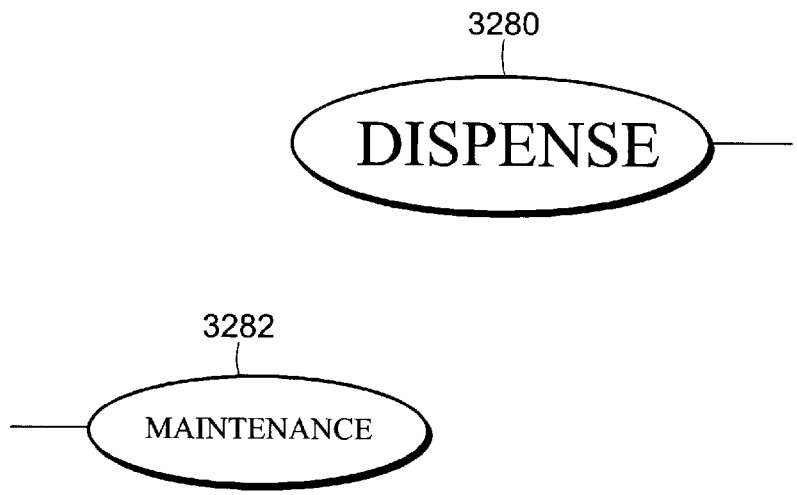
FIGS. 96A–96D illustrate display screens in a user interface that is used in a system for dispensing samples of medical products showing the methods for re-entering or editing medical products to an inventory in accordance with a preferred embodiment of the present invention.
Figure 96B:
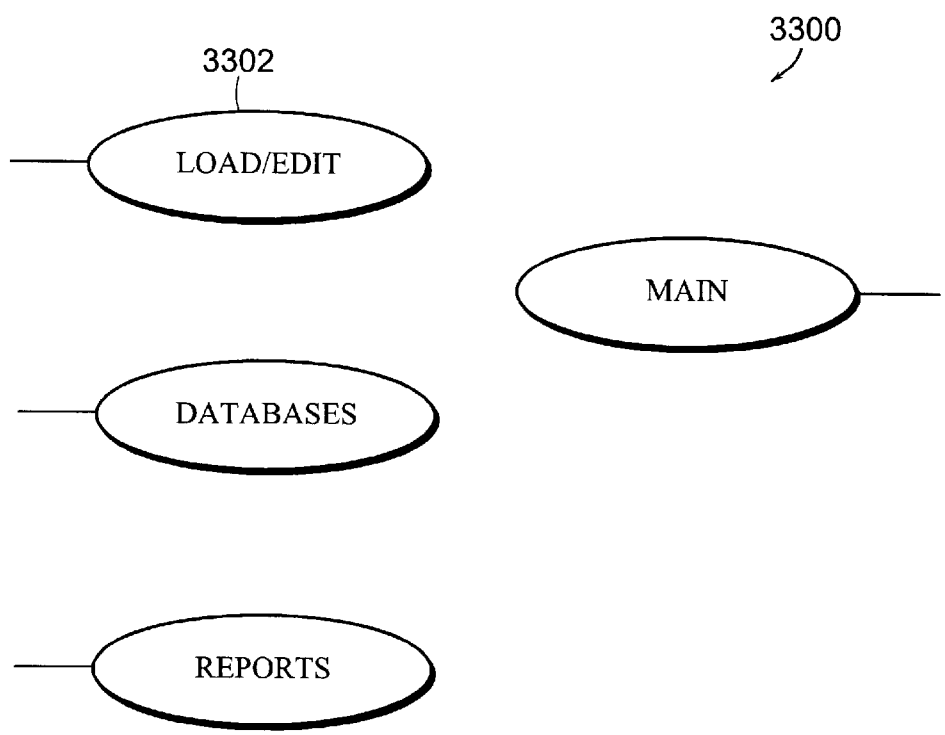
Figure 96C:
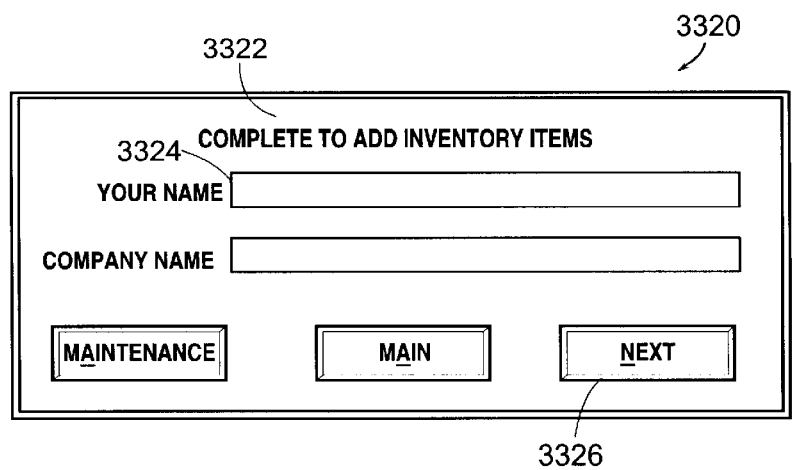
Figure 96D:
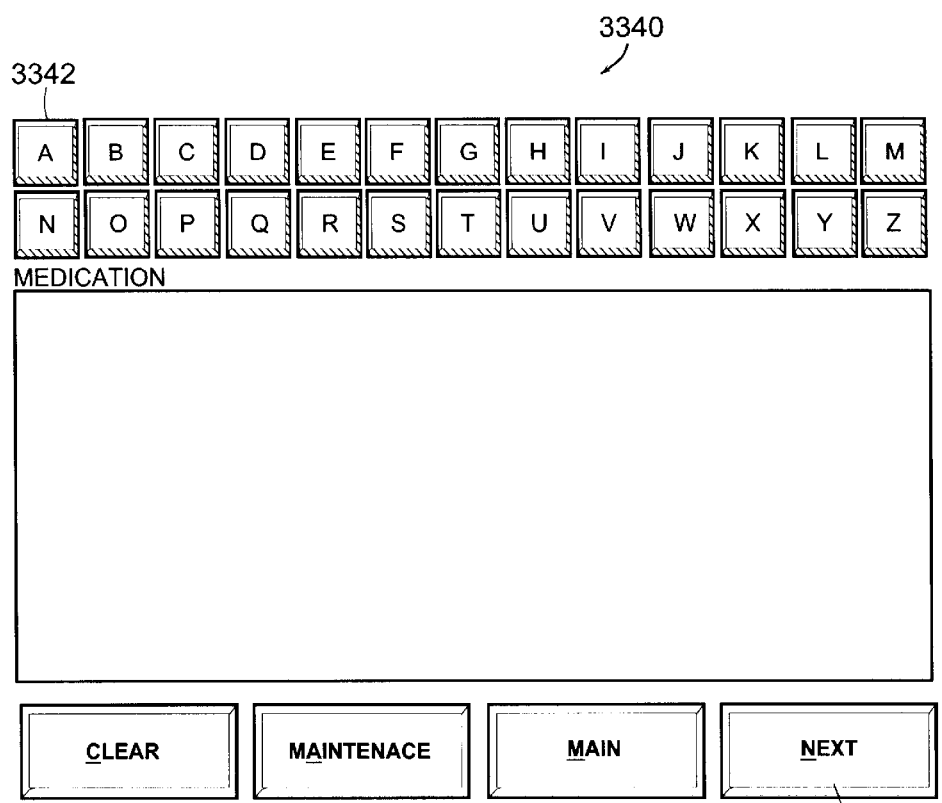
Figure 97A:
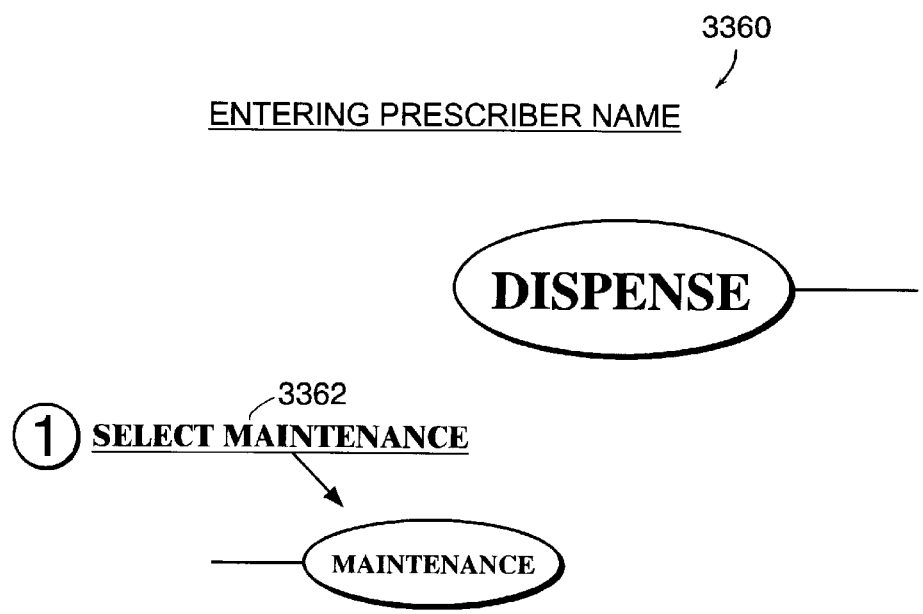
FIGS. 97A–97D illustrate display screens in a user interface that is used in a system for dispensing samples of medical products showing the steps of the method associated with the databases functions to include a prescriber name in accordance with a preferred embodiment of the present invention.
Figure 97B:
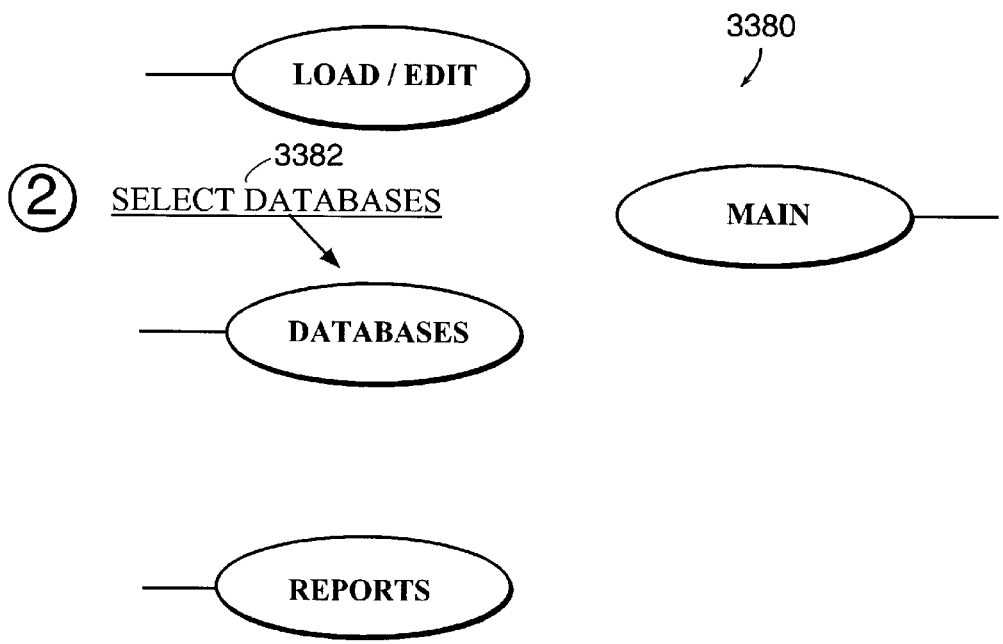
Figure 97C:
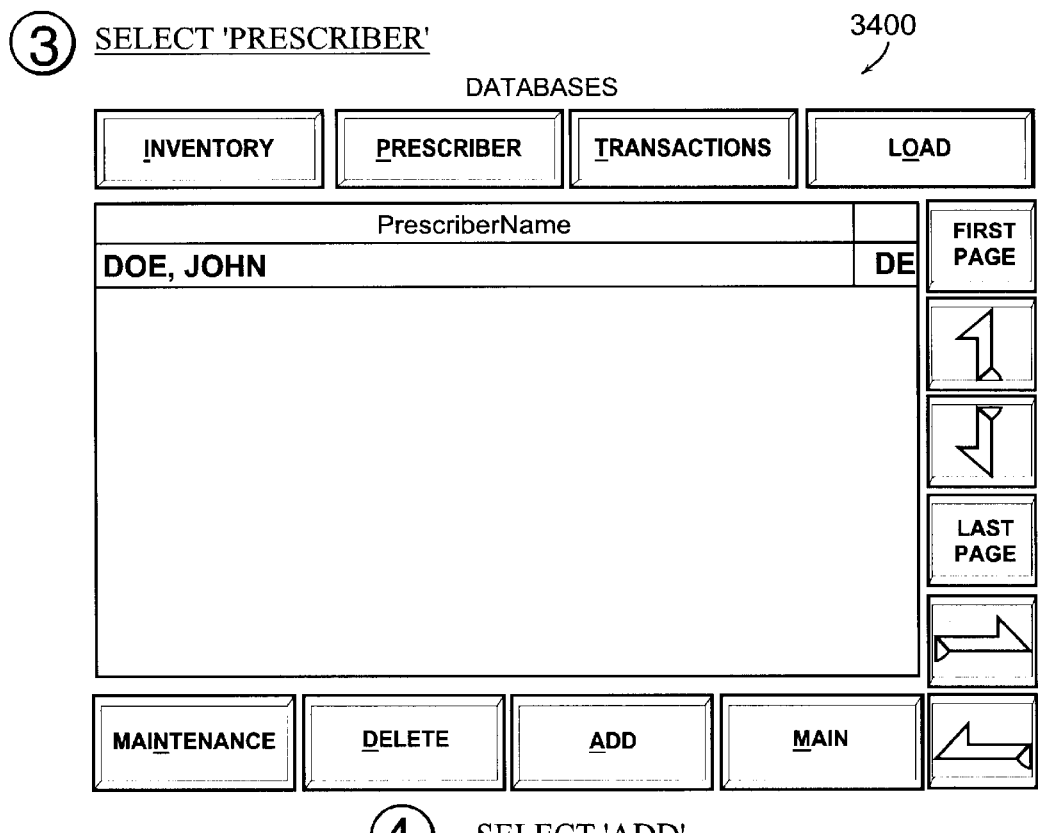
Figure 97D:
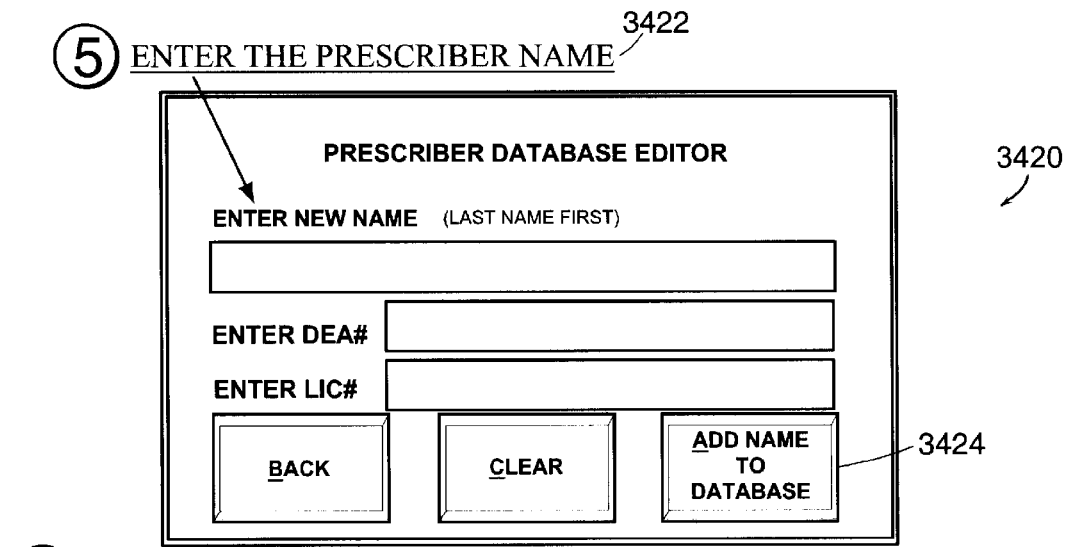

FIG. 95D is a screen 3200 that requires the entry into the name and company fields 3202, 3204. By selecting the drug or medical product name in FIG. 95E using the interface button 3222 a view into the inventory database editor is provided. As depicted in FIG. 95F, the interface 3242 can be used to select a letter to search for the medical product. This interface allows for data to be entered quickly and easily and enforces naming conventions for consistency. Using interface button 3244 a number of packages is entered. The product can be added to the database using the add interface button 3246. In the subsequent screens further information such as lot, expiration data, and quantity added. The save button 3262 is used to save data.

FIGS. 96A–96D illustrate display screens in a user interface that is used in a system for dispensing samples of medical products showing the methods for re-entering or editing medical products to an inventory in accordance with a preferred embodiment of the present invention. The method includes using the maintenance interface button 3282 to enter the screen 3300 from where the load/edit interface button 3302 can be accessed. The user is then prompted to add a name and company information. In this case the user may be an agent of a medical pharmaceutical company or another distributor. The first initial of the drug can be accessed and then selected from the alphabetized list. The use of on screen 3320 next interface button 3344 on screen 3340 brings up the inventory database editor screen described in FIG. 95E. It should be noted that the inventory database editor utilizes a number of utility programs such as a drug name utility that allows the user to search through a drug sample database, a "Mfg" button that allows a search through a database containing names of drug manufacturers, and a get new gcn interface utility that retrieves a number which determines the proper patient monograph for a sample. All these utilities, reduce and preferably eliminate the need for excess typing and maintain naming conventions.

Whether a drug name is manually created, or selected with the drug name utility, the following applies: the PIC number (minimum quantity required) must be entered. Another utility examines this field and sends an email if shortage exist; the lot and expiration data must be entered next. Samples are always stored and entered in the same order, closest expiration data first; enter the lot, depress the 'tab' or 'enter' key to give the date (YYYY) focus. Type the numeric value for the following eight characters (YYYYMMDD), after the required number of elements in each field is realized, focus automatically shifts to the next open field on its right. Further, samples with different lot and expiration numbers are entered separately. Each quantity field is specific to their own specific lot and expiration. When sample data is saved the sum of the individual quantities are placed into the 'OnHand' text field. When the quantity of samples dispensed exceeds the quantity of a specific lot, the balance is subtracted from the next lot. The lot and expiration fields also automatically shifts to the left. The first sig, 'TAKE AS DIRECTED' is posted automatically whenever the 'CLEAR ALL FIELDS' button is selected. The remaining fields can be filled in and saved. There is an additional field called 'COMMENT'. This field can be used to capture all other data of interest. For example: If a sample reaches its expiration date and is removed, the number, date, and reason for removal can be entered in this field.

FIGS. 97A–97D illustrate display screens in a user interface that is used in a system for dispensing samples of medical products showing the steps of the method associated with the databases functions to include a prescriber name in accordance with a preferred embodiment of the present invention. The method begins with selecting the maintenance interface button 3362 which allows access to the screen 3380 from which the database interface is selected using button 3382. Once the prescriber is selected in screen 3400 and added, the screen 3420 prompts the user to enter the prescriber's name and license number and other pertinent information.

Figure 98A:
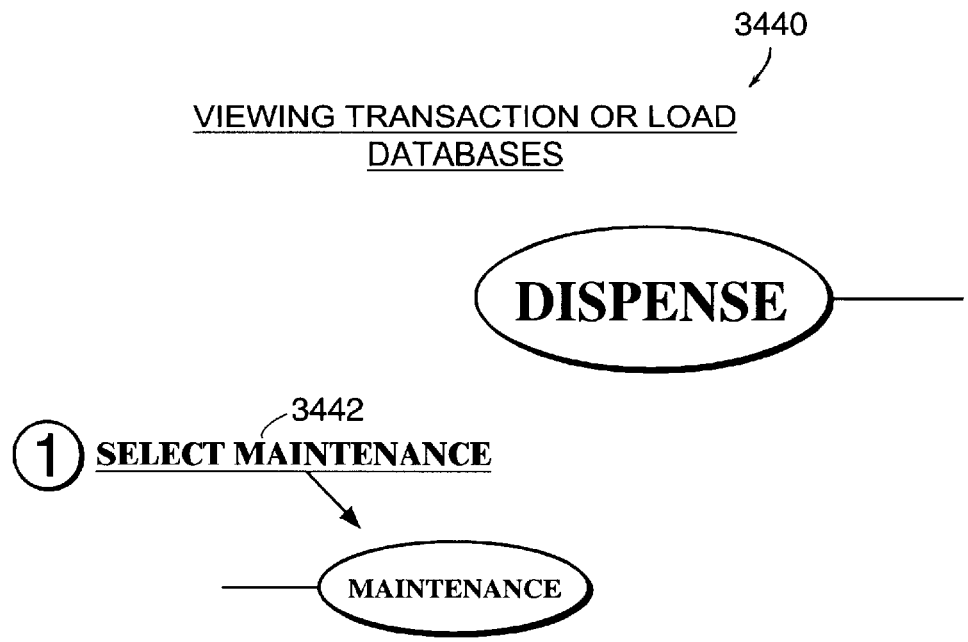
Figure 98B:
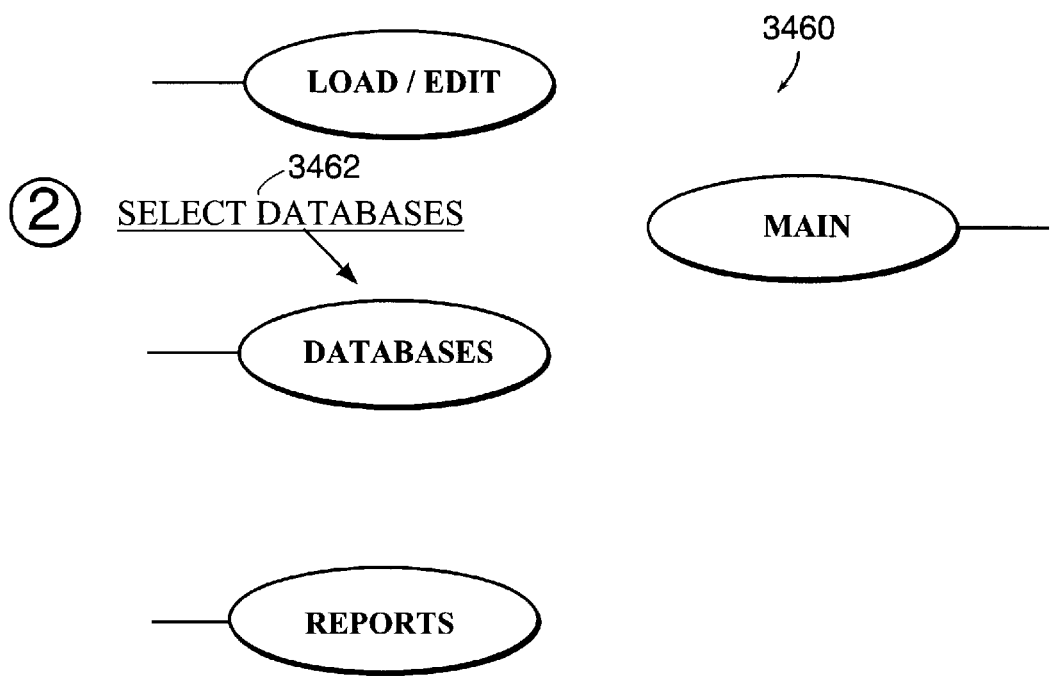
Figure 99A:
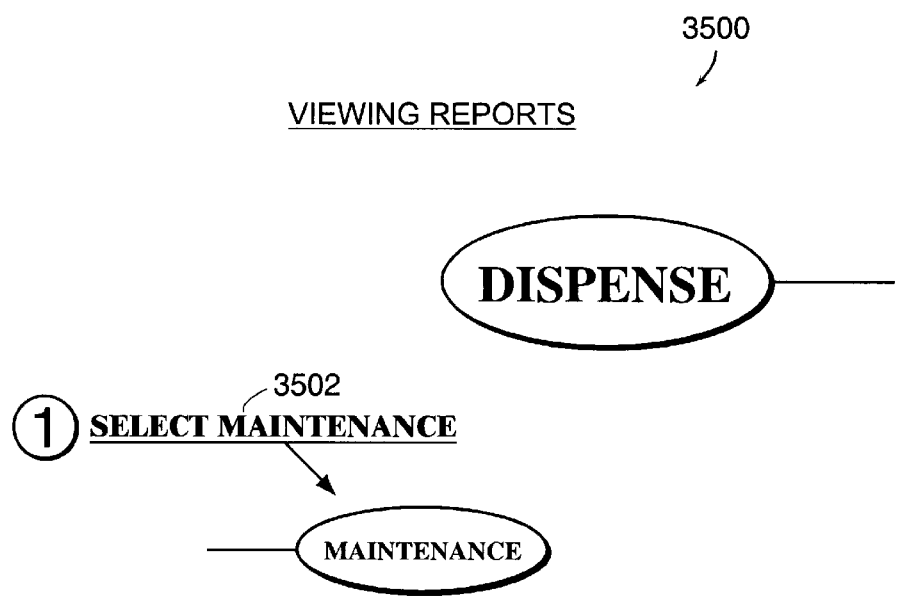
FIGS. 99A–99D illustrate display screens in a user interface that is used in a system for dispensing samples of medical products showing the method to view multiple reports in accordance with a preferred embodiment of the present invention.
Figure 99B:
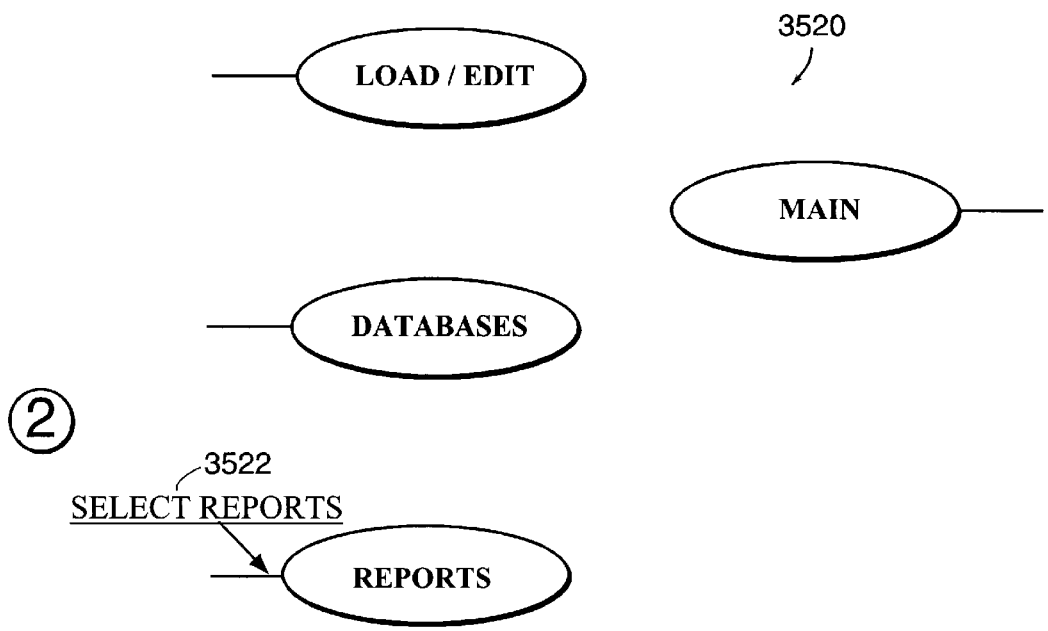
Figure 99C:
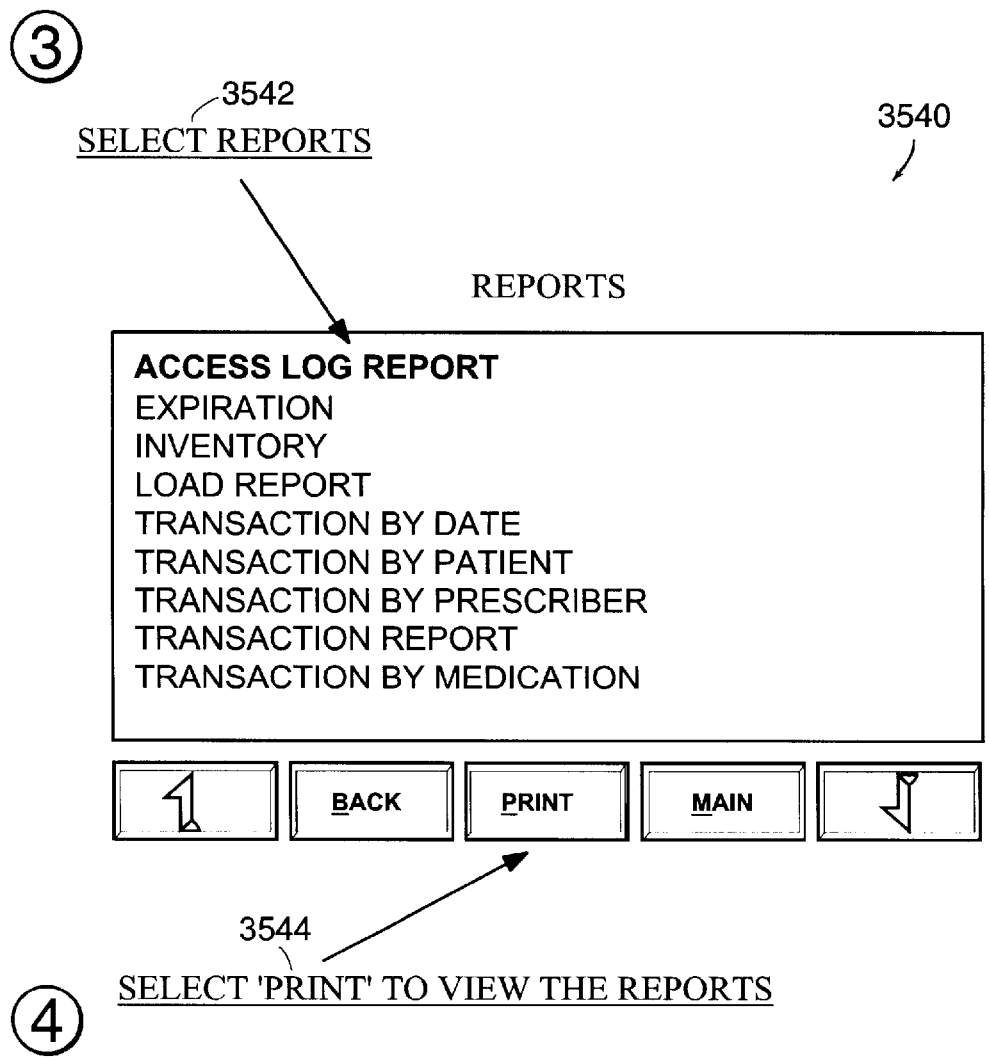
Figure 99D:
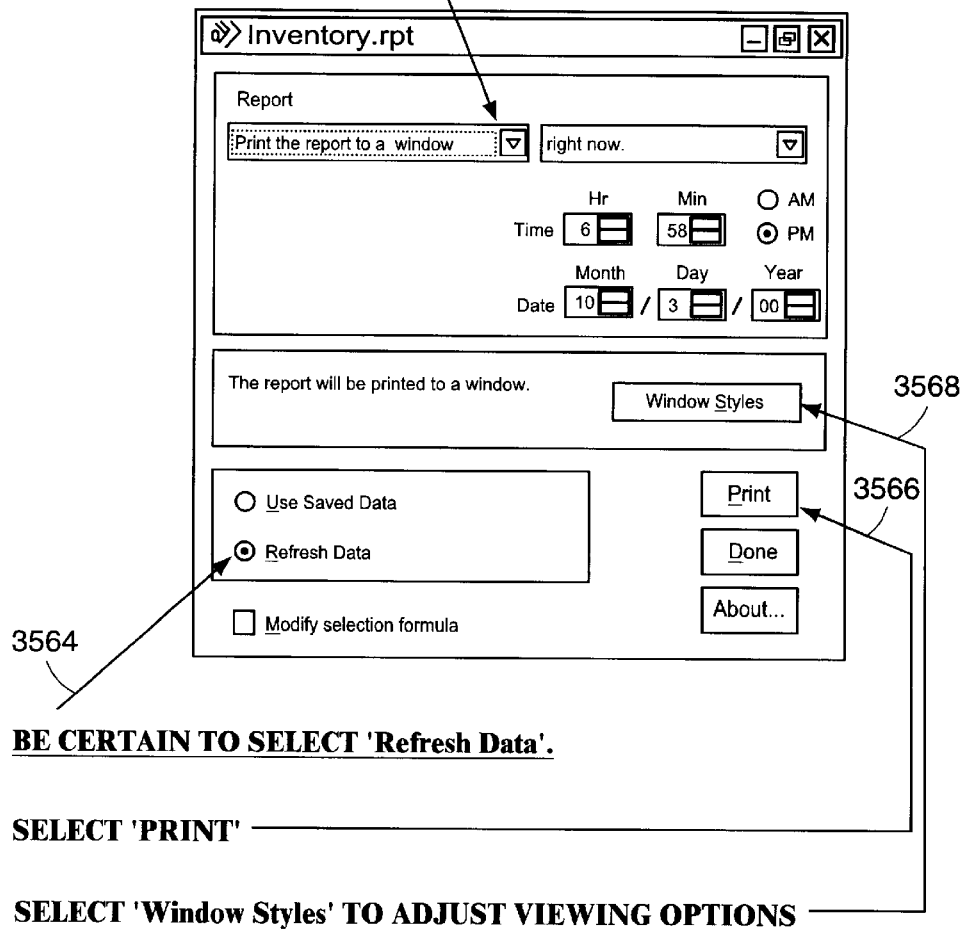

FIGS. 98A–98C illustrate display screens in a user interface that is used in a system for dispensing samples of medical products showing the methods for viewing a transaction or loading databases in accordance with a preferred embodiment of the present invention. Similar to the previous description herein the maintenance interface button 3442 is used to enter the databases on screen 3460. The database to be viewed can be selected from display screen 3480. In a preferred embodiment the transaction and load databases are for viewing purposes only.

FIGS. 99A–99D illustrate display screens in a user interface that is used in a system for dispensing samples of medical products showing the method to view multiple reports in accordance with a preferred embodiment of the present invention. The executable instructions for viewing reports can be accessed using the maintenance button 3502 which access screen 3520 allowing the user the interface with the reports button 3522. A multiple listing of reports are provided to the user in screen 3540. The type of report needed can be selected 3542 by touching the screen and then printed using a print interface 3544. The options for viewing the report are provided in field 3562 along with a print interface 3566.

FIGS. 100A–100C illustrate display screens in a user interface that is used in a system for dispensing samples of medical products showing the method to determine the software version of the medical products in accordance with a preferred embodiment of the present invention. Upon selecting the maintenance interface button 3582 and subsequently accessing executable instructions with respect to databases via the display screen 3580, the current version of the executable instruction in use.

Figure 101A:
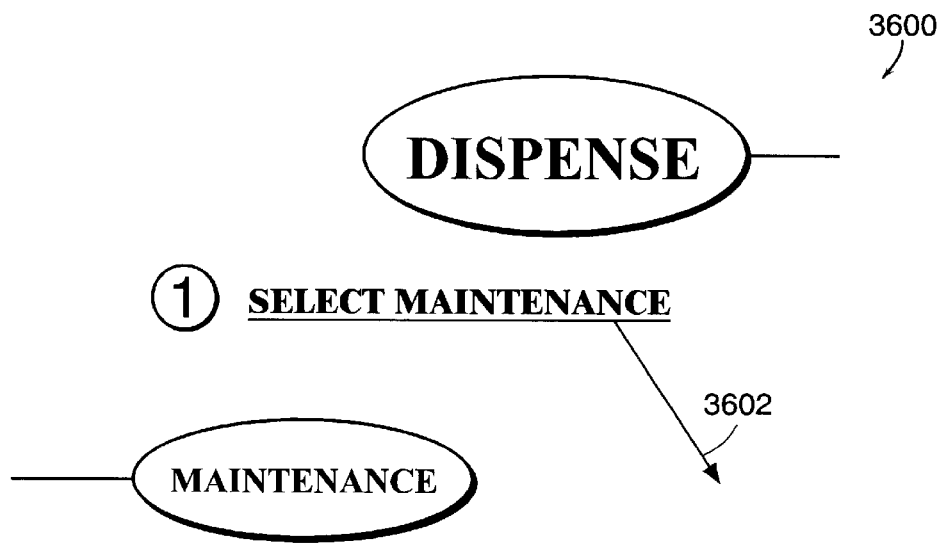
FIGS. 101A–101B illustrate display screens in a user interface that is used in a system for dispensing samples of medical products showing the method to access a desktop computing processor in accordance with a preferred embodiment of the present invention.
Figure 101B:
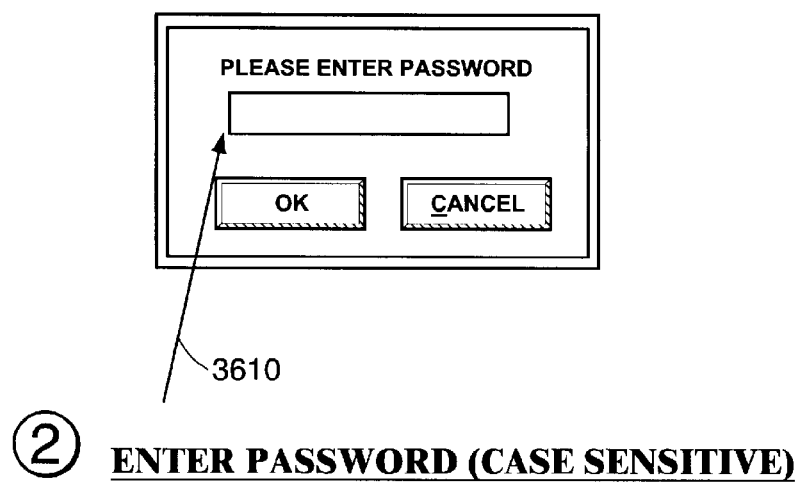

FIGS. 101A–101B illustrate display screens in a user interface that is used in a system for dispensing samples of medical products showing the method to access a desktop computing processor in accordance with a preferred embodiment of the present invention. The maintenance interface button in display screen 3600 allows the access to a screen 3610 for entry of a password which enables executable instructions to exit to a desktop computing interface.

Figure 102:
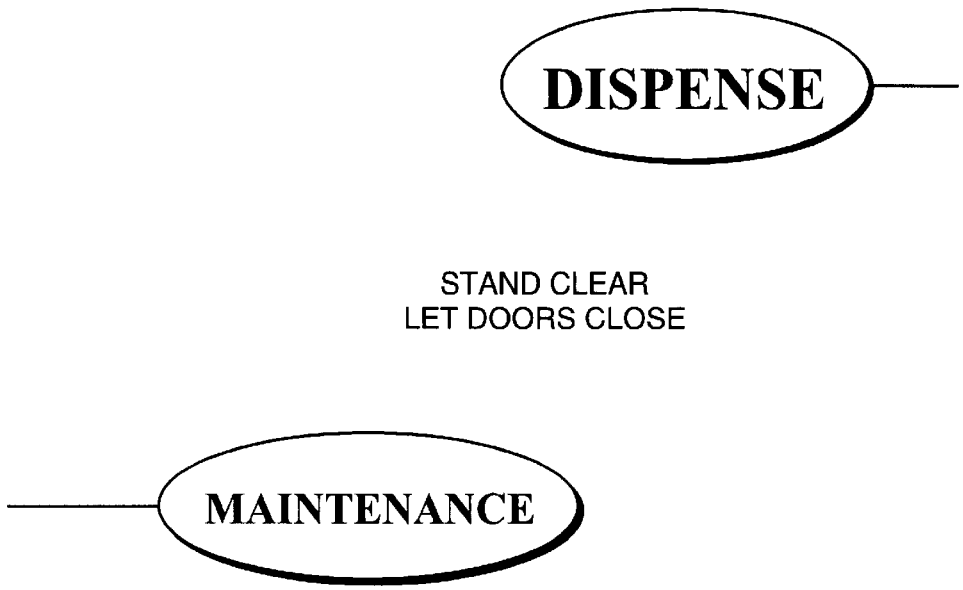
FIG. 102 illustrates warning screen in a user interface that is used in a system for dispensing samples of medical products in accordance with a preferred embodiment of the present invention.

FIG. 102 illustrates a warning 3620 screen in a user interface that is used in a system for dispensing samples of medical products in accordance with a preferred embodiment of the present invention. Once the process for dispensing the samples of medical products is completed by selecting the close button the screen 3620 is displayed.

Figure 103:
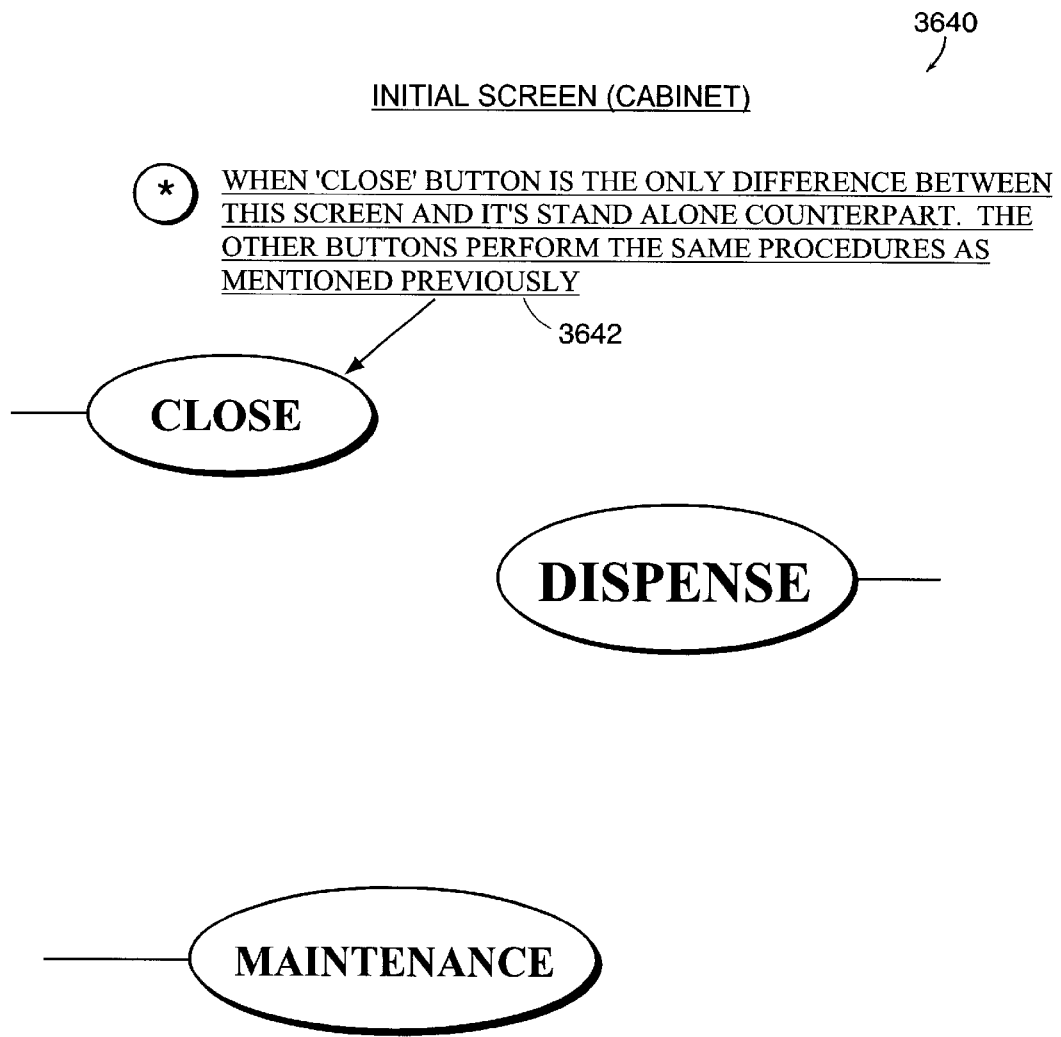
FIG. 103 illustrates an initial screen in a system for dispensing samples of medical products in accordance with a preferred embodiment of the present invention.

FIG. 103 illustrates an initial screen 3640 in a system for dispensing samples of medical products in accordance with a preferred embodiment of the present invention. As indicated in the figure, the close interface button 3642 is the only difference between the interface at a cabinet or in a stand alone version.

Figure 104:
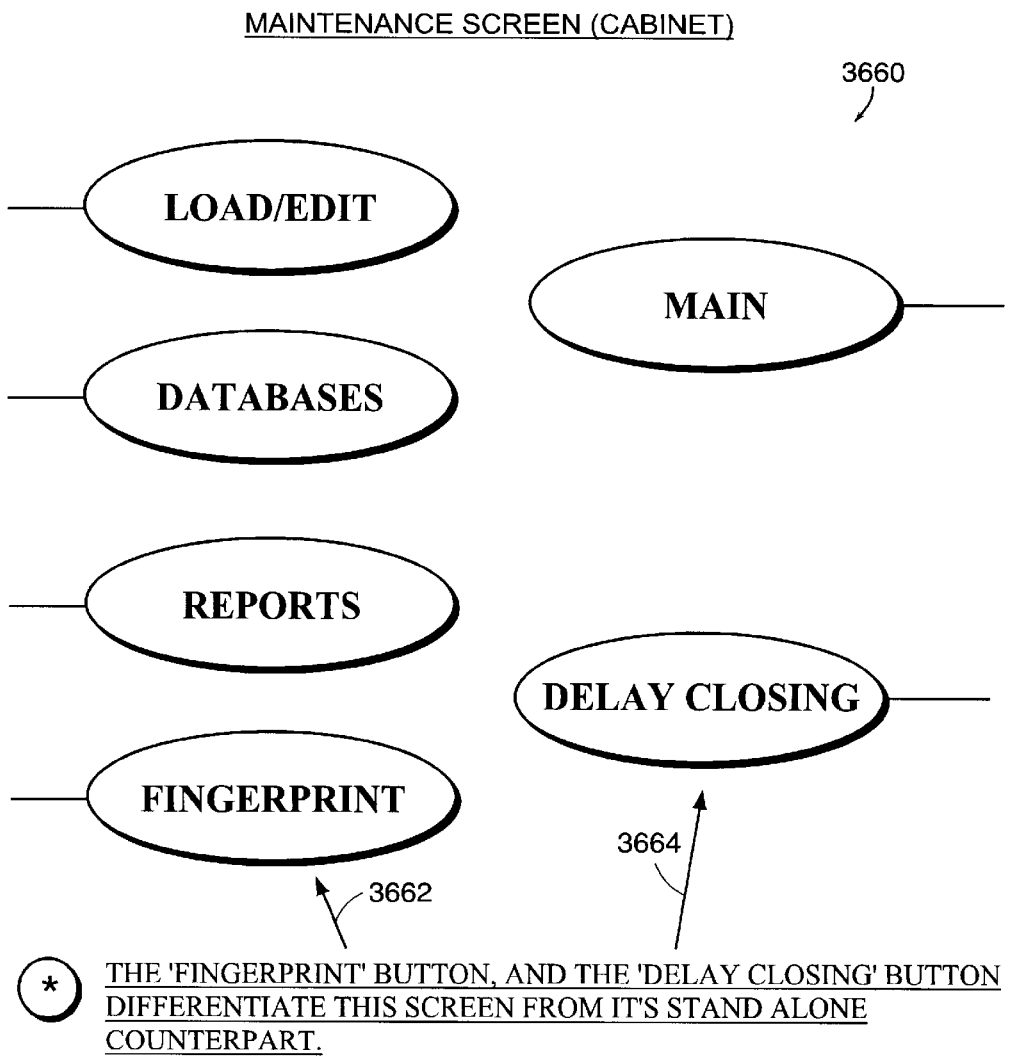
FIG. 104 illustrates a maintenance screen in a system for dispensing samples of medical products in accordance with a preferred embodiment of the present invention.

FIG. 104 illustrates a maintenance screen 3660 in a system for dispensing samples of medical products in accordance with a preferred embodiment of the present invention. A fingerprint interface button 3662 and a delay closing interface button 3664 and a delay closing interface button 3664 are present in the system integral with the dispensing cabinet.

Figure 105B:
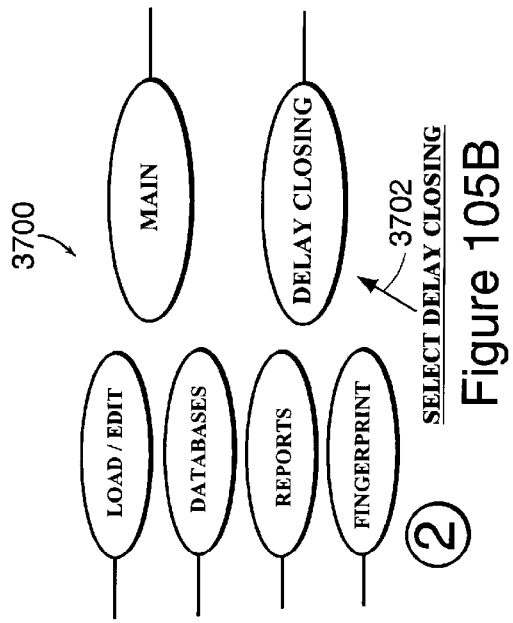
FIGS. 105A–105C illustrate display screens in a user interface that is used in a system for dispensing samples of medical products showing a method used for delaying the closing of a cabinet in accordance with a preferred embodiment of the present invention.
Figure 105A:
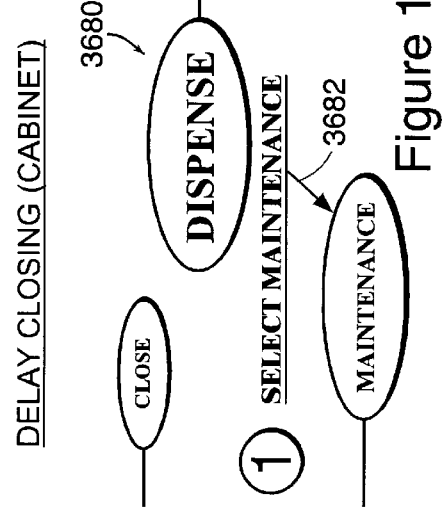
Figure 105C:
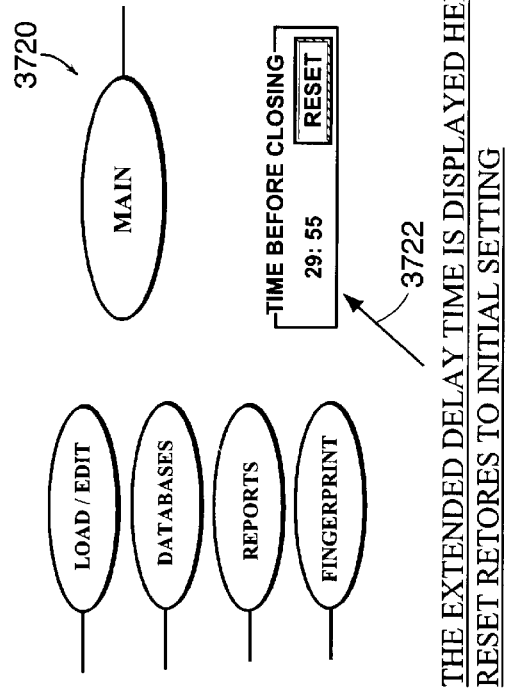
Figure 106A:
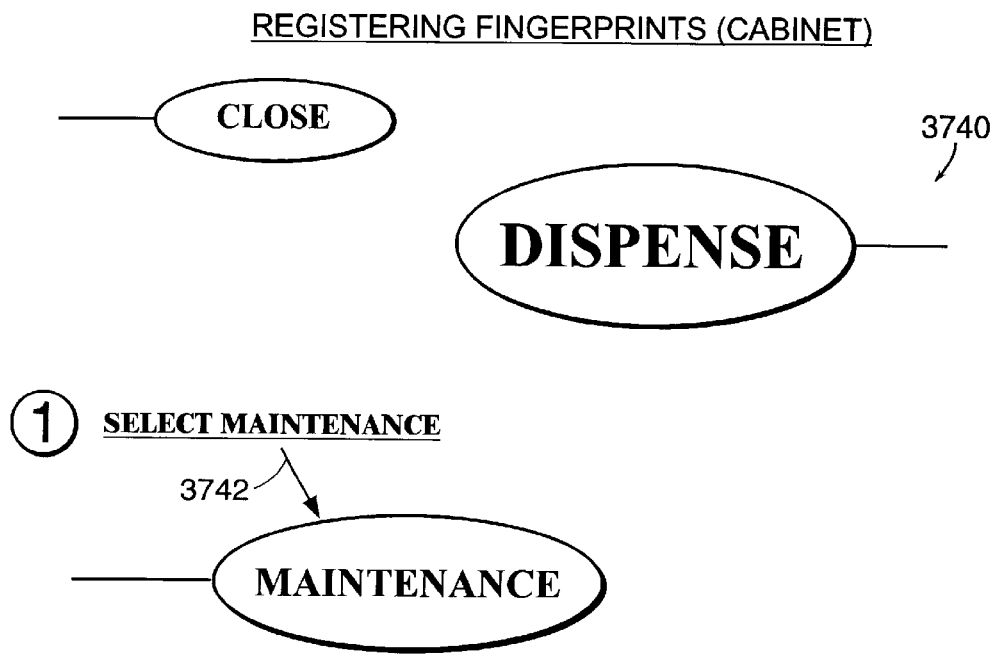
FIGS. 106A–106D illustrate display screens in a user interface that is used in a system for dispensing samples of medical products showing a method used for registering fingerprints in accordance with a preferred embodiment of the present invention.
Figure 106B:
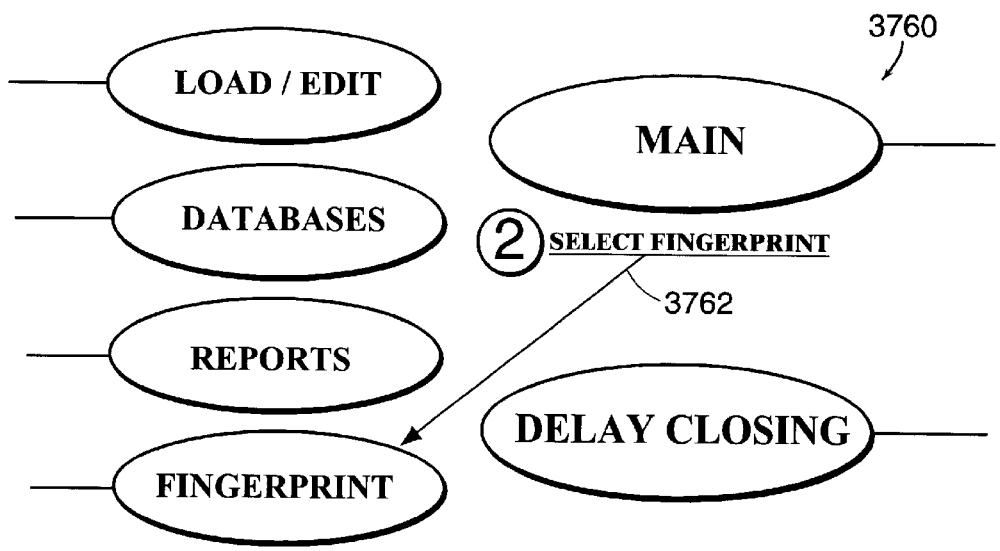
Figure 106C:
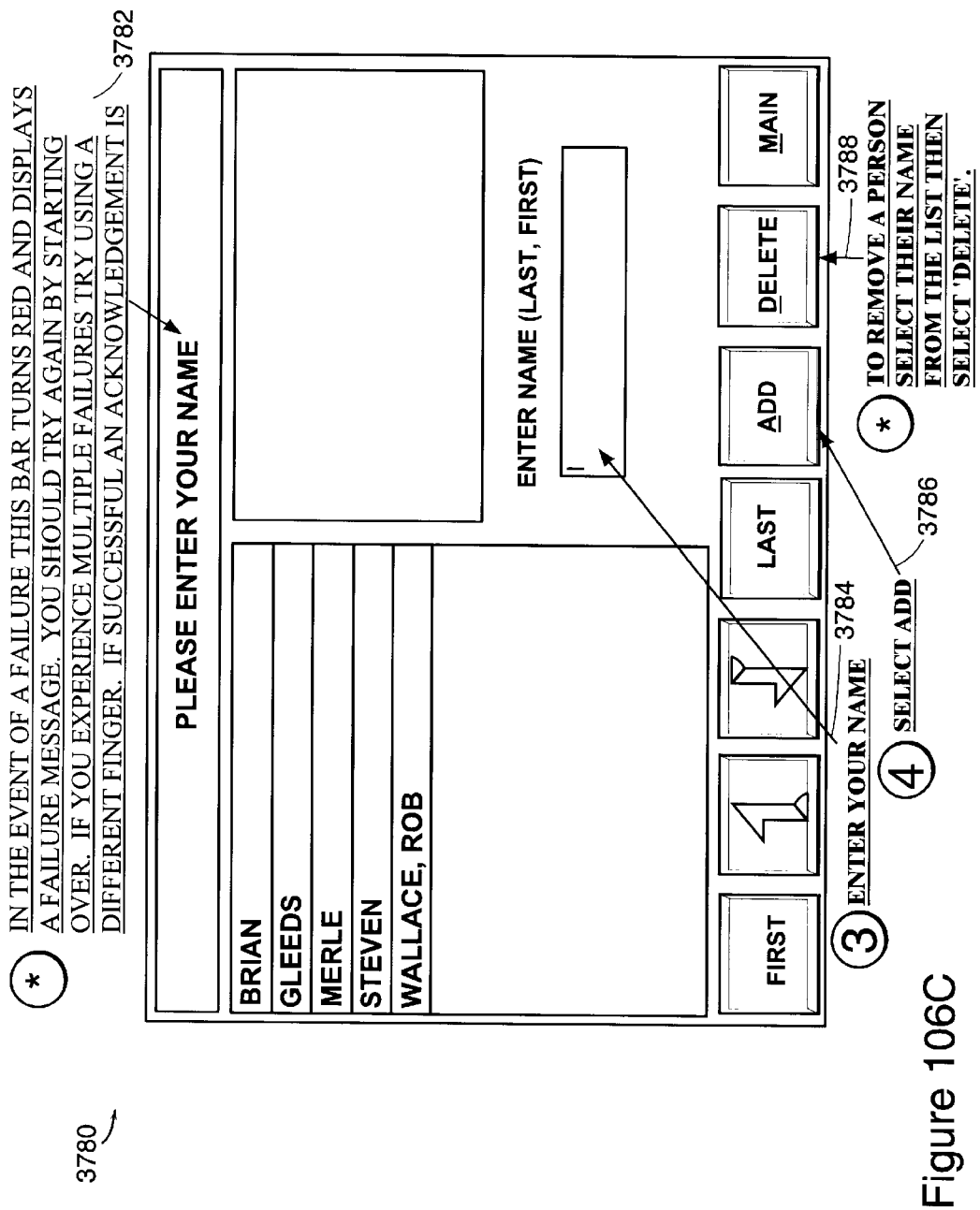
Figure 106D:
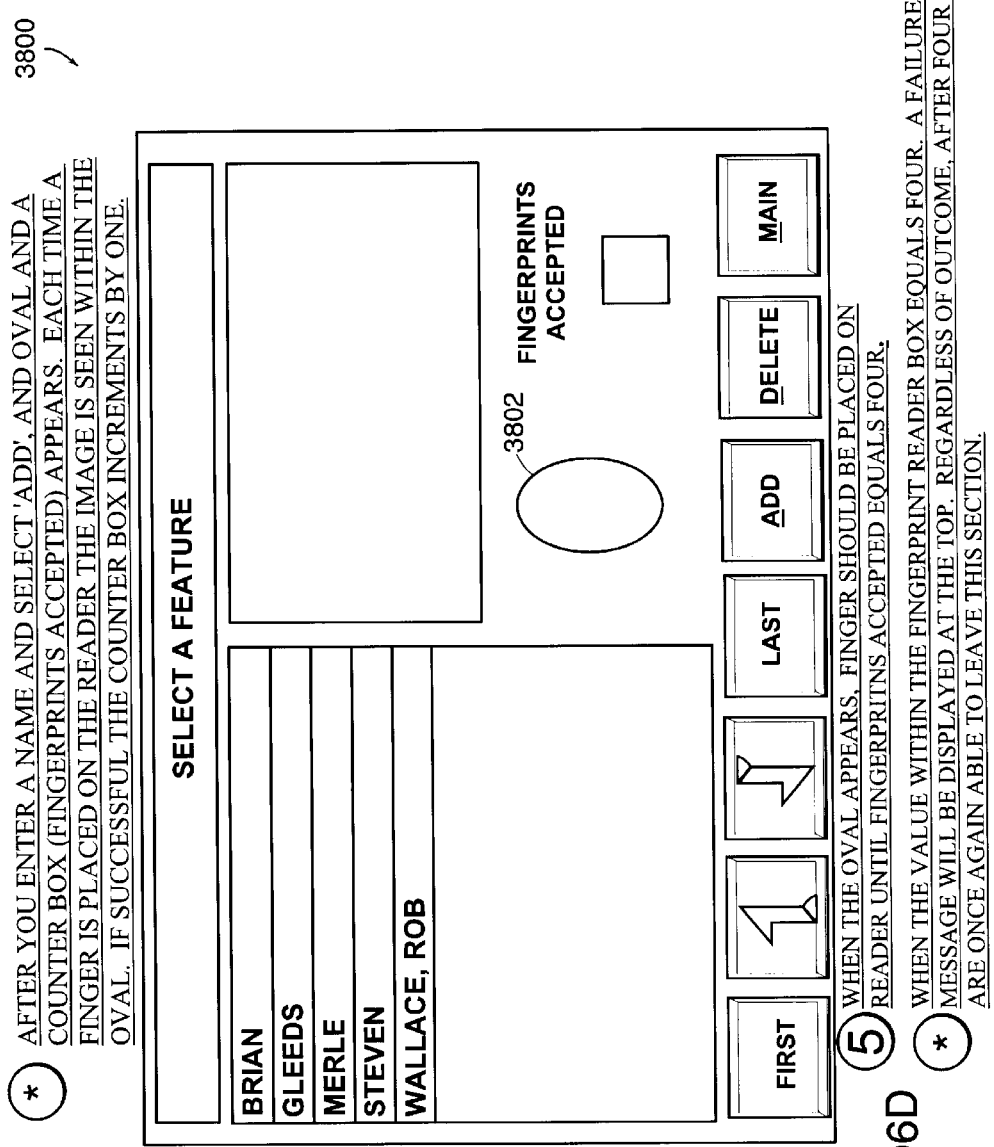

FIGS. 105A–105C illustrate display screens in a user interface that is used in a system for dispensing samples of medical products showing a method used for delaying the closing of a cabinet in accordance with a preferred embodiment of the present invention. Upon selecting the maintenance interface section 3682 in the main screen 3680 and accessing the delay closing interface 3702 from the maintenance screens the delay closing executable instructions are processed. The user can set the delay time and visually confirm the delay time in the field 3722.

FIGS. 106A–106D illustrate display screens in a user interface that is used in a system for dispensing samples of medical products showing a method used for registering fingerprints in accordance with a preferred embodiment of the present invention. The method for registering fingerprints includes accessing the fingerprint interface button 3762 from the maintenance screen 3760. the user is prompted by the messages on screen 3780 to add their name, and place their finger in the interface field 3802 for accepting and registering their fingerprint. The registered fingerprint provides a controlled access to the user at a subsequent time.

The systems and methods to dispense medical products in the preferred embodiments have an information display device for retrieving and caching information from a communication network during periodically established communication sessions. The display device includes a graphical display device, a communication transceiver connectable to a communication network that receives display data. The network can include the Internet or other local and wide area networks. The device also includes a microprocessor and a memory device that stores display data, at least one display template, and program information. The display templates include variable field identifiers. Further the program information comprises a display generator providing a modified template by replacing the variable field identifiers with corresponding display data, and displaying the modified template on the graphical display device. The microprocessor and the memory device record at least one dispensing operation value for a subset of data that are subsequently sent to the communication network. The display device formats textual data and graphical data for display on the touch screen. The microprocessor may include an operating system, as well as application and communication software to implement the functions with respect to dispensing medical products. The operating system for the system of the present invention includes a processing system with at least one high sped processing unit and a memory system. In accordance with the practice of persons skilled in the art of computer programming, the present invention has been described herein with reference to acts and symbolic representations of operations or instructions that are performed by the processing system. Such acts, operations and instructions are also referred to sometimes as being computer executed or processing unit executed.

It will be appreciated that the acts and symbolically represent operations or instructions include the manipulation of electrical signals by the processing unit. An electrical system with data bits causes a resulting transformation or reduction of the electrical signal representation, and the maintenance of data bits at memory location in the memory system to thereby reconfigure or otherwise alter the processing unit's operation, as well as other processing of signals. The memory locations where data bits are maintained are physical locations that have particular electrical, magnetic, optical, or organic properties corresponding to the data bits.

The data bits may also be maintained on a computer readable medium including magnetic disks, optical disks, organic disks, and any other volatile or non-volatile mass storage system readable by the processing unit. The computer readable medium includes cooperating or interconnected computer readable media, which exist exclusively on the processing system or is distributed among multiple interconnected processing systems that may be local or remote to the processing system.

It should be understood that the programs, processes, methods and systems described herein are not related or limited to any particular type of computer or network system (hardware or software), unless indicated otherwise. Various types of general purpose or specialized computer systems may be used with or perform operations in accordance with the teaching described herein.

In view of the wide variety of embodiments to which the principles of the present invention can be applied, it should be understood that the illustrated embodiments are exemplary only, and should not be taken as limiting the scope of the present invention. For example, the steps of the flow diagrams may be taken in sequences other than those described, and more or fewer elements may be used in the block diagrams. While various elements of the preferred embodiments have been described as being implemented in software, in other embodiments in hardware or firmware implementations may alternatively be used, and vice-versa.

It will be apparent to those of ordinary skill in the art that methods involved in the dispensing of medical products may be embodied in a computer program product that includes a computer usable medium. For example, such a computer usable medium can include a readable memory device, such as, a hard drive device, a CD-ROM, a DVD-ROM, or a computer diskette, having computer readable program code segments stored thereon. The computer readable medium can also include a communications or transmission medium, such as, a bus or a communications link, either optical, wired, or wireless having program code segments carried thereon as digital or analog data signals.

The claims should not be read as limited to the described order or elements unless stated to that effect. Therefore, all embodiments that come within the scope and spirit of the following claims and equivalents thereto are claimed as the invention.

While this invention has been particularly shown and described with references to preferred embodiments thereof, it will be understood by those skilled in the art that various changes in form and details may be made therein without departing from the scope of the invention.

What is claimed:

1. A drug sample dispenser comprising:
   a dispenser housing in which a plurality of packaged medical products are stored, the dispenser housing having a door that opens to provide access to the packaged medical products;
   a computer mounted within the housing; and
   a control system that opens and closes the door of the dispenser housing in response to an instruction from the computer.

2. The drug sample dispenser of claim 1 wherein the drug dispenser further comprises at least one door mounted to the housing the, at least one door having a plurality of bins.

3. The drug sample dispenser of claim 1 wherein the dispenser further comprises a barcode reader.

4. The drug sample dispenser of claim 1 wherein the at least one door comprises a proximity sensor.

5. The drug sample dispenser of claim 1 wherein the computer is in communication with a database data processor.

6. The drug sample dispenser of claim 5 wherein the communication between the computer and the database data processor includes transmission using one of at least the Internet, a telephone system, a satellite system, a wireless system, and a pager system.

7. The drug sample dispenser of claim 1 wherein the drug dispenser further comprises a camera.

8. The drug sample dispenser of claim 7 wherein the drug dispenser comprises a proximity detector coupled to the camera.

9. The drug sample dispenser of claim 7 wherein the drug sample dispenser comprises a user identification system coupled to the camera.

10. The drug sample dispenser of claim 7 wherein the camera is coupled to the at least one door such that opening of the at least one door causes the camera to take a picture.

11. The drug sample dispenser of claim 7 wherein the drug sample dispenser comprises a control system connected to the camera.

12. The drug sample dispenser of claim 1 wherein the dispenser further comprises a user identification system.

13. The drug sample dispenser of claim 12 wherein the user identification system comprises a keypad.

14. The sample dispenser of claim 12 wherein the user identification system comprises a card reader.

15. The drug sample dispenser of claim 12 wherein the drug dispenser comprises a control system connected to the identification system.

16. A method for obtaining drug samples from a drug sample dispenser comprising the steps of:
   providing a drug sample dispenser housing with a plurality of drug samples stored in the housing;
   providing a valid user identification to a database interfaced with the drug sample dispenser;
   inputting request signals to dispense a drug sample;
   selecting a drug sample to be removed from the drug sample dispenser from the database;
   removing the selected drug sample from the drug sample dispenser; and
   automatically closing the dispenser housing with a control system to prevent further access to drug samples stored in the housing.

17. The method of claim 16 further comprising the step of entering a prescriber's name into the database interfaced with the drug sample dispenser.

18. The method of claim 16 further comprising the step of entering a patient's name into the database interfaced with the drug sample dispenser.

19. The method of claim 16 further comprising the step of providing the user access to the drug samples by opening a door on the housing.

20. The method of claim 16 further comprising the step of securing the drug samples from further access by closing a pair of doors on the dispenser with a control system.

21. The method of claim 16 wherein the step of user identification includes using a fingerprint identification system.

22. The method of claim 16 wherein the step of user identification includes using a card identification system.

23. The method of claim 16 further comprises automatically closing the doors after a programmed period of time.

24. The method of claim 16 further comprising accessing the database with a computer in the dispenser housing.

25. The method of claim 24 further comprising actuating a control system to open and close a door to the housing with the computer.

26. A method for dispensing drug samples from a drug sample dispenser comprising the steps of:

storing a plurality of drug samples in a drug sample dispenser having a computer;

verifying a user's identification and access to remove drug samples from the drug sample dispenser;

using a control system in response to a first instruction from the computer to open a housing door to provide user access to the drug samples;

allowing a user to remove the drug samples and record the removed samples in a database; and using the control system to prevent further user access to the drug samples in response to a second instruction from the computer to close the door.

* * * * *